United States Patent
Lyman et al.

(10) Patent No.: US 11,328,798 B2
(45) Date of Patent: May 10, 2022

(54) UTILIZING MULTIPLE SUB-MODELS VIA A MULTI-MODEL MEDICAL SCAN ANALYSIS SYSTEM

(71) Applicant: Enlitic, Inc., San Francisco, CA (US)

(72) Inventors: Kevin Lyman, Fords, NJ (US); Li Yao, San Francisco, CA (US); Eric C. Poblenz, Palo Alto, CA (US); Jordan Prosky, San Francisco, CA (US); Ben Covington, Berkeley, CA (US); Anthony Upton, Malvern (AU)

(73) Assignee: Enlitic, Inc., San Francisco, CA (US)

( * ) Notice: Subject to any disclaimer, the term of this patent is extended or adjusted under 35 U.S.C. 154(b) by 236 days.

(21) Appl. No.: 16/365,772

(22) Filed: Mar. 27, 2019

(65) Prior Publication Data
US 2020/0160971 A1    May 21, 2020

Related U.S. Application Data

(60) Provisional application No. 62/770,334, filed on Nov. 21, 2018.

(51) Int. Cl.
*G16H 50/20* (2018.01)
*G16H 10/60* (2018.01)
(Continued)

(52) U.S. Cl.
CPC .......... *G16H 10/60* (2018.01); *A61B 5/7264* (2013.01); *G06F 3/0482* (2013.01);
(Continued)

(58) Field of Classification Search
CPC ........................ G06Q 50/22–24; G16H 10/60
See application file for complete search history.

(56) References Cited

U.S. PATENT DOCUMENTS 6,470,092 B1 * 10/2002 Li .................... G06T 7/0012
                                                             382/132
6,524,246 B1    2/2003 Kelly
(Continued)

FOREIGN PATENT DOCUMENTS

CN             106551704 A       4/2017
WO     WO-2016013004 A1 *  1/2016  ............ A61B 6/482

OTHER PUBLICATIONS

"Medical Image Classification Based on Deep Features Extracted by Deep Model and Statistic Feature Fusion with Multilayer Perceptron"; Lai et al.; Sep. 12, 2018 (Year: 2018).*
(Continued)

*Primary Examiner* — John A Pauls
(74) *Attorney, Agent, or Firm* — Garlick & Markison; Katherine C. Stuckman; Bruce E. Stuckman

(57) ABSTRACT

A multi-model medical scan analysis system is operable to generate a plurality of training sets from a plurality of medical scans. Each of a set of sub-models can be generated by performing a training step on a corresponding one of the plurality of training sets. A subset of the set of sub-models is selected for a new medical scan. A set of abnormality data is generated by applying a subset of a set of inference functions on the new medical scan, where the subset of the set of inference functions utilize the subset of the set of sub-models. Final abnormality data is generated by performing a final inference function on the set of abnormality data. The final abnormality data can be to a client device for display via a display device.

19 Claims, 64 Drawing Sheets

(51) Int. Cl.

| | | |
|---|---|---|
| H04L 67/01 | (2022.01) | |
| G16H 30/40 | (2018.01) | |
| G16H 15/00 | (2018.01) | |
| G06K 9/62 | (2022.01) | |
| G06T 5/00 | (2006.01) | |
| G06T 5/50 | (2006.01) | |
| G06T 7/00 | (2017.01) | |
| G06T 11/00 | (2006.01) | |
| G06N 5/04 | (2006.01) | |
| G16H 30/20 | (2018.01) | |
| G06N 20/00 | (2019.01) | |
| G06F 9/54 | (2006.01) | |
| G06T 7/187 | (2017.01) | |
| G06T 7/11 | (2017.01) | |
| G06F 3/0482 | (2013.01) | |
| G06T 3/40 | (2006.01) | |
| A61B 5/00 | (2006.01) | |
| G06F 21/62 | (2013.01) | |
| G06Q 20/14 | (2012.01) | |
| G16H 40/20 | (2018.01) | |
| G06F 3/0484 | (2022.01) | |
| G06Q 10/06 | (2012.01) | |
| G16H 10/20 | (2018.01) | |
| G06T 7/10 | (2017.01) | |
| G06T 11/20 | (2006.01) | |
| G06F 16/245 | (2019.01) | |
| G06T 7/44 | (2017.01) | |
| G06N 20/20 | (2019.01) | |
| H04L 67/12 | (2022.01) | |
| G06V 10/22 | (2022.01) | |
| G16H 50/70 | (2018.01) | |
| G06T 7/70 | (2017.01) | |
| G16H 50/30 | (2018.01) | |
| A61B 5/055 | (2006.01) | |
| A61B 6/03 | (2006.01) | |
| A61B 8/00 | (2006.01) | |
| A61B 6/00 | (2006.01) | |
| G06Q 50/22 | (2018.01) | |
| G06F 40/295 | (2020.01) | |
| G06V 30/194 | (2022.01) | |

(52) U.S. Cl.
CPC ............ *G06F 3/0484* (2013.01); *G06F 9/542* (2013.01); *G06F 16/245* (2019.01); *G06F 21/6254* (2013.01); *G06K 9/6231* (2013.01); *G06K 9/6254* (2013.01); *G06K 9/6256* (2013.01); *G06K 9/6262* (2013.01); *G06K 9/6277* (2013.01); *G06N 5/04* (2013.01); *G06N 5/045* (2013.01); *G06N 20/00* (2019.01); *G06N 20/20* (2019.01); *G06Q 10/06315* (2013.01); *G06Q 20/14* (2013.01); *G06T 3/40* (2013.01); *G06T 5/002* (2013.01); *G06T 5/008* (2013.01); *G06T 5/50* (2013.01); *G06T 7/0012* (2013.01); *G06T 7/0014* (2013.01); *G06T 7/10* (2017.01); *G06T 7/11* (2017.01); *G06T 7/187* (2017.01); *G06T 7/44* (2017.01); *G06T 7/97* (2017.01); *G06T 11/001* (2013.01); *G06T 11/006* (2013.01); *G06T 11/206* (2013.01); *G06V 10/225* (2022.01); *G16H 10/20* (2018.01); *G16H 15/00* (2018.01); *G16H 30/20* (2018.01); *G16H 30/40* (2018.01); *G16H 40/20* (2018.01); *G16H 50/20* (2018.01); *H04L 67/12* (2013.01); *H04L 67/42* (2013.01); *A61B 5/055* (2013.01); *A61B 6/032* (2013.01); *A61B 6/5217* (2013.01); *A61B 8/4416* (2013.01); *G06F 40/295* (2020.01); *G06K 9/6229* (2013.01); *G06K 9/6267* (2013.01); *G06Q 50/22* (2013.01); *G06T 7/70* (2017.01); *G06T 2200/24* (2013.01); *G06T 2207/10048* (2013.01); *G06T 2207/10081* (2013.01); *G06T 2207/10088* (2013.01); *G06T 2207/10116* (2013.01); *G06T 2207/10132* (2013.01); *G06T 2207/20076* (2013.01); *G06T 2207/20081* (2013.01); *G06T 2207/20084* (2013.01); *G06T 2207/30004* (2013.01); *G06T 2207/30008* (2013.01); *G06T 2207/30016* (2013.01); *G06T 2207/30061* (2013.01); *G06V 30/194* (2022.01); *G06V 2201/03* (2022.01); *G16H 50/30* (2018.01); *G16H 50/70* (2018.01)

(56) References Cited

U.S. PATENT DOCUMENTS

| | | | |
|---|---|---|---|
| 6,937,776 | B2 | 8/2005 | Li |
| 7,123,762 | B2 | 10/2006 | Giger |
| 7,418,123 | B2 | 8/2008 | Giger |
| 7,813,822 | B1 | 10/2010 | Hoffberg |
| 8,121,362 | B2 | 2/2012 | Zhan |
| 8,303,505 | B2 | 11/2012 | Webler |
| 9,165,360 | B1 | 10/2015 | Bates |
| 9,569,736 | B1 | 2/2017 | Ghesu |
| 9,579,518 | B2 | 2/2017 | Gertner |
| 9,760,978 | B1 | 9/2017 | Lu |
| 2002/0186818 | A1 | 12/2002 | Arnaud |
| 2004/0147840 | A1 | 7/2004 | Duggirala |
| 2004/0252870 | A1 | 12/2004 | Reeves |
| 2005/0010445 | A1* | 1/2005 | Krishnan .............. G06T 7/0012 705/2 |
| 2005/0251013 | A1* | 11/2005 | Krishnan .............. G06T 7/0012 600/407 |
| 2005/0283450 | A1 | 12/2005 | Matsugu |
| 2006/0018524 | A1* | 1/2006 | Suzuki ................. G06V 10/25 382/128 |
| 2008/0015418 | A1 | 1/2008 | Jarrell |
| 2008/0021834 | A1 | 1/2008 | Holla |
| 2008/0205717 | A1 | 8/2008 | Reeves |
| 2008/0267483 | A1 | 10/2008 | Zhan |
| 2009/0148010 | A1* | 6/2009 | Boroczky ............ G06K 9/3233 382/128 |
| 2009/0177495 | A1 | 7/2009 | Abousy |
| 2009/0222388 | A1 | 9/2009 | Hua |
| 2010/0177942 | A1* | 7/2010 | Kolatt ................. G06T 7/90 382/128 |
| 2011/0103675 | A1* | 5/2011 | Marshall .............. G06T 7/0012 382/132 |
| 2014/0341471 | A1 | 11/2014 | Ono et al. |
| 2015/0031979 | A1 | 1/2015 | Rappaport et al. |
| 2015/0063667 | A1 | 3/2015 | Sprencz |
| 2015/0278457 | A1* | 10/2015 | De la Torre ........... G16H 50/20 705/3 |
| 2015/0305706 | A1 | 10/2015 | Kanik |
| 2016/0019695 | A1 | 1/2016 | Chukka |
| 2016/0027175 | A1 | 1/2016 | Kim et al. |
| 2016/0104281 | A1 | 4/2016 | Grady |
| 2016/0203281 | A1 | 7/2016 | Zalis |
| 2016/0314588 | A1 | 10/2016 | Harper |
| 2016/0343127 | A1 | 11/2016 | Miller |
| 2017/0116497 | A1 | 4/2017 | Georgescu |
| 2018/0025255 | A1* | 1/2018 | Poole ..................... G06T 7/337 382/131 |
| 2018/0033144 | A1 | 2/2018 | Risman |
| 2018/0060535 | A1 | 3/2018 | Reicher |
| 2018/0060691 | A1 | 3/2018 | Bernal |
| 2018/0114595 | A1 | 4/2018 | Stern |
| 2018/0204111 | A1 | 7/2018 | Zadeh |

(56) References Cited

U.S. PATENT DOCUMENTS

2018/0365281 A1* 12/2018 Patel .................. G06F 16/2365
2020/0334228 A1* 10/2020 Matyska ............... G06F 16/278

OTHER PUBLICATIONS

Andersch, Michael; Inference: The Next Step in GPU-Accelerated Deep Learning; https://devblogs.nvidia.com/parallelforall/inference-next-step-gpu-accelerated-deep-learning/; Nov. 11, 2015; 7 pages.
International Searching Authority; International Search Report and Written Opinion; International Application No. PCT/US2018/032927; dated Sep. 14, 2018; 9 pgs.
Minnaar, Alex; Deep Learning Basics: Neural Networks, Backpropagation and Stochastic Gradient Descent; http://alexminnaar.com/deep-learning-basics-neural-networks-backpropagation-and-stochastic-gradient-descent.html; Feb. 14, 2015; 11 pages.
Olah, Christopher; Calculus on Computational Graphs: Backpropagation; http://colah.github.io/posts/2015-08-Backprop/; Aug. 31, 2015; 7 pages.
Reid, Stuart; 10 misconceptions about Neural Networks; http://www.turingfinance.com/misconceptions-about-neural-networks/; May 8, 2014; 24 pages.
Wikipedia: Backpropagation; https://en.wikipedia.org/wiki/Backpropagation#Assumptions_about_the_loss_function; downloaded from the internet on 18/15/18; 12 pages.
Wikipedia, Convolutional neural network; https://en.wikipedia.org/wiki/Convolutional_neural_network#Pooling_layer; downloaded from the internet on Jan. 15, 18; 21 pages.
Pre Conference Proceedings of the 7th MICCAI BraTS Challenge (2018); BraTS Multimodal Brain Tumor Segmentation Challenge; Granada, Spain; Sep. 16, 2018; 578 pages.

* cited by examiner

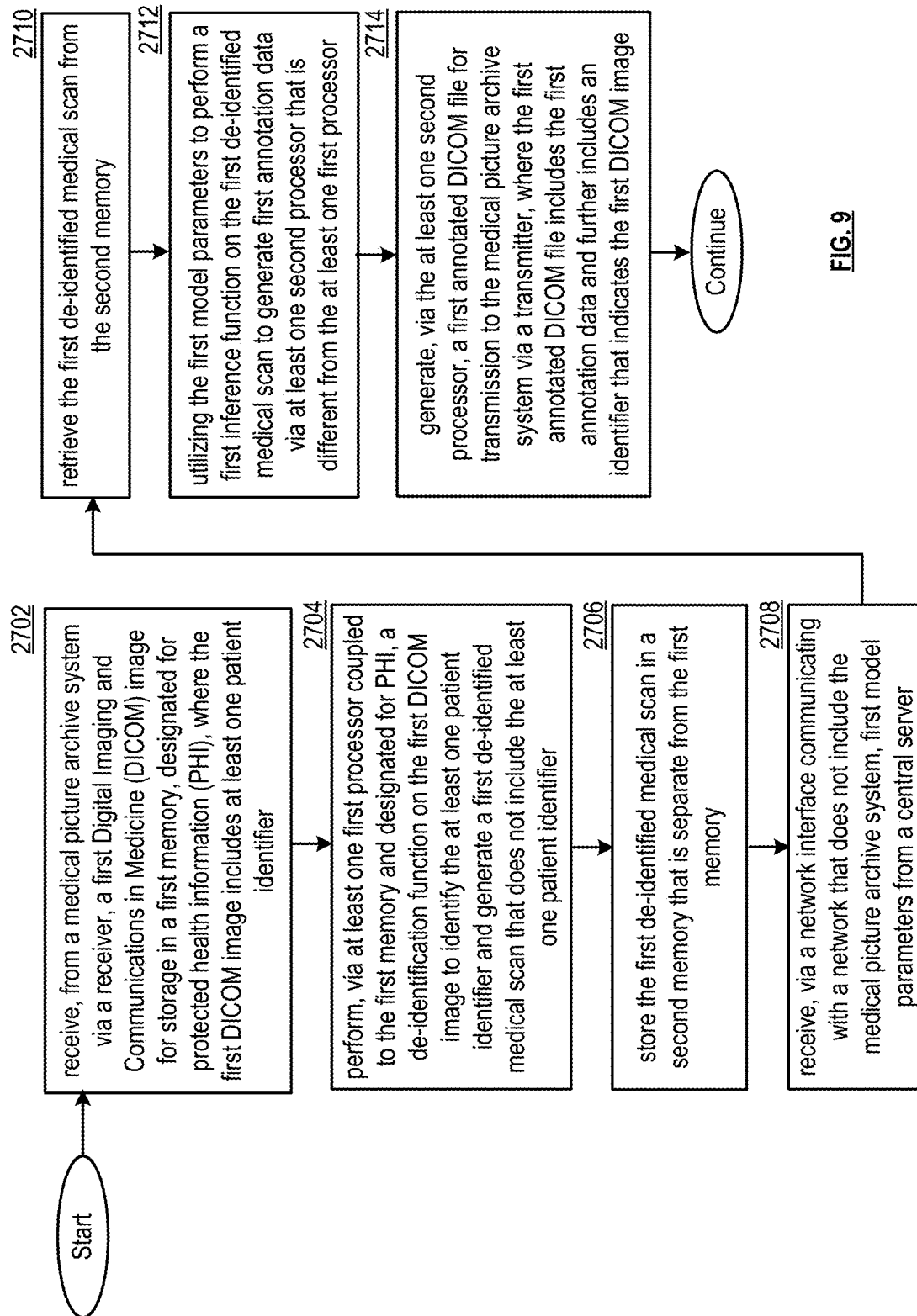

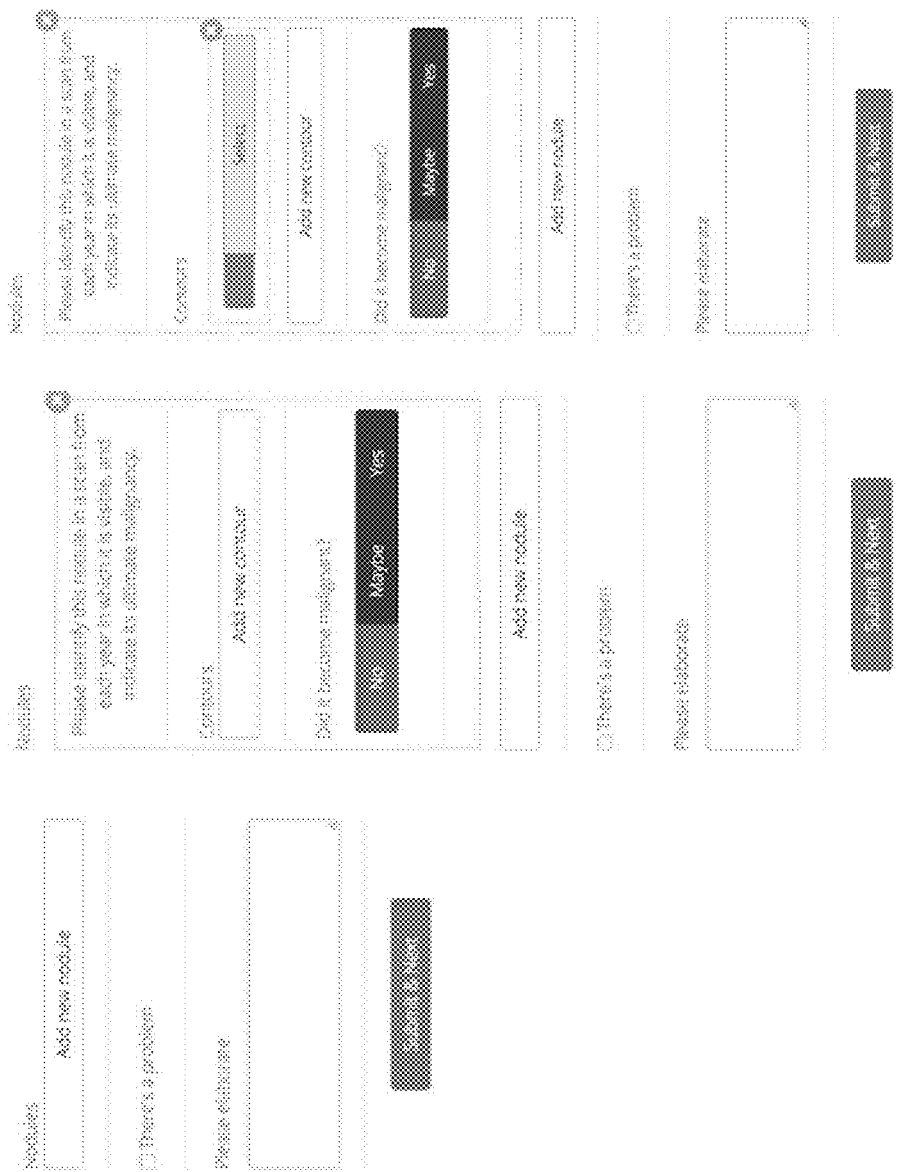

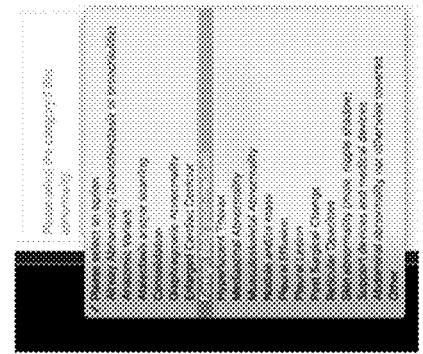
FIG. 13O
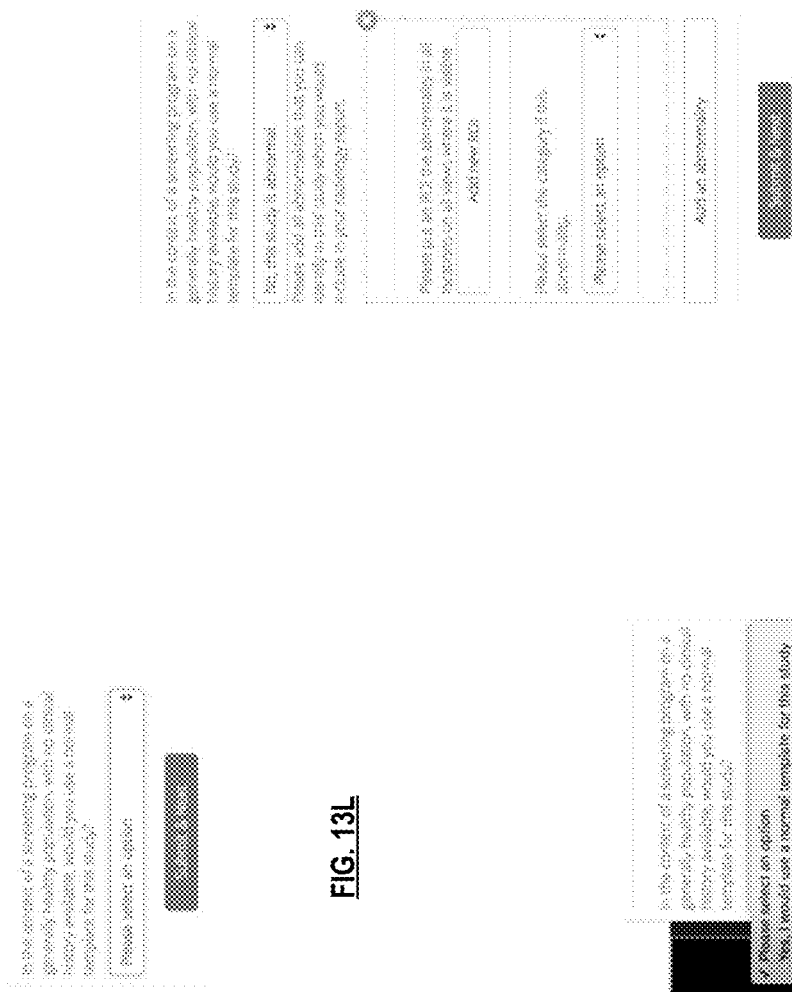
FIG. 13N
FIG. 13L
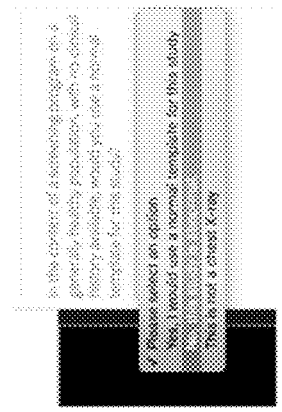
FIG. 13M

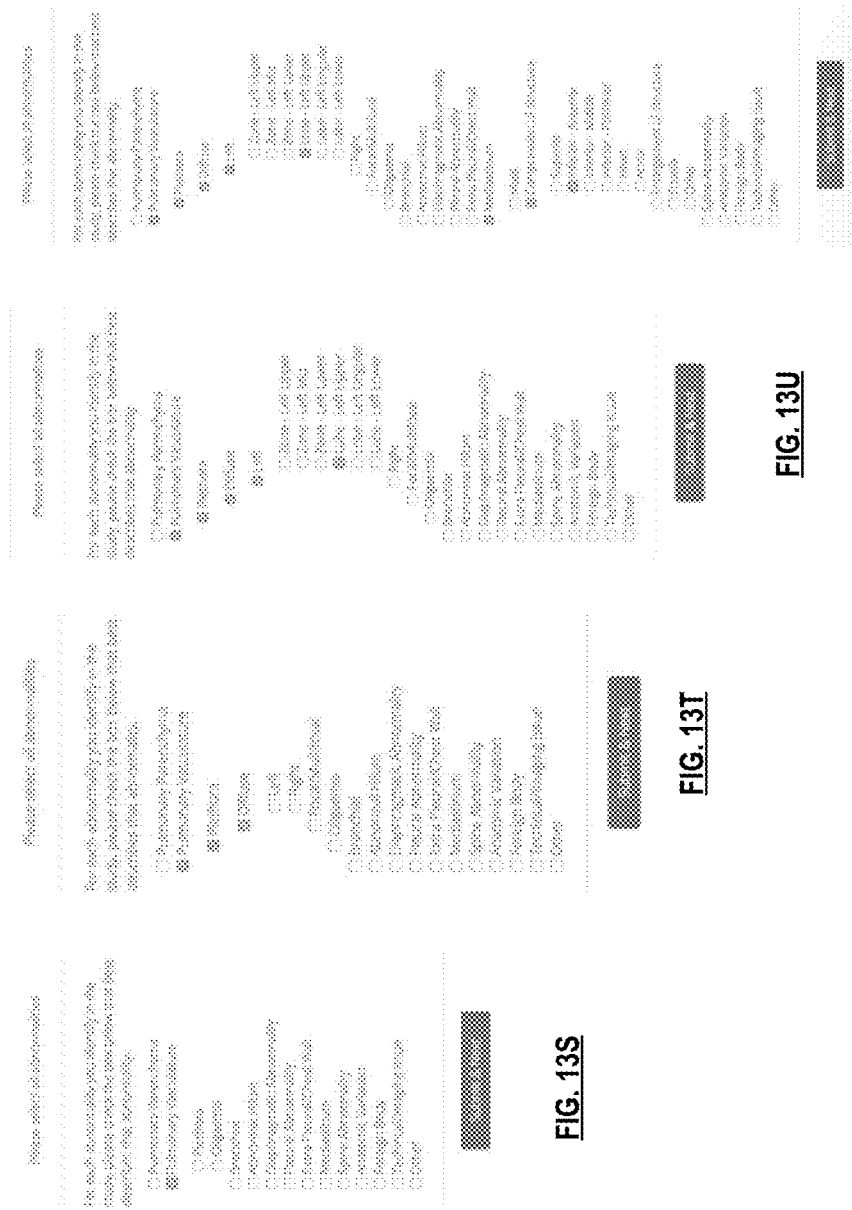

| | | AUC | | | DICE | | |
|---|---|---|---|---|---|---|---|
| | | $r_0 = 0$ | $r_0 = 5$ | $r_0 = 10$ | $r_0 = 0$ | $r_0 = 5$ | $r_0 = 10$ |
| Atelectasis | 0.7003 | 0.733 | 0.728 | 0.724 | 0.204 | 0.240 | 0.211 |
| Cardiomegaly | 0.8100 | 0.856 | 0.858 | 0.854 | 0.180 | 0.114 | 0.076 |
| Effusion | 0.7585 | 0.806 | 0.803 | 0.795 | 0.293 | 0.294 | 0.242 |
| Infiltration | 0.6614 | 0.673 | 0.675 | 0.668 | 0.325 | 0.312 | 0.286 |
| Nodule | 0.6687 | 0.718 | 0.724 | 0.727 | 0.202 | 0.238 | 0.196 |
| Mass | 0.6933 | 0.777 | 0.777 | 0.778 | 0.295 | 0.295 | 0.241 |
| Pneumonia | 0.6580 | 0.684 | 0.690 | 0.687 | 0.112 | 0.104 | 0.072 |
| Pneumothorax | 0.7993 | 0.805 | 0.791 | 0.763 | 0.039 | 0.023 | 0.028 |
| Consolidation | 0.7032 | 0.711 | 0.714 | 0.717 | – | – | – |
| Edema | 0.8052 | 0.806 | 0.804 | 0.801 | – | – | – |
| Emphysema | 0.8330 | 0.842 | 0.822 | 0.771 | – | – | – |
| Fibrosis | 0.7859 | 0.743 | 0.757 | 0.731 | – | – | – |
| Pleural thickening | 0.6835 | 0.724 | 0.715 | 0.712 | – | – | – |
| Hernia | 0.8717 | 0.775 | 0.764 | 0.824 | – | – | – |
| A.V.G. | 0.738 | 0.761 | 0.760 | 0.754 | – | – | – |

FIG. 15B

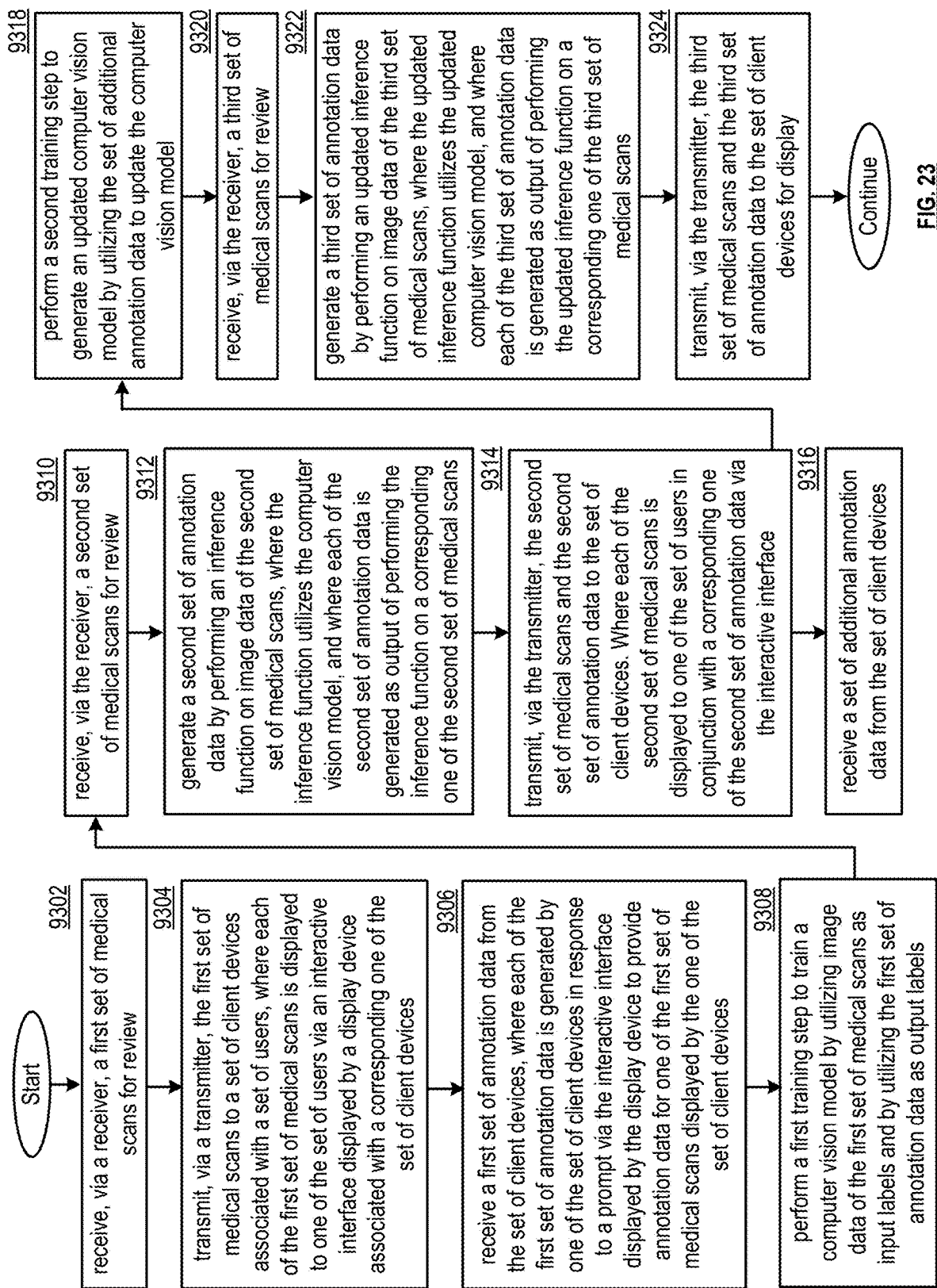

UTILIZING MULTIPLE SUB-MODELS VIA A MULTI-MODEL MEDICAL SCAN ANALYSIS SYSTEM

CROSS REFERENCE TO RELATED APPLICATIONS

The present U.S. Utility patent application claims priority pursuant to 35 U.S.C. § 119(e) to U.S. Provisional Application No. 62/770,334, entitled "LESION TRACKING SYSTEM", filed Nov. 21, 2018, which is hereby incorporated herein by reference in its entirety and made part of the present U.S. Utility patent application for all purposes.

STATEMENT REGARDING FEDERALLY SPONSORED RESEARCH OR DEVELOPMENT

Not applicable.

INCORPORATION-BY-REFERENCE OF MATERIAL SUBMITTED ON A COMPACT DISC

Not applicable.

BACKGROUND

Technical Field

This invention relates generally to medical imaging devices and knowledge-based systems used in conjunction with client/server network architectures.

Description of Related Art

BRIEF DESCRIPTION OF THE SEVERAL VIEWS OF THE DRAWING(S)

FIG. 9 is a flowchart representation of a method for execution by a medical picture archive integration system in accordance with various embodiments;

Figure 11:
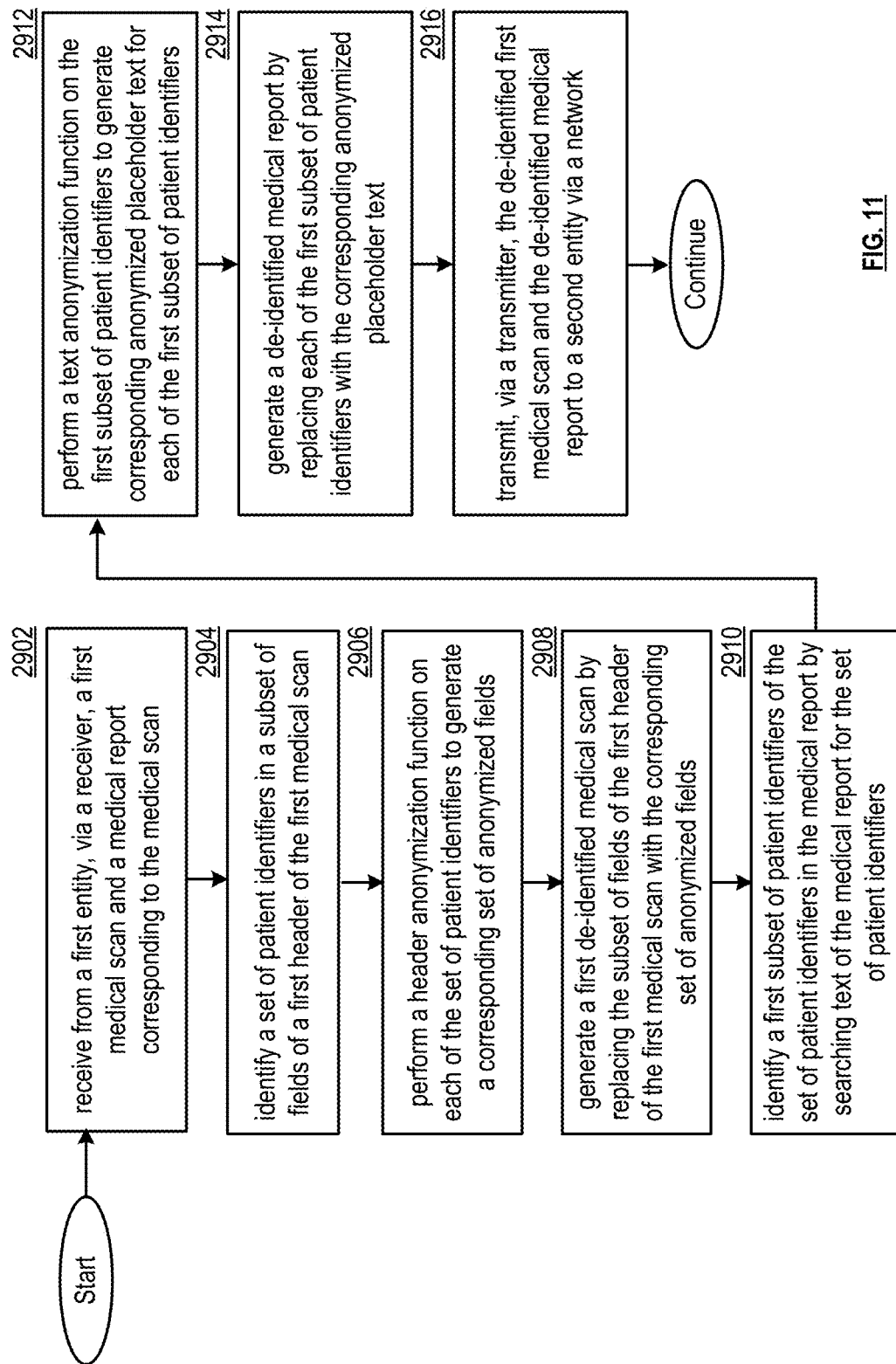
Figure 12A:
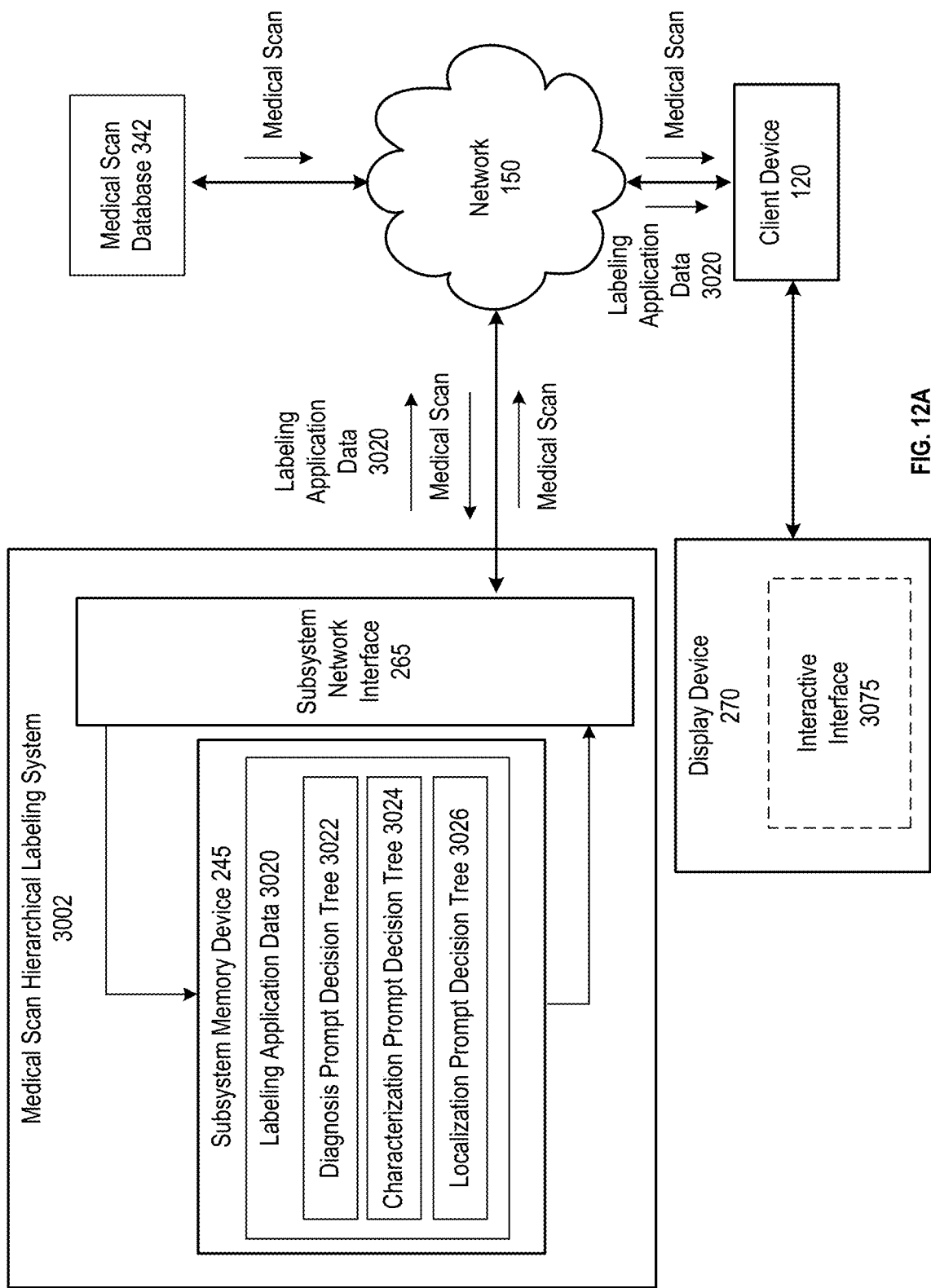
Figure 12B:
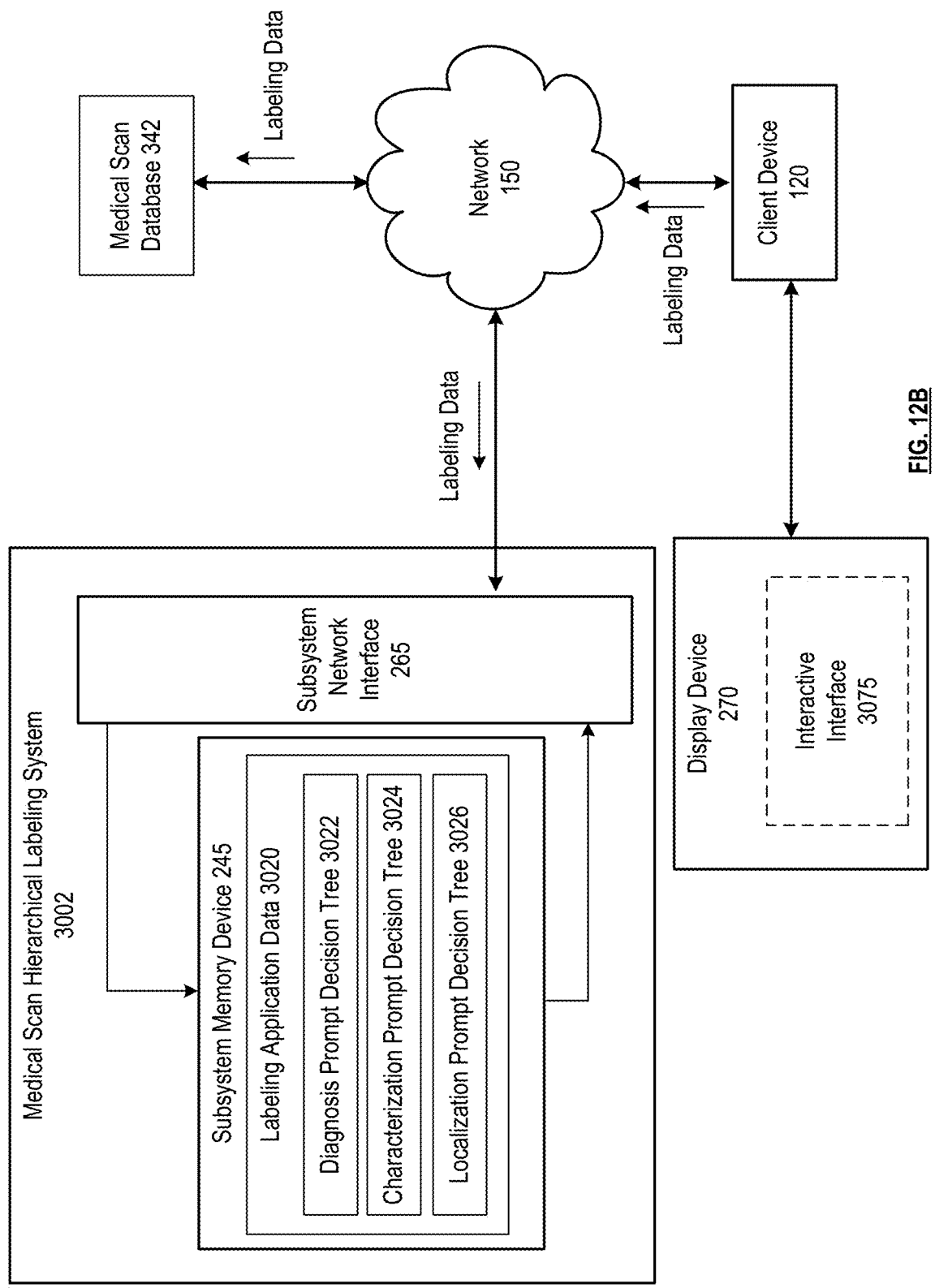
Figure 12C:
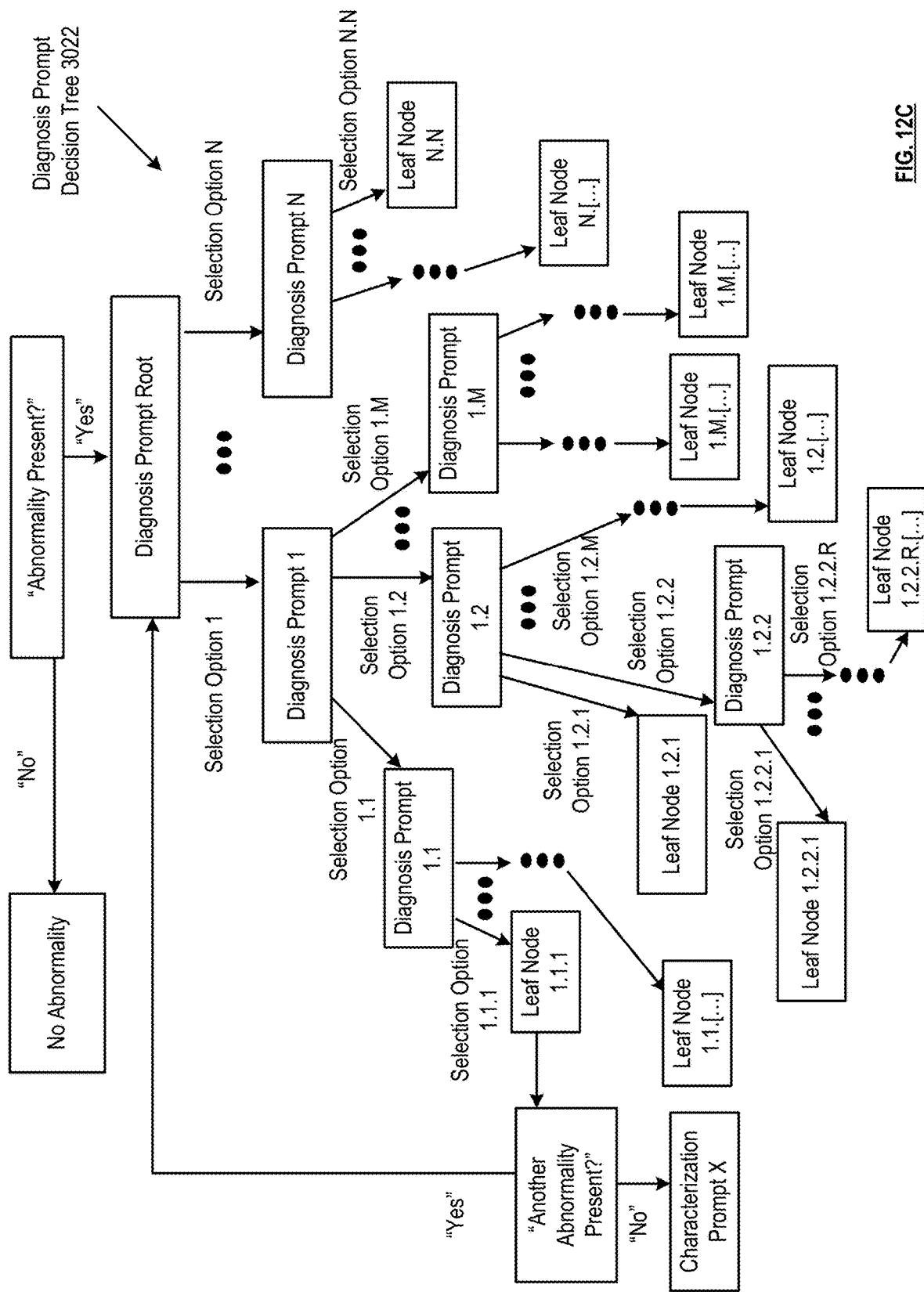
Figure 12D:
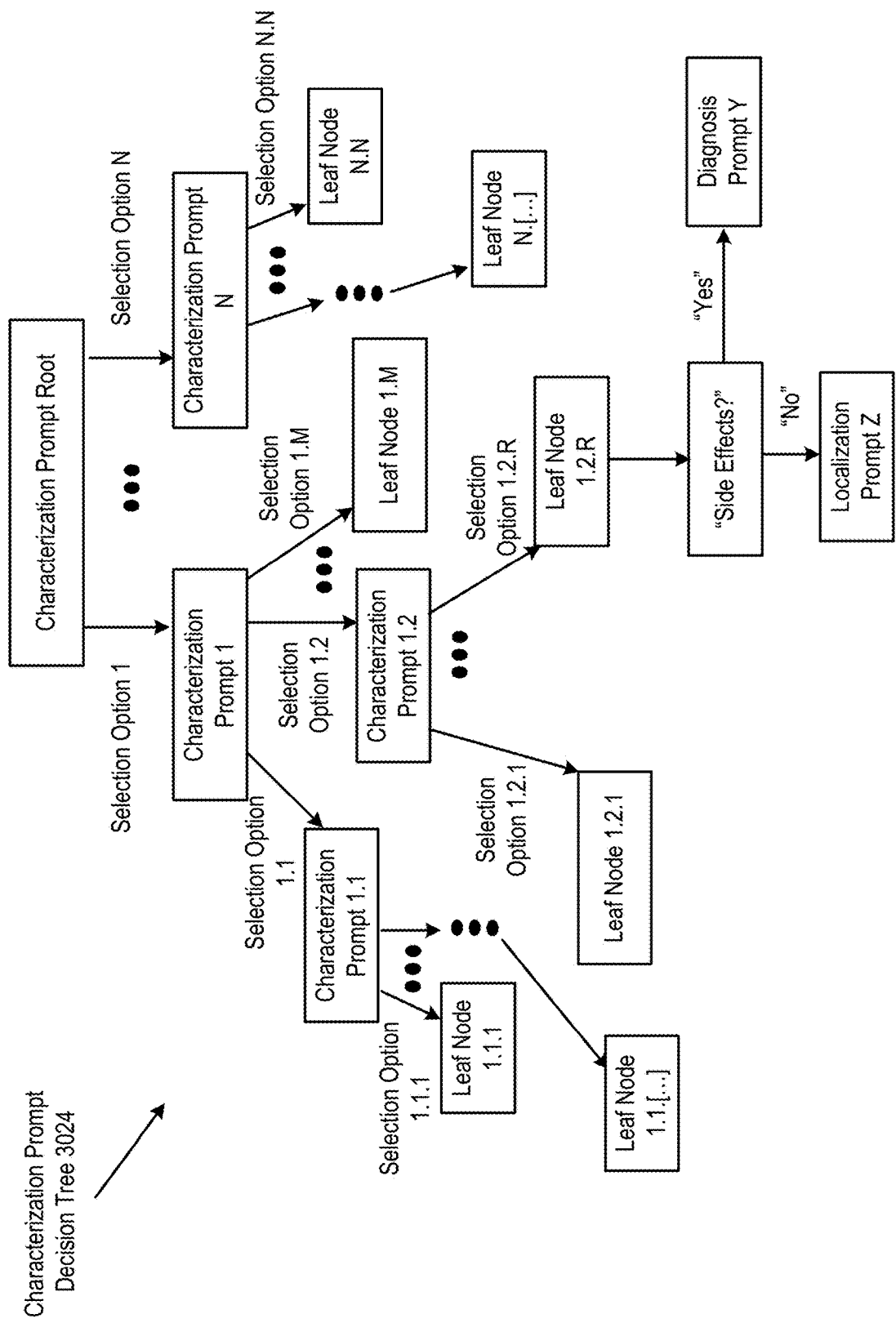
Figure 12E:
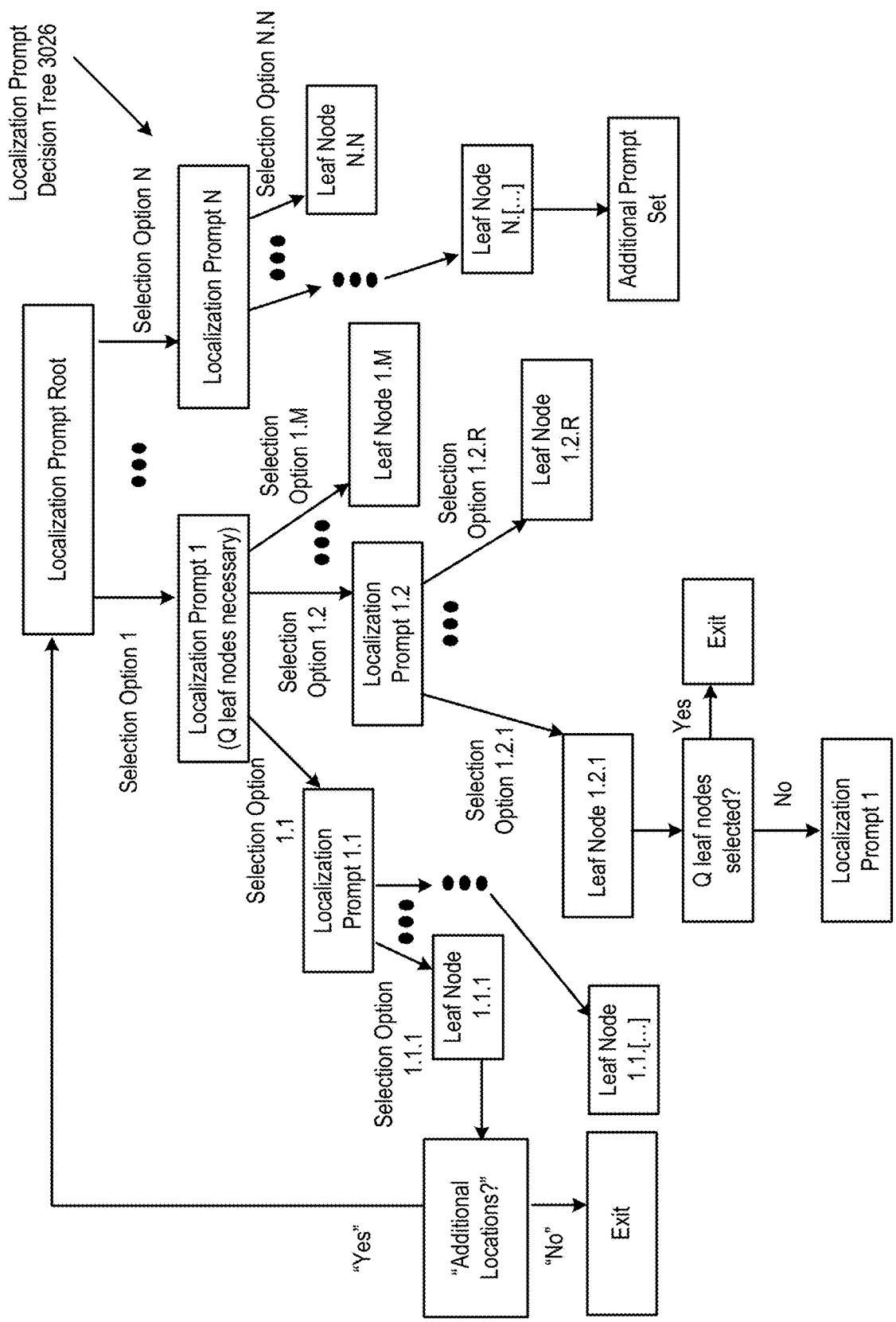
Figure 12F:
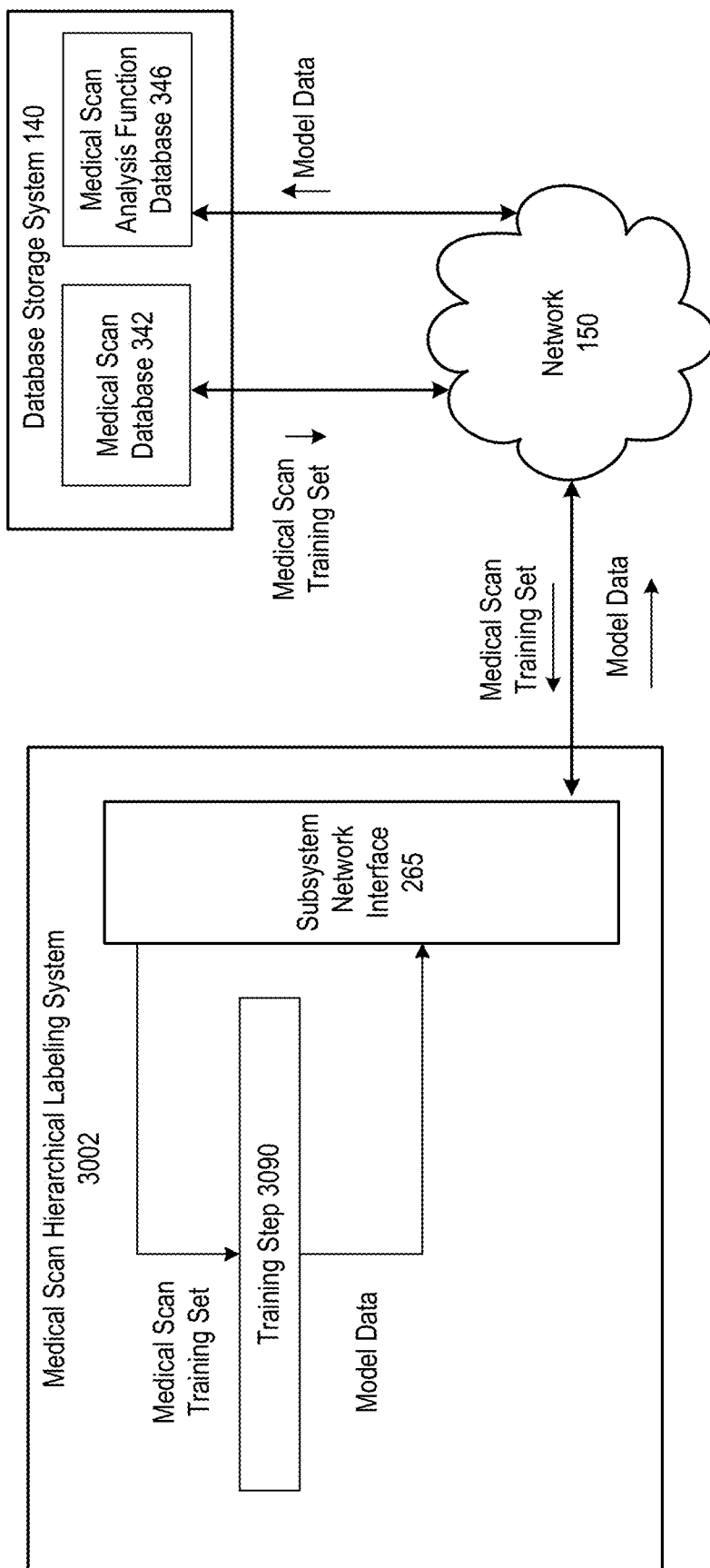
Figure 12G:
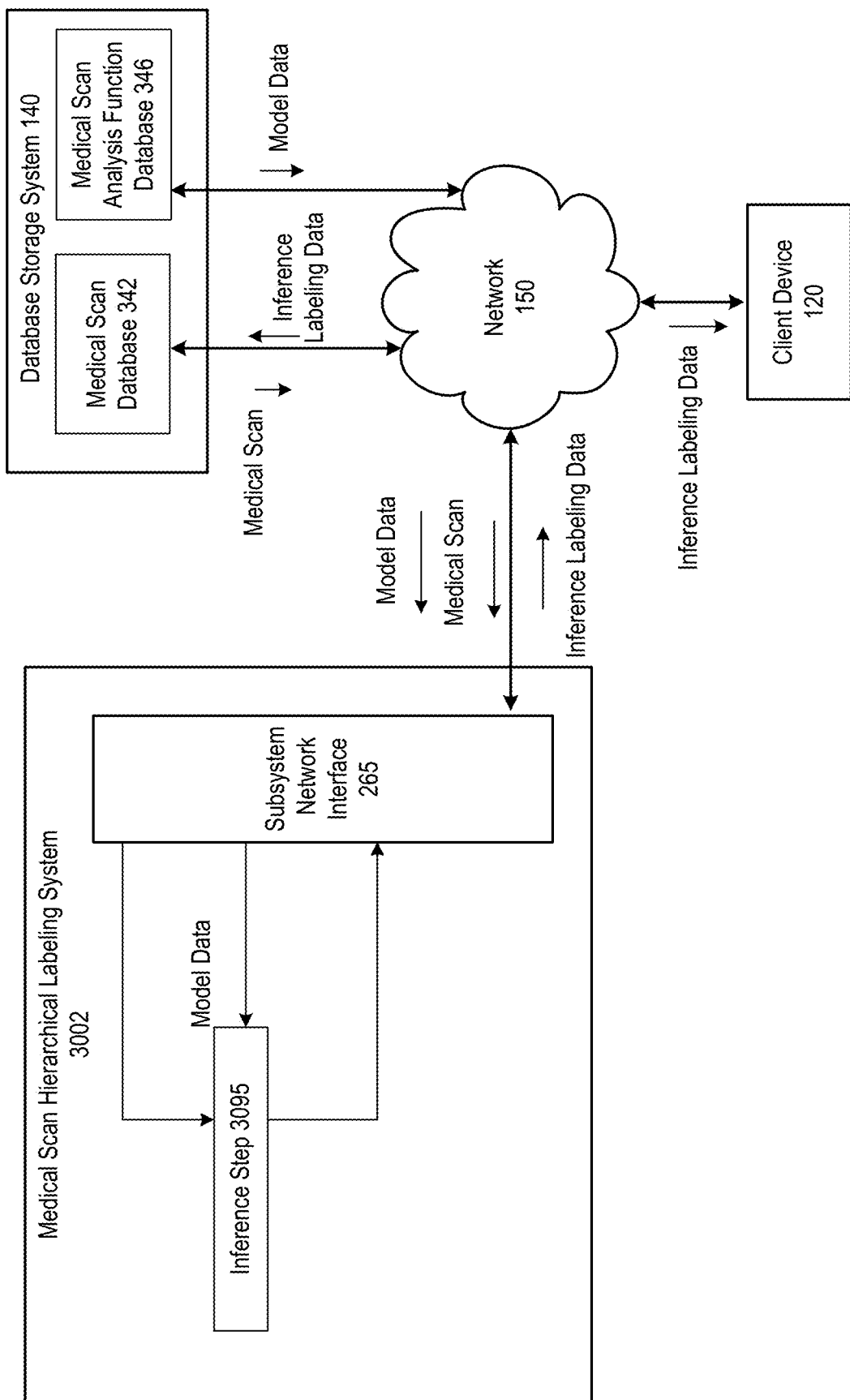
Figure 13A:
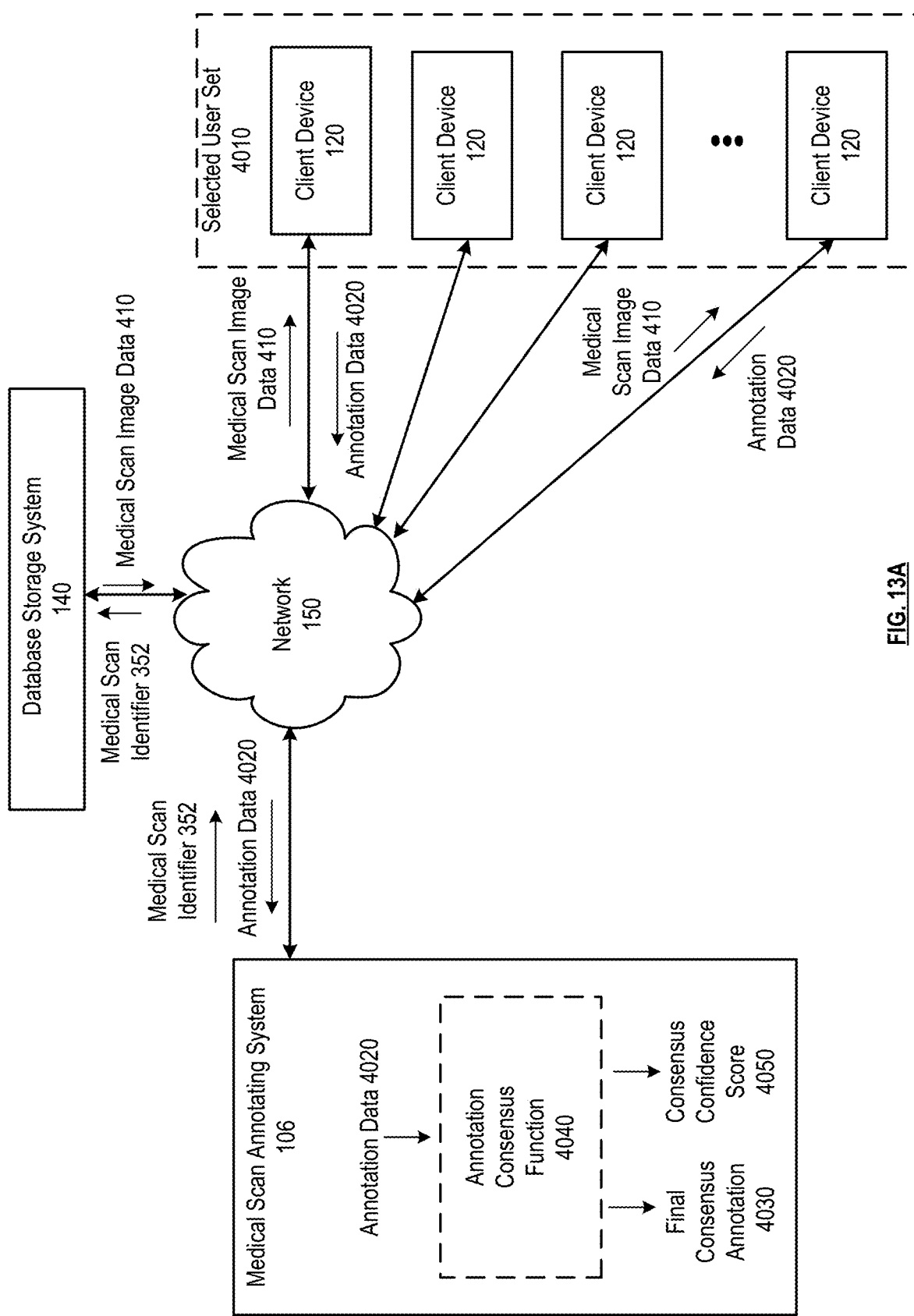
Figure 13B:
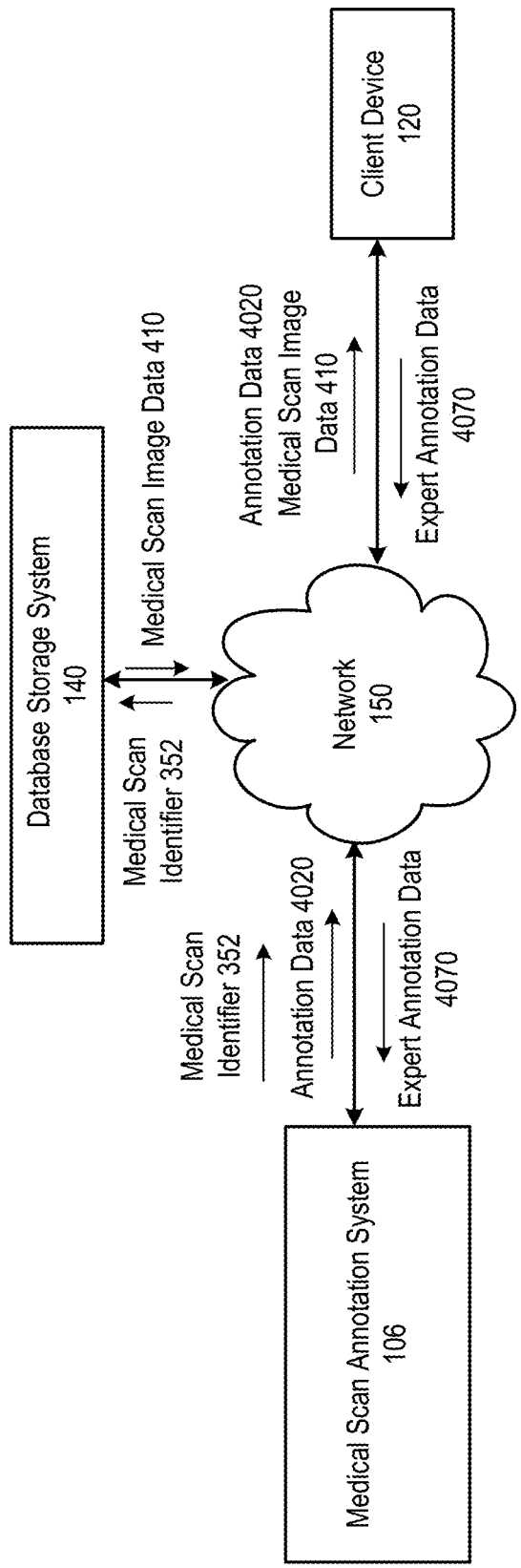
Figures 13C, 13D, 13E, 13F, 13G:
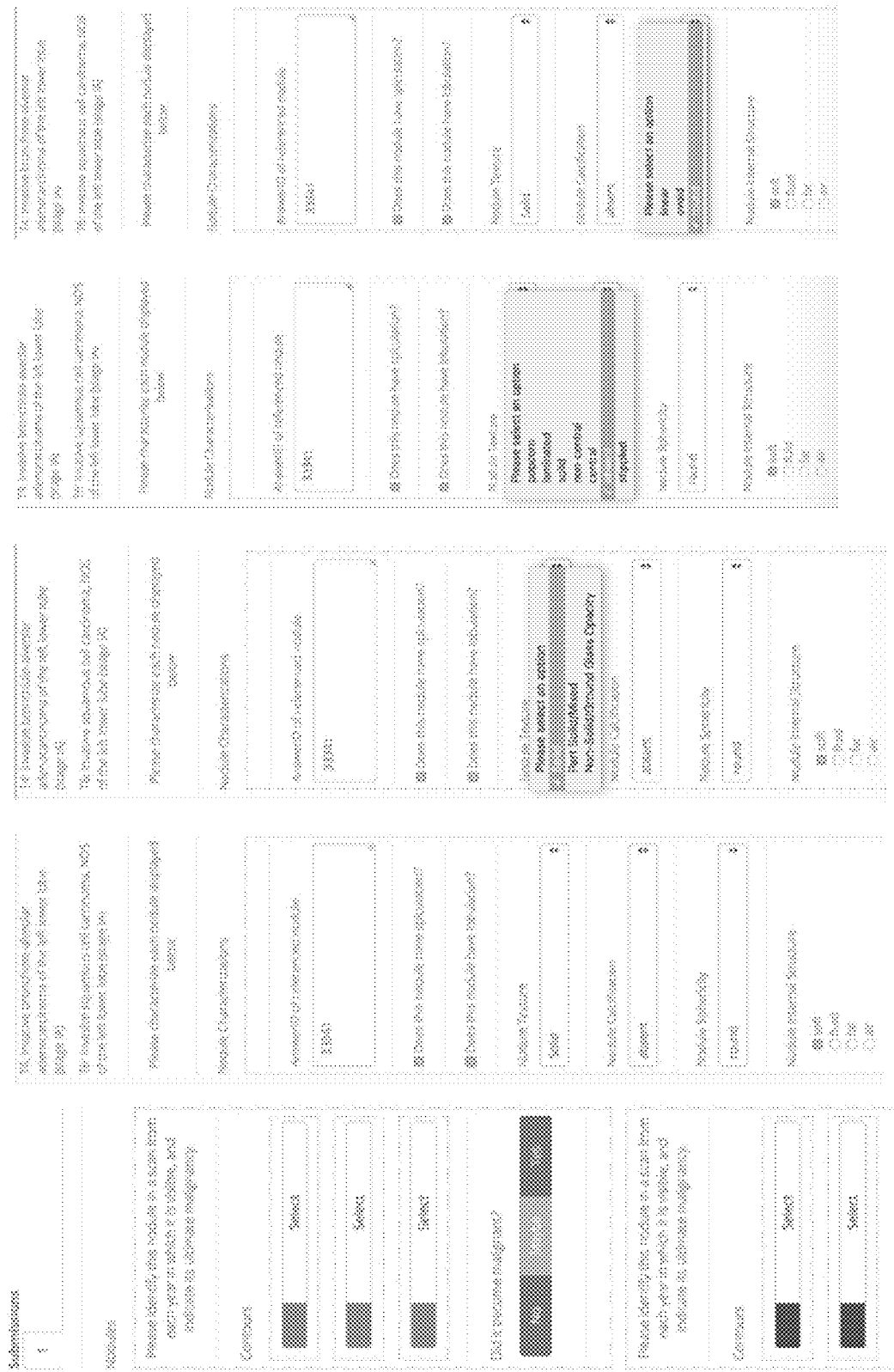
Figure 14A:
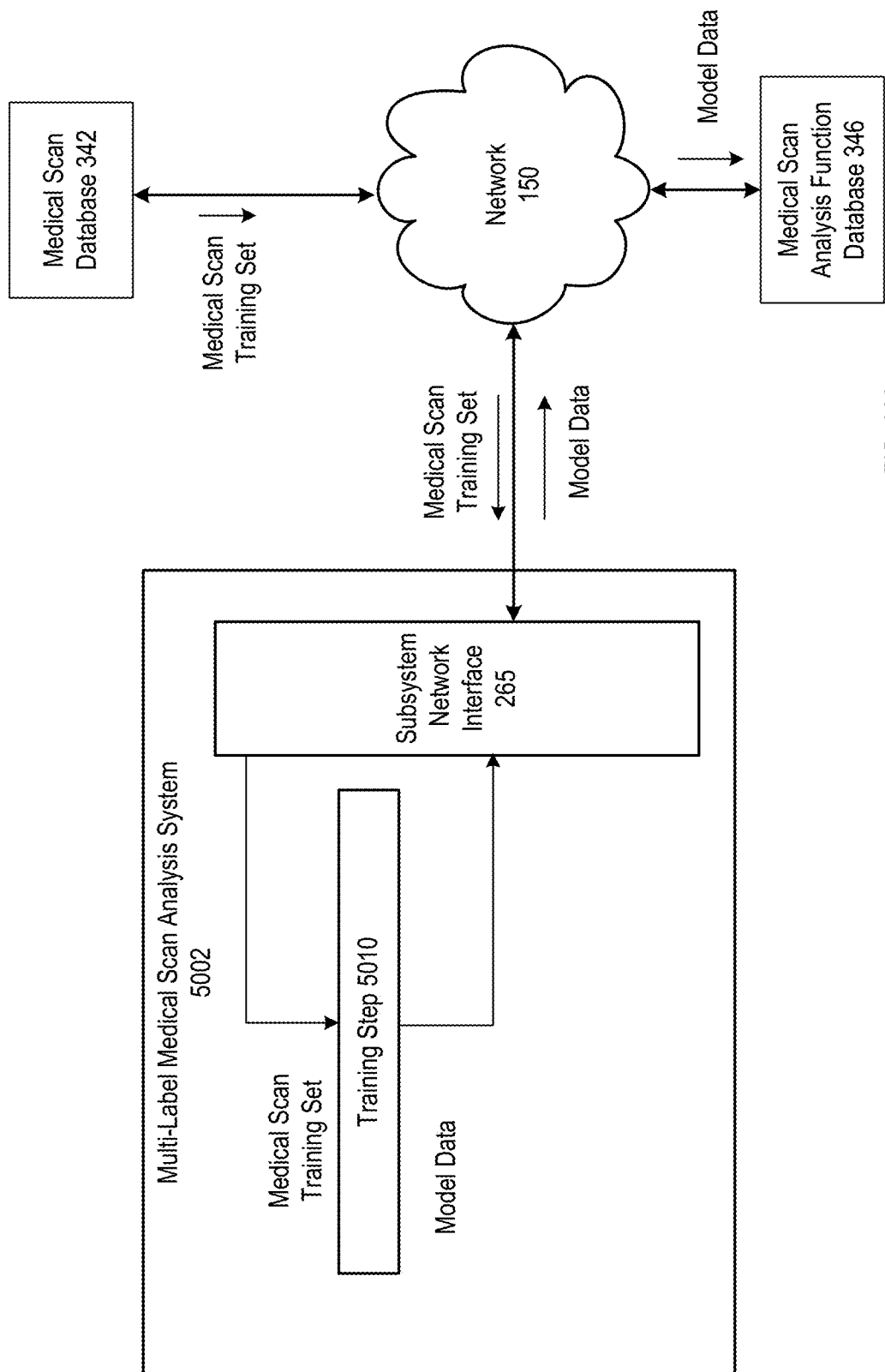
Figure 14B:
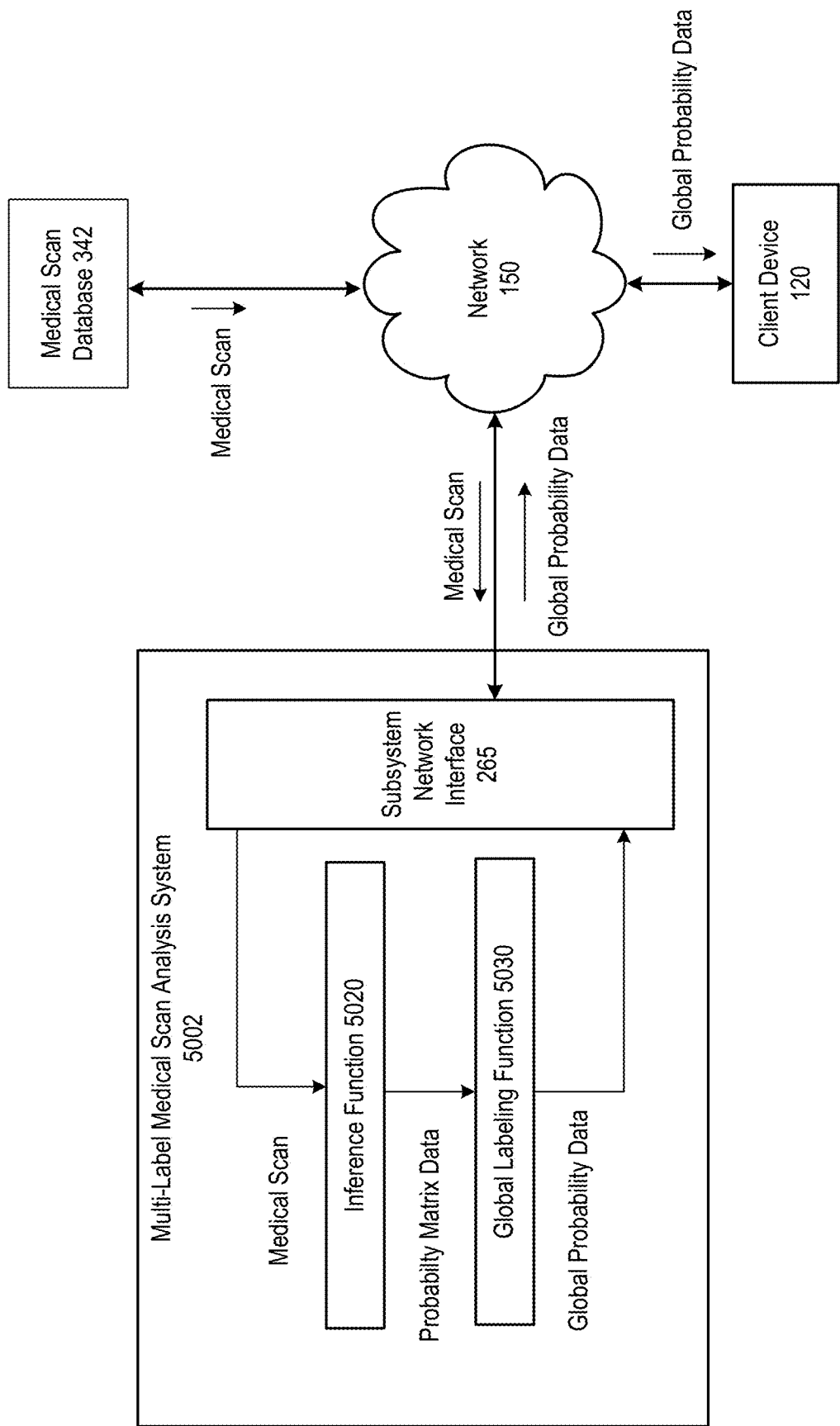
Figure 14C:
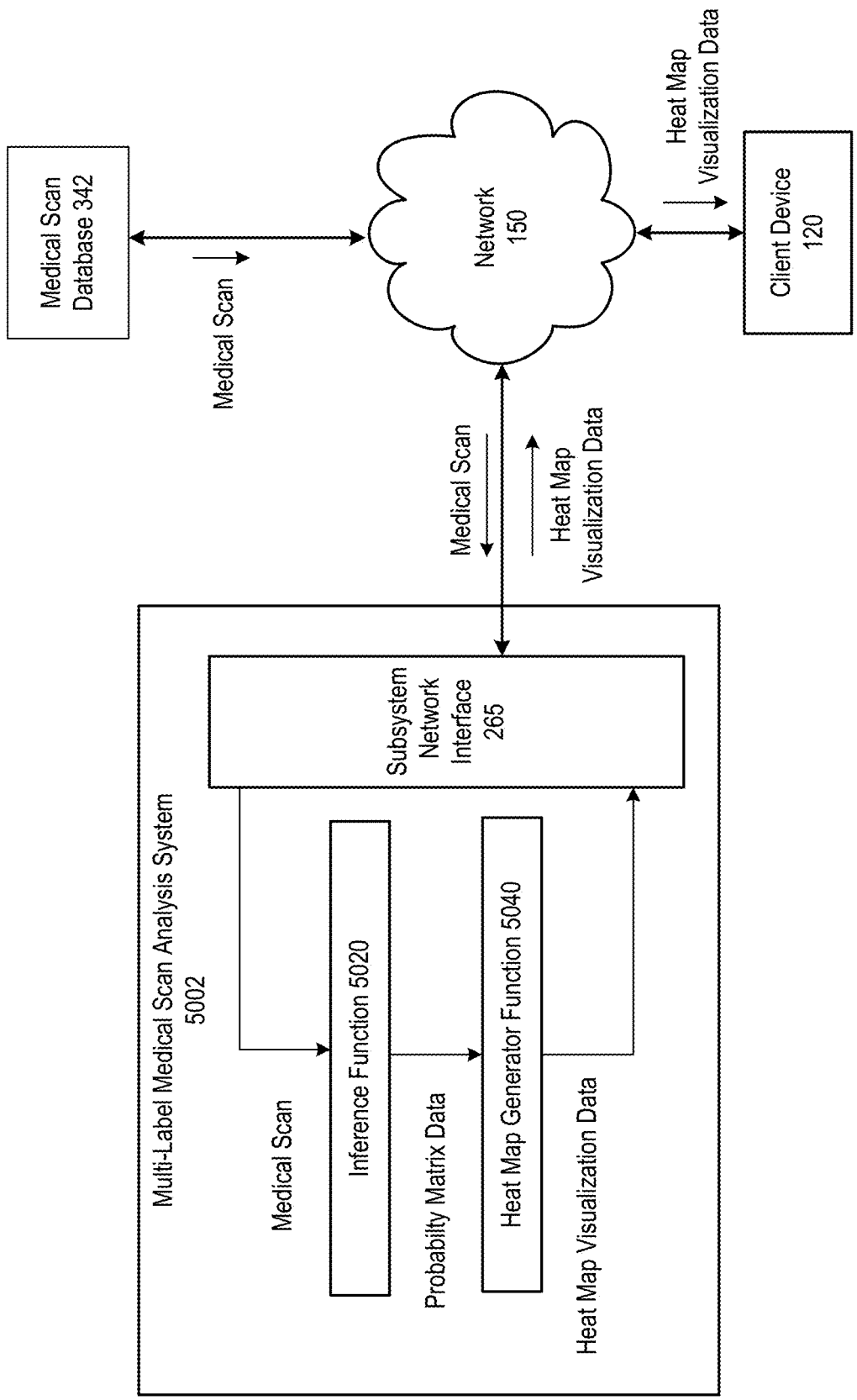
Figure 15A:
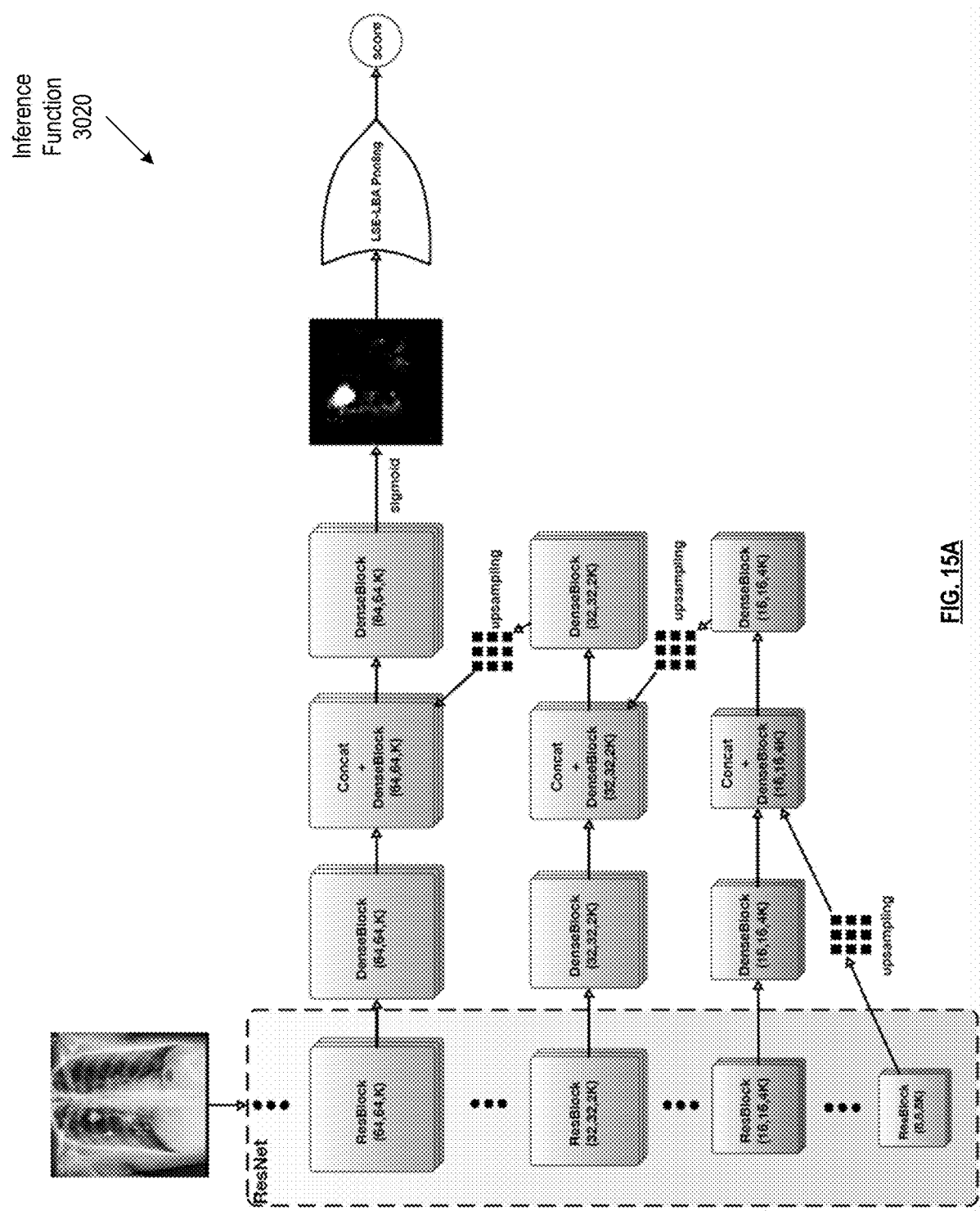
Figure 15C:
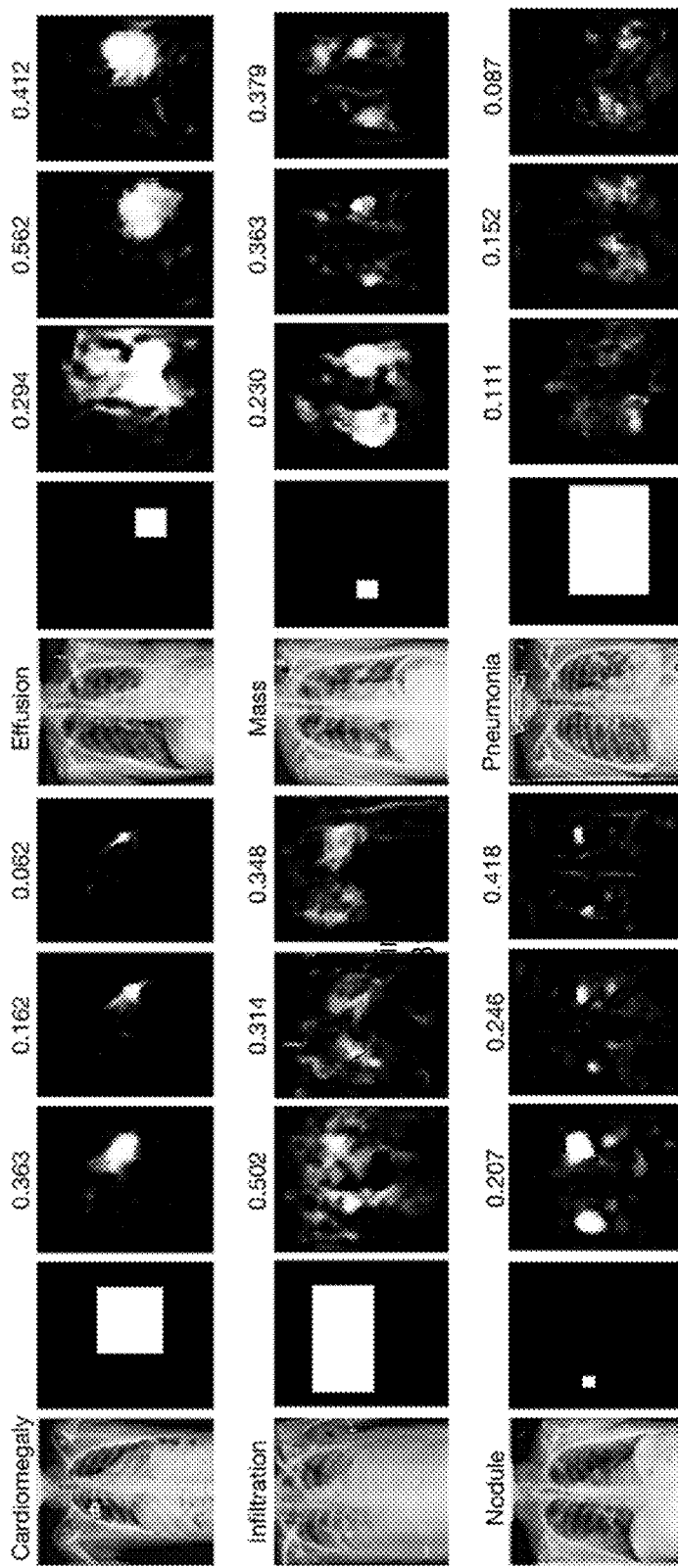
Figure 15D:
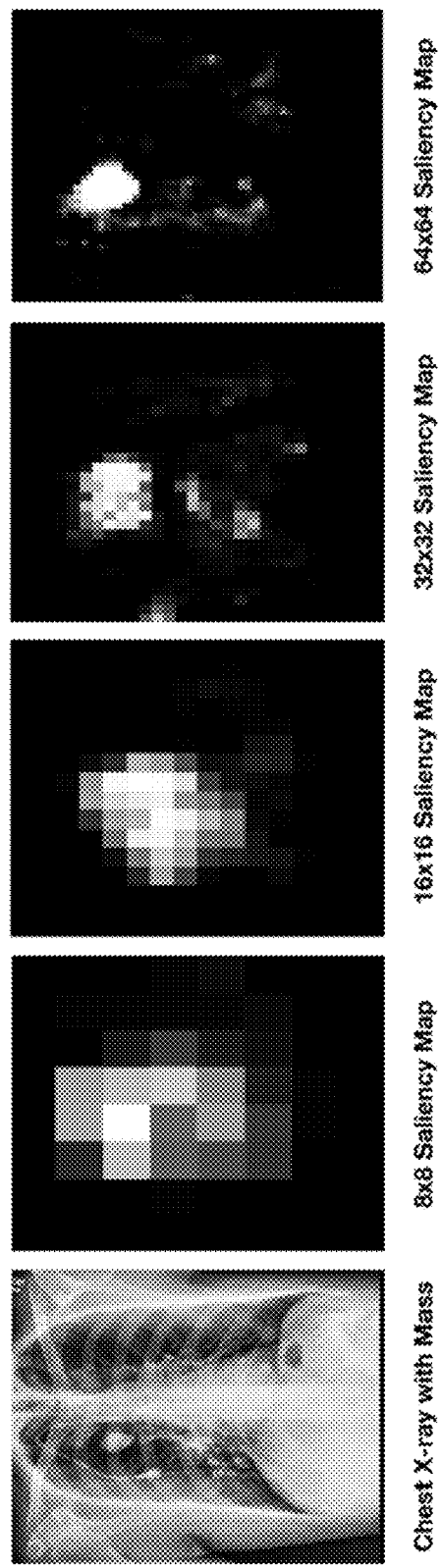
Figure 17:
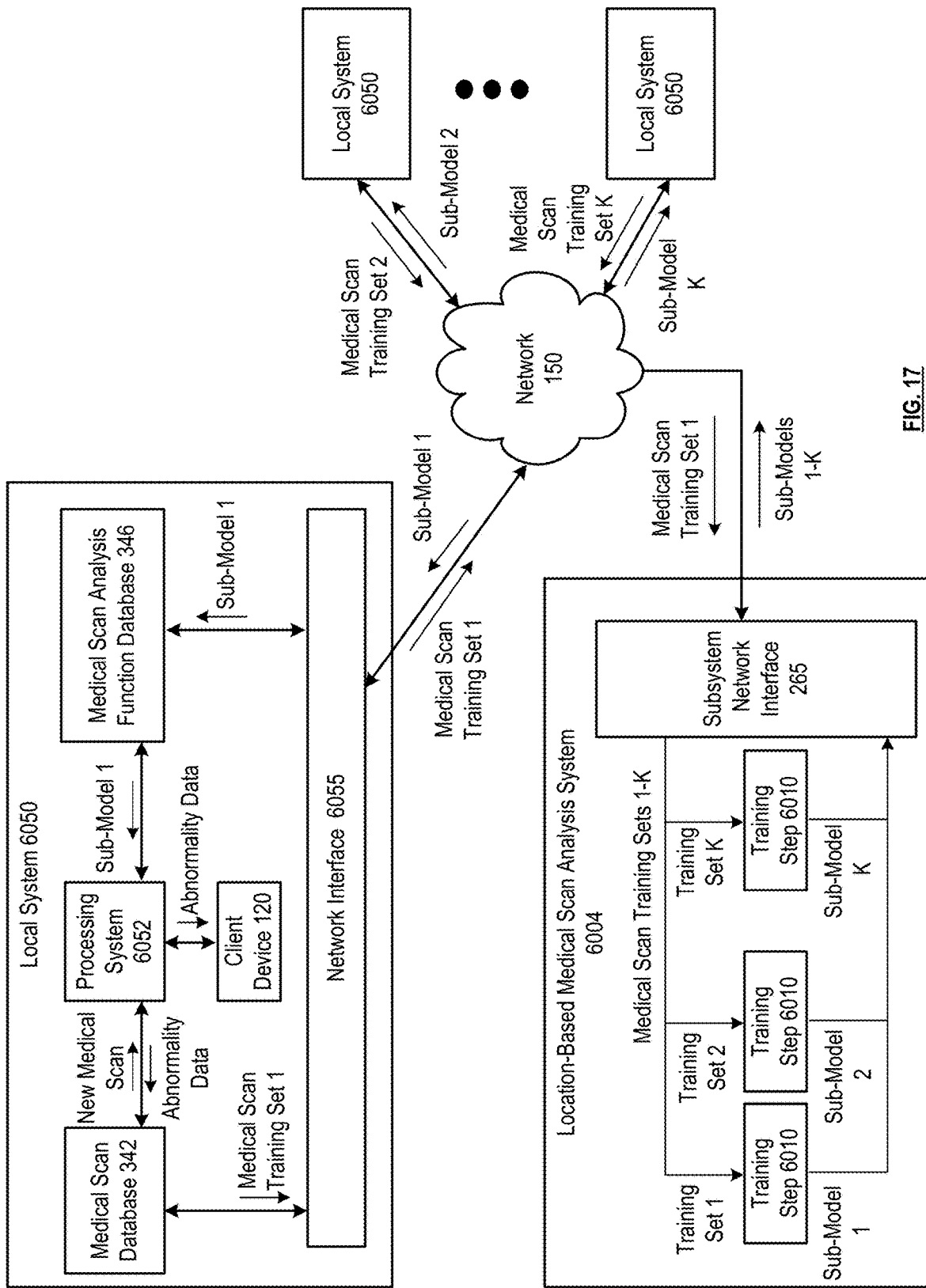
Figure 19:
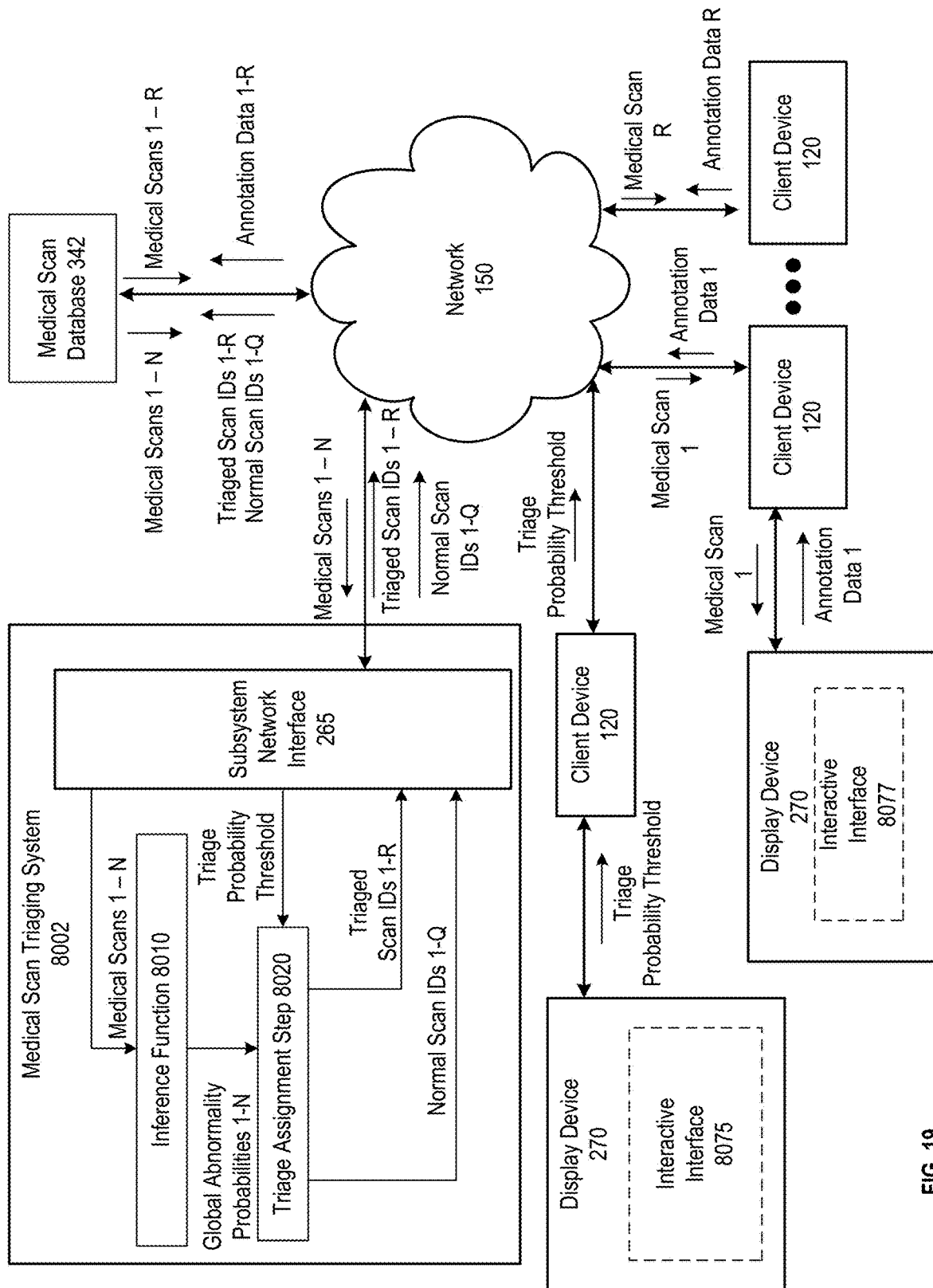
Figure 20:
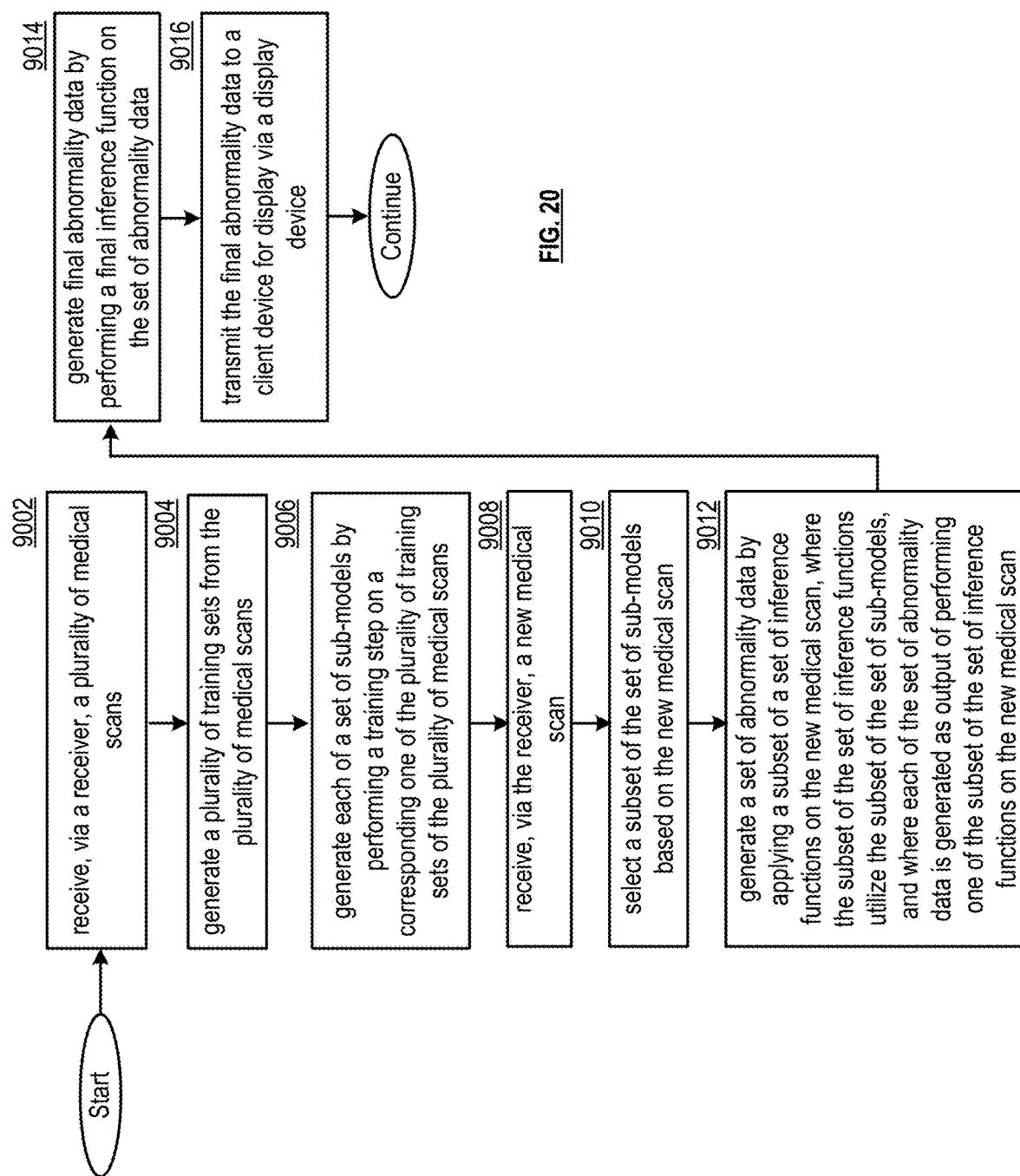
Figure 21:
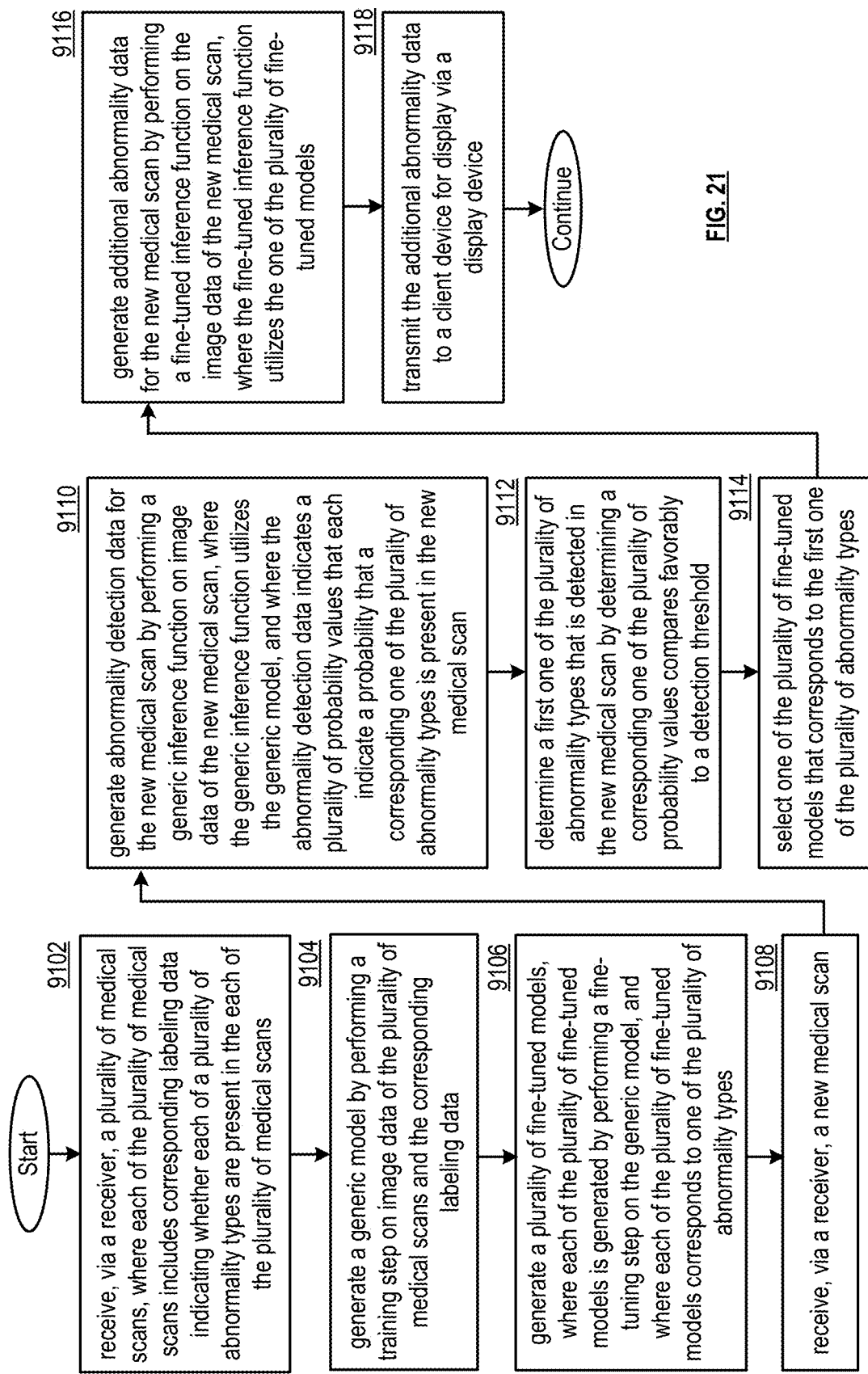
Figure 22A:
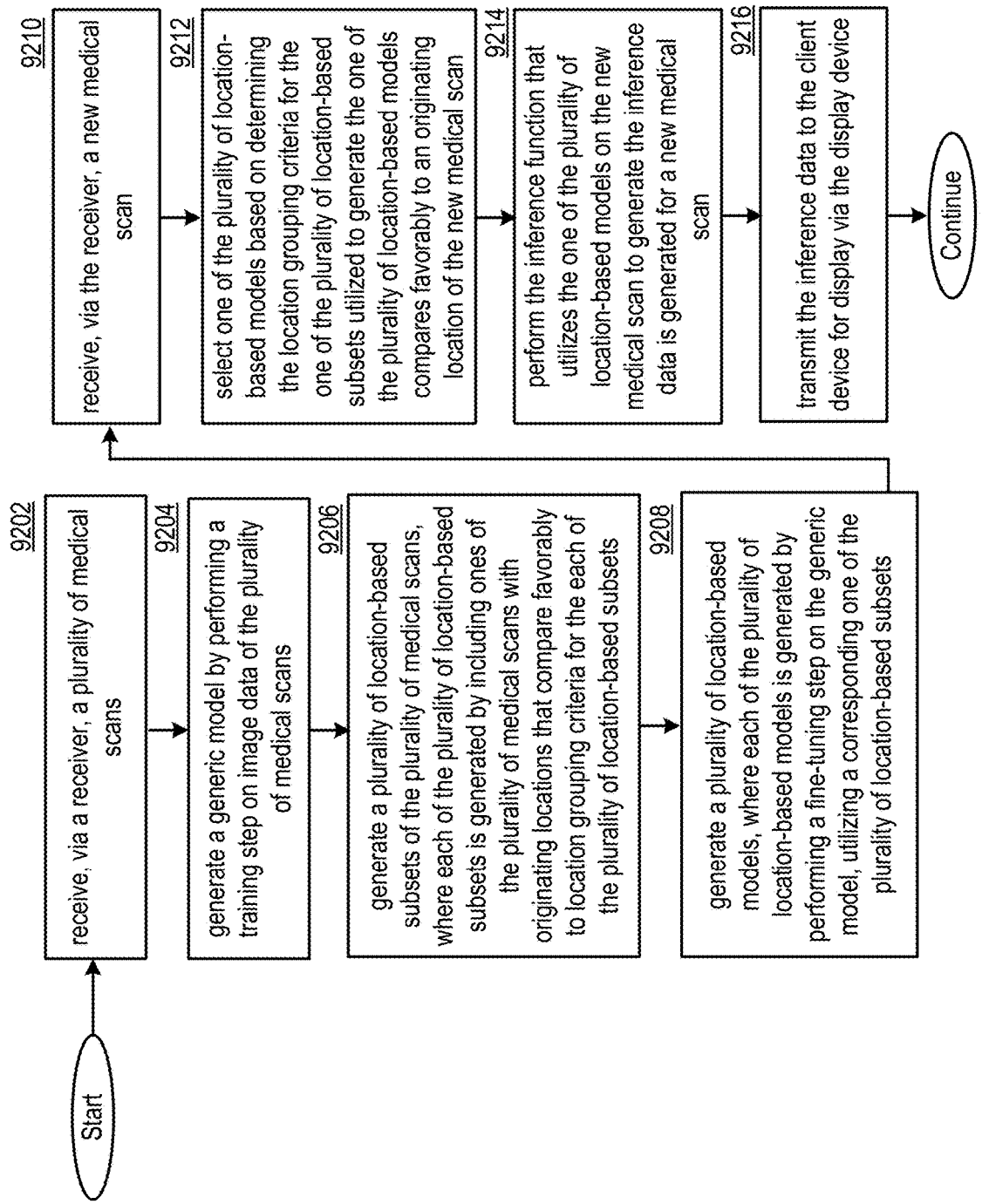
Figure 22B:
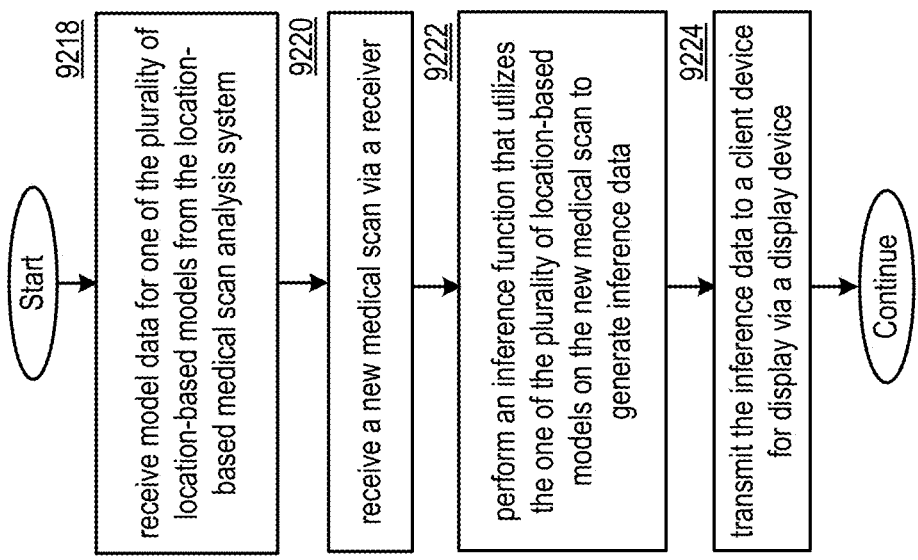
Figure 24:
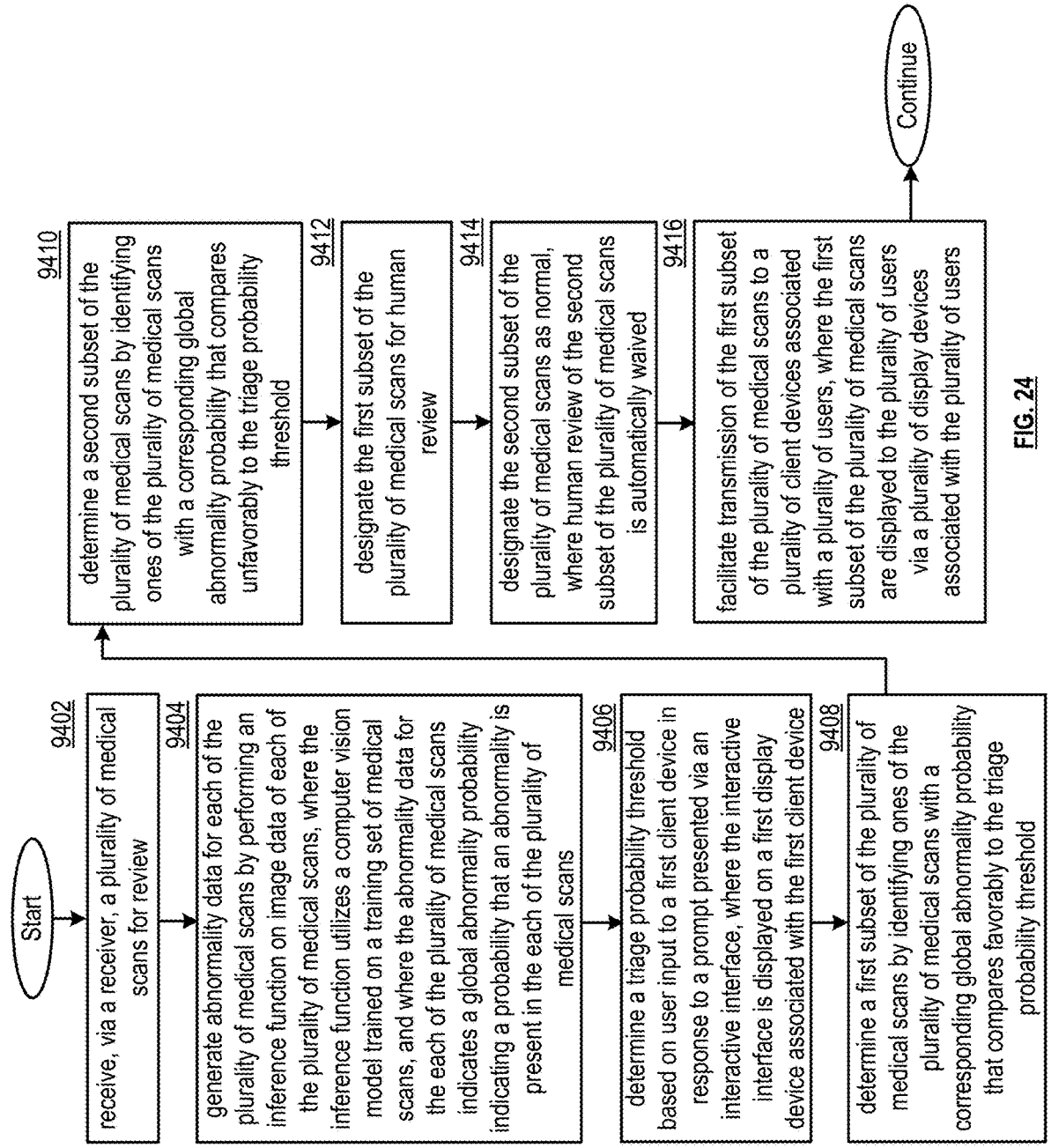

FIG. 11 presents a flowchart illustrating a method for execution by a de-identification system in accordance with various embodiments;

FIGS. 12A-12B are schematic block diagrams of a medical scan hierarchical labeling system in accordance with various embodiments;

FIG. 12C is an illustration of an example of a diagnosis prompt decision tree in accordance with various embodiments;

FIG. 12D is an illustration of an example of a characterization prompt decision tree in accordance with various embodiments;

FIG. 12E is an illustration of an example of a localization prompt decision tree in accordance with various embodiments;

FIGS. 12F-12G are schematic block diagrams of a medical scan hierarchical labeling system in accordance with various embodiments;

FIGS. 13A-13B are schematic block diagrams of a medical scan annotating system in accordance with various embodiments;

FIGS. 13C-13V are graphical illustrations of an example interactive interface displayed on a client device in conjunction with various embodiments;

FIGS. 14A-14C are a schematic block diagrams of a multi-label medical scan analysis system in accordance with various embodiments;

FIG. 15A illustrates an example embodiment of a model that is be utilized by the multi-label medical scan analysis system;

FIGS. 15B-15D illustrate example embodiments of the multi-label medical scan analysis system;

FIGS. 16A-16E are schematic block diagrams of a multi-model medical scan analysis system in accordance with various embodiments;

FIG. 17 is a schematic block diagram of a location-based medical scan analysis system in accordance with various embodiments;

FIGS. 18A-18E are schematic block diagrams of a model-assisted annotating system in accordance with various embodiments;

FIG. 19 is a schematic block diagram of a medical scan triaging system in accordance with various embodiments;

FIG. 20 presents a flowchart illustrating a method for execution by a multi-model medical scan analysis system in accordance with various embodiments;

FIG. 21 presents a flowchart illustrating a method for execution by a multi-model medical scan analysis system in accordance with various embodiments;

FIG. 22A presents a flowchart illustrating a method for execution by a location-based medical scan analysis system in accordance with various embodiments;

FIG. 22B presents a flowchart illustrating a method for execution by a local system communicating with a location-based medical scan analysis system in accordance with various embodiments;

FIG. 23 presents a flowchart illustrating a method for execution by a model-assisted annotating system in accordance with various embodiments; and FIG. 24 presents a flowchart illustrating a method for execution by a medical scan triaging system in accordance with various embodiments.

DETAILED DESCRIPTION

The present U.S. Utility patent application is related to U.S. Utility application Ser. No. 15/627,644, entitled "MEDICAL SCAN ASSISTED REVIEW SYSTEM", filed 20 Jun. 2017, which claims priority pursuant to 35 U.S.C. § 119(e) to U.S. Provisional Application No. 62/511,150, entitled "MEDICAL SCAN ASSISTED REVIEW SYSTEM AND METHODS", filed 25 May 2017, both of which are hereby incorporated herein by reference in their entirety and made part of the present U.S. Utility patent application for all purposes.

Figure 1:
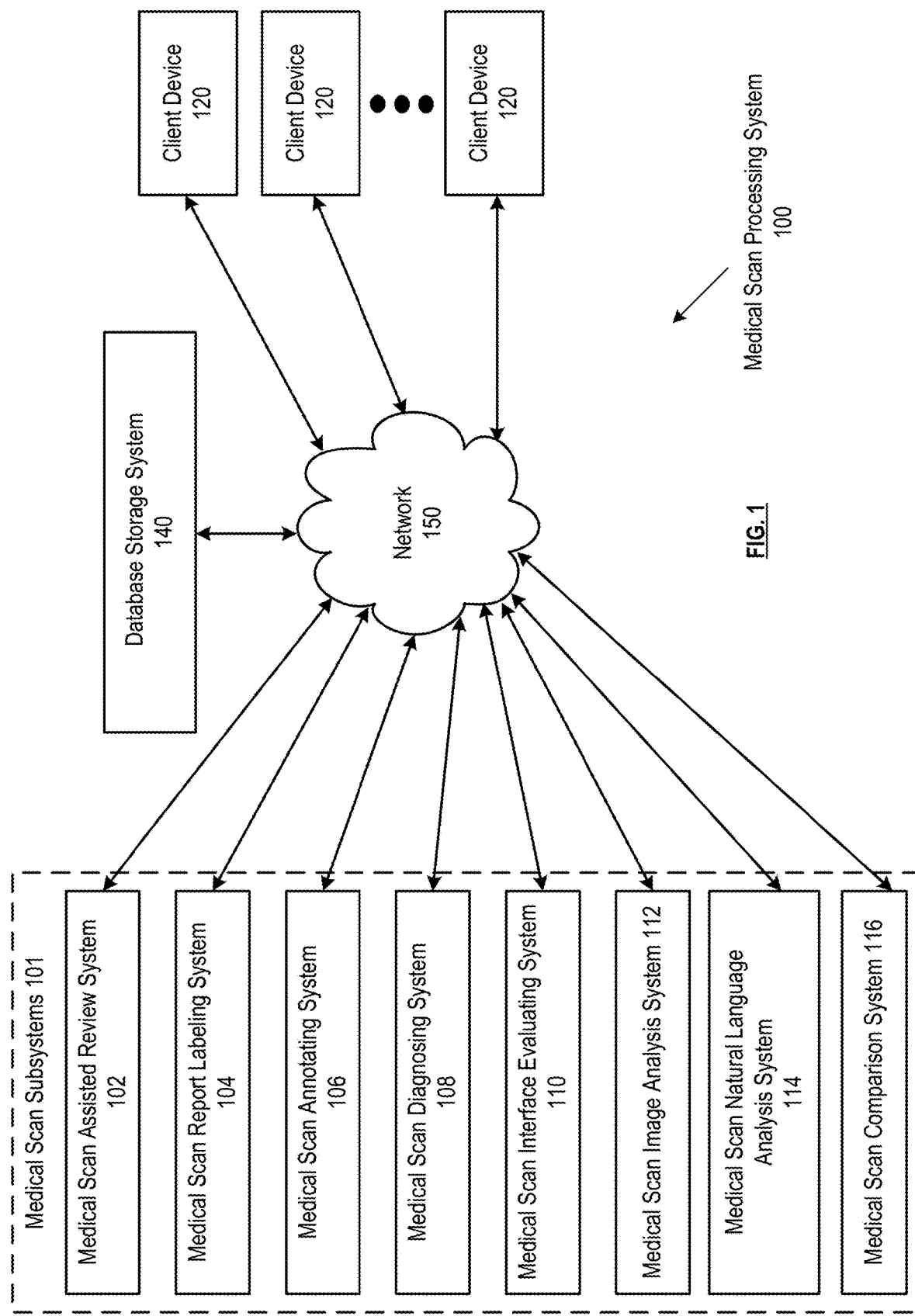
FIG. 1 is a schematic block diagram of an embodiment of a medical scan processing system.

FIG. 1 presents a medical scan processing system 100, which can include one or more medical scan subsystems 101 that communicate bidirectionally with one or more client devices 120 via a wired and/or wireless network 150. The medical scan subsystems 101 can include a medical scan assisted review system 102, medical scan report labeling system 104, a medical scan annotator system 106, a medical scan diagnosing system 108, a medical scan interface feature evaluator system 110, a medical scan image analysis system 112, a medical scan natural language analysis system 114, and/or a medical scan comparison system 116. Some or all of the subsystems 101 can utilize the same processing devices, memory devices, and/or network interfaces, for example, running on a same set of shared servers connected to network 150. Alternatively or in addition, some or all of the subsystems 101 be assigned their own processing devices, memory devices, and/or network interfaces, for example, running separately on different sets of servers connected to network 150. Some or all of the subsystems 101 can interact directly with each other, for example, where one subsystem's output is transmitted directly as input to another subsystem via network 150. Network 150 can include one or more wireless and/or wired communication systems; one or more non-public intranet systems and/or public internet systems; and/or one or more local area networks (LAN) and/or wide area networks (WAN).

The medical scan processing system 100 can further include a database storage system 140, which can include one or more servers, one or more memory devices of one or more subsystems 101, and/or one or more other memory devices connected to network 150. The database storage system 140 can store one or more shared databases and/or one or more files stored on one or more memory devices that include database entries as described herein. The shared databases and/or files can each be utilized by some or all of the subsystems of the medical scan processing system, allowing some or all of the subsystems and/or client devices to retrieve, edit, add, or delete entries to the one or more databases and/or files.

The one or more client devices 120 can each be associated with one or more users of one or more subsystems of the medical scan processing system. Some or all of the client devices can be associated with hospitals or other medical institutions and/or associated with medical professionals, employees, or other individual users for example, located at one or more of the medical institutions. Some of the client devices 120 can correspond to one or more administrators of one or more subsystems of the medical scan processing system, allowing administrators to manage, supervise, or override functions of one or more subsystems for which they are responsible.

Some or all of the subsystems 101 of the medical scan processing system 100 can include a server that presents a website for operation via a browser of client devices 120. Alternatively or in addition, each client device can store application data corresponding to some or all subsystems, for example, a subset of the subsystems that are relevant to the user in a memory of the client device, and a processor of the client device can display the interactive interface based on instructions in the interface data stored in memory. For example, the website presented by a subsystem can operate via the application. Some or all of the web sites presented can correspond to multiple subsystems, for example, where the multiple subsystems share the server presenting the web site. Furthermore, the network 150 can be configured for secure and/or authenticated communications between the medical scan subsystems 101, the client devices 120 and the database storage system 140 to protect the data stored in the database storage system and the data communicated between the medical scan subsystems 101, the client devices 120 and the database storage system 140 from unauthorized access.

The medical scan assisted review system 102 can be used to aid medical professionals or other users in diagnosing, triaging, classifying, ranking, and/or otherwise reviewing medical scans by presenting a medical scan for review by a user by transmitting medical scan data of a selected medical scan and/or interface feature data of selected interface features of to a client device 120 corresponding to a user of the medical scan assisted review system for display via a display device of the client device. The medical scan assisted review system 102 can generate scan review data for a medical scan based on user input to the interactive interface displayed by the display device in response to prompts to provide the scan review data, for example, where the prompts correspond to one or more interface features.

The medical scan assisted review system 102 can be operable to receive, via a network, a medical scan for review. Abnormality annotation data can be generated by identifying one or more of abnormalities in the medical scan by utilizing a computer vision model that is trained on a plurality of training medical scans. The abnormality annotation data can include location data and classification data for each of the plurality of abnormalities and/or data that facilitates the visualization of the abnormalities in the scan image data. Report data including text describing each of the plurality of abnormalities is generated based on the abnormality data. The visualization and the report data, which can collectively be displayed annotation data, can be transmitted to a client device. A display device associated with the client device can display the visualization in conjunction with the medical scan via an interactive interface, and the display device can further display the report data via the interactive interface.

In various embodiments, longitudinal data, such as one or more additional scans of longitudinal data 433 of the medical scan or of similar scans, can be displayed in conjunction with the medical scan automatically, or in response to the user electing to view longitudinal data via user input. For example, the medical scan assisted review system can retrieve a previous scan or a future scan for the patient from a patient database or from the medical scan database automatically or in response to the user electing to view past patient data. One or more previous scans can be displayed in one or more corresponding windows adjacent to the current medical scan. For example, the user can select a past scan from the longitudinal data for display. Alternatively or in addition, the user can elect longitudinal parameters such as amount of time elapsed, scan type, electing to select the most recent and/or least recent scan, electing to select a future scan, electing to select a scan at a date closest to the scan, or other criteria, and the medical scan assisted review system can automatically select a previous scan that compares most favorably to the longitudinal parameters. The selected additional scan can be displayed in an adjacent window alongside the current medical scan. In some embodiments, multiple additional scans will be selected and can be displayed in multiple adjacent windows.

In various embodiments, a first window displaying an image slice 412 of the medical scan and an adjacent second window displaying an image slice of a selected additional scan will display image slices 412 determined to correspond with the currently displayed slice 412 of the medical scan. As described with respect to selecting a slice of a selected similar medical scan for display, this can be achieved based on selecting the image slice with a matching slice number, based on automatically determining the image slice that most closely matches the anatomical region corresponding to the currently displayed slice of the current scan, and/or based on determining the slice in the previous scan with the most similar view of the abnormality as the currently displayed slice. The user can use a single scroll bar or other single user input indication to jump to a different image slice, and the multiple windows can simultaneously display the same numbered image slice, or can scroll or jump by the same number of slices if different slice numbers are initially displayed. In some embodiments, three or more adjacent windows corresponding to the medical scan and two or more additional scans are displayed, and can all be controlled with the single scroll bar in a similar fashion.

The medical scan assisted review system 102 can automatically detect previous states of the identified abnormalities based on the abnormality data, such as the abnormality location data. The detected previous states of the identified abnormality can be circled, highlighted, or otherwise indicated in their corresponding window. The medical scan assisted review system 102 can retrieve classification data for the previous state of the abnormality by retrieving abnormality annotation data 442 of the similar abnormality mapped to the previous scan from the medical scan database 342. This data may not be assigned to the previous scan, and the medical scan assisted review system can automatically determine classification or other diagnosis data for the previous medical scan by utilizing the medical scan image analysis system as discussed. Alternatively or in addition, some or all of the abnormality classification data 445 or other diagnosis data 440 for the previous scan can be assigned values determined based on the abnormality classification data or other diagnosis data determined for the current scan. Such abnormality classification data 445 or other diagnosis data 440 determined for the previous scan can be mapped to the previous scan, and or mapped to the longitudinal data 433, in the database and/or transmitted to a responsible entity via the network.

The medical assisted review system can automatically generate state change data such as a change in size, volume, malignancy, or other changes to various classifiers of the abnormality. This can be achieved by automatically comparing image data of one or more previous scans and the current scan and/or by comparing abnormality data of the previous scan to abnormality data of the current scan. In some embodiments, such metrics can be calculated by utilizing the medical scan similarity analysis function, for example, where the output of the medical scan similarity analysis function such as the similarity score indicates distance, error, or other measured discrepancy in one or more abnormality classifier categories 444 and/or abnormality pattern categories 446. This calculated distance, error, or other measured discrepancy in each category can be used to quantify state change data, indicate a new classifier in one or more categories, to determine if a certain category has become more or less severe, or otherwise determine how the abnormality has changed over time. In various embodiments, this data can be displayed in one window, for example, where an increase in abnormality size is indicated by overlaying or highlighting an outline of the current abnormality over the corresponding image slice of the previous abnormality, or vice versa. In various embodiments where several past scans are available, such state change data can be determined over time, and statistical data showing growth rate changes over time or malignancy changes over time can be generated, for example, indicating if a growth rate is lessening or worsening over time. Image slices corresponding to multiple past scans can be displayed in sequence, for example, where a first scroll bar allows a user to scroll between image slice numbers, and a second scroll bar allows a user to scroll between the same image slice over time. In various embodiments the abnormality data, heat map data, or other interface features will be displayed in conjunction with the image slices of the past image data.

The medical scan report labeling system 104 can be used to automatically assign medical codes to medical scans based on user identified keywords, phrases, or other relevant medical condition terms of natural text data in a medical scan report of the medical scan, identified by users of the medical scan report labeling system 104. The medical scan report labeling system 104 can be operable to transmit a medical report that includes natural language text to a first client device for display. Identified medical condition term data can be received from the first client device in response. An alias mapping pair in a medical label alias database can be identified by determining that a medical condition term of the alias mapping pair compares favorably to the identified medical condition term data. A medical code that corresponds to the alias mapping pair and a medical scan that corresponds to the medical report can be transmitted to a second client device of an expert user for display, and accuracy data can be received from the second client device in response. The medical code is mapped to the first medical scan in a medical scan database when the accuracy data indicates that the medical code compares favorably to the medical scan.

The medical scan annotator system 106 can be used to gather annotations of medical scans based on review of the medical scan image data by users of the system such as radiologists or other medical professionals. Medical scans that require annotation, for example, that have been triaged from a hospital or other triaging entity, can be sent to multiple users selected by the medical scan annotator system 106, and the annotations received from the multiple medical professionals can be processed automatically by a processing system of the medical scan annotator system, allowing the medical scan annotator system to automatically determine a consensus annotation of each medical scan. Furthermore, the users can be automatically scored by the medical scan annotator system based on how closely their annotation matches to the consensus annotation or some other truth annotation, for example, corresponding to annotations of the medical scan assigned a truth flag. Users can be assigned automatically to annotate subsequent incoming medical scans based on their overall scores and/or based on categorized scores that correspond to an identified category of the incoming medical scan.

The medical scan annotator system 106 can be operable to select a medical scan for transmission via a network to a first client device and a second client device for display via an interactive interface, and annotation data can be received from the first client device and the second client device in response. Annotation similarity data can be generated by comparing the first annotation data to the second annotation data, and consensus annotation data can be generated based on the first annotation data and the second annotation data in response to the annotation similarity data indicating that the difference between the first annotation data and the second annotation data compares favorably to an annotation discrepancy threshold. The consensus annotation data can be mapped to the medical scan in a medical scan database.

A medical scan diagnosing system 108 can be used by hospitals, medical professionals, or other medical entities to automatically produce inference data for given medical scans by utilizing computer vision techniques and/or natural language processing techniques. This automatically generated inference data can be used to generate and/or update diagnosis data or other corresponding data of corresponding medical scan entries in a medical scan database. The medical scan diagnosing system can utilize a medical scan database, user database, and/or a medical scan analysis function database by communicating with the database storage system 140 via the network 150, and/or can utilize another medical scan database, user database, and/or function database stored in local memory.

The medical scan diagnosing system 108 can be operable to receive a medical scan. Diagnosis data of the medical scan can be generated by performing a medical scan inference function on the medical scan. The first medical scan can be transmitted to a first client device associated with a user of the medical scan diagnosing system in response to the diagnosis data indicating that the medical scan corresponds to a non-normal diagnosis. The medical scan can be displayed to the user via an interactive interface displayed by a display device corresponding to the first client device. Review data can be received from the first client device, where the review data is generated by the first client device in response to a prompt via the interactive interface. Updated diagnosis data can be generated based on the review data. The updated diagnosis data can be transmitted to a second client device associated with a requesting entity.

A medical scan interface feature evaluating system 110 can be used evaluate proposed interface features or currently used interface features of an interactive interface to present medical scans for review by medical professionals or other users of one or more subsystems 101. The medical scan interface feature evaluator system 110 can be operable to generate an ordered image-to-prompt mapping by selecting a set of user interface features to be displayed with each of an ordered set of medical scans. The set of medical scans and the ordered image-to-prompt mapping can be transmitted to a set of client devices. A set of responses can be generated by each client device in response to sequentially displaying each of the set of medical scans in conjunction with a mapped user interface feature indicated in the ordered image-to-prompt mapping via a user interface. Response score data can be generated by comparing each response to truth annotation data of the corresponding medical scan. Interface feature score data corresponding to each user interface feature can be generated based on aggregating the response score data, and is used to generate a ranking of the set of user interface features.

A medical scan image analysis system 112 can be used to generate and/or perform one or more medical scan image analysis functions by utilizing a computer vision-based learning algorithm 1350 on a training set of medical scans with known annotation data, diagnosis data, labeling and/or medical code data, report data, patient history data, patient risk factor data, and/or other metadata associated with medical scans. These medical scan image analysis functions can be used to generate inference data for new medical scans that are triaged or otherwise require inferred annotation data, diagnosis data, labeling and/or medical code data, and/or report data. For example, some medical scan image analysis functions can correspond to medical scan inference functions of the medical scan diagnosing system or other medical scan analysis functions of a medical scan analysis function database. The medical scan image analysis functions can be used to determine whether or not a medical scan is normal, to detect the location of an abnormality in one or more slices of a medical scan, and/or to characterize a detected abnormality. The medical scan image analysis system can be used to generate and/or perform computer vision based medical scan image analysis functions utilized by other subsystems of the medical scan processing system as described herein, aiding medical professionals to diagnose patients and/or to generate further data and models to characterize medical scans. The medical scan image analysis system can include a processing system that includes a processor and a memory that stores executable instructions that, when executed by the processing system, facilitate performance of operations.

The medical scan image analysis system 112 can be operable to receive a plurality of medical scans that represent a three-dimensional anatomical region and include a plurality of cross-sectional image slices. A plurality of three-dimensional subregions corresponding to each of the plurality of medical scans can be generated by selecting a proper subset of the plurality of cross-sectional image slices from each medical scan, and by further selecting a two-dimensional subregion from each proper subset of cross-sectional image slices. A learning algorithm can be performed on the plurality of three-dimensional subregions to generate a neural network. Inference data corresponding to a new medical scan received via the network can be generated by performing an inference algorithm on the new medical scan by utilizing the neural network. An inferred abnormality can be identified in the new medical scan based on the inference data.

The medical scan natural language analysis system 114 can determine a training set of medical scans with medical codes determined to be truth data. Corresponding medical reports and/or other natural language text data associated with a medical scan can be utilized to train a medical scan natural language analysis function by generating a medical report natural language model. The medical scan natural language analysis function can be utilized to generate inference data for incoming medical reports for other medical scans to automatically determine corresponding medical codes, which can be mapped to corresponding medical scans. Medical codes assigned to medical scans by utilizing the medical report natural language model can be utilized by other subsystems, for example, to train other medical scan analysis functions, to be used as truth data to verify annotations provided via other subsystems, to aid in diagnosis, or otherwise be used by other subsystems as described herein.

A medical scan comparison system 116 can be utilized by one or more subsystems to identify and/or display similar medical scans, for example, to perform or determine function parameters for a medical scan similarity analysis function, to generate or retrieve similar scan data, or otherwise compare medical scan data. The medical scan comparison system 116 can also utilize some or all features of other subsystems as described herein. The medical scan comparison system 116 can be operable to receive a medical scan via a network and can generate similar scan data. The similar scan data can include a subset of medical scans from a medical scan database and can be generated by performing an abnormality similarity function, such as medical scan similarity analysis function, to determine that a set of abnormalities included in the subset of medical scans compare favorably to an abnormality identified in the medical scan. At least one cross-sectional image can be selected from each medical scan of the subset of medical scans for display on a display device associated with a user of the medical scan comparison system in conjunction with the medical scan.

Figure 2A:
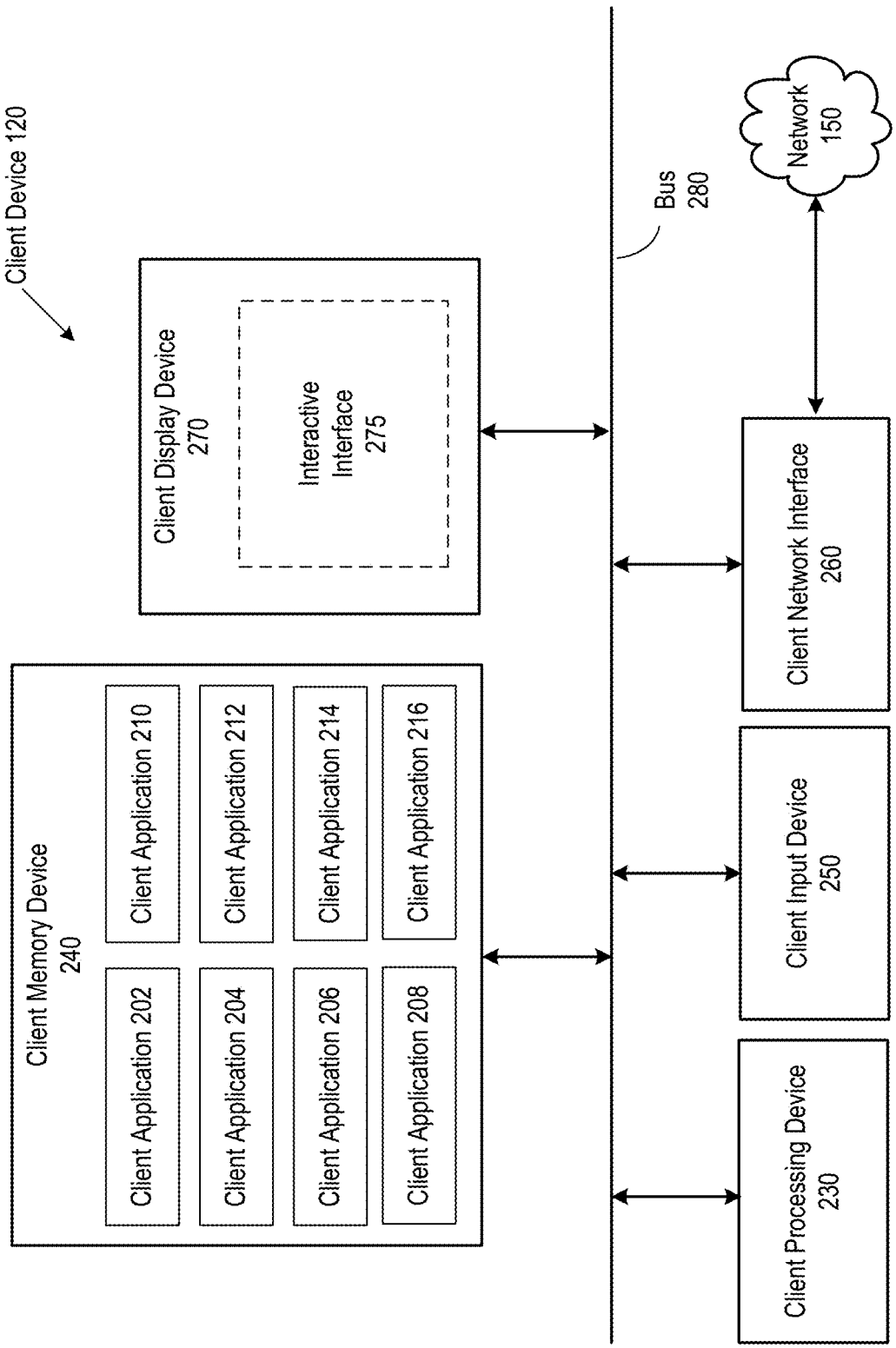
FIG. 2A is a schematic block diagram of a client device in accordance with various embodiments.

FIG. 2A presents an embodiment of client device 120. Each client device 120 can include one or more client processing devices 230, one or more client memory devices 240, one or more client input devices 250, one or more client network interfaces 260 operable to more support one or more communication links via the network 150 indirectly and/or directly, and/or one or more client display devices 270, connected via bus 280. Client applications 202, 204, 206, 208, 210, 212, 214, and/or 216 correspond to subsystems 102, 104, 106, 108, 110, 112, 114, and/or 116 of the medical scan processing system respectfully. Each client device 120 can receive the application data from the corresponding subsystem via network 150 by utilizing network interface 260, for storage in the one or more memory devices 240. In various embodiments, some or all client devices 120 can include a computing device associated with a radiologist, medical entity, or other user of one or more subsystems as described herein.

The one or more processing devices 230 can display interactive interface 275 on the one or more client display devices 270 in accordance with one or more of the client applications 202, 204, 206, 208, 210, 212, 214, and/or 216, for example, where a different interactive interface 275 is displayed for some or all of the client applications in accordance with the website presented by the corresponding subsystem 102, 104, 106, 108, 110, 112, 114 and/or 116. The user can provide input in response to menu data or other prompts presented by the interactive interface via the one or more client input devices 250, which can include a microphone, mouse, keyboard, touchscreen of display device 270 itself or other touchscreen, and/or other device allowing the user to interact with the interactive interface. The one or more processing devices 230 can process the input data and/or send raw or processed input data to the corresponding subsystem, and/or can receive and/or generate new data in response for presentation via the interactive interface 275 accordingly, by utilizing network interface 260 to communicate bidirectionally with one or more subsystems and/or databases of the medical scan processing system via network 150.

Figure 2B:
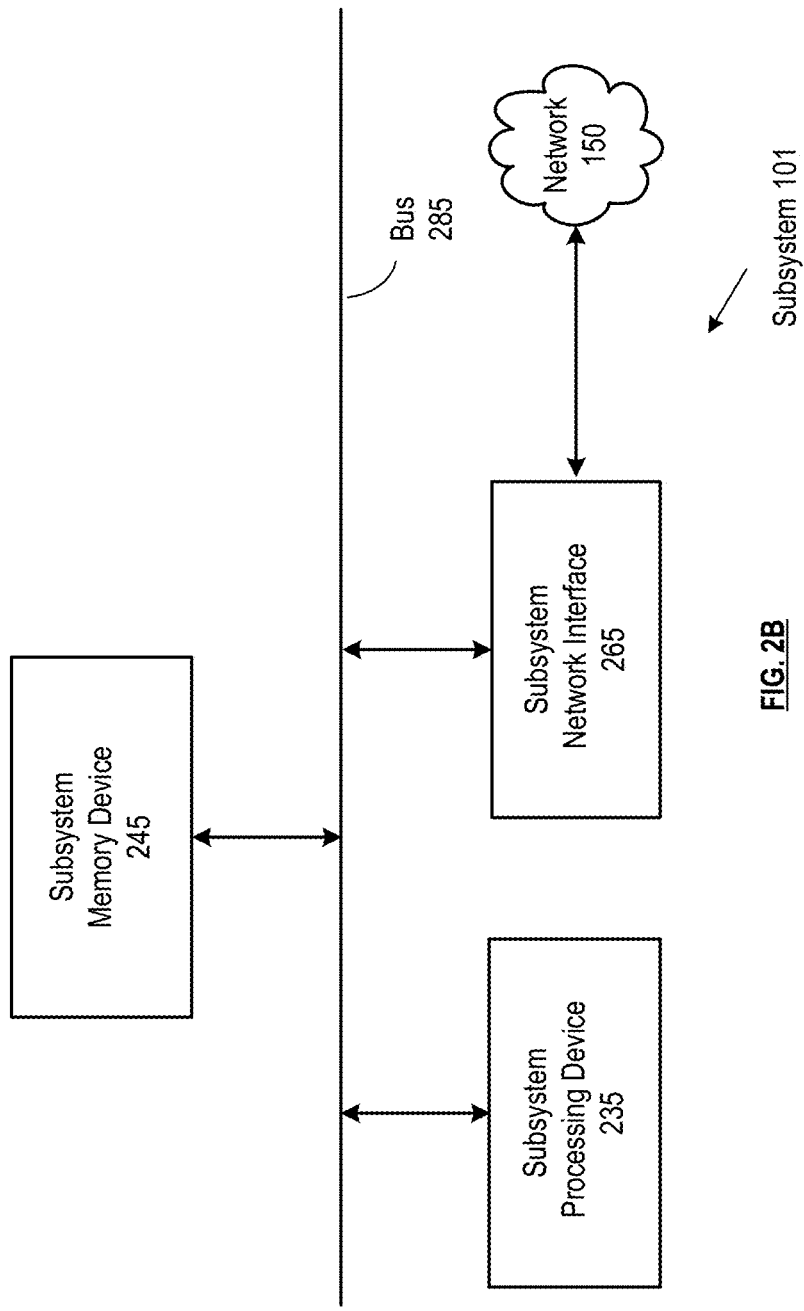
FIG. 2B is a schematic block diagram of one or more subsystems in accordance with various embodiments.

FIG. 2B presents an embodiment of a subsystem 101, which can be utilized in conjunction with subsystem 102, 104, 106, 108, 110, 112, 114 and/or 116. Each subsystem 101 can include one or more subsystem processing devices 235, one or more subsystem memory devices 245, and/or one or more subsystem network interfaces 265, connected via bus 285. The subsystem memory devices 245 can store executable instructions that, when executed by the one or more subsystem processing devices 235, facilitate performance of operations by the subsystem 101, as described for each subsystem herein.

Figure 3:
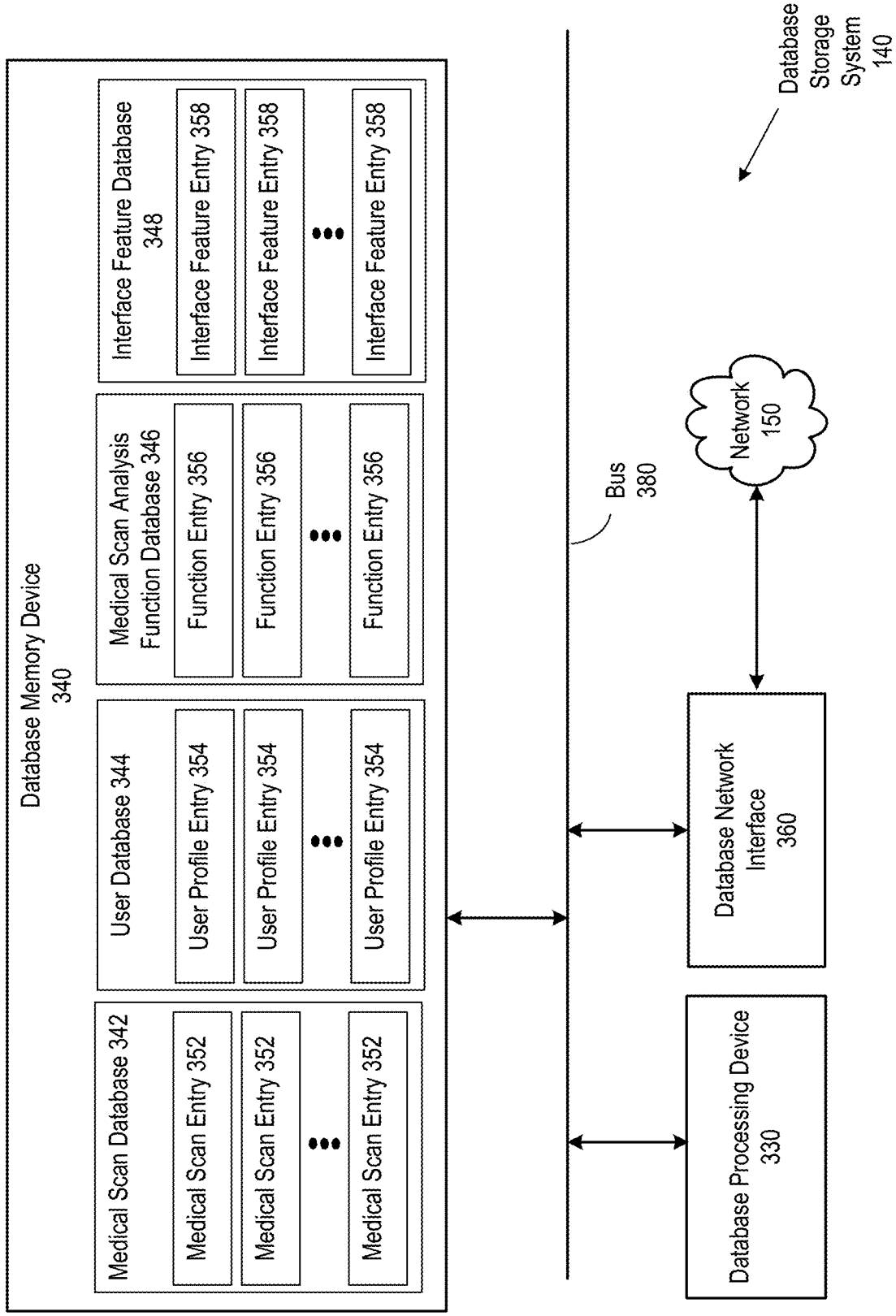
FIG. 3 is a schematic block diagram of a database storage system in accordance with various embodiments.

FIG. 3 presents an embodiment of the database storage system 140. Database storage system 140 can include at least one database processing device 330, at least one database memory device 340, and at least one database network interface 360, operable to more support one or more communication links via the network 150 indirectly and/or directly, all connected via bus 380. The database storage system 140 can store one or more databases the at least one memory 340, which can include a medical scan database 342 that includes a plurality medical scan entries 352, a user database 344 that includes a plurality of user profile entries 354, a medical scan analysis function database 346 that includes a plurality of medical scan analysis function entries 356, an interface feature database 348 can include a plurality of interface feature entries 358, and/or other databases that store data generated and/or utilized by the subsystems 101. Some or all of the databases 342, 344, 346 and/or 348 can consist of multiple databases, can be stored relationally or non-relationally, and can include different types of entries and different mappings than those described herein. A database entry can include an entry in a relational table or entry in a non-relational structure. Some or all of the data attributes of an entry 352, 354, 356, and/or 358 can refer to data included in the entry itself or that is otherwise mapped to an identifier included in the entry and can be retrieved from, added to, modified, or deleted from the database storage system 140 based on a given identifier of the entry. Some or all of the databases 342, 344, 346, and/or 348 can instead be stored locally by a corresponding subsystem, for example, if they are utilized by only one subsystem.

The processing device 330 can facilitate read/write requests received from subsystems and/or client devices via the network 150 based on read/write permissions for each database stored in the at least one memory device 340. Different subsystems can be assigned different read/write permissions for each database based on the functions of the subsystem, and different client devices 120 can be assigned different read/write permissions for each database. One or more client devices 120 can correspond to one or more administrators of one or more of the databases stored by the database storage system, and database administrator devices can manage one or more assigned databases, supervise can assess and/or efficiency, edit permissions, or otherwise oversee database processes based on input to the client device via interactive interface 275.

Figure 4A:
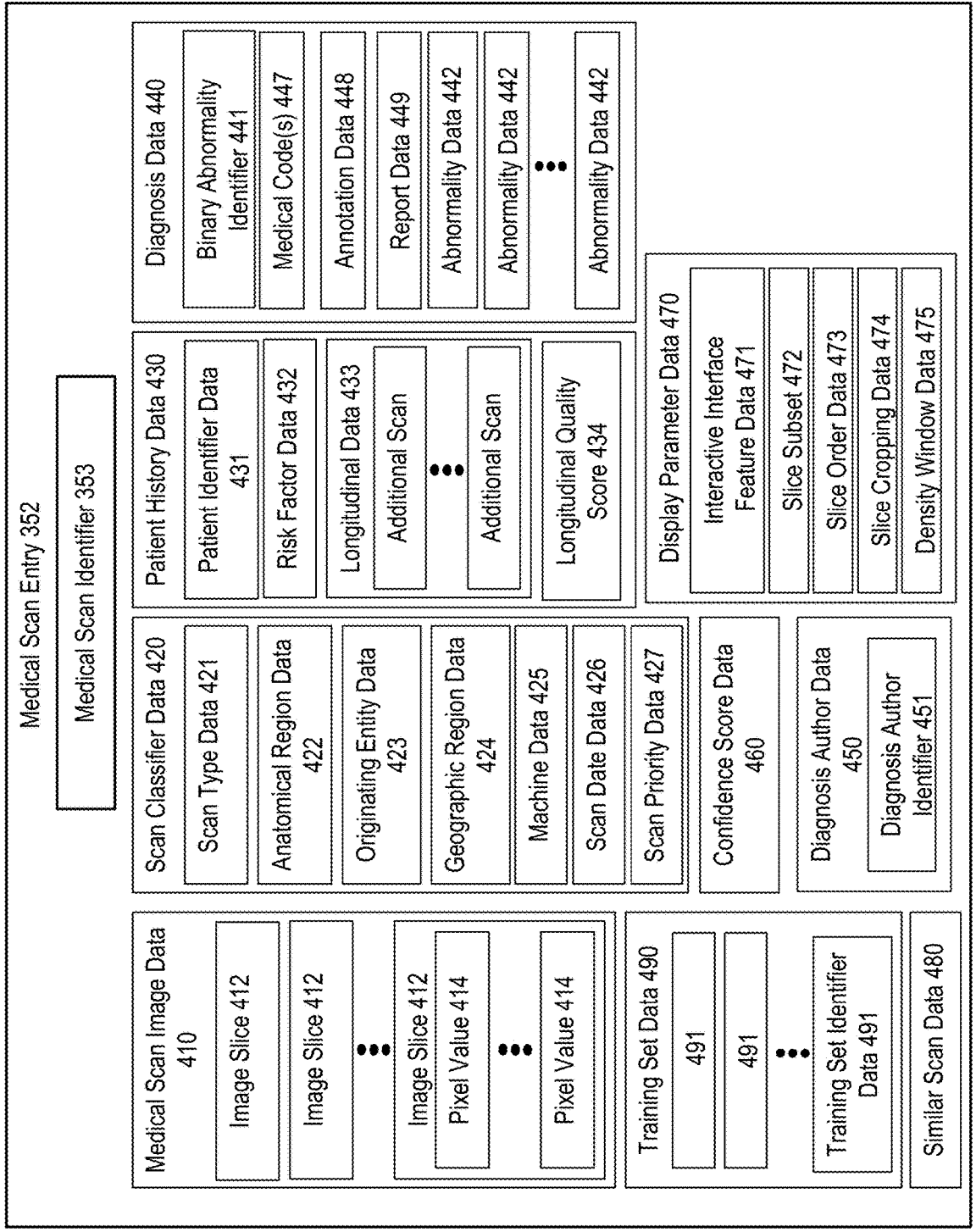
FIG. 4A is schematic block diagram of a medical scan entry in accordance with various embodiments.

FIG. 4A presents an embodiment of a medical scan entry 352, stored in medical scan database 342, included in metadata of a medical scan, and/or otherwise associated with a medical scan. A medical scan can include imaging data corresponding to a CT scan, x-ray, MRI, PET scan, Ultrasound, EEG, mammogram, or other type of radiological scan or medical scan taken of an anatomical region of a human body, animal, organism, or object and further can include metadata corresponding to the imaging data. Some or all of the medical scan entries can be formatted in accordance with a Digital Imaging and Communications in Medicine (DICOM) format or other standardized image format, and some or more of the fields of the medical scan entry 352 can be included in a DICOM header or other standardized header of the medical scan. Medical scans can be awaiting review or can have already been reviewed by one or more users or automatic processes and can include tentative diagnosis data automatically generated by a subsystem, generated based on user input, and/or generated from another source. Some medical scans can include final, known diagnosis data generated by a subsystem and/or generated based on user input, and/or generated from another source, and can included in training sets used to train processes used by one or more subsystems such as the medical scan image analysis system 112 and/or the medical scan natural language analysis sy stem 114.

Some medical scans can include one or more abnormalities, which can be identified by a user or can be identified automatically. Abnormalities can include nodules, for example malignant nodules identified in a chest CT scan. Abnormalities can also include and/or be characterized by one or more abnormality pattern categories such as such as cardiomegaly, consolidation, effusion, emphysema, and/or fracture, for example identified in a chest x-ray. Abnormalities can also include any other unknown, malignant or benign feature of a medical scan identified as not normal. Some scans can contain zero abnormalities, and can be identified as normal scans. Some scans identified as normal scans can include identified abnormalities that are classified as benign, and include zero abnormalities classified as either unknown or malignant. Scans identified as normal scans may include abnormalities that were not detected by one or more subsystems and/or by an originating entity. Thus, some scans may be improperly identified as normal. Similarly, scans identified to include at least one abnormality may include at least one abnormality that was improperly detected as an abnormality by one or more subsystems and/or by an originating entity. Thus, some scans may be improperly identified as containing abnormalities.

Each medical scan entry 352 can be identified by its own medical scan identifier 353, and can include or otherwise map to medical scan image data 410, and metadata such as scan classifier data 420, patient history data 430, diagnosis data 440, annotation author data 450, confidence score data 460, display parameter data 470, similar scan data 480, training set data 490, and/or other data relating to the medical scan. Some or all of the data included in a medical scan entry 352 can be used to aid a user in generating or editing diagnosis data 440, for example, in conjunction with the medical scan assisted review system 102, the medical scan report labeling system 104, and/or the medical scan annotator system 106. Some or all of the data included in a medical scan entry 352 can be used to allow one or more subsystems 101, such as automated portions of the medical scan report labeling system 104 and/or the medical scan diagnosing system 108, to automatically generate and/or edit diagnosis data 440 or other data the medical scan. Some or all of the data included in a medical scan entry 352 can be used to train some or all medical scan analysis functions of the medical scan analysis function database 346 such as one or more medical scan image analysis functions, one or more medical scan natural language analysis functions, one or more medical scan similarity analysis functions, one or more medical report generator functions, and/or one or more medical report analysis functions, for example, in conjunction with the medical scan image analysis system 112, the medical scan natural language analysis system 114, and/or the medical scan comparison system 116.

The medical scan entries 352 and the associated data as described herein can also refer to data associated with a medical scan that is not stored by the medical scan database, for example, that is uploaded by a client device for direct transmission to a subsystem, data generated by a subsystem and used as input to another subsystem or transmitted directly to a client device, data stored by a Picture Archive and Communication System (PACS) communicating with the medical scan processing system 100, or other data associated with a medical scan that is received and or generated without being stored in the medical scan database 342. For example, some or all of the structure and data attributes described with respect to a medical scan entry 352 can also correspond to structure and/or data attribute of data objects or other data generated by and/or transmitted between subsystems and/or client devices that correspond to a medical scan. Herein, any of the data attributes described with respect to a medical scan entry 352 can also correspond to data extracted from a data object generated by a subsystem or client device or data otherwise received from a subsystem, client device, or other source via network 150 that corresponds to a medical scan.

The medical scan image data 410 can include one or more images corresponding to a medical scan. The medical scan image data 410 can include one or more image slices 412, for example, corresponding to a single x-ray image, a plurality of cross-sectional, tomographic images of a scan such as a CT scan, or any plurality of images taken from the same or different point at the same or different angles. The medical scan image data 410 can also indicate an ordering of the one or more image slices 412. Herein, a "medical scan" can refer a full scan of any type represented by medical scan image data 410. Herein, an "image slice" can refer to one of a plurality of cross-sectional images of the medical scan image data 410, one of a plurality of images taken from different angles of the medical scan image data 410, and/or the single image of the medical scan image data 410 that includes only one image. Furthermore "plurality of image slices" can refer to all of the images of the associated medical scan, and refers to only a single image if the medical scan image data 410 includes only one image. Each image slice 412 can include a plurality of pixel values 414 mapped to each pixel of the image slice. Each pixel value can correspond to a density value, such as a Hounsfield value or other measure of density. Pixel values can also correspond to a grayscale value, a RGB (Red-Green-Blue) or other color value, or other data stored by each pixel of an image slice 412.

Scan classifier data 420 can indicate classifying data of the medical scan. Scan classifier data can include scan type data 421, for example, indicating the modality of the scan. The scan classifier data can indicate that the scan is a CT scan, x-ray, Mill, PET scan, Ultrasound, EEG, mammogram, or other type of scan. Scan classifier data 420 can also include anatomical region data 422, indicating for example, the scan is a scan of the chest, head, right knee, or other anatomical region. Scan classifier data can also include originating entity data 423, indicating the hospital where the scan was taken and/or a user that uploaded the scan to the system. If the originating entity data corresponds to a user of one or more subsystems 101, the originating entity data can include a corresponding user profile identifier and/or include other data from the user profile entry 354 of the user. Scan classifier data 420 can include geographic region data 424, indicating a city, state, and/or country from which the scan originated, for example, based on the user data retrieved from the user database 344 based on the originating entity. Scan classifier data can also include machine data 425, which can include machine identifier data, machine model data, machine calibration data, and/or contrast agent data, for example based on imaging machine data retrieved from the user database 344 based on the originating entity data 423. The scan classifier data 420 can include scan date data 426 indicating when the scan was taken. The scan classifier data 420 can include scan priority data 427, which can indicate a priority score, ranking, number in a queue, or other priority data with regard to triaging and/or review. A priority score, ranking, or queue number of the scan priority data 427 can be generated by automatically by a subsystem based on the scan priority data 427, based on a severity of patient symptoms or other indicators in the risk factor data 432, based on a priority corresponding to the originating entity, based on previously generated diagnosis data 440 for the scan, and/or can be assigned by the originating entity and/or a user of the system.

The scan classifier data 420 can include other classifying data not pictured in FIG. 4A. For example, a set of scans can include medical scan image data 410 corresponding to different imaging planes. The scan classifier data can further include imaging plane data indicating one or more imaging planes corresponding to the image data. For example, the imaging plane data can indicate the scan corresponds to the axial plane, sagittal plane, or coronal plane. A single medical scan entry 352 can include medical scan image data 410 corresponding multiple planes, and each of these planes can be tagged appropriately in the image data. In other embodiments, medical scan image data 410 corresponding to each plane can be stored as separate medical scan entries 352, for example, with a common identifier indicating these entries belong to the same set of scans.

Alternatively or in addition, the scan classifier data 420 can include sequencing data. For example, a set of scans can include medical scan image data 410 corresponding to different sequences. The scan classifier data can further include sequencing data indicating one or more of a plurality of sequences of the image data corresponds to, for example, indicating whether an MRI scan corresponds to a T2 sequence, a T1 sequence, a T1 sequence with contrast, a diffusion sequence, a FLAIR sequence, or other MRI sequence. A single medical scan entry 352 can include medical scan image data 410 corresponding to multiple sequences, and each of these sequences can be tagged appropriately in the entry. In other embodiments, medical scan image data 410 corresponding to each sequence can be stored as separate medical scan entries 352, for example, with a common identifier indicating these entries belong to the same set of scans.

Alternatively or in addition, the scan classifier data 420 can include an image quality score. This score can be determined automatically by one or more subsystems 101, and/or can be manually assigned the medical scan. The image quality score can be based on a resolution of the image data 410, where higher resolution image data is assigned a more favorable image quality score than lower resolution image data. The image quality score can be based on whether the image data 410 corresponds to digitized image data received directly from the corresponding imaging machine, or corresponds to a hard copy of the image data that was later scanned in. In some embodiments, the image quality score can be based on a detected corruption, and/or detected external factor that determined to negatively affect the quality of the image data during the capturing of the medical scan and/or subsequent to the capturing of the medical scan. In some embodiments, the image quality score can be based on detected noise in the image data, where a medical scan with a higher level of detected noise can receive a less favorable image quality score than a medical scan with a lower level of detected noise. Medical scans with this determined corruption or external factor can receive a less favorable image quality score than medical scans with no detected corruption or external factor.

In some embodiments, the image quality score can be based on include machine data 425. In some embodiments, one or more subsystems can utilize the image quality score to flag medical scans with image quality scores that fall below an image quality threshold. The image quality threshold can be the same or different for different subsystems, medical scan modalities, and/or anatomical regions. For example, the medical scan image analysis system can automatically filter training sets based on selecting only medical scans with image quality scores that compare favorably to the image quality threshold. As another example, one or more subsystems can flag a particular imaging machine and/or hospital or other medical entity that have produced at least a threshold number and/or percentage of medical scan with image quality scores that compare unfavorably to the image quality threshold. As another example, a de-noising algorithm can be automatically utilized to clean the image data when the image quality score compares unfavorably to the image quality threshold. As another example, the medical scan image analysis system can select a particular medical image analysis function from a set of medical image analysis functions to utilize on a medical scan to generate inference data for the medical scan. Each of this set of medical image analysis function can be trained on different levels of image quality, and the selected image analysis function can be selected based on the determined image quality score falling within a range of image quality scores the image analysis function was trained on and/or is otherwise suitable for.

The patient history data 430 can include patient identifier data 431 which can include basic patient information such as name or an identifier that may be anonymized to protect the confidentiality of the patient, age, and/or gender. The patient identifier data 431 can also map to a patient entry in a separate patient database stored by the database storage system, or stored elsewhere. The patient history data can include patient risk factor data 432 which can include previous medical history, family medical history, smoking and/or drug habits, pack years corresponding to tobacco use, environmental exposures, patient symptoms, etc. The patient history data 430 can also include longitudinal data 433, which can identify one or more additional medical scans corresponding to the patient, for example, retrieved based on patient identifier data 431 or otherwise mapped to the patient identifier data 431. Some or all additional medical scans can be included in the medical scan database, and can be identified based on their corresponding identifiers medical scan identifiers 353. Some or all additional medical scans can be received from a different source and can otherwise be identified. Alternatively or in addition, the longitudinal data can simply include some or all relevant scan entry data of a medical scan entry 352 corresponding to the one or more additional medical scans. The additional medical scans can be the same type of scan or different types of scans. Some or all of the additional scans may correspond to past medical scans, and/or some or all of the additional scans may correspond to future medical scans. The longitudinal data 433 can also include data received and/or determined at a date after the scan such as final biopsy data, or some or all of the diagnosis data 440. The patient history data can also include a longitudinal quality score 434, which can be calculated automatically by a subsystem, for example, based on the number of additional medical scans, based on how many of the additional scans in the file were taken before and/or after the scan based on the scan date data 426 of the medical scan and the additional medical scans, based on a date range corresponding to the earliest scan and corresponding to the latest scan, based on the scan types data 421 these scans, and/or based on whether or not a biopsy or other final data is included. As used herein, a "high" longitudinal quality score refers to a scan having more favorable longitudinal data than that with a "low" longitudinal quality score.

Diagnosis data 440 can include data that indicates an automated diagnosis, a tentative diagnosis, and/or data that can otherwise be used to support medical diagnosis, triage, medical evaluation and/or other review by a medical professional or other user. The diagnosis data 440 of a medical scan can include a binary abnormality identifier 441 indicating whether the scan is normal or includes at least one abnormality. In some embodiments, the binary abnormality identifier 441 can be determined by comparing some or all of confidence score data 460 to a threshold, can be determined by comparing a probability value to a threshold, and/or can be determined by comparing another continuous or discrete value indicating a calculated likelihood that the scan contains one or more abnormalities to a threshold. In some embodiments, non-binary values, such as one or more continuous or discrete values indicating a likelihood that the scan contains one or more abnormalities, can be included in diagnosis data 440 in addition to, or instead of, binary abnormality identifier 441. One or abnormalities can be identified by the diagnosis data 440, and each identified abnormality can include its own set of abnormality annotation data 442. Alternatively, some or all of the diagnosis data 440 can indicate and/or describe multiple abnormalities, and thus will not be presented for each abnormality in the abnormality annotation data 442. For example, the report data 449 of the diagnosis data 440 can describe all identified abnormalities, and thus a single report can be included in the diagnosis.

Figure 4B:
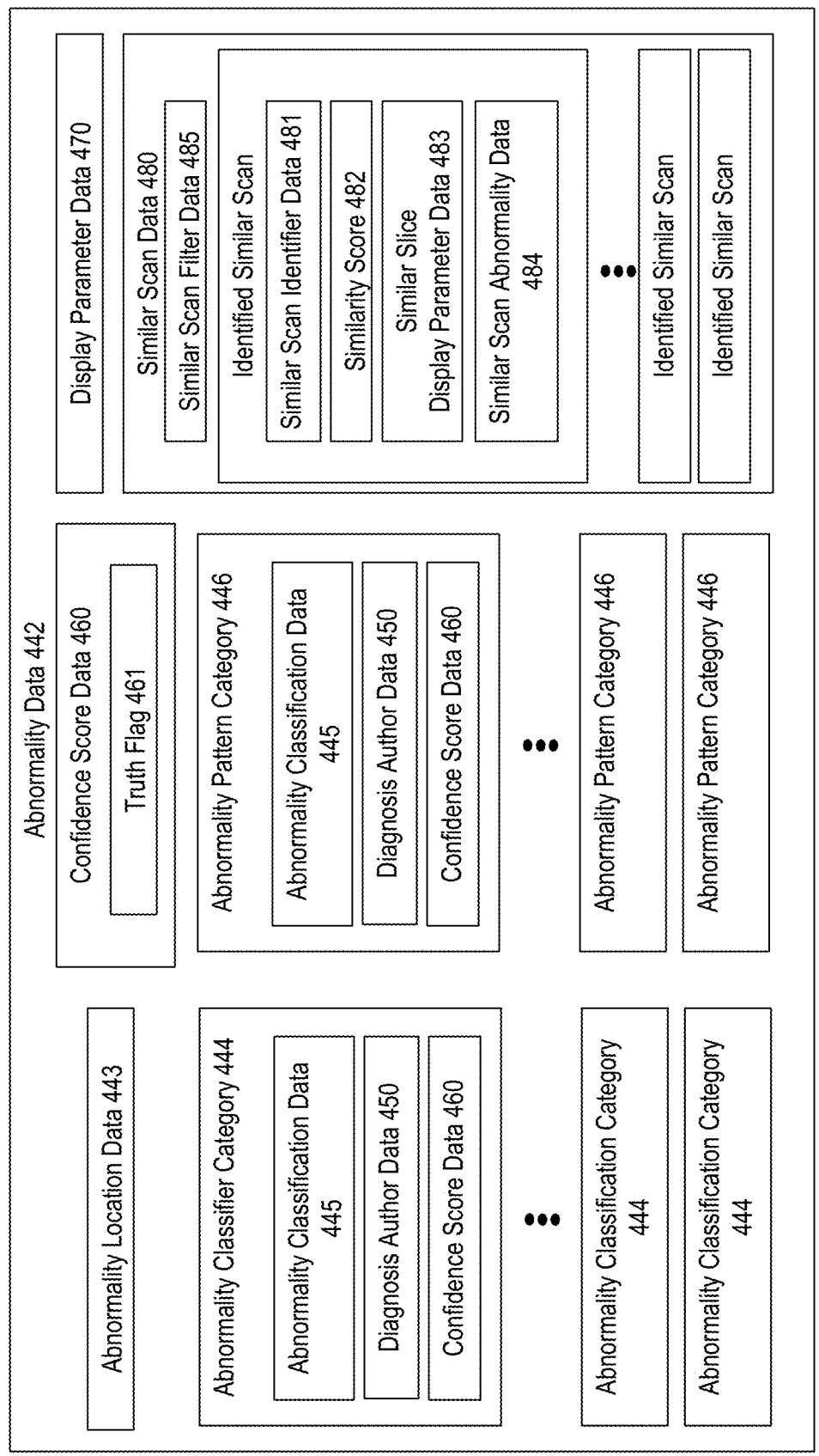
FIG. 4B is a schematic block diagram of abnormality data in accordance with various embodiments.

FIG. 4B presents an embodiment of the abnormality annotation data 442. The abnormality annotation data 442 for each abnormality can include abnormality location data 443, which can include an anatomical location and/or a location specific to pixels, image slices, coordinates or other location information identifying regions of the medical scan itself. The abnormality annotation data 442 can include abnormality classification data 445 which can include binary, quantitative, and/or descriptive data of the abnormality as a whole, or can correspond to one or more abnormality classifier categories 444, which can include size, volume, pre-post contrast, doubling time, calcification, components, smoothness, spiculation, lobulation, sphericity, internal structure, texture, or other categories that can classify and/or otherwise characterize an abnormality. Abnormality classifier categories 444 can be assigned a binary value, indicating whether or not such a category is present. For example, this binary value can be determined by comparing some or all of confidence score data 460 to a threshold, can be determined by comparing a probability value to a threshold, and/or can be determined by comparing another continuous or discrete value indicating a calculated likelihood that a corresponding abnormality classifier category 444 is present to a threshold, which can be the same or different threshold for each abnormality classifier category 444. In some embodiments, abnormality classifier categories 444 can be assigned one or more non-binary values, such as one or more continuous or discrete values indicating a likelihood that the corresponding classifier category 444 is present.

The abnormality classifier categories 444 can also include a malignancy category, and the abnormality classification data 445 can include a malignancy rating such as a Lung-RADS score, a Fleischner score, and/or one or more calculated values that indicate malignancy level, malignancy severity, and/or probability of malignancy. Alternatively or in addition, the malignancy category can be assigned a value of "yes", "no", or "maybe". The abnormality classifier categories 444 can also include abnormality pattern categories 446 such as cardiomegaly, consolidation, effusion, emphysema, and/or fracture, and the abnormality classification data 445 for each abnormality pattern category 446 can indicate whether or not each of the abnormality patterns is present.

The abnormality classifier categories can correspond to Response Evaluation Criteria in Solid Tumors (RECIST) eligibility and/or RECIST evaluation categories. For example, an abnormality classifier category 444 corresponding to RECIST eligibility can have corresponding abnormality classification data 445 indicating a binary value "yes" or "no", and/or can indicate if the abnormality is a "target lesion" and/or a "non-target lesion." As another example, an abnormality classifier category 444 corresponding to a RECIST evaluation category can be determined based on longitudinal data 433 and can have corresponding abnormality classification data 445 that includes one of the set of possible values "Complete Response", "Partial Response", "Stable Disease", or "Progressive Disease."

The diagnosis data 440 as a whole, and/or the abnormality annotation data 442 for each abnormality, can include custom codes or datatypes identifying the binary abnormality identifier 441, abnormality location data 443 and/or some or all of the abnormality classification data 445 of one or more abnormality classifier categories 444. Alternatively or in addition, some or all of the abnormality annotation data 442 for each abnormality and/or other diagnosis data 440 can be presented in a DICOM format or other standardized image annotation format, and/or can be extracted into custom datatypes based on abnormality annotation data originally presented in DICOM format. Alternatively or in addition, the diagnosis data 440 and/or the abnormality annotation data 442 for each abnormality can be presented as one or more medical codes 447 such as SNOMED codes, Current Procedure Technology (CPT) codes, ICD-9 codes, ICD-10 codes, or other standardized medical codes used to label or otherwise describe medical scans.

Alternatively or in addition, the diagnosis data 440 can include natural language text data 448 annotating or otherwise describing the medical scan as a whole, and/or the abnormality annotation data 442 can include natural language text data 448 annotating or otherwise describing each corresponding abnormality. In some embodiments, some or all of the diagnosis data 440 is presented only as natural language text data 448. In some embodiments, some or all of the diagnosis data 440 is automatically generated by one or more subsystems based on the natural language text data 448, for example, without utilizing the medical scan image data 410, for example, by utilizing one or more medical scan natural language analysis functions trained by the medical scan natural language analysis system 114. Alternatively or in addition, some embodiments, some or all of the natural language text data 448 is generated automatically based on other diagnosis data 440 such as abnormality annotation data 442, for example, by utilizing a medical scan natural language generating function trained by the medical scan natural language analysis system 114.

The diagnosis data can include report data 449 that includes at least one medical report, which can be formatted to include some or all of the medical codes 447, some or all of the natural language text data 448, other diagnosis data 440, full or cropped images slices formatted based on the display parameter data 470 and/or links thereto, full or cropped images slices or other data based on similar scans of the similar scan data 480 and/or links thereto, full or cropped images or other data based on patient history data 430 such as longitudinal data 433 and/or links thereto, and/or other data or links to data describing the medical scan and associated abnormalities. The diagnosis data 440 can also include finalized diagnosis data corresponding to future scans and/or future diagnosis for the patient, for example, biopsy data or other longitudinal data 433 determined subsequently after the scan. The medical report of report data 449 can be formatted based on specified formatting parameters such as font, text size, header data, bulleting or numbering type, margins, file type, preferences for including one or more full or cropped image slices 412, preferences for including similar medical scans, preferences for including additional medical scans, or other formatting to list natural language text data and/or image data, for example, based on preferences of a user indicated in the originating entity data 423 or other responsible user in the corresponding report formatting data.

Annotation author data 450 can be mapped to the diagnosis data for each abnormality, and/or mapped to the scan as a whole. This can include one or more annotation author identifiers 451, which can include one or more user profile identifiers of a user of the system, such as an individual medical professional, medical facility and/or medical entity that uses the system. Annotation author data 450 can be used to determine the usage data of a user profile entry 354. Annotation author data 450 can also include one or more medical scan analysis function identifiers 357 or other function identifier indicating one or more functions or other processes of a subsystem responsible for automatically generating and/or assisting a user in generating some or all of the diagnosis data, for example an identifier of a particular type and/or version of a medical scan image analysis functions that was used by the medical scan diagnosing system 108 used to generate part or all of the diagnosis data 440 and/or an interface feature identifier, indicating an one or more interface features presented to a user to facilitate entry of and/or reviewing of the diagnosis data 440. The annotation author data can also simply indicate, for one or more portions of the diagnosis data 440, if this portion was generated by a human or automatically generated by a subsystem of the medical scan processing system.

In some embodiments, if a medical scan was reviewed by multiple entities, multiple, separate diagnosis data entries 440 can be included in the medical scan entry 352, mapped to each diagnosis author in the annotation author data 450. This allows different versions of diagnosis data 440 received from multiple entities. For example, annotation author data of a particular medical scan could indicate that the annotation data was written by a doctor at medical entity A, and the medical code data was generated by user Y by utilizing the medical scan report labeling system 104, which was confirmed by expert user X. The annotation author data of another medical scan could indicate that the medical code was generated automatically by utilizing version 7 of the medical scan image analysis function relating to chest x-rays, and confirmed by expert user X. The annotation author data of another medical scan could indicate that the location and a first malignancy rating were generated automatically by utilizing version 7 of the medical scan image analysis function relating to chest x-rays, and that a second malignancy rating was entered by user Z. In some embodiments, one of the multiple diagnosis entries can include consensus annotation data, for example, generated automatically by a subsystem such as the medical scan annotating system 106 based on the multiple diagnosis data 440, based on confidence score data 460 of each of the multiple diagnosis data 440, and/or based on performance score data of a corresponding user, a medical scan analysis function, or an interface feature, identified in the annotation author data for each corresponding one of the multiple diagnosis data 440.

Confidence score data 460 can be mapped to some or all of the diagnosis data 440 for each abnormality, and/or for the scan as a whole. This can include an overall confidence score for the diagnosis, a confidence score for the binary indicator of whether or not the scan was normal, a confidence score for the location a detected abnormality, and/or confidence scores for some or all of the abnormality classifier data. This may be generated automatically by a subsystem, for example, based on the annotation author data and corresponding performance score of one or more identified users and/or subsystem attributes such as interactive interface types or medical scan image analysis functions indicated by the annotation author data. In the case where multiple diagnosis data entries 440 are included from different sources, confidence score data 460 can be computed for each entry and/or an overall confidence score, for example, corresponding to consensus diagnosis data, can be based on calculated distance or other error and/or discrepancies between the entries, and/or can be weighted on the confidence score data 460 of each entry. In various embodiments, the confidence score data 460 can include a truth flag 461 indicating the diagnosis data is considered as "known" or "truth", for example, flagged based on user input, flagged automatically based on the author data, and/or flagged automatically based on the calculated confidence score of the confidence score data exceeding a truth threshold. As used herein, a "high" confidence score refers to a greater degree or more favorable level of confidence than a "low" confidence score.

Display parameter data 470 can indicate parameters indicating an optimal or preferred display of the medical scan by an interactive interface 275 and/or formatted report for each abnormality and/or for the scan as a whole. Some or all of the display parameter data can have separate entries for each abnormality, for example, generated automatically by a subsystem 101 based on the abnormality annotation data 442. Display parameter data 470 can include interactive interface feature data 471, which can indicate one or more selected interface features associated with the display of abnormalities and/or display of the medical scan as a whole, and/or selected interface features associated with user interaction with a medical scan, for example, based on categorized interface feature performance score data and a category associated with the abnormality and/or with the medical scan itself. The display parameter data can include a slice subset 472, which can indicate a selected subset of the plurality of image slices that includes a single image slice 412 or multiple image slices 412 of the medical scan image data 410 for display by a user interface. The display parameter data 470 can include slice order data 473 that indicates a selected custom ordering and/or ranking for the slice subset 472, or for all of the slices 412 of the medical scan. The display parameter data 470 can include slice cropping data 474 corresponding to some or all of the slice subset 472, or all of the image slices 412 of the medical scan, and can indicating a selected custom cropped region of each image slice 412 for display, or the same selected custom cropped region for the slice subset 472 or for all slices 412. The display parameter data can include density window data 475, which can indicate a selected custom density window for display of the medical scan as a whole, a selected custom density window for the slice subset 472, and/or selected custom density windows for each of the image slices 412 of the slice subset 472, and/or for each image slice 412 of the medical scan. The density window data 475 can indicate a selected upper density value cut off and a selected lower density value cut off, and/or can include a selected deterministic function to map each density value of a pixel to a grayscale value based on the preferred density window. The interactive interface feature data 471, slice subset 472, slice order data 473, slice cropping data 474, and/or the density window data 475 can be selected via user input and/or generated automatically by one or more subsystems 101, for example, based on the abnormality annotation data 442 and/or based on performance score data of different interactive interface versions.

Similar scan data 480 can be mapped to each abnormality, or the scan as a whole, and can include similar scan identifier data 481 corresponding to one or more identified similar medical scans, for example, automatically identified by a subsystem 101, for example, by applying a similar scan identification step of the medical scan image analysis system 112 and/or applying medical scan similarity analysis function to some or all of the data stored in the medical scan entry of the medical scan, and/or to some or all corresponding data of other medical scans in the medical scan database. The similar scan data 480 can also correspond to medical scans received from another source. The stored similarity data can be used to present similar cases to users of the system and/or can be used to train medical scan image analysis functions or medical scan similarity analysis functions.

Each identified similar medical scan can have its own medical scan entry 352 in the medical scan database 342 with its own data, and the similar scan identifier data 481 can include the medical scan identifier 353 each similar medical scan. Each identified similar medical scan can be a scan of the same scan type or different scan type than medical scan.

The similar scan data 480 can include a similarity score 482 for each identified similar scan, for example, generated based on some or all of the data of the medical scan entry 352 for medical scan and based on some or all of the corresponding data of the medical scan entry 352 for the identified similar medical scan. For example, the similarity score 482 can be generated based on applying a medical scan similarity analysis function to the medical image scan data of medical scans and 402, to some or all of the abnormality annotation data of medical scans and 402, and/or to some or all of the patient history data 430 of medical scans and 402 such as risk factor data 432. As used herein, a "high" similarity score refers a higher level of similarity that a "low" similarity score.

The similar scan data 480 can include its own similar scan display parameter data 483, which can be determined based on some or all of the display parameter data 470 of the identified similar medical scan. Some or all of the similar scan display parameter data 483 can be generated automatically by a subsystem, for example, based on the display parameter data 470 of the identified similar medical scan, based on the abnormality annotation data 442 of the medical scan itself and/or based on display parameter data 470 of the medical scan itself. Thus, the similar scan display parameter data 483 can be the same or different than the display parameter data 470 mapped to the identified similar medical scan and/or can be the same or different than the display parameter data 470 of the medical scan itself. This can be utilized when displaying similar scans to a user via interactive interface 275 and/or can be utilized when generating report data 449 that includes similar scans, for example, in conjunction with the medical scan assisted review system 102.

The similar scan data 480 can include similar scan abnormality data 484, which can indicate one of a plurality of abnormalities of the identified similar medical scan and its corresponding abnormality annotation data 442. For example, the similarity scan abnormality data 484 can include an abnormality pair that indicates one of a plurality of abnormalities of the medical scan, and indicates one of a plurality of abnormalities of the identified similar medical scan, for example, that was identified as the similar abnormality.

The similar scan data 480 can include similar scan filter data 485. The similar scan filter data can be generated automatically by a subsystem, and can include a selected ordered or un-ordered subset of all identified similar scans of the similar scan data 480, and/or a ranking of all identified similar scans. For example, the subset can be selected and/or some or all identified similar scans can be ranked based on each similarity score 482, and/or based on other factors such as based on a longitudinal quality score 434 of each identified similar medical scan.

The training set data 490 can indicate one or more training sets that the medical scan belongs to. For example, the training set data can indicate one or more training set identifiers 491 indicating one or more medical scan analysis functions that utilized the medical scan in their training set, and/or indicating a particular version identifier 641 of the one or more medical scan analysis functions that utilized the medical scan in their training set. The training set data 490 can also indicate which portions of the medical scan entry were utilized by the training set, for example, based on model parameter data 623 of the corresponding medical scan analysis functions. For example, the training set data 490 can indicate that the medical scan image data 410 was included in the training set utilized to train version X of the chest x-ray medical scan image analysis function, or that the natural language text data 448 of this medical scan was used to train version Y of the natural language analysis function.

Figure 5A:
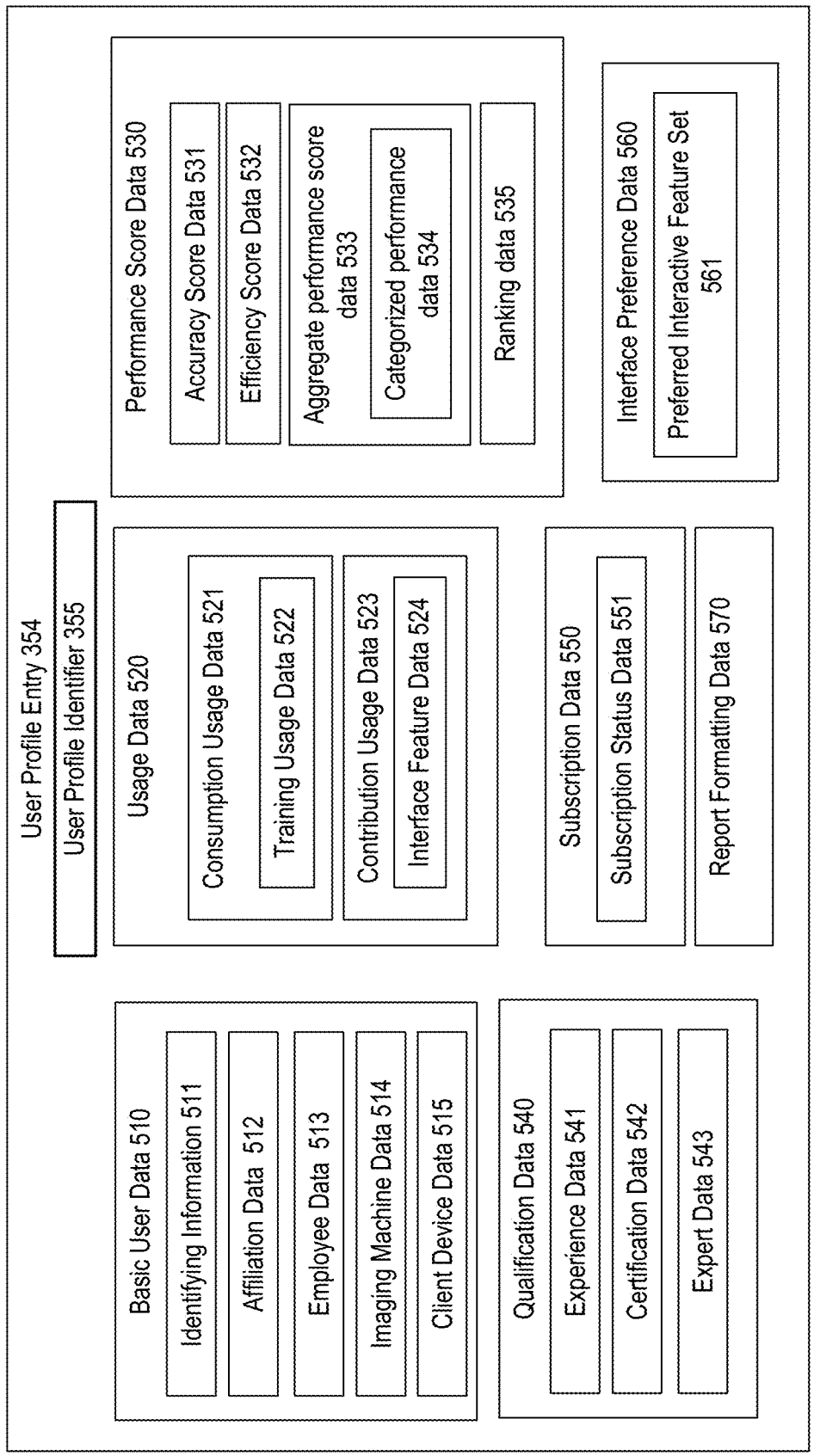
FIG. 5A is a schematic block diagram of a user profile entry in accordance with various embodiments.

FIG. 5A presents an embodiment of a user profile entry 354, stored in user database 344 or otherwise associated with a user. A user can correspond to a user of one or more of the subsystems such as a radiologist, doctor, medical professional, medical report labeler, administrator of one or more subsystems or databases, or other user that uses one or more subsystems 101. A user can also correspond to a medical entity such as a hospital, medical clinic, establishment that utilizes medical scans, establishment that employs one or more of the medical professionals described, an establishment associated with administering one or more subsystems, or other entity. A user can also correspond to a particular client device 120 or account that can be accessed one or more medical professionals or other employees at the same or different medical entities. Each user profile entry can have a corresponding user profile identifier 355.

A user profile entry 354 can include basic user data 510, which can include identifying information 511 corresponding to the user such as a name, contact information, account/login/password information, geographic location information such as geographic region data 424, and/or other basic information. Basic user data 510 can include affiliation data 512, which can list one or more medical entities or other establishments the user is affiliated with, for example, if the user corresponds to a single person such as a medical professional, or if the user corresponds to a hospital in a network of hospitals. The affiliation data 512 can include one or more corresponding user profile identifiers 355 and/or basic user data 510 if the corresponding affiliated medical entity or other establishment has its own entry in the user database. The user identifier data can include employee data 513 listing one or more employees, such as medical professionals with their own user profile entries 354, for example, if the user corresponds to a medical entity or supervising medical professional of other medical professional employees, and can list a user profile identifier 355 and/or basic user data 510 for each employee. The basic user data 510 can also include imaging machine data 514, which can include a list of machines affiliated with the user which can include machine identifiers, model information, calibration information, scan type information, or other data corresponding to each machine, for example, corresponding to the machine data 425. The user profile entry can include client device data 515, which can include identifiers for one or more client devices associated with the user, for example, allowing subsystems 101 to send data to a client device 120 corresponding to a selected user based on the client device data and/or to determine a user that data was received by determining the client device from which the data was received.

The user profile entry can include usage data 520 which can include identifying information for a plurality of usages by the user in conjunction with using one or more subsystems 101. This can include consumption usage data 521, which can include a listing of, or aggregate data associated with, usages of one or more subsystems by the user, for example, where the user is utilizing the subsystem as a service. For example, the consumption usage data 521 can correspond to each instance where diagnosis data was sent to the user for medical scans provided to the user in conjunction with the medical scan diagnosing system 108 and/or the medical scan assisted review system 102. Some or all of consumption usage data 521 can include training usage data 522, corresponding to usage in conjunction with a certification program or other user training provided by one or more subsystems. The training usage data 522 can correspond to each instance where diagnosis feedback data was provided by user for a medical scan with known diagnosis data, but diagnosis feedback data is not utilized by a subsystem to generate, edit, and/or confirm diagnosis data 440 of the medical scan, as it is instead utilized to train a user and/or determine performance data for a user.

Usage data 520 can include contribution usage data 523, which can include a listing of, or aggregate data associated with, usages of one or more subsystems 101 by the user, for example, where the user is generating and/or otherwise providing data and/or feedback that can is utilized by the subsystems, for example, to generate, edit, and/or confirm diagnosis data 440 and/or to otherwise populate, modify, or confirm portions of the medical scan database or other subsystem data. For example, the contribution usage data 523 can correspond to diagnosis feedback data received from user, used to generate, edit, and/or confirm diagnosis data. The contribution usage data 523 can include interactive interface feature data 524 corresponding to the interactive interface features utilized with respect to the contribution.

The consumption usage data 521 and/or the contribution usage data 523 can include medical scan entry 352 whose entries the user utilized and/or contributed to, can indicate one or more specific attributes of a medical scan entry 352 that a user utilized and/or contributed to, and/or a log of the user input generated by a client device of the user in conjunction with the data usage. The contribution usage data 523 can include the diagnosis data that the user may have generated and/or reviewed, for example, indicated by, mapped to, and/or used to generate the annotation author data 450 of corresponding medical scan entries 352. Some usages may correspond to both consumption usage of the consumption usage data 521 and contribution usage of the contribution usage data 523. The usage data 520 can also indicate one or more subsystems 101 that correspond to each consumption and/or contribution.

The user profile entry can include performance score data 530. This can include one or more performance scores generated based on the contribution usage data 523 and/or training usage data 522. The performance scores can include separate performance scores generated for every contribution in the contribution usage data 523 and/or training usage data 522 and/or generated for every training consumption usages corresponding to a training program. As used herein, a "high" performance score refers to a more favorable performance or rating than a "low" performance score.

The performance score data can include accuracy score data 531, which can be generated automatically by a subsystem for each contribution, for example, based on comparing diagnosis data received from a user to data to known truth data such as medical scans with a truth flag 461, for example, retrieved from the corresponding medical scan entry 352 and/or based on other data corresponding to the medical scan, for example, received from an expert user that later reviewed the contribution usage data of the user and/or generated automatically by a subsystem. The accuracy score data 531 can include an aggregate accuracy score generated automatically by a subsystem, for example, based on the accuracy data of multiple contributions by the user over time.

The performance data can also include efficiency score data 532 generated automatically by a subsystem for each contribution based on an amount of time taken to complete a contribution, for example, from a time the request for a contribution was sent to the client device to a time that the contribution was received from the client device, based on timing data received from the client device itself, and/or based on other factors. The efficiency score can include an aggregate efficiency score, which can be generated automatically by a subsystem based on the individual efficiency scores over time and/or based on determining a contribution completion rate, for example based on determining how many contributions were completed in a fixed time window.

Aggregate performance score data 533 can be generated automatically by a subsystem based on the aggregate efficiency and/or accuracy data. The aggregate performance data can include categorized performance data 534, for example, corresponding to different scan types, different anatomical regions, different subsystems, different interactive interface features and/or display parameters. The categorized performance data 534 can be determined automatically by a subsystem based on the scan type data 421 and/or anatomical region data 422 of the medical scan associated with each contribution, one or more subsystems 101 associated with each contribution, and/or interactive interface feature data 524 associated with each contribution. The aggregate performance data can also be based on performance score data 530 of individual employees if the user corresponds to a medical entity, for example, retrieved based on user profile identifiers 355 included in the employee data 513. The performance score data can also include ranking data 535, which can include an overall ranking or categorized rankings, for example, generated automatically by a subsystem or the database itself based on the aggregate performance data.

In some embodiments, aggregate data for each user can be further broken down based on scores for distinct scan categories, for example, based on the scan classifier data 420, for example, where a first aggregate data score is generated for a user "A" based on scores from all knee x-rays, and a second aggregate data score is generated for user A based on scores from all chest CT scans. Aggregate data for each user can be further based on scores for distinct diagnosis categories, where a first aggregate data score is generated for user A based on scores from all normal scans, and a second aggregate data score is generated for user A based on scores from all scans that contain an abnormality. This can be further broken down, where a first aggregate score is generated for user A based on all scores from scans that contain an abnormality of a first type and/or in a first anatomical location, and a second aggregate score is generated for A based on all scores from scans that contain an abnormality of a second type and/or in a second location. Aggregate data for each user can be further based on affiliation data, where a ranking is generated for a medical professional "B" based on scores from all medical professionals with the same affiliation data, and/or where a ranking is generated for a hospital "C" based on scores for all hospitals, all hospitals in the same geographical region, etc. Aggregate data for each user can be further based on scores for interface features, where a first aggregate data score is generated for user A based on scores using a first interface feature, and a second aggregate data score is generated for user A based on scores using a first interface feature.

The user profile entry can include qualification data 540. The qualification data can include experience data 541 such as education data, professional practice data, number of years practicing, awards received, etc. The qualification data 540 can also include certification data 542 corresponding to certifications earned based on contributions to one or more subsystems, for example, assigned to users automatically by a subsystem based on the performance score data 530 and/or based on a number of contributions in the contribution usage data 523 and/or training usage data 522. For example, the certifications can correspond to standard and/or recognized certifications to train medical professionals and/or incentivize medical professionals to use the system. The qualification data 540 can include expert data 543. The expert data 543 can include a binary expert identifier, which can be generated automatically by a subsystem based on experience data 541, certification data 542, and/or the performance score data 530, and can indicate whether the user is an expert user. The expert data 543 can include a plurality of categorized binary expert identifiers corresponding to a plurality of qualification categories corresponding to corresponding to scan types, anatomical regions, and/or the particular subsystems. The categorized binary expert identifiers can be generated automatically by a subsystem based on the categorized performance data 534 and/or the experience data 541. The categories be ranked by performance score in each category to indicate particular specialties. The expert data 543 can also include an expert ranking or categorized expert ranking with respect to all experts in the system.

The user profile entry can include subscription data 550, which can include a selected one of a plurality of subscription options that the user has subscribed to. For example, the subscription options can correspond to allowed usage of one or more subsystems, such as a number of times a user can utilize a subsystem in a month, and/or to a certification program, for example paid for by a user to receive training to earn a subsystem certification of certification data 542. The subscription data can include subscription expiration information, and/or billing information. The subscription data can also include subscription status data 551, which can for example indicate a number of remaining usages of a system and/or available credit information. For example, the remaining number of usages can decrease and/or available credit can decrease in response to usages that utilize one or more subsystems as a service, for example, indicated in the consumption usage data 521 and/or training usage data 522. In some embodiments, the remaining number of usages can increase and/or available credit can increase in response to usages that correspond to contributions, for example, based on the contribution usage data 523. An increase in credit can be variable, and can be based on a determined quality of each contribution, for example, based on the performance score data 530 corresponding to the contribution where a higher performance score corresponds to a higher increase in credit, based on scan priority data 427 of the medical scan where contributing to higher priority scans corresponds to a higher increase in credit, or based on other factors.

The user profile entry 354 can include interface preference data 560. The interface preference data can include a preferred interactive interface feature set 561, which can include one or more interactive interface feature identifiers and/or one or more interactive interface version identifiers of interface feature entries 358 and/or version identifiers of the interface features. Some or all of the interface features of the preferred interactive interface feature set 561 can correspond to display parameter data 470 of medical scans. The preferred interactive interface feature set 561 can include a single interactive feature identifier for one or more feature types and/or interface types, and/or can include a single interactive interface version identifier for one or more interface categories. The preferred interactive interface feature set 561 can include a ranking of multiple features for the same feature type and/or interface type. The ranked and/or unranked preferred interactive interface feature set 561 can be generated based on user input to an interactive interface of the client device to select and/or rank some or all of the interface features and/or versions. Some or all of the features and/or versions of the preferred interactive feature set can be selected and/or ranked automatically by a subsystem such as the medical scan interface evaluator system, for example based on interface feature performance score data and/or feature popularity data. Alternatively or in addition, the performance score data 530 can be utilized by a subsystem to automatically determine the preferred interactive feature set, for example, based on the scores in different feature-based categories of the categorized performance data 534.

The user profile entry 354 can include report formatting data 570, which can indicate report formatting preferences indicated by the user. This can include font, text size, header data, bulleting or numbering type, margins, file type, preferences for including one or more full or cropped image slices 412, preferences for including similar medical scans, preferences for including additional medical scans in reports, or other formatting preference to list natural language text data and/or image data corresponding to each abnormality. Some or all of the report formatting data 570 can be based on interface preference data 560. The report formatting data 570 can be used by one or more subsystems to automatically generate report data 449 of medical scans based on the preferences of the requesting user.

Figure 5B:
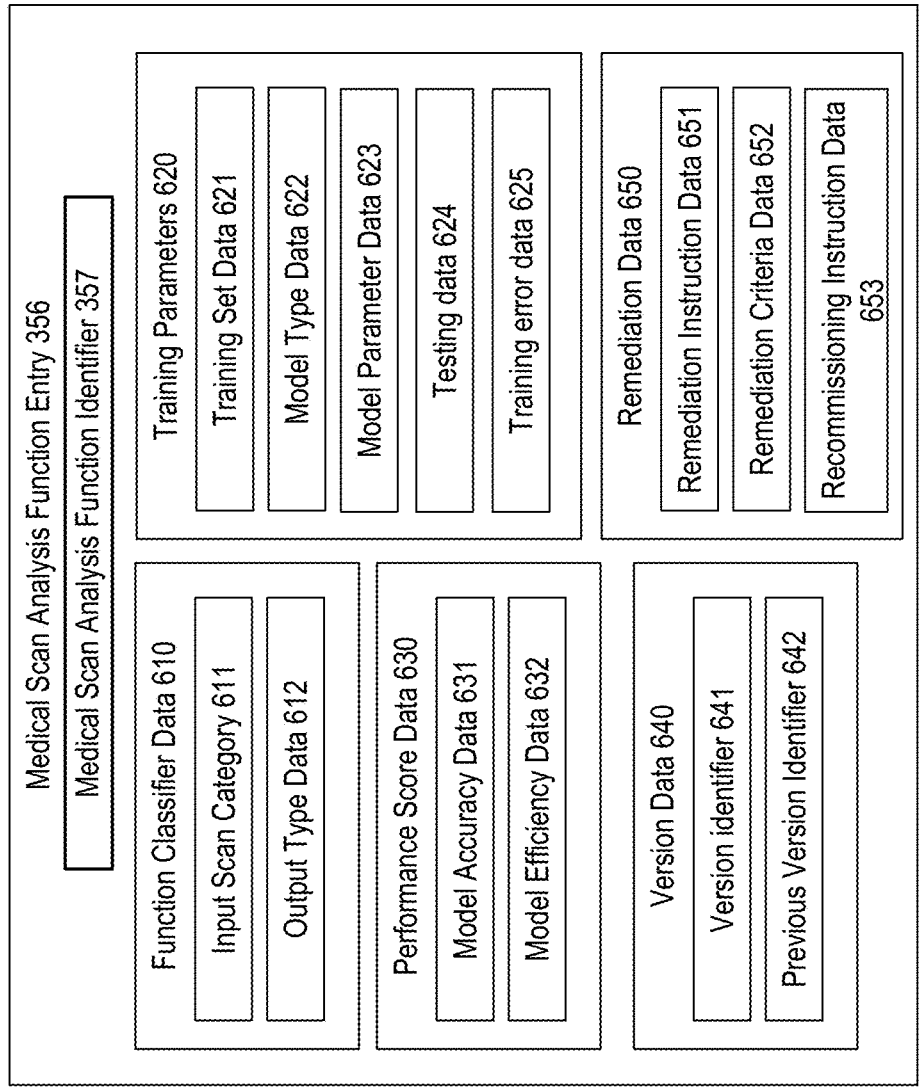
FIG. 5B is a schematic block diagram of a medical scan analysis function entry in accordance with various embodiments.

FIG. 5B presents an embodiment of a medical scan analysis function entry 356, stored in medical scan analysis function database 346 or otherwise associated with one of a plurality of medical scan analysis functions trained by and/or utilized by one or more subsystems 101. For example, a medical scan analysis function can include one or more medical scan image analysis functions trained by the medical scan image analysis system 112; one or more medical scan natural language analysis functions trained by the medical scan natural language analysis system 114; one or more medical scan similarity analysis function trained by the medical scan image analysis system 112, the medical scan natural language analysis system 114, and/or the medical scan comparison system 116; one or more medical report generator functions trained by the medical scan natural language analysis system 114 and/or the medical scan image analysis system 112, and/or the medical report analysis function trained by the medical scan natural language analysis system 114. Some or all of the medical scan analysis functions can correspond to medical scan inference functions of the medical scan diagnosing system 108, the de-identification function and/or the inference functions utilized by a medical picture archive integration system as discussed in conjunction with FIGS. 8A-8F, or other functions and/or processes described herein in conjunction with one or more subsystems 101. Each medical scan analysis function entry 356 can include a medical scan analysis function identifier 357.

A medical scan analysis function entry 356 can include function classifier data 610. Function classifier data 610 can include input and output types corresponding to the function. For example the function classifier data can include input scan category 611 that indicates which types of scans can be used as input to the medical scan analysis function. For example, input scan category 611 can indicate that a medical scan analysis function is for chest CT scans from a particular hospital or other medical entity. The input scan category 611 can include one or more categories included in scan classifier data 420. In various embodiments, the input scan category 611 corresponds to the types of medical scans that were used to train the medical scan analysis function. Function classifier data 610 can also include output type data 612 that characterizes the type of output that will be produced by the function, for example, indicating that a medical scan analysis function is used to generate medical codes 447. The input scan category 611 can also include information identifying which subsystems 101 are responsible for running the medical scan analysis function.

A medical scan analysis function entry 356 can include training parameters 620. This can include training set data 621, which can include identifiers for the data used to train the medical scan analysis function, such as a set of medical scan identifiers 353 corresponding to the medical scans used to train the medical scan analysis function, a list of medical scan reports and corresponding medical codes used to train the medical scan analysis function, etc. Alternatively or in addition to identifying particular scans of the training set, the training set data 621 can identify training set criteria, such as necessary scan classifier data 420, necessary abnormality locations, classifiers, or other criteria corresponding to abnormality annotation data 442, necessary confidence score data 460, for example, indicating that only medical scans with diagnosis data 440 assigned a truth flag 461 or with confidence score data 460 otherwise comparing favorably to a training set confidence score threshold are included, a number of medical scans to be included and proportion data corresponding to different criteria, or other criteria used to populate a training set with data of medical scans. Training parameters 620 can include model type data 622 indicating one or more types of model, methods, and/or training functions used to determine the medical scan analysis function by utilizing the training set 621. Training parameters 620 can include model parameter data 623 that can include a set of features of the training data selected to train the medical scan analysis function, determined values for weights corresponding to selected input and output features, determined values for model parameters corresponding to the model itself, etc. The training parameter data can also include testing data 624, which can identify a test set of medical scans or other data used to test the medical scan analysis function. The test set can be a subset of training set 621, include completely separate data than training set 621, and/or overlap with training set 621. Alternatively or in addition, testing data 624 can include validation parameters such as a percentage of data that will be randomly or pseudo-randomly selected from the training set for testing, parameters characterizing a cross validation process, or other information regarding testing. Training parameters 620 can also include training error data 625 that indicates a training error associated with the medical scan analysis function, for example, based on applying cross validation indicated in testing data 624.

A medical scan analysis function entry 356 can include performance score data 630. Performance data can include model accuracy data 631, for example, generated and/or updated based on the accuracy of the function when performed on new data. For example, the model accuracy data 631 can include or be calculated based on the model error for determined for individual uses, for example, generated by comparing the output of the medical scan analysis function to corresponding data generated by user input to interactive interface 275 in conjunction with a subsystem 101 and/or generated by comparing the output of the medical scan analysis function to medical scans with a truth flag 461. The model accuracy data 631 can include aggregate model accuracy data computed based on model error of individual uses of the function over time. The performance score data 630 can also include model efficiency data 632, which can be generated based on how quickly the medical scan analysis function performs, how much memory is utilized by medical scan analysis function, or other efficiency data relating to the medical scan analysis function. Some or all of the performance score data 630 can be based on training error data 625 or other accuracy and/or efficiency data determined during training and/or validation. As used herein, a "high" performance score refers to a more favorable performance or rating than a "low" performance score.

A medical scan analysis function entry 356 can include version data 640. The version data can include a version identifier 641. The version data can indicate one or more previous version identifiers 642, which can map to version identifiers 641 stored in other medical scan analysis function entry 356 that correspond to previous versions of the function. Alternatively or in addition, the version data can indicate multiple versions of the same type based on function classifier data 610, can indicate the corresponding order and/or rank of the versions, and/or can indicate training parameters 620 associated with each version.

A medical scan analysis function entry 356 can include remediation data 650. Remediation data 650 can include remediation instruction data 651 which can indicate the steps in a remediation process indicating how a medical scan analysis function is taken out of commission and/or reverted to a previous version in the case that remediation is necessary. The version data 640 can further include remediation criteria data 652, which can include threshold data or other criteria used to automatically determine when remediation is necessary. For example, the remediation criteria data 652 can indicate that remediation is necessary at any time where the model accuracy data and/or the model efficiency data compares unfavorably to an indicated model accuracy threshold and/or indicated model efficiency threshold. The remediation data 650 can also include recommissioning instruction data 653, identifying required criteria for recommissioning a medical scan analysis function and/or updating a medical scan analysis function. The remediation data 650 can also include remediation history, indicating one or more instances that the medical scan analysis function was taken out of commission and/or was recommissioned.

Figure 6A:
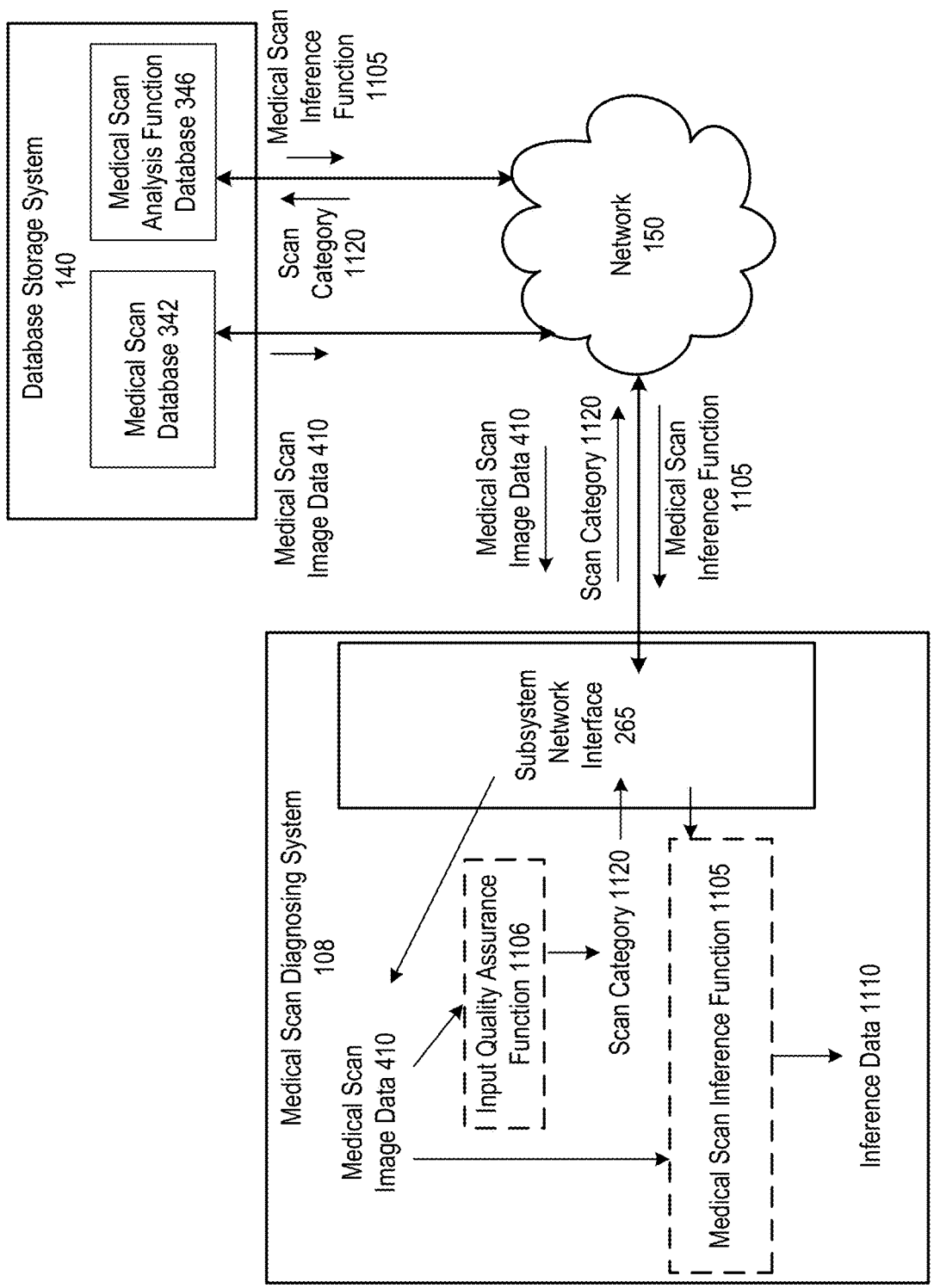
FIGS. 6A-6B are schematic block diagram of a medical scan diagnosing system in accordance with various embodiments.
Figure 6B:
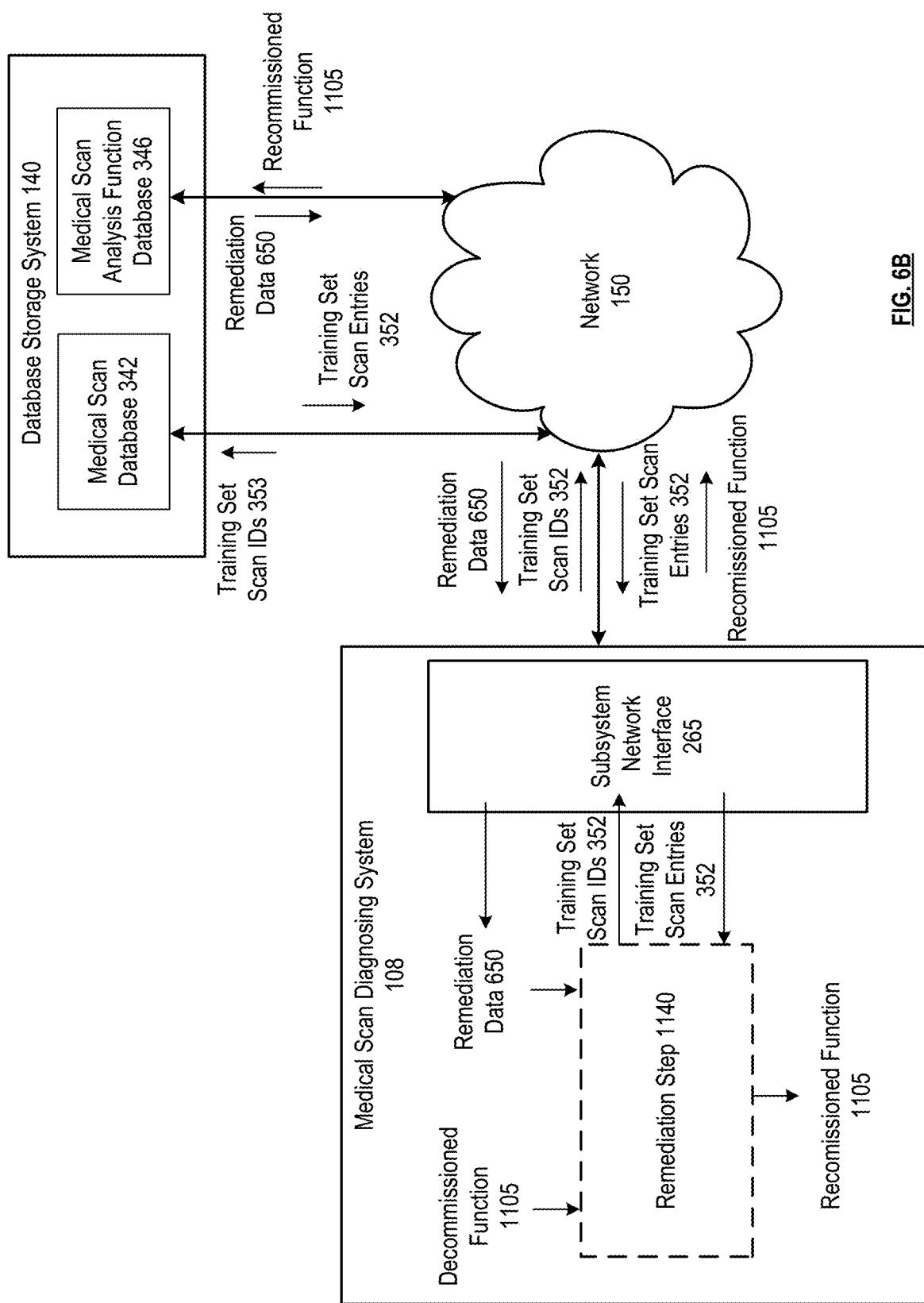

FIGS. 6A and 6B present an embodiment of a medical scan diagnosing system 108.

The medical scan diagnosing system 108 can generate inference data 1110 for medical scans by utilizing a set of medical scan inference functions 1105, stored and run locally, stored and run by another subsystem 101, and/or stored in the medical scan analysis function database 346, where the function and/or parameters of the function can be retrieved from the database by the medical scan diagnosing system. For example, the set of medical scan inference function 1105 can include some or all medical scan analysis functions described herein or other functions that generate inference data 1110 based on some or all data corresponding to a medical scan such as some or all data of a medical scan entry 352. Each medical scan inference function 1105 in the set can correspond to a scan category 1120, and can be trained on a set of medical scans that compare favorably to the scan category 1120. For example, each inference function can be trained on a set of medical scans of the one or more same scan classifier data 420, such as the same and/or similar scan types, same and/or similar anatomical regions locations, same and/or similar machine models, same and/or similar machine calibration, same and/or similar contrasting agent used, same and/or similar originating entity, same and/or similar geographical region, and/or other classifiers. Thus, the scan categories 1120 can correspond to one or more of a scan type, scan anatomical region data, hospital or other originating entity data, machine model data, machine calibration data, contrast agent data, geographic region data, and/or other scan classifying data 420. For example, a first medical scan inference function can be directed to characterizing knee x-rays, and a second medical scan inference function can be directed to chest CT scans. As another example, a first medical scan inference function can be directed to characterizing CT scans from a first hospital, and a second medical scan image analysis function can be directed to characterizing CT scans from a second hospital.

Training on these categorized sets separately can ensure each medical scan inference function 1105 is calibrated according to its scan category 1120, for example, allowing different inference functions to be calibrated on type specific, anatomical region specific, hospital specific, machine model specific, and/or region-specific tendencies and/or discrepancies. Some or all of the medical scan inference functions 1105 can be trained by the medical scan image analysis system and/or the medical scan natural language processing system, and/or some medical scan inference functions 1105 can utilize both image analysis and natural language analysis techniques to generate inference data 1110. For example, some or all of the inference functions can utilize image analysis of the medical scan image data 410 and/or natural language data extracted from abnormality annotation data 442 and/or report data 449 as input, and generate diagnosis data 440 such as medical codes 447 as output. Each medical scan inference function can utilize the same or different learning models to train on the same or different features of the medical scan data, with the same or different model parameters, for example indicated in the model type data 622 and model parameter data 623. Model type and/or parameters can be selected for a particular medical scan inference function based on particular characteristics of the one or more corresponding scan categories 1120, and some or all of the indicated in the model type data 622 and model parameter data 623 can be selected automatically by a subsystem during the training process based on the particular learned and/or otherwise determined characteristics of the one or more corresponding scan categories 1120.

As shown in FIG. 6A, the medical scan diagnosing system 108 can automatically select a medical scan for processing in response to receiving it from a medical entity via the network. Alternatively, the medical scan diagnosing system 108 can automatically retrieve a medical scan from the medical scan database that is selected based on a request received from a user for a particular scan and/or based on a queue of scans automatically ordered by the medical scan diagnosing system 108 or another subsystem based on scan priority data 427.

Once a medical scan to be processed is determined, the medical scan diagnosing system 108 can automatically select an inference function 1105 based on a determined scan category 1120 of the selected medical scan and based on corresponding inference function scan categories. The scan category 1120 of a scan can be determined based one some or all of the scan classifier data 420 and/or based on other metadata associated with the scan. This can include determining which one of the plurality of medical scan inference functions 1105 matches or otherwise compares favorably to the scan category 1120, for example, by comparing the scan category 1120 to the input scan category of the function classifier data 610.

Alternatively or in addition, the medical scan diagnosing system 108 can automatically determine which medical scan inference function 1105 is utilized based on an output preference that corresponding to a desired type of inference data 1110 that is outputted by an inference function 1105. The output preference designated by a user of the medical scan diagnosing system 108 and/or based on the function of a subsystem 101 utilizing the medical scan diagnosing system 108. For example, the set of inference functions 1105 can include inference functions that are utilized to indicate whether or not a medical scan is normal, to automatically identify at least one abnormality in the scan, to automatically characterize the at least one abnormality in the scan, to assign one or more medical codes to the scan, to generate natural language text data and/or a formatted report for the scan, and/or to automatically generate other diagnosis data such as some or all of diagnosis data 440 based on the medical scan. Alternatively or in addition, some inference functions can also be utilized to automatically generate confidence score data 460, display parameter data 470, and/or similar scan data 480. The medical scan diagnosing system 108 can compare the output preference to the output type data 612 of the medical scan inference function 1105 to determine the selected inference function 1105. For example, this can be used to decide between a first medical scan inference function that automatically generates medical codes and a second medical scan inference function that automatically generates natural language text for medical reports based on the desired type of inference data 1110.

Prior to performing the selected medical scan inference function 1105, the medical scan diagnosing system 108 can automatically perform an input quality assurance function 1106 to ensure the scan classifier data 420 or other metadata of the medical scan accurately classifies the medical scan such that the appropriate medical scan inference function 1105 of the appropriate scan category 1120 is selected. The input quality assurance function can be trained on, for example, medical scan image data 410 of plurality of previous medical scans with verified scan categories. Thus, the input quality assurance function 1106 can take medical scan image data 410 as input and can generate an inferred scan category as output. The inferred scan category can be compared to the scan category 1120 of the scan, and the input quality assurance function 1106 can determine whether or not the scan category 1120 is appropriate by determining whether the scan category 1120 compares favorably to the automatically generated inferred scan category. The input quality assurance function 1106 can also be utilized to reassign the generated inferred scan category to the scan category 1120 when the scan category 1120 compares favorably to the automatically generated inferred scan category. The input quality assurance function 1106 can also be utilized to assign the generated inferred scan category to the scan category 1120 for incoming medical scans that do not include any classifying data, and/or to add classifiers in scan classifier data 420 to medical scans missing one or more classifiers.

In various embodiments, upon utilizing the input quality assurance function 1106 to determine that the scan category 1120 determined by a scan classifier data 420 or other metadata is inaccurate, the medical scan diagnosing system 108 can transmit an alert and/or an automatically generated inferred scan category to the medical entity indicating that the scan is incorrectly classified in the scan classifier data 420 or other metadata. In some embodiments, the medical scan diagnosing system 108 can automatically update performance score data corresponding to the originating entity of the scan indicated in originating entity data 423, or another user or entity responsible for classifying the scan, for example, where a lower performance score is generated in response to determining that the scan was incorrectly classified and/or where a higher performance score is generated in response to determining that the scan was correctly classified.

In some embodiments, the medical scan diagnosing system 108 can transmit the medical scan and/or the automatically generated inferred scan category to a selected user. The user can be presented the medical scan image data 410 and/or other data of the medical scan via the interactive interface 275, for example, displayed in conjunction with the medical scan assisted review system 102. The interface can prompt the user to indicate the appropriate scan category 1120 and/or prompt the user to confirm and/or edit the inferred scan category, also presented to the user. For example, scan review data can be automatically generated to reflect the user generated and/or verified scan category 1120, This user indicated scan category 1120 can be utilized to select to the medical scan inference function 1105 and/or to update the scan classifier data 420 or other metadata accordingly. In some embodiments, for example, where the scan review data indicates that the selected user disagrees with the automatically generated inferred scan category created by the input quality assurance function 1106, the medical scan diagnosing system 108 can automatically update performance score data 630 of the input quality assurance function 1106 by generating a low performance score and/or determine to enter the remediation step 1140 for the input quality assurance function 1106.

The medical scan diagnosing system 108 can also automatically perform an output quality assurance step after a medical scan inference function 1105 has been performed on a medical scan to produce the inference data 1110, as illustrated in the embodiment presented in FIG. 6B. The output quality assurance step can be utilized to ensure that the selected medical scan inference function 1105 generated appropriate inference data 1110 based on expert feedback. The inference data 1110 generated by performing the selected medical scan inference function 1105 can be sent to a client device 120 of a selected expert user, such as an expert user in the user database selected based on categorized performance data and/or qualification data that corresponds to the scan category 1120 and/or the inference itself, for example, by selecting an expert user best suited to review an identified abnormality classifier category 444 and/or abnormality pattern category 446 in the inference data 1110 based on categorized performance data and/or qualification data of a corresponding user entry. The selected user can also correspond to a medical professional or other user employed at the originating entity and/or corresponding to the originating medical professional, indicated in the originating entity data 423.

FIG. 6B illustrates an embodiment of the medical scan diagnosing system 108 in conjunction with performing a remediation step 1140. The medical scan diagnosing system 108 can monitor the performance of the set of medical scan inference functions 1105, for example, based on evaluating inference accuracy data outputted by an inference data evaluation function and/or based monitoring on the performance score data 630 in the medical scan analysis function database, and can determine whether or not if the corresponding medical scan inference function 1105 is performing properly. This can include, for example, determining if a remediation step 1140 is necessary for a medical scan inference function 1105, for example, by comparing the performance score data 630 and/or inference accuracy data to remediation criteria data 652. Determining if a remediation step 1140 is necessary can also be based on receiving an indication from the expert user or another user that remediation is necessary for one or more identified medical scan inference functions 1105 and/or for all of the medical scan inference functions 1105.

In various embodiments, a remediation evaluation function is utilized to determine if a remediation step 1140 is necessary for medical scan inference function 1105. The remediation evaluation function can include determining that remediation is necessary when recent accuracy data and/or efficiency data of a particular medical scan inference function 1105 is below the normal performance level of the particular inference function. The remediation evaluation function can include determining that remediation is necessary when recent or overall accuracy data and/or efficiency data of a particular medical scan inference function 1105 is below a recent or overall average for all or similar medical scan inference functions 1105. The remediation evaluation function can include determining that remediation is necessary only after a threshold number of incorrect diagnoses are made. In various embodiments, multiple threshold number of incorrect diagnoses correspond to different diagnoses categories. For example, the threshold number of incorrect diagnoses for remediation can be higher for false negative diagnoses than false positive diagnoses. Similarly, categories corresponding to different diagnosis severities and/or rarities can have different thresholds, for example where a threshold number of more severe and/or more rare diagnoses that were inaccurate to necessitate remediation is lower than a threshold number of less severe and/or less rare diagnoses that were inaccurate.

The remediation step 1140 can include automatically updating an identified medical inference function 1105. This can include automatically retraining identified medical inference function 1105 on the same training set or on a new training set that includes new data, data with higher corresponding confidence scores, or data selected based on new training set criteria. The identified medical inference function 1105 can also be updated and/or changed based on the review data received from the client device. For example, the medical scan and expert feedback data can be added to the training set of the medical scan inference function 1105, and the medical scan inference function 1105 can be retrained on the updated training set. Alternatively or in addition, the expert user can identify additional parameters and/or rules in the expert feedback data based on the errors made by the inference function in generating the inference data 1110 for the medical scan, and these parameters and/or rules can be applied to update the medical scan inference function, for example, by updating the model type data 622 and/or model parameter data 623.

The remediation step 1140 can also include determining to split a scan category 1120 into two or more subcategories. Thus, two or more new medical scan inference functions 1105 can be created, where each new medical scan inference functions 1105 is trained on a corresponding training set that is a subset of the original training set and/or includes new medical scan data corresponding to the subcategory. This can allow medical scan inference functions 1105 to become more specialized and/or allow functions to utilize characteristics and/or discrepancies specific to the subcategory when generating inference data 1110. Similarly, a new scan category 1120 that was not previously represented by any of the medical scan inference functions 1105 can be added in the remediation step, and a new medical scan inference functions 1105 can be trained on a new set of medical scan data that corresponds to the new scan category 1120. Splitting a scan category and/or adding a scan category can be determined automatically by the medical scan diagnosing system 108 when performing the remediation step 1140, for example, based on performance score data 630. This can also be determined based on receiving instructions to split a category and/or add a new scan category from the expert user or other user of the system.

After a medical scan inference function 1105 is updated or created for the first time, the remediation step 1140 can further undergo a commissioning test, which can include rigorous testing of the medical scan inference function 1105 on a testing set, for example, based on the training parameters 620. For example, the commissioning test can be passed when the medical scan inference function 1105 generates a threshold number of correct inference data 1110 and/or the test can be passed if an overall or average discrepancy level between the inference data and the test data is below a set error threshold. The commissioning test can also evaluate efficiency, where the medical scan inference function 1105 only passes the commissioning test if it performs at or exceeds a threshold efficiency level. If the medical scan inference function 1105 fails the commissioning test, the model type and/or model parameters can be modified automatically or based on user input, and the medical scan inference function can be retested, continuing this process until the medical scan inference function 1105 passes the commissioning test.

The remediation step 1140 can include decommissioning the medical scan inference function 1105, for example, while the medical scan inference function is being retrained and/or is undergoing the commissioning test. Incoming scans to the medical scan diagnosing system 108 with a scan category 1120 corresponding to a decommissioned medical scan inference function 1105 can be sent directly to review by one or more users, for example, in conjunction with the medical scan annotator system 106. These user-reviewed medical scans and corresponding annotations can be included in an updated training set used to train the decommissioned medical scan inference function 1105 as part of the remediation step 1140. In some embodiments, previous versions of the plurality of medical scan image analysis functions can be stored in memory of the medical scan diagnosing system and/or can be determined based on the version data 640 of a medical scan inference function 1105. A previous version of a medical scan inference function 1105, such as most recent version or version with the highest performance score, can be utilized during the remediation step 1140 as an alternative to sending all medical scans to user review.

A medical scan inference function can also undergo the remediation step 1140 automatically in response to a hardware and/or software update on processing, memory, and/or other computing devices where the medical scan inference function 1105 is stored and/or performed. Different medical scan inference functions 1105 can be containerized on their own devices by utilizing a micro-service architecture, so hardware and/or software updates may only necessitate that one of the medical scan inference functions 1105 undergo the remediation step 1140 while the others remain unaffected. A medical scan inference function 1105 can also undergo the remediation step 1140 automatically in response to normal system boot-up, and/or periodically in fixed intervals. For example, in response to a scheduled or automatically detected hardware and/or software update, change, or issue, one or more medical scan inference functions 1105 affected by this hardware or software can be taken out of commission until they each pass the commissioning test. Such criteria can be indicated in the remediation criteria data 652.

The medical scan diagnosing system 108 can automatically manage usage data, subscription data, and/or billing data for the plurality of users corresponding to user usage of the system, for example, by utilizing, generating, and/or updating some or all of the subscription data of the user database. Users can pay for subscriptions to the system, which can include different subscription levels that can correspond to different costs. For example, a hospital can pay a monthly cost to automatically diagnose up to 100 medical scans per month. The hospital can choose to upgrade their subscription or pay per-scan costs for automatic diagnosing of additional scans received after the quota is reached and/or the medical scan diagnosing system 108 can automatically send medical scans received after the quota is reached to an expert user associated with the hospital. In various embodiments incentive programs can be used by the medical scan diagnosing system to encourage experts to review medical scans from different medical entities. For example, an expert can receive credit to their account and/or subscription upgrades for every medical scan reviewed, or after a threshold number of medical scans are reviewed. The incentive programs can include interactions by a user with other subsystems, for example, based on contributions made to medical scan entries via interaction with other subsystems.

Figure 7A:
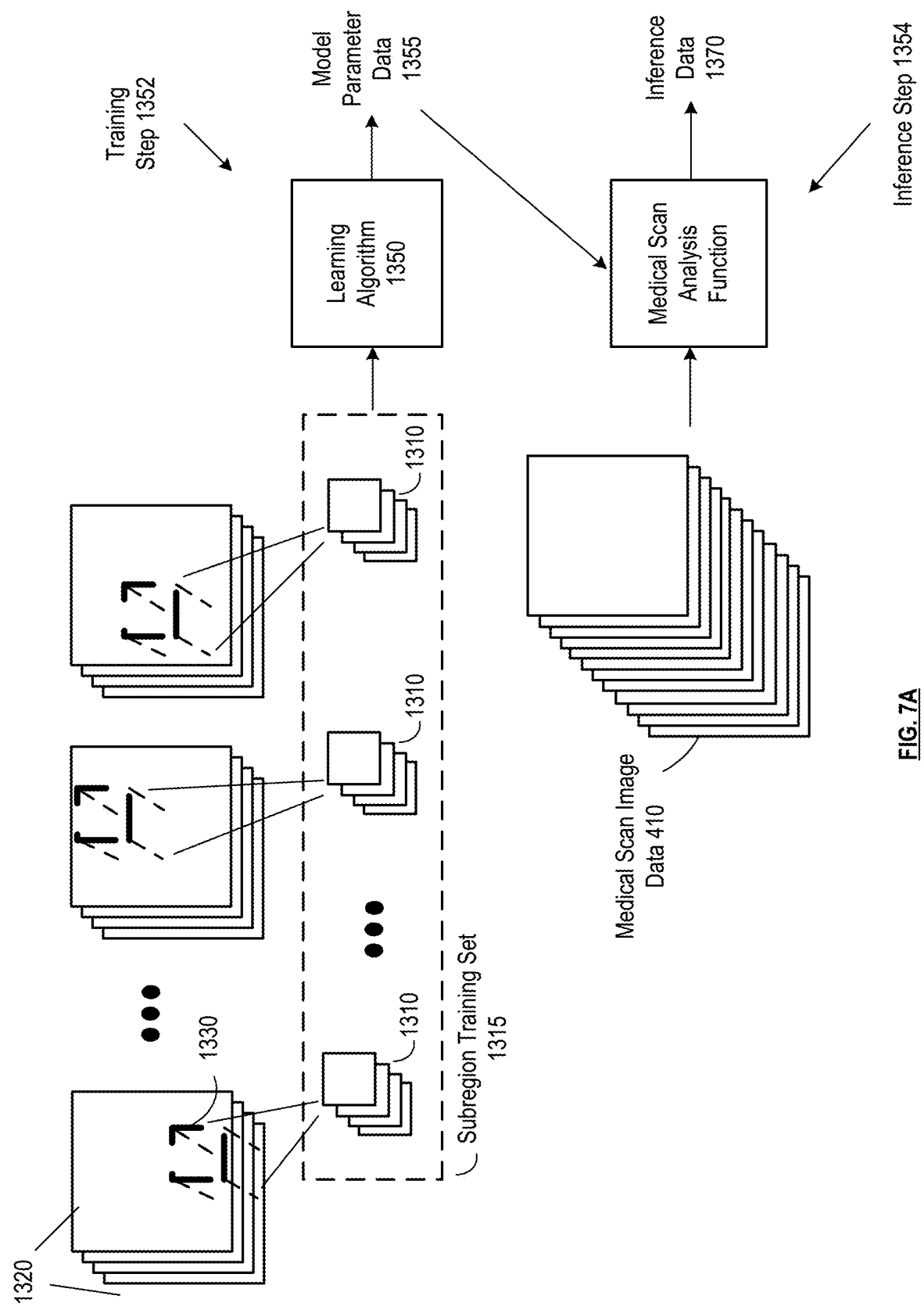
FIG. 7A is a flowchart representation of an inference step in accordance with various embodiments.

FIG. 7A presents an embodiment of a medical scan image analysis system 112. A training set of medical scans used to train one more medical scan image analysis functions can be received from one or more client devices via the network and/or can be retrieved from the medical scan database 342, for example, based on training set data 621 corresponding to medical scan image analysis functions. Training set criteria, for example, identified in training parameters 620 of the medical scan image analysis function, can be utilized to automatically identify and select medical scans to be included in the training set from a plurality of available medical scans. The training set criteria can be automatically generated based on, for example, previously learned criteria, and/or training set criteria can be received via the network, for example, from an administrator of the medical scan image analysis system. The training set criteria can include a minimum training set size. The training set criteria can include data integrity requirements for medical scans in the training set such as requiring that the medical scan is assigned a truth flag 461, requiring that performance score data for a hospital and/or medical professional associated with the medical scan compares favorably to a performance score threshold, requiring that the medical scan has been reviewed by at least a threshold number of medical professionals, requiring that the medical scan and/or a diagnosis corresponding to a patient file of the medical scan is older than a threshold elapsed time period, or based on other criteria intended to insure that the medical scans and associated data in the training set is reliable enough to be considered "truth" data. The training set criteria can include longitudinal requirements such the number of required subsequent medical scans for the patient, multiple required types of additional scans for the patient, and/or other patient file requirements.

The training set criteria can include quota and/or proportion requirements for one or more medical scan classification data. For example, the training set criteria can include meeting quota and/or proportion requirements for one or more scan types and/or human body location of scans, meeting quota or proportion requirements for a number of normal medical scans and a number of medicals scans with identified abnormalities, meeting quota and/or proportion requirements for a number of medical scans with abnormalities in certain locations and/or a number of medical scans with abnormalities that meet certain size, type, or other characteristics, meeting quota and/or proportion data for a number of medical scans with certain diagnosis or certain corresponding medical codes, and/or meeting other identified quota and/or proportion data relating to metadata, patient data, or other data associated with the medical scans.

In some embodiments, multiple training sets are created to generate corresponding medical scan image analysis functions, for example, corresponding to some or all of the set of medical scan inference functions 1105. Some or all training sets can be categorized based on some or all of the scan classifier data 420 as described in conjunction with the medical scan diagnosing system 108, where medical scans are included in a training set based on their scan classifier data 420 matching the scan category of the training set. In some embodiments, the input quality assurance function 1106 or another input check step can be performed on medical scans selected for each training set to confirm that their corresponding scan classifier data 420 is correct. In some embodiments, the input quality assurance function can correspond to its own medical scan image analysis function, trained by the medical scan image analysis system, where the input quality assurance function utilizes high level computer vision technology to determine a scan category 1120 and/or to confirm the scan classifier data 420 already assigned to the medical scan.

In some embodiments, the training set will be used to create a single neural network model, or other model corresponding to model type data 622 and/or model parameter data 623 of the medical scan image analysis function that can be trained on some or all of the medical scan classification data described above and/or other metadata, patient data, or other data associated with the medical scans. In other embodiments, a plurality of training sets will be created to generate a plurality of corresponding neural network models, where the multiple training sets are divided based on some or all of the medical scan classification data described above and/or other metadata, patient data, or other data associated with the medical scans. Each of the plurality of neural network models can be generated based on the same or different learning algorithm that utilizes the same or different features of the medical scans in the corresponding one of the plurality of training sets. The medical scan classifications selected to segregate the medical scans into multiple training sets can be received via the network, for example based on input to an administrator client device from an administrator. The medical scan classifications selected to segregate the medical scans can be automatically determined by the medical scan image analysis system, for example, where an unsupervised clustering algorithm is applied to the original training set to determine appropriate medical scan classifications based on the output of the unsupervised clustering algorithm.

In embodiments where the medical scan image analysis system is used in conjunction with the medical scan diagnosing system, each of the medical scan image analysis functions associated with each neural network model can correspond to one of the plurality of neural network models generated by the medical scan image analysis system. For example, each of the plurality of neural network models can be trained on a training set classified on scan type, scan human body location, hospital or other originating entity data, machine model data, machine calibration data, contrast agent data, geographic region data, and/or other scan classifying data as discussed in conjunction with the medical scan diagnosing system. In embodiments where the training set classifiers are learned, the medical scan diagnosing system can determine which of the medical scan image analysis functions should be applied based on the learned classifying criteria used to segregate the original training set.

A computer vision-based learning algorithm used to create each neural network model can include selecting a three-dimensional subregion 1310 for each medical scan in the training set. This three-dimensional subregion 1310 can correspond to a region that is "sampled" from the entire scan that may represent a small fraction of the entire scan. Recall that a medical scan can include a plurality of ordered cross-sectional image slices. Selecting a three-dimensional subregion 1310 can be accomplished by selecting a proper image slice subset 1320 of the plurality of cross-sectional image slices from each of the plurality of medical scans, and by further selecting a two-dimensional subregion 1330 from each of the selected subset of cross-sectional image slices of the each of the medical scans. In some embodiments, the selected image slices can include one or more non-consecutive image slices and thus a plurality of disconnected three-dimensional subregions will be created. In other embodiments, the selected proper subset of the plurality of image slices correspond to a set of consecutive image slices, as to ensure that a single, connected three-dimensional subregion is selected. In some embodiments, entire scans of the training set are used to train the neural network model. In such embodiment, as used herein, the three-dimensional subregion 1310 can refer to all of the medical scan image data 410 of a medical scan.

In some embodiments, a density windowing step can be applied to the full scan or the selected three-dimensional subregion. The density windowing step can include utilizing a selected upper density value cut off and/or a selected lower density value cut off, and masking pixels with higher values than the upper density value cut off and/or masking pixels with lower values than the lower density value cut off. The upper density value cut off and/or a selected lower density value cut off can be determined based on based on the range and/or distribution of density values included in the region that includes the abnormality, and/or based on the range and/or distribution of density values associated with the abnormality itself, based on user input to a subsystem, based on display parameter data associated with the medical scan or associated with medical scans of the same type, and/or can be learned in the training step. In some embodiments, a non-linear density windowing function can be applied to alter the pixel density values, for example, to stretch or compress contrast. In some embodiments, this density windowing step can be performed as a data augmenting step, to create additional training data for a medical scan in accordance with different density windows.

Having determined the subregion training set 1315 of three-dimensional subregions 1310 corresponding to the set of full medical scans in the training set, the medical scan image analysis system can complete a training step 1352 by performing a learning algorithm on the plurality of three-dimensional subregions to generate model parameter data 1355 of a corresponding learning model. The learning model can include one or more of a neural network, an artificial neural network, a convolutional neural network, a Bayesian model, a support vector machine model, a cluster analysis model, or other supervised or unsupervised learning model. The model parameter data 1355 can generated by performing the learning algorithm 1350, and the model parameter data 1355 can be utilized to determine the corresponding medical scan image analysis functions. For example, some or all of the model parameter data 1355 can be mapped to the medical scan analysis function in the model parameter data 623 or can otherwise define the medical scan analysis function.

The training step 1352 can include creating feature vectors for each three-dimensional subregion of the training set for use by the learning algorithm 1350 to generate the model parameter data 1355. The feature vectors can include the pixel data of the three-dimensional subregions such as density values and/or grayscale values of each pixel based on a determined density window. The feature vectors can also include other features as additional input features or desired output features, such as known abnormality data such as location and/or classification data, patient history data such as risk factor data or previous medical scans, diagnosis data, responsible medical entity data, scan machinery model or calibration data, contrast agent data, medical code data, annotation data that can include raw or processed natural language text data, scan type and/or anatomical region data, or other data associated with the image, such as some or all data of a medical scan entry 352. Features can be selected based on administrator instructions received via the network and/or can be determined based on determining a feature set that reduces error in classifying error, for example, by performing a cross-validation step on multiple models created using different feature sets. The feature vector can be split into an input feature vector and output feature vector. The input feature vector can include data that will be available in subsequent medical scan input, which can include for example, the three-dimensional subregion pixel data and/or patient history data. The output feature vector can include data that will be inferred in in subsequent medical scan input and can include single output value, such as a binary value indicating whether or not the medical scan includes an abnormality or a value corresponding to one of a plurality of medical codes corresponding to the image. The output feature vector can also include multiple values which can include abnormality location and/or classification data, diagnosis data, or other output. The output feature vector can also include a determined upper density value cut off and/or lower density value cut off, for example, characterizing which pixel values were relevant to detecting and/or classifying an abnormality. Features included in the output feature vector can be selected to include features that are known in the training set, but may not be known in subsequent medical scans such as triaged scans to be diagnosed by the medical scan diagnosing system, and/or scans to be labeled by the medical scan report labeling system. The set of features in the input feature vector and output feature vector, as well as the importance of different features where each feature is assigned a corresponding weight, can also be designated in the model parameter data 1355.

Consider a medical scan image analysis function that utilizes a neural network. The neural network can include a plurality of layers, where each layer includes a plurality of neural nodes. Each node in one layer can have a connection to some or all nodes in the next layer, where each connection is defined by a weight value. Thus, the model parameter data 1355 can include a weight vector that includes weight values for every connection in the network. Alternatively or in addition, the model parameter data 1355 can include any vector or set of parameters associated with the neural network model, which can include an upper density value cut off and/or lower density value cut off used to mask some of the pixel data of an incoming image, kernel values, filter parameters, bias parameters, and/or parameters characterizing one or more of a plurality of convolution functions of the neural network model. The medical scan image analysis function can be utilized to produce the output vector as a function of the input feature vector and the model parameter data 1355 that characterizes the neural network model. In particular, the medical scan image analysis function can include performing a forward propagation step plurality of neural network layers to produce an inferred output vector based on the weight vector or other model parameter data 1355. Thus, the learning algorithm 1350 utilized in conjunction with a neural network model can include determining the model parameter data 1355 corresponding to the neural network model, for example, by populating the weight vector with optimal weights that best reduce output error.

In particular, determining the model parameter data 1355 can include utilizing a backpropagation strategy. The forward propagation algorithm can be performed on at least one input feature vector corresponding to at least one medical scan in the training set to propagate the at least one input feature vector through the plurality of neural network layers based on initial and/or default model parameter data 1355, such as an initial weight vector of initial weight values set by an administrator or chosen at random. The at least one output vector generated by performing the forward propagation algorithm on the at least one input feature vector can be compared to the corresponding at least one known output feature vector to determine an output error. Determining the output error can include, for example, computing a vector distance such as the Euclidian distance, or squared Euclidian distance, between the produced output vector and the known output vector, and/or determining an average output error such as an average Euclidian distance or squared Euclidian distance if multiple input feature vectors were employed. Next, gradient descent can be performed to determine an updated weight vector based on the output error or average output error. This gradient descent step can include computing partial derivatives for the error with respect to each weight, or other parameter in the model parameter data 1355, at each layer starting with the output layer. Chain rule can be utilized to iteratively compute the gradient with respect to each weight or parameter at each previous layer until all weight's gradients are computed. Next updated weights, or other parameters in the model parameter data 1355, are generated by updating each weight based on its corresponding calculated gradient. This process can be repeated on at least one input feature vector, which can include the same or different at least one feature vector used in the previous iteration, based on the updated weight vector and/or other updated parameters in the model parameter data 1355 to create a new updated weight vector and/or other new updated parameters in the model parameter data 1355. This process can continue to repeat until the output error converges, the output error is within a certain error threshold, or another criterion is reached to determine the most recently updated weight vector and/or other model parameter data 1355 is optimal or otherwise determined for selection.

Figure 7B:
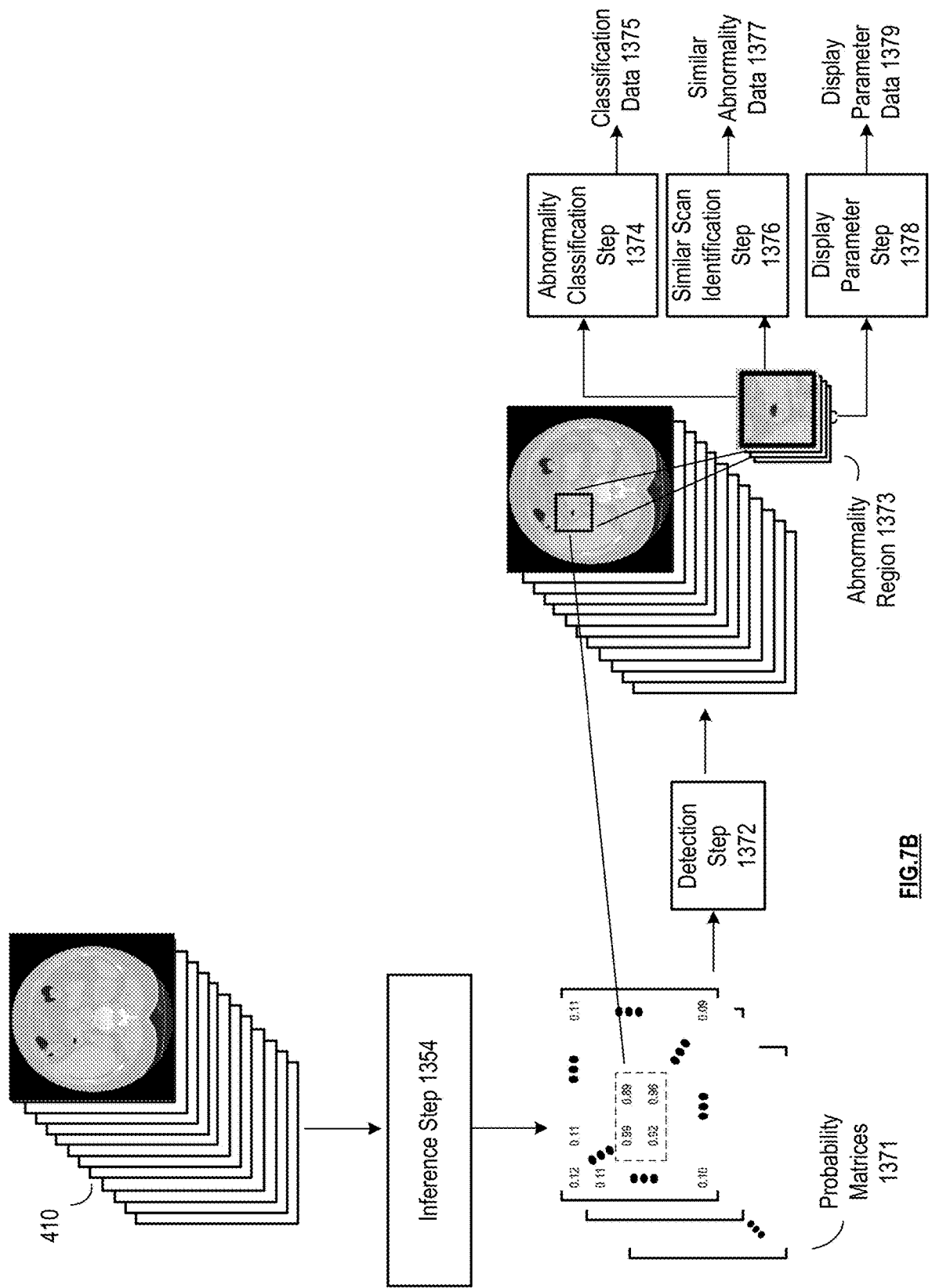
FIG. 7B is a flowchart representation of a detection step in accordance with various embodiments.

Having determined the medical scan neural network and its final other model parameter data 1355, an inference step 1354 can be performed on new medical scans to produce inference data 1370, such as inferred output vectors, as shown in FIG. 7B. The inference step can include performing the forward propagation algorithm to propagate an input feature vector through a plurality of neural network layers based on the final model parameter data 1355, such as the weight values of the final weight vector, to produce the inference data. This inference step 1354 can correspond to performing the medical scan image analysis function, as defined by the final model parameter data 1355, on new medical scans to generate the inference data 1370, for example, in conjunction with the medical scan diagnosing system 108 to generate inferred diagnosis data or other selected output data for triaged medical scans based on its corresponding the input feature vector.

The inference step 1354 can include applying the density windowing step to new medical scans. Density window cut off values and/or a non-linear density windowing function that are learned can be automatically applied when performing the inference step. For example, if the training step 1352 was used to determine optimal upper density value cut off and/or lower density value cut off values to designate an optimal density window, the inference step 1354 can include masking pixels of incoming scans that fall outside of this determined density window before applying the forward propagation algorithm. As another example, if learned parameters of one or more convolutional functions correspond to the optimal upper density value cut off and/or lower density value cut off values, the density windowing step is inherently applied when the forward propagation algorithm is performed on the new medical scans.

In some embodiments where a medical scan analysis function is defined by model parameter data 1355 corresponding to a neutral network model, the neural network model can be a fully convolutional neural network. In such embodiments, only convolution functions are performed to propagate the input feature vector through the layers of the neural network in the forward propagation algorithm. This enables the medical scan image analysis functions to process input feature vectors of any size. For example, as discussed herein, the pixel data corresponding to the three-dimensional subregions is utilized input to the forward propagation algorithm when the training step 1352 is employed to populate the weight vector and/or other model parameter data 1355. However, when performing the forward propagation algorithm in the inference step 1354, the pixel data of full medical scans can be utilized as input, allowing the entire scan to be processed to detect and/or classify abnormalities, or otherwise generate the inference data 1370. This may be a preferred embodiment over other embodiments where new scans must also be sampled by selecting a three-dimensional subregions and/or other embodiments where the inference step requires "piecing together" inference data 1370 corresponding to multiple three-dimensional subregions processed separately.

The inferred output vector of the inference data 1370 can include a plurality of abnormality probabilities mapped to a pixel location of each of a plurality of cross-sectional image slices of the new medical scan. For example, the inferred output vector can indicate a set of probability matrices 1371, where each matrix in the set corresponds to one of the plurality of image slices of the medical scan, where each matrix is a size corresponding to the number of pixels in each image slice, where each cell of each matrix corresponds to a pixel of the corresponding image slice, whose value is the abnormality probability of the corresponding pixel.

A detection step 1372 can include determining if an abnormality is present in the medical scan based on the plurality of abnormality probabilities. Determining if an abnormality is present can include, for example, determining that a cluster of pixels in the same region of the medical scan correspond to high abnormality probabilities, for example, where a threshold proportion of abnormality probabilities must meet or exceed a threshold abnormality probability, where an average abnormality probability of pixels in the region must meet or exceed a threshold abnormality probability, where the region that includes the cluster of pixels must be at least a certain size, etc. Determining if an abnormality is present can also include calculating a confidence score based on the abnormality probabilities and/or other data corresponding to the medical scan such as patient history data. The location of the detected abnormality can be determined in the detection step 1372 based on the location of the pixels with the high abnormality probabilities. The detection step can further include determining an abnormality region 1373, such as a two-dimensional subregion on one or more image slices that includes some or all of the abnormality. The abnormality region 1373 determined in the detection step 1372 can be mapped to the medical scan to populate some or all of the abnormality location data 443 for use by one or more other subsystems 101 and/or client devices 120. Furthermore, determining whether or not an abnormality exists in the detection step 1372 can be used to populate some or all of the diagnosis data 440 of the medical scan, for example, to indicate that the scan is normal or contains an abnormality in the diagnosis data 440.

An abnormality classification step 1374 can be performed on a medical scan in response to determining an abnormality is present. Classification data 1375 corresponding to one or more classification categories such as abnormality size, volume, pre-post contract, doubling time, calcification, components, smoothness, texture, diagnosis data, one or more medical codes, a malignancy rating such as a Lung-RADS score, or other classifying data as described herein can be determined based on the detected abnormality. The classification data 1375 generated by the abnormality classification step 1374 can be mapped to the medical scan to populate some or all of the abnormality classification data 445 of the corresponding abnormality classifier categories 444 and/or abnormality pattern categories 446 and/or to determine one or more medical codes 447 of the medical scan. The abnormality classification step 1374 can include performing an abnormality classification function on the full medical scan, or the abnormality region 1373 determined in the detection step 1372. The abnormality classification function can be based on another model trained on abnormality data such as a support vector machine model, another neural network model, or any supervised classification model trained on medical scans, or portions of medical scans, that include known abnormality classifying data to generate inference data for some or all of the classification categories. For example, the abnormality classification function can include another medical scan analysis function. Classification data 1375 in each of a plurality of classification categories can also be assigned their own calculated confidence score, which can also be generated by utilizing the abnormality classification function. Output to the abnormality classification function can also include at least one identified similar medical scan and/or at least one identified similar cropped image, for example, based on the training data. The abnormality classification step can also be included in the inference step 1354, where the inferred output vector or other inference data 1370 of the medical scan image analysis function includes the classification data 1375.

The abnormality classification function can be trained on full medical scans and/or one or more cropped or full selected image slices from medical scans that contain an abnormality. For example, the abnormality classification function can be trained on a set of two-dimensional cropped slices that include abnormalities. The selected image slices and/or the cropped region in each selected image slice for each scan in the training set can be automatically selected based upon the known location of the abnormality. Input to the abnormality classification function can include the full medical scan, one or more selected full image slices, and/or one or more selected image slices cropped based on a selected region. Thus, the abnormality classification step can include automatically selecting one or more image slices that include the detected abnormality. The slice selection can include selecting the center slice in a set of consecutive slices that are determined to include the abnormality or selecting a slice that has the largest cross-section of the abnormality, or selecting one or more slices based on other criteria. The abnormality classification step can also include automatically generating one or more cropped two-dimensional images corresponding to the one or more of the selected image slices based on an automatically selected region that includes the abnormality.

Input to the abnormality classification function can also include other data associated with the medical scan, including patient history, risk factors, or other metadata. The abnormality classification step can also include determining some or all of the characteristics based on data of the medical scan itself. For example, the abnormality size and volume can be determined based on a number of pixels determined to be part of the detected abnormality. Other classifiers such as abnormality texture and/or smoothness can be determined by performing one or more other preprocessing functions on the image specifically designed to characterize such features. Such preprocessed characteristics can be included in the input to the abnormality classification function to the more difficult task of assigning a medical code or generating other diagnosis data. The training data can also be preprocessed to include such preprocessed features.

A similar scan identification step 1376 can also be performed on a medical scan with a detected abnormality and/or can be performed on the abnormality region 1373 determined in the detection step 1372. The similar scan identification step 1376 can include generating similar abnormality data 1377, for example, by identifying one or more similar medical scans or one or more similar cropped two-dimensional images from a database of medical scans and/or database of cropped two-dimensional images. Similar medical scans and/or cropped images can include medical scans or cropped images that are visually similar, medical scans or cropped images that have known abnormalities in a similar location to an inferred abnormality location of the given medical scan, medical scans that have known abnormalities with similar characteristics to inferred characteristics of an abnormality in the given scan, medical scans with similar patient history and/or similar risk factors, or some combination of these factors and/or other known and/or inferred factors. The similar abnormality data 1377 can be mapped to the medical scan to populate some or all of its corresponding similar scan data 480 for use by one or more other subsystems 101 and/or client devices 120.

The similar scans identification step 1376 can include performing a scan similarity algorithm, which can include generating a feature vector for the given medical scan and for medical scans in the set of medical scans, where the feature vector can be generated based on quantitative and/or category based visual features, inferred features, abnormality location and/or characteristics such as the predetermined size and/or volume, patient history and/or risk factor features, or other known or inferred features. A medical scan similarity analysis function can be applied to the feature vector of the given medical scan and one or more feature vectors of medical scans in the set. The medical scan similarity analysis function can include computing a similarity distance such as the Euclidian distance between the feature vectors, and assigning the similarity distance to the corresponding medical scan in the set. Similar medical scans can be identified based on determining one or more medical scans in the set with a smallest computed similarity distance, based on ranking medical scans in the set based on the computed similarity distances and identifying a designated number of top ranked medical scans, and/or based on determining if a similarity distance between the given medical scan and a medical scan in the set is smaller than a similarity threshold. Similar medical scans can also be identified based on determining medical scans in a database that mapped to a medical code that matches the medical code of the medical scan, or mapped to other matching classifying data. A set of identified similar medical scans can also be filtered based on other inputted or automatically generated criteria, where for example only medical scans with reliable diagnosis data or rich patient reports, medical scans with corresponding with longitudinal data in the patient file such as multiple subsequent scans taken at later dates, medical scans with patient data that corresponds to risk factors of the given patient, or other identified criteria, where only a subset of scans that compare favorably to the criteria are selected from the set and/or only a highest ranked single scan or subset of scans are selected from the set, where the ranking is automatically computed based on the criteria. Filtering the similar scans in this fashion can include calculating, or can be based on previously calculated, one or more scores as discussed herein. For example, the ranking can be based on a longitudinal quality score, such as the longitudinal quality score 434, which can be calculated for an identified medical scan based on a number of subsequent and/or previous scans for the patient. Alternatively or in addition, the ranking can be based on a confidence score associated with diagnosis data of the scan, such as confidence score data 460, based on performance score data associated with a user or medical entity associated with the scan, based on an amount of patient history data or data in the medical scan entry 352, or other quality factors. The identified similar medical scans can be filtered based on ranking the scans based on their quality score and/or based on comparing their quality score to a quality score threshold. In some embodiments, a longitudinal threshold must be reached, and only scans that compare favorably to the longitudinal threshold will be selected. For example, only scans with at least three scans on file for the patient and final biopsy data will be included.

In some embodiments, the similarity algorithm can be utilized in addition to or instead of the trained abnormality classification function to determine some or all of the inferred classification data 1375 of the medical scan, based on the classification data such as abnormality classification data 445 or other diagnosis data 440 mapped to one or more of the identified similar scans. In other embodiments, the similarity algorithm is merely used to identify similar scans for review by medical professionals to aid in review, diagnosis, and/or generating medical reports for the medical image.

A display parameter step 1378 can be performed based on the detection and/or classification of the abnormality. The display parameter step can include generating display parameter data 1379, which can include parameters that can be used by an interactive interface to best display each abnormality. The same or different display parameters can be generated for each abnormality. The display parameter data generated in the display parameter step 1378 can be mapped to the medical scan to populate some or all of its corresponding display parameter data 470 for use by one or more other subsystems 101 and/or client devices 120.

Performing the display parameter step 1378 can include selecting one or more image slices that include the abnormality by determining the one or more image slices that include the abnormality and/or determining one or more image slices that has a most optimal two-dimensional view of the abnormality, for example by selecting the center slice in a set of consecutive slices that are determined to include the abnormality, selecting a slice that has the largest cross-section of the abnormality, selecting a slice that includes a two-dimensional image of the abnormality that is most similar to a selected most similar two-dimensional-image, selecting the slice that was used as input to the abnormality classification step and/or similar scan identification step, or based on other criteria. This can also include automatically cropping one or more selected image slices based on an identified region that includes the abnormality. This can also select an ideal Hounsfield window that best displays the abnormality. This can also include selecting other display parameters based on data generated by the medical scan interface evaluating system and based on the medical scan.

FIGS. 8A-8F illustrate embodiments of a medical picture archive integration system 2600. The medical picture archive integration system 2600 can provide integration support for a medical picture archive system 2620, such as a PACS that stores medical scans. The medical picture archive integration system 2600 can utilize model parameters received from a central server system 2640 via a network 2630 to perform an inference function on de-identified medical scans of medical scans received from the medical picture archive system 2620. The annotation data produced by performing the inference function can be transmitted back to the medical picture archive system. Furthermore, the annotation data and/or de-identified medical scans can be sent to the central server system 2640, and the central server system can train on this information to produce new and/or updated model parameters for transmission back to the medical picture archive integration system 2600 for use on subsequently received medical scans.

In various embodiments, medical picture archive integration system 2600 includes a de-identification system that includes a first memory designated for protected health information (PHI), operable to perform a de-identification function on a DICOM image, received from a medical picture archive system, to identify at least one patient identifier and generate a de-identified medical scan that does not include the at least one patient identifier. The medical picture archive integration system further includes a de-identified image storage system that stores the de-identified medical scan in a second memory that is separate from the first memory, and an annotating system, operable to utilize model parameters received from a central server to perform an inference function on the de-identified medical scan, retrieved from the second memory to generate annotation data for transmission to the medical picture archive system as an annotated DICOM file.

The first memory and the second memory can be implemented by utilizing separate storage systems: the first memory can be implemented by a first storage system designated for PHI storage, and the second memory can be implemented by a second storage system designated for storage of de-identified data. The first storage system can be protected from access by the annotating system, while the second storage system can be accessible by the annotating system. The medical picture archive integration system 2600 can be operable to perform the de-identification function on data in first storage system to generate de-identified data. The de-identified data can then be stored in the second storage system for access by the annotating system. The first and second storage systems can be physically separate, each utilizing at least one of their own, separate memory devices. Alternatively, the first and second storage systems can be virtually separate, where data is stored in separate virtual memory locations on the same set of memory devices. Firewalls, virtual machines, and/or other protected containerization can be utilized to enforce the separation of data in each storage system, to protect the first storage system from access by the annotating system and/or from other unauthorized access, and/or to ensure that only data of the first storage system that has been properly de-identified through application of the de-identification function can be stored in the second storage system.

Figure 8A:
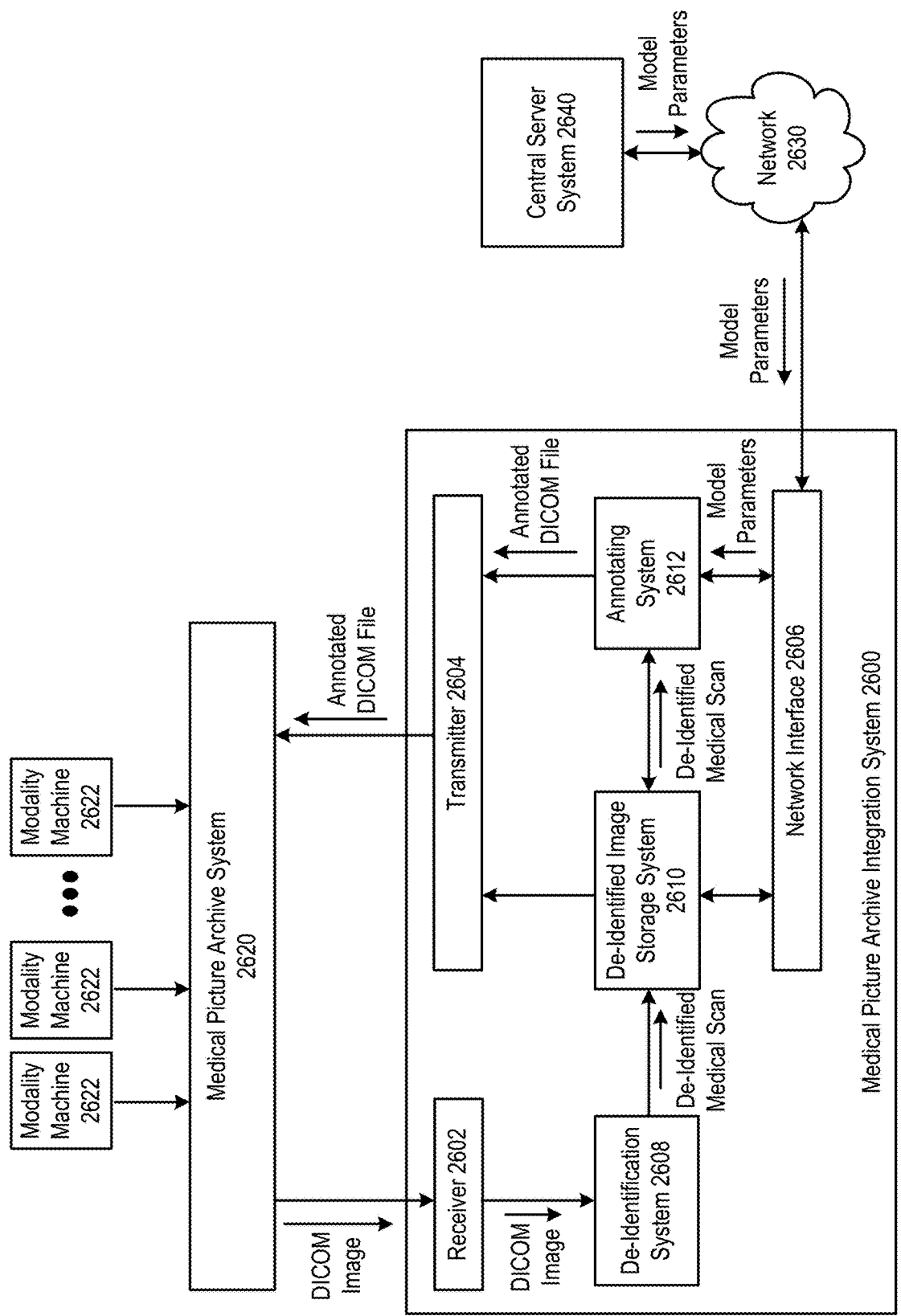
FIGS. 8A-8F are schematic block diagrams of a medical picture archive integration system in accordance with various embodiments.

As shown in FIG. 8A, the medical picture archive system 2620 can receive image data from a plurality of modality machines 2622, such as CT machines, Mill machines, x-ray machines, and/or other medical imaging machines that produce medical scans. The medical picture archive system 2620 can store this image data in a DICOM image format and/or can store the image data in a plurality of medical scan entries 352 as described in conjunction with some or all of the attributes described in conjunction with FIGS. 4A and 4B. While "DICOM image" will be used herein to refer to medical scans stored by the medical picture archive system 2620, the medical picture archive integration system 2600 can provide integration support for medical picture archive systems 2620 that store medical scans in other formats.

The medical picture archive integration system 2600 can include a receiver 2602 and a transmitter 2604, operable to transmit and receive data from the medical picture archive system 2620, respectively. For example, the receiver 2602 and transmitter 2604 can be configured to receive and transmit data, respectively, in accordance with a DICOM communication protocol and/or another communication protocol recognized by the medical image archive system 2620. The receiver can receive DICOM images from the medical picture archive system 2620. The transmitter 2604 can send annotated DICOM files to the medical picture archive system 2620.

DICOM images received via receiver 2602 can be sent directly to a de-identification system 2608. The de-identification system 2608 can be operable to perform a de-identification function on the first DICOM image to identify at least one patient identifier in the DICOM image, and to generate a de-identified medical scan that does not include the identified at least one patient identifier. As used herein, a patient identifier can include any patient identifying data in the image data, header, and/or metadata of a medical scan, such as a patient ID number or other unique patient identifier, an accession number, a service-object pair (SOP) instance unique identifier (UID) field, scan date and/or time that can be used to determine the identity of the patient that was scanned at that date and/or time, and/or other private data corresponding to the patient, doctor, or hospital. In some embodiments, the de-identified medical scan is still in a DICOM image format. For example, a duplicate DICOM image that does not include the patient identifiers can be generated, and/or the original DICOM image can be altered such that the patient identifiers of the new DICOM image are masked, obfuscated, removed, replaced with a custom fiducial, and/or otherwise anonymized. In other embodiments, the de-identified medical scan is formatted in accordance with a different image format and/or different data format that does not include the identifying information. In some embodiments, other private information, for example, associated with a particular doctor or other medical professional, can be identified and anonymized as well.

Some patient identifying information can be included in a DICOM header of the DICOM image, for example, in designated fields for patient identifiers. These corresponding fields can be anonymized within the corresponding DICOM header field. Other patient identifying information can be included in the image itself, such as in medical scan image data 410. For example, the image data can include a patient name or other identifier that was handwritten on a hard copy of the image before the image was digitized. As another example, a hospital administered armband or other visual patient information in the vicinity of the patient may have been captured in the image itself. A computer vision model can detect the presence of these identifiers for anonymization, for example, where a new DICOM image includes a fiducial image that covers the identifying portion of the original DICOM image. In some embodiments, patient information identified in the DICOM header can be utilized to detect corresponding patient information in the image itself. For example, a patient name extracted from the DICOM header before anonymization can be used to search for the patient name in the image and/or to detect a location of the image that includes the patient name. In some embodiments, the de-identification system 2608 is implemented by the de-identification system discussed in conjunction with FIGS. 10A, 10B and 11, and/or utilizes functions and/or operations discussed in conjunction with FIGS. 10A, 10B and 11.

The de-identified medical scan can be stored in de-identified image storage system 2610 and the annotating system 2612 can access the de-identified medical scan from the de-identified image storage system 2610 for processing. The de-identified storage system can archive a plurality of de-identified DICOM images and/or can serve as temporary storage for the de-identified medical scan until processing of the de-identified medical scan by the annotating system 2612 is complete. The annotating system 2612 can generate annotation data by performing an inference function on the de-identified medical scan, utilizing the model parameters received from the central server system 2640. The annotation data can correspond to some or all of the diagnosis data 440 as discussed in conjunction with FIGS. 4A and 4B. In come embodiments, the annotating system 2612 can utilize the model parameters to perform inference step 1354, the detection step 1372, the abnormality classification step 1374, the similar scan identification step 1376, and/or the display parameter step 1378 of the medical scan image analysis system 112, as discussed in conjunction with FIG. 7B, on de-identified medical scans received from the medical picture archive system 2620.

In some embodiments, model parameters for a plurality of inference functions can be received from the central server system 2640, for example, where each inference function corresponds to one of a set of different scan categories. Each scan category can correspond to a unique combination of one or a plurality of scan modalities, one of a plurality of anatomical regions, and/or other scan classifier data 420. For example, a first inference function can be trained on and intended for de-identified medical scans corresponding chest CT scans, and a second inference function can be trained on and intended for de-identified medical scans corresponding to head MRI scans. The annotating system can select one of the set of inference functions based on determining the scan category of the DICOM image, indicated in the de-identified medical scan, and selecting the inference function that corresponds to the determined scan category.

To ensure that scans received from the medical picture archive system 2620 match the set of scan categories for which the annotating system is operable to perform a corresponding inference function, the transmitter can transmit requests, such as DICOM queries, indicating image type parameters such as parameters corresponding to scan classifier data 420, for example indicating one or more scan modalities, one or more anatomical regions, and/or other parameters. For example, the request can indicate that all incoming scans that match the set of scan categories corresponding to a set of inference functions the annotating system 2612 for which the annotating system has obtained model parameters from the central server system 2640 and is operable to perform.

Once the annotation data is generated by performing the selected inference function, the annotating system 2612 can generate an annotated DICOM file for transmission to the medical image archive system 2620 for storage. The annotated DICOM file can include some or all of the fields of the diagnosis data 440 and/or abnormality annotation data 442 of FIGS. 4A and 4B. The annotated DICOM file can include scan overlay data, providing location data of an identified abnormality and/or display data that can be used in conjunction with the original DICOM image to indicate the abnormality visually in the DICOM image and/or to otherwise visually present the annotation data, for example, for use with the medical scan assisted review system 102. For example, a DICOM presentation state file can be generated to indicate the location of an abnormality identified in the de-identified medical scan. The DICOM presentation state file can include an identifier of the original DICOM image, for example, in metadata of the DICOM presentation state file, to link the annotation data to the original DICOM image. In other embodiments, a full, duplicate DICOM image is generated that includes the annotation data with an identifier linking this duplicate annotated DICOM image to the original DICOM image.

The identifier linking the annotated DICOM file to the original DICOM image can be extracted from the original DICOM file by the de-identification system 2608, thus enabling the medical picture archive system 2620 to link the annotated DICOM file to the original DICOM image in its storage. For example, the de-identified medical scan can include an identifier that links the de-identified medical scan to the original DICOM file, but does not link the de-identified medical scan to a patient identifier or other private data.

In some embodiments, generating the annotated DICOM file includes altering one or more fields of the original DICOM header. For example, standardized header formatting function parameters can be received from the central server system and can be utilized by the annotating system to alter the original DICOM header to match a standardized DICOM header format. The standardized header formatting function can be trained in a similar fashion to other medical scan analysis functions discussed herein and/or can be characterized by some or all fields of a medical scan analysis function entry 356. The annotating system can perform the standardized header formatting function on a de-identified medical scan to generate a new, standardized DICOM header for the medical scan to be sent back to the medical picture archive system 2620 in the annotated DICOM file and/or to replace the header of the original DICOM file. The standardized header formatting function can be run in addition to other inference functions utilized to generate annotation data. In other embodiments, the medical picture archive integration system 2600 is implemented primarily for header standardization for medical scans stored by the medical picture archive system 2620. In such embodiments, only the standardized header formatting function is performed on the de-identified data to generate a modified DICOM header for the original DICOM image, but the de-identified medical scan is not annotated.

In some embodiments of header standardization, the annotation system can store a set of acceptable, standardized entries for some or all of the DICOM header fields, and can select one of the set of acceptable, standardized entries in populating one or more fields of the new DICOM header for the annotated DICOM file. For example, each of the set of scan categories determined by the annotating system can correspond to a standardized entry of one or more fields of the DICOM header. The new DICOM header can thus be populated based on the determined scan category.

In some embodiments, each of the set of standardized entries can be mapped to a set of related, non-standardized entries, such as entries in a different order, commonly misspelled entries, or other similar entries that do not follow a standardized format. For example, one of the set of acceptable, standardized entries for a field corresponding to a scan category can include "Chest CT", which can be mapped to a set of similar, non-standardized entries which can include "CT chest", "computerized topography CT", and/or other entries that are not standardized. In such embodiments, the annotating system can determine the original DICOM header is one of the similar non-standardized entries, and can select the mapped, standardized entry as the entry for the modified DICOM header. In other embodiments, the image data itself and/or or other header data can be utilized by the annotation system to determine a standardized field. For example, an input quality assurance function 1106 can be trained by the central server system and sent to the annotating system to determine one or more appropriate scan classifier fields, or one or more other DICOM header fields, based on the image data or other data of the de-identified medical scan. One or more standardized labels can be assigned to corresponding fields of the modified DICOM header based on the one or more fields determined by the input quality assurance function.

In some embodiments, the DICOM header is modified based on the annotation data generated in performing the inference function. In particular, a DICOM priority header field can be generated and/or modified automatically based on the severity and/or time-sensitivity of the abnormalities detected in performing the inference function. For example, a DICOM priority header field can be changed from a low priority to a high priority in response to annotation data indicating a brain bleed in the de-identified medical scan of a DICOM image corresponding to a head CT scan, and a new DICOM header that includes the high priority DICOM priority header field can be sent back to the medical picture archive system 2620 to replace or otherwise be mapped to the original DICOM image of the head CT scan.

In various embodiments, the medical picture archive system 2620 is disconnected from network 2630, for example, to comply with requirements regarding Protected Health Information (PHI), such as patient identifiers and other private patient information included in the DICOM images and/or otherwise stored by the medical picture archive system 2620. The medical picture archive integration system 2600 can enable processing of DICOM images while still protecting private patient information by first de-identifying DICOM data by utilizing de-identification system 2608. The de-identification system 2608 can utilize designated processors and memory of the medical picture archive integration system, for example, designated for PHI. The de-identification system 2608 can be decoupled from the network 2630 to prevent the DICOM images that still include patient identifiers from being accessed via the network 2630. For example, as shown in FIG. 8A, the de-identification system 2608 is not connected to network interface 2606. Furthermore, only the de-identification system 2608 has access to the original DICOM files received from the medical picture archive system 2620 via receiver 2602. The de-identified image storage system 2610 and annotating system 2612, as they are connected to network 2630 via network interface 2606, only store and have access to the de-identified medical scan produced by the de-identification system 2608.

Figure 8B:
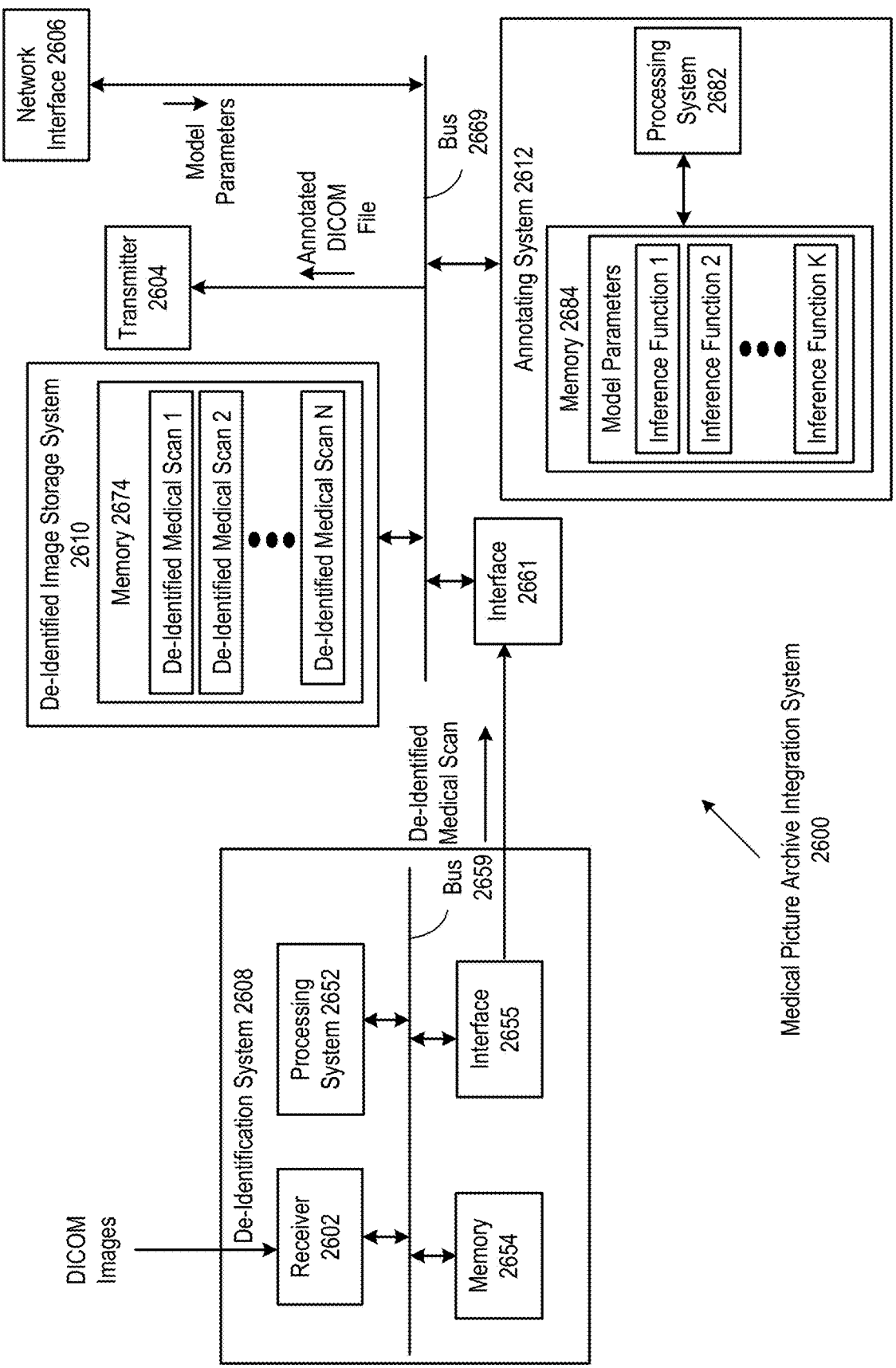

This containerization that separates the de-identification system 2608 from the de-identified image storage system 2610 and the annotating system 2612 is further illustrated in FIG. 8B, which presents an embodiment of the medical picture archive integration system 2600. The de-identification system 2608 can include its own designated memory 2654 and processing system 2652, connected to receiver 2602 via bus 2659. For example, this memory 2654 and processing system 2652 can be designated for PHI, and can adhere to requirements for handling PHI. The memory 2654 can store executable instructions that, when executed by the processing system 2652, enable the de-identification system to perform the de-identification function on DICOM images received via receiver 2602 of the de-identification system. The incoming DICOM images can be temporarily stored in memory 2654 for processing, and patient identifiers detected in performing the de-identification function can be temporarily stored in memory 2654 to undergo anonymization. Interface 2655 can transmit the de-identified medical scan to interface 2661 for use by the de-identified image storage system 2610 and the annotating system 2612. Interface 2655 can be protected from transmitting original DICOM files and can be designated for transmission of de-identified medical scan only.

Bus 2669 connects interface 2661, as well as transmitter 2604 and network interface 2606, to the de-identified image storage system 2610 and the annotating system 2612. The de-identified image storage system 2610 and annotating system 2612 can utilize separate processors and memory, or can utilize shared processors and/or memory. For example, the de-identified image storage system 2610 can serve as temporary memory of the annotating system 2612 as de-identified images are received and processed to generate annotation data.

As depicted in FIG. 8B, the de-identified image storage system 2610 can include memory 2674 that can temporarily store incoming de-identified medical scans as it undergoes processing by the annotating system 2612 and/or can archive a plurality of de-identified medical scans corresponding to a plurality of DICOM images received by the medical picture archive integration system 2600. The annotating system 2612 can include a memory 2684 that stores executable instructions that, when executed by processing system 2682, cause the annotating system 2612 perform a first inference function on de-identified medical scan to generate annotation data by utilizing the model parameters received via interface 2606, and to generate an annotated DICOM file based on the annotation data for transmission via transmitter 2604. The model parameters can be stored in memory 2684, and can include model parameters for a plurality of inference functions, for example, corresponding to a set of different scan categories.

The medical picture archive integration system can be an onsite system, installed at a first geographic site, such as a hospital or other medical entity that is affiliated with the medical picture archive system 2620. The hospital or other medical entity can further be responsible for the PHI of the de-identification system, for example, where the memory 2654 and processing system 2652 are owned by, maintained by, and/or otherwise affiliated with the hospital or other medical entity. The central server system 2640 can be located at a second, separate geographic site that is not affiliated with the hospital or other medical entity and/or at a separate geographic site that is not affiliated with the medical picture archive system 2620. The central server system 2640 can be a server configured to be outside the network firewall and/or out outside the physical security of the hospital or other medical entity or otherwise not covered by the particular administrative, physical and technical safeguards of the hospital or other medical entity.

Figure 8C:
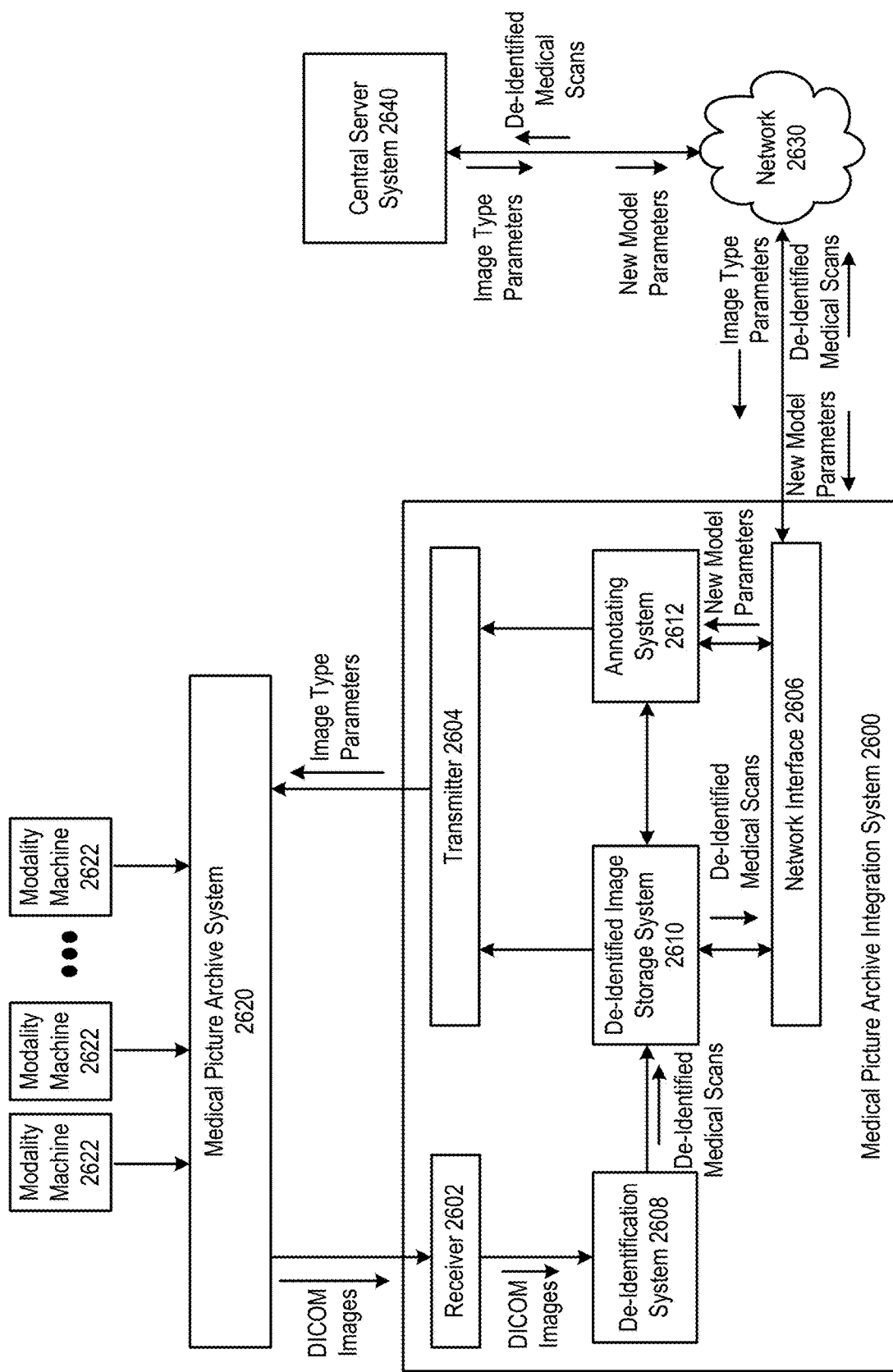

FIG. 8C further illustrates how model parameters can be updated over time to improve existing inference functions and/or to add new inference functions, for example corresponding to new scan categories. In particular, the some or all of the de-identified medical scans generated by the de-identification system 2608 can be transmitted back to the central server system, and the central server system 2640 can train on this data to improve existing models by producing updated model parameters of an existing inference function and/or to generate new models, for example, corresponding to new scan categories, by producing new model parameters for new inference functions. For example, the central server system 2640 can produce updated and/or new model parameters by performing the training step 1352 of the medical scan image analysis system 112, as discussed in conjunction with FIG. 7A, on a plurality of de-identified medical scans received from the medical picture archive integration system 2600.

The image type parameters can be determined by the central server system to dictate characteristics of the set of de-identified medical scans to be received to train and/or retrain the model. For example, the image type parameters can correspond to one or more scan categories, can indicate scan classifier data 420, can indicate one or more scan modalities, one or more anatomical regions, a date range, and/or other parameters. The image type parameters can be determined by the central server system based on training parameters 620 determined for the corresponding inference function to be trained, and/or based on characteristics of a new and/or existing scan category corresponding to the inference function to be trained. The image type parameters can be sent to the medical picture archive integration system 2600, and a request such as a DICOM query can be sent to the medical picture archive system 2620, via transmitter 2604, that indicates the image type parameters. For example, the processing system 2682 can be utilized to generate the DICOM query based on the image type parameters received from the central server system 2640. The medical picture archive system can automatically transmit one or more DICOM images to the medical picture archive integration system in response to determining that the one or more DICOM images compares favorably to the image type parameters. The DICOM images received in response can be de-identified by the de-identification system 2608. In some embodiments, the de-identified medical scans can be transmitted directly to the central server system 2640, for example, without generating annotation data.

The central server system can generate the new and/or updated model parameters by training on the received set of de-identified medical scans, and can transmit the new and/or updated model parameters to the de-identified storage system. If the model parameters correspond to a new inference function for a new scan category, the medical picture archive integration system 2600 can generate a request, such as a DICOM query, for transmission to the medical picture archive system indicating that incoming scans corresponding to image type parameters corresponding to the new scan category be sent to the medical picture archive integration system. The annotating system can update the set of inference functions to include the new inference function, and the annotating system can select the new inference function from the set of inference functions for subsequently generated de-identified medical scans by the de-identification system by determining each of these de-identified medical scans indicate the corresponding DICOM image corresponds to the new scan category. The new model parameters can be utilized to perform the new inference function on each of these de-identified medical scans to generate corresponding annotation data, and an annotated DICOM file corresponding to each of these de-identified medical scans can be generated for transmission to the medical picture archive system via the transmitter.

In some embodiments, the central server system 2640 receives a plurality of de-identified medical scans from a plurality of medical picture archive integration system 2600, for example, each installed at a plurality of different hospitals or other medical entities, via the network 2630. The central server system can generate training sets by integrating de-identified medical scans from some or all of the plurality of medical picture archive integration systems 2600 to train one or more inference functions and generate model parameters. The plurality of medical picture archive integration systems 2600 can utilize the same set of inference functions or different sets of inference functions. In some embodiments, the set of inference functions utilized by the each of the plurality of medical picture archive systems 2620 are trained on different sets of training data. For example, the different sets of training data can correspond to the set of de-identified medical scans received from the corresponding medical picture archive integration system 2600.

In some embodiments, the medical scan diagnosing system 108 can be utilized to implement the annotating system 2612, where the corresponding subsystem processing device 235 and subsystem memory device 245 of the medical scan diagnosing system 108 are utilized to implement the processing system 2682 and the memory 2684, respectively. Rather than receiving the medical scans via the network 150 as discussed in conjunction with FIG. 6A, the medical scan diagnosing system 108 can perform a selected medical scan inference function 1105 on an incoming de-identified medical scan generated by the de-identification system 2608 and/or retrieved from the de-identified image storage system 2610. Memory 2684 can store the set of medical scan inference functions 1105, each corresponding to a scan category 1120, where the inference function is selected from the set based on determining the scan category of the de-identified medical scan and selecting the corresponding inference function. The processing system 2682 can perform the selected inference function 1105 to generate the inference data 1110, which can be further utilized by the annotating system 2612 to generate the annotated DICOM file for transmission back to the medical picture archive system 2620. New medical scan inference functions 1105 can be added to the set when corresponding model parameters are received from the central server system. The remediation step 1140 can be performed locally by the annotating system 2612 and/or can be performed by the central server system 2640 by utilizing one or more de-identified medical scans and corresponding annotation data sent to the central server system 2640. Updated model parameters can be generated by the central server system 2640 and sent to the medical picture archive integration system 2600 as a result of performing the remediation step 1140.

The central server system 2640 can be implemented by utilizing one or more of the medical scan subsystems 101, such as the medical scan image analysis system 112 and/or the medical scan diagnosing system 108, to produce model parameters for one or more inference functions. The central server system can store or otherwise communicate with a medical scan database 342 that includes the de-identified medical scans and/or annotation data received from one or more medical picture archive integration systems 2600. Some or all entries of the medical scan database 342 can be utilized to as training data to produce model parameters for one or more inference functions. These entries of the medical scan database 342 can be utilized by other subsystems 101 as discussed herein. For example, other subsystems 101 can utilize the central server system 2640 to fetch medical scans and/or corresponding annotation data that meet specified criteria. The central server system 2640 can query the medical picture archive integration system 2600 based on this criteria, and can receive de-identified medical scans and/or annotation data in response. This can be sent to the requesting subsystem 101 directly and/or can be added to the medical scan database 342 or another database of the database storage system 140 for access by the requesting subsystem 101.

Alternatively or in addition, the central server system 2640 can store or otherwise communicate with a user database 344 storing user profile entries corresponding to each of a plurality of medical entities that each utilize a corresponding one of a plurality of medical picture archive integration systems 2600. For example, basic user data corresponding to the medical entity can be stored as basic user data, a number of scans or other consumption information indicating usage of one or more inference functions by corresponding medical picture archive integration system can be stored as consumption usage data, and/or a number of scans or other contribution information indicating de-identified scans sent to the central server system as training data can be stored as contribution usage data. The user profile entry can also include inference function data, for example, with a list of model parameters or function identifiers, such as medical scan analysis function identifiers 357, of inference functions currently utilized by the corresponding medical picture archive integration system 2600. These entries of the user database 344 can be utilized by other subsystems 101 as discussed herein.

Alternatively or in addition, the central server system 2640 can store or otherwise communicate with a medical scan analysis function database 346 to store model parameters, training data, or other information for one or more inference functions as medical scan analysis function entries 356. In some embodiments, model parameter data 623 can indicate the model parameters and function classifier data 610 can indicate the scan category of inference function entries. In some embodiments, the medical scan analysis function entry 356 can further include usage identifying information indicating a medical picture archive integration system identifier, medical entity identifier, and/or otherwise indicating which medical archive integration systems and/or medical entities have received the corresponding model parameters to utilize the inference function corresponding to the medical scan analysis function entry 356. These entries of the medical scan analysis function database 346 can be utilized by other subsystems 101 as discussed herein.

In some embodiments, the de-identification function is a medical scan analysis function, for example, with a corresponding medical scan analysis function entry 356 in the medical scan analysis function database 346. In some embodiments, the de-identification function is trained by the central server system 2640. For example, the central server system 2640 can send de-identification function parameters to the medical picture archive integration system 2600 for use by the de-identification system 2608. In embodiments with a plurality of medical picture archive integration systems 2600, each of the plurality of medical picture archive integration systems 2600 can utilize the same or different de-identification functions. In some embodiments, the de-identification function utilized by the each of the plurality of medical picture archive integration systems 2600 are trained on different sets of training data. For example, the different sets of training data can correspond to each different set of de-identified medical scans received from each corresponding medical picture archive integration system 2600.

Figure 8D:
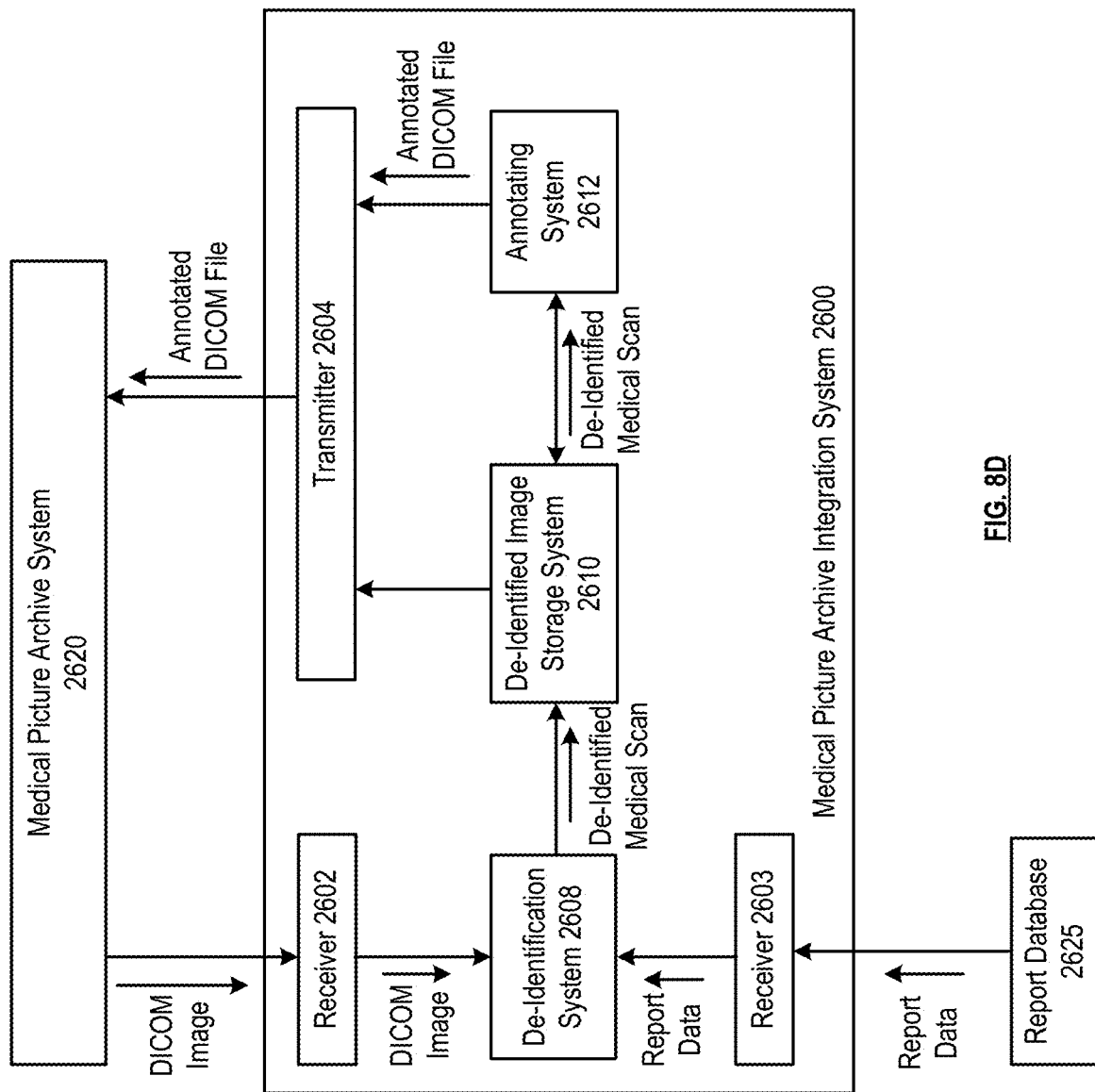
Figure 8E:
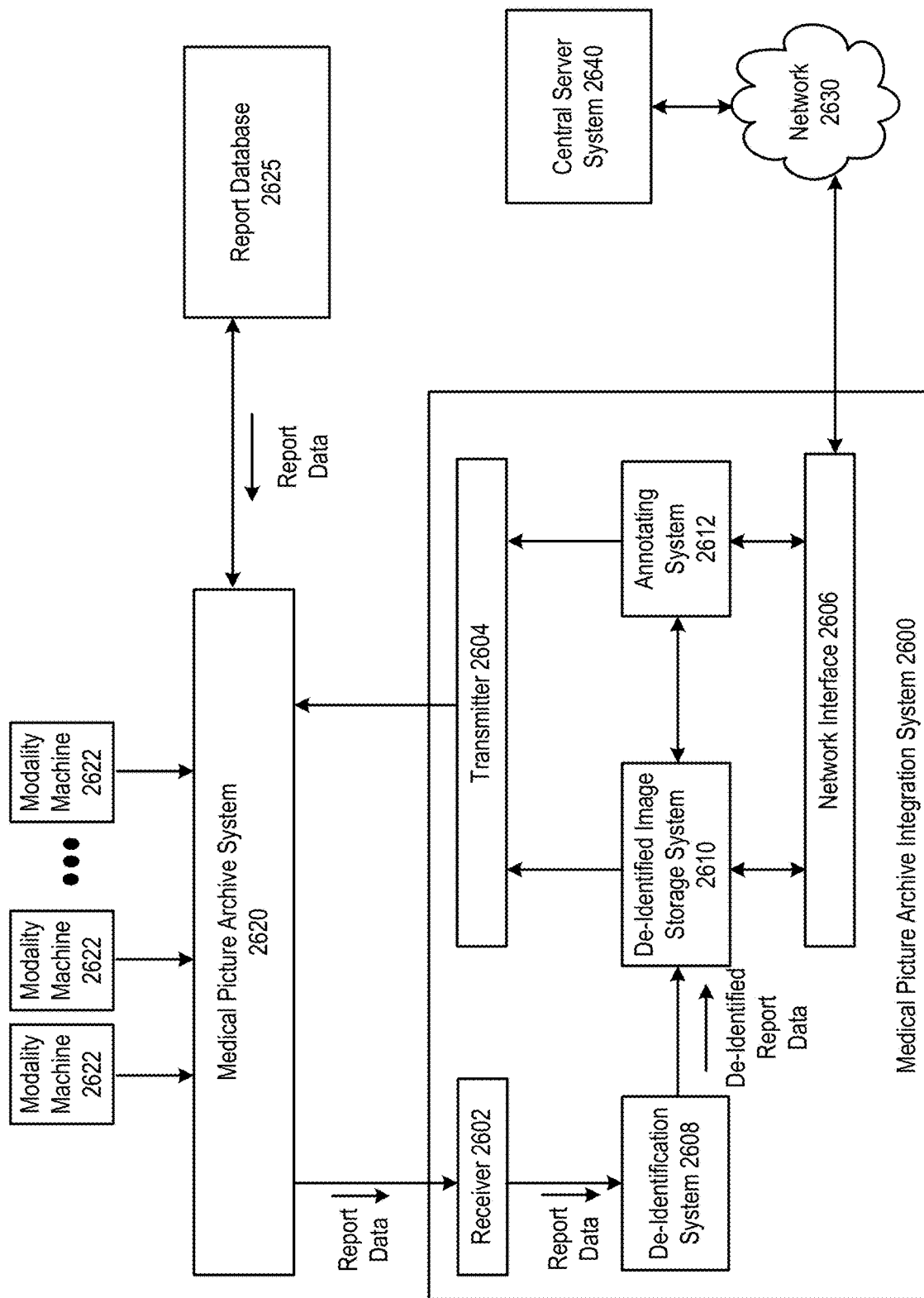
Figure 8F:
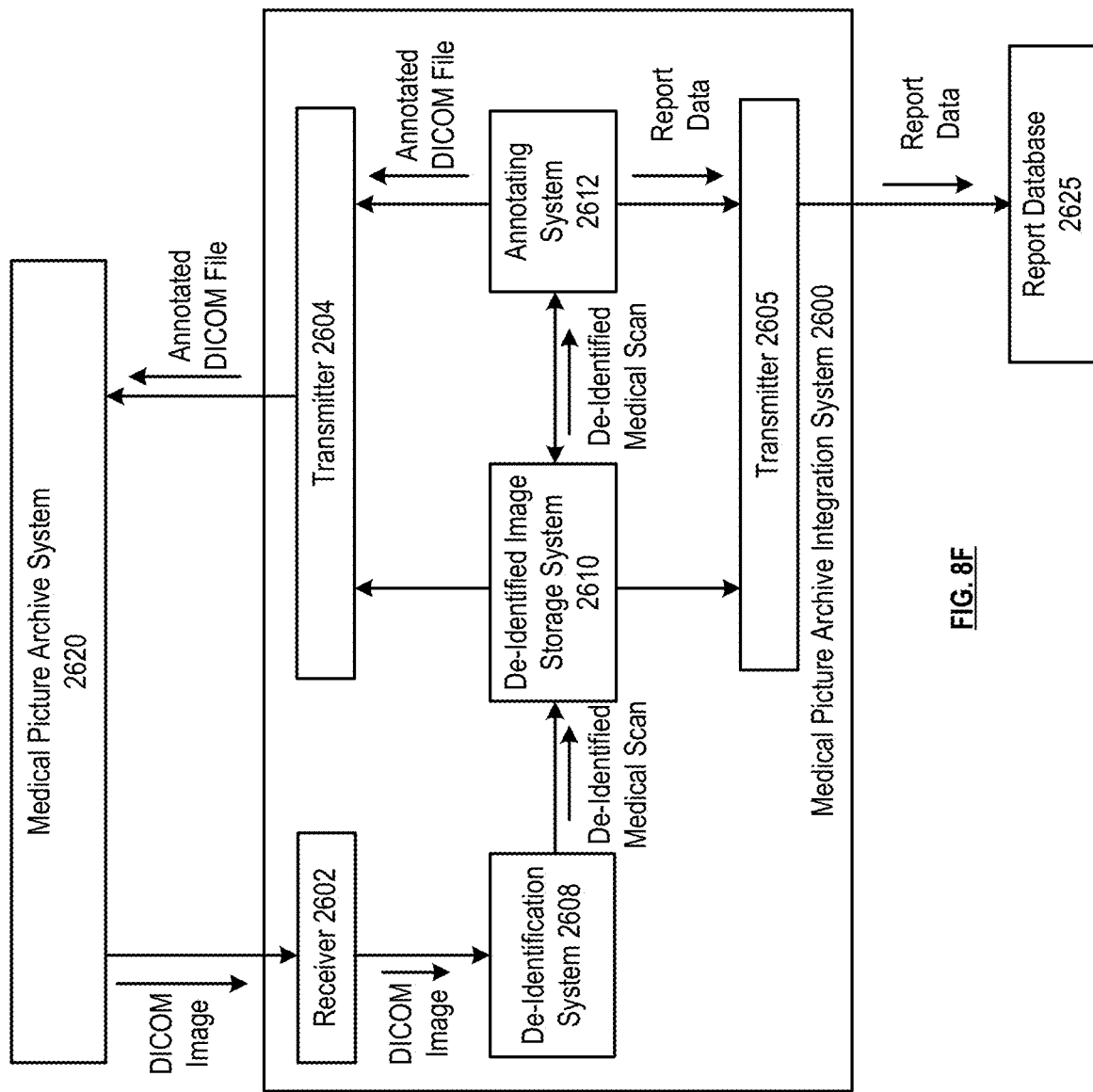

In some embodiments, as illustrated in FIGS. 8D-8F, the medical picture archive integration system 2600 can further communicate with a report database 2625, such as a Radiology Information System (RIS), that includes a plurality of medical reports corresponding to the DICOM images stored by the medical picture archive system 2620.

As shown in FIG. 8D, the medical picture archive integration system 2600 can further include a receiver 2603 that receives report data, corresponding to the DICOM image, from report database 2625. The report database 2625 can be affiliated with the medical picture archive system 2620 and can store report data corresponding to DICOM images stored in the medical picture archive system. The report data of report database 2625 can include PHI, and the report database 2625 can thus be disconnected from network 2630.

The report data can include natural language text, for example, generated by a radiologist that reviewed the corresponding DICOM image. The report data can be used to generate the de-identified medical scan, for example, where the de-identification system 2608 performs a natural language analysis function on the report data to identify patient identifying text in the report data. The de-identification system 2608 can utilize this patient identifying text to detect matching patient identifiers in the DICOM image to identify the patient identifiers of the DICOM image and generate the de-identified medical scan. In some embodiments, the report data can be de-identified by obfuscating, hashing, removing, replacing with a fiducial, or otherwise anonymizing the identified patient identifying text to generate de-identified report data.

The de-identified report data can be utilized by the annotating system 2612, for example, in conjunction with the DICOM image, to generate the annotation data. For example, the annotating system 2612 can perform a natural language analysis function on the de-identified natural language text of the report data to generate some or all of the annotation data. In some embodiments, the de-identified report data is sent to the central server system, for example, to be used as training data for inference functions, for natural language analysis functions, for other medical scan analysis functions, and/or for use by at least one other subsystem 101. For example, other subsystems 101 can utilize the central server system 2640 to fetch medical reports that correspond to particular medical scans or otherwise meet specified criteria. The central server system 2640 can query the medical picture archive integration system 2600 based on this criteria, and can receive de-identified medical reports in response. This can be sent to the requesting subsystem 101 directly, can be added to the medical scan database 342, a de-identified report database, or another database of the database storage system 140 for access by the requesting subsystem 101.

In some embodiments the medical picture archive integration system 2600 can query the report database 2625 for the report data corresponding to a received DICOM image by utilizing a common identifier extracted from the DICOM image.

In some embodiments, the report data can correspond to a plurality of DICOM images. For example, the report data can include natural language text describing a plurality of medical scans of a patient that can include multiple sequences, multiple modalities, and/or multiple medical scans taken over time. In such embodiments, the patient identifying text and/or annotation data detected in the report data can also be applied to de-identify and/or generate annotation data for the plurality of DICOM images it describes. In such embodiments, the medical picture archive integration system 2600 can query the medical picture archive system 2620 for one or more additional DICOM images corresponding to the report data, and de-identified data and annotation data for these additional DICOM images can be generated accordingly by utilizing the report data.

In some embodiments, as shown in FIG. 8E, the medical picture archive system 2620 communicates with the report database 2625. The medical picture archive system 2620 can request the report data corresponding to the DICOM image from the report database 2625, and can transmit the report data to the medical picture archive integration system 2600 via a DICOM communication protocol for receipt via receiver 2602. The medical picture archive system 2620 can query the report database 2625 for the report data, utilizing a common identifier extracted from the corresponding DICOM image, in response to determining to send the corresponding DICOM image to the medical picture archive integration system 2600.

FIG. 8F presents an embodiment where report data is generated by the annotating system 2612 and is transmitted, via a transmitter 2605, to the report database 2625, for example via a DICOM communication protocol or other protocol recognized by the report database 2625. In other embodiments, the report data is instead transmitted via transmitter 2604 to the medical picture archive system 2620, and the medical picture archive system 2620 transmits the report data to the report database 2625.

The report data can be generated by the annotating system 2612 as output of performing the inference function on the de-identified medical scan. The report data can include natural language text data 448 generated automatically based on other diagnosis data 440 such as abnormality annotation data 442 determined by performing the inference function, for example, by utilizing a medical scan natural language generating function trained by the medical scan natural language analysis system 114. The report data can be generated instead of, or in addition to, the annotated DICOM file.

FIG. 9 presents a flowchart illustrating a method for execution by a medical picture archive integration system 2600 that includes a first memory and a second memory that store executable instructions that, when executed by at least one first processor and at least one second processor, respectfully, cause the medical picture archive integration system to perform the steps below. In various embodiments, the first memory and at least one first processor are implemented by utilizing, respectfully, the memory 2654 and processing system 2652 of FIG. 8B. In various embodiments, the second memory is implemented by utilizing the memory 2674 and/or the memory 2684 of FIG. 8B. In various embodiments, the at least one second processor is implemented by utilizing the processing system 2682 of FIG. 8B.

Step 2702 includes receiving, from a medical picture archive system via a receiver, a first DICOM image for storage in the first memory, designated for PHI, where the first DICOM image includes at least one patient identifier. Step 2704 includes performing, via at least one first processor coupled to the first memory and designated for PHI, a de-identification function on the first DICOM image to identify the at least one patient identifier and generate a first de-identified medical scan that does not include the at least one patient identifier.

Step 2706 includes storing the first de-identified medical scan in a second memory that is separate from the first memory. Step 2708 includes receiving, via a network interface communicating with a network that does not include the medical picture archive system, first model parameters from a central server.

Step 2710 includes retrieving the first de-identified medical scan from the second memory. Step 2712 includes utilizing the first model parameters to perform a first inference function on the first de-identified medical scan to generate first annotation data via at least one second processor that is different from the at least one first processor. Step 2714 includes generating, via the at least one second processor, a first annotated DICOM file for transmission to the medical picture archive system via a transmitter, where the first annotated DICOM file includes the first annotation data and further includes an identifier that indicates the first DICOM image. In various embodiments, the first annotated DICOM file is a DICOM presentation state file.

In various embodiments, the second memory further includes operational instructions that, when executed by the at least one second processor, further cause the medical picture archive integration system to retrieve a second de-identified medical scan from the de-identified image storage system, where the second de-identified medical scan was generated by the at least one first processor by performing the de-identification function on a second DICOM image received from the medical picture archive system. The updated model parameters are utilized to perform the first inference function on the second de-identified medical scan to generate second annotation data. A second annotated DICOM file is generated for transmission to the medical picture archive system via the transmitter, where the second annotated DICOM file includes the second annotation data and further includes an identifier that indicates the second DICOM image.

In various embodiments, the second memory stores a plurality of de-identified medical scans generated by the at least one first processor by performing the de-identification function on a corresponding plurality of DICOM images received from the medical picture archive system via the receiver. The plurality of de-identified medical scans is transmitted to the central server via the network interface, and the central server generates the first model parameters by performing a training function on training data that includes the plurality of de-identified medical scans.

In various embodiments, the central server generates the first model parameters by performing a training function on training data that includes a plurality of de-identified medical scans received from a plurality of medical picture archive integration systems via the network. Each of the plurality of medical picture archive integration systems communicates bidirectionally with a corresponding one of a plurality of medical picture archive systems, and the plurality of de-identified medical scans corresponds to a plurality of DICOM images stored by the plurality of medical picture archive integration systems.

In various embodiments, the first de-identified medical scan indicates a scan category of the first DICOM image. The second memory further stores operational instructions that, when executed by the at least one second processor, further cause the medical picture archive integration system to select the first inference function from a set of inference functions based on the scan category. The set of inference functions corresponds to a set of unique scan categories that includes the scan category. In various embodiments, each unique scan category of the set of unique scan categories is characterized by one of a plurality of modalities and one of a plurality of anatomical regions.

In various embodiments, the first memory further stores operational instructions that, when executed by the at least one first processor, further cause the medical picture archive integration system to receive a plurality of DICOM image data from the medical picture archive system via the receiver for storage in the first memory in response to a query transmitted to the medical picture archive system via the transmitter. The query is generated by the medical picture archive integration system in response to a request indicating a new scan category received from the central server via the network. The new scan category is not included in the set of unique scan categories, and the plurality of DICOM image data corresponds to the new scan category. The de-identification function is performed on the plurality of DICOM image data to generate a plurality of de-identified medical scans for transmission to the central server via the network.

The second memory further stores operational instructions that, when executed by the at least one second processor, further cause the medical picture archive integration system to receive second model parameters from the central server via the network for a new inference function corresponding to the new scan category. The set of inference functions is updated to include the new inference function. The second de-identified medical scan is retrieved from the first memory, where the second de-identified medical scan was generated by the at least one first processor by performing the de-identification function on a second DICOM image received from the medical picture archive system. The new inference function is selected from the set of inference functions by determining the second de-identified medical scan indicates the second DICOM image corresponds to the new scan category. The second model parameters are utilized to perform the new inference function on the second de-identified medical scan to generate second annotation data. A second annotated DICOM file is generated for transmission to the medical picture archive system via the transmitter, where the second annotated DICOM file includes the second annotation data and further includes an identifier that indicates the second DICOM image.

In various embodiments, the medical picture archive integration system generates parameter data for transmission to the medical picture archive system that indicates the set of unique scan categories. The medical picture archive system automatically transmits the first DICOM image to the medical picture archive integration system in response to determining that the first DICOM image compares favorably to one of the set of unique scan categories.

In various embodiments, the second memory further stores operational instructions that, when executed by the at least one second processor, cause the medical picture archive integration system to generate a natural language report data is based on the first annotation data and to transmit, via a second transmitter, the natural language report data to a report database associated with the medical picture archive integration system, where the natural language report data includes an identifier corresponding to the first DICOM image.

In various embodiments, the first memory further stores operational instructions that, when executed by the at least one first processor, cause the medical picture archive integration system to receive, via a second receiver, a natural language report corresponding to the first DICOM image from the report database. A set of patient identifying text included in the natural language report are identified. Performing the de-identification function on the first DICOM image includes searching the first DICOM image for the set of patient identifying text to identify the at least one patient identifier.

In various embodiments, the first memory is managed by a medical entity associated with the medical picture archive system. The medical picture archive integration system is located at a first geographic site corresponding to the medical entity, and the central server is located at a second geographic site. In various embodiments, the first memory is decoupled from the network to prevent the first DICOM image that includes the at least one patient identifier from being communicated via the network. In various embodiments, the medical picture archive system is a Picture Archive and Communication System (PACS) server, and the first DICOM image is received in response to a query sent to the medical picture archive system by the transmitter in accordance with a DICOM communication protocol.

Figure 10A:
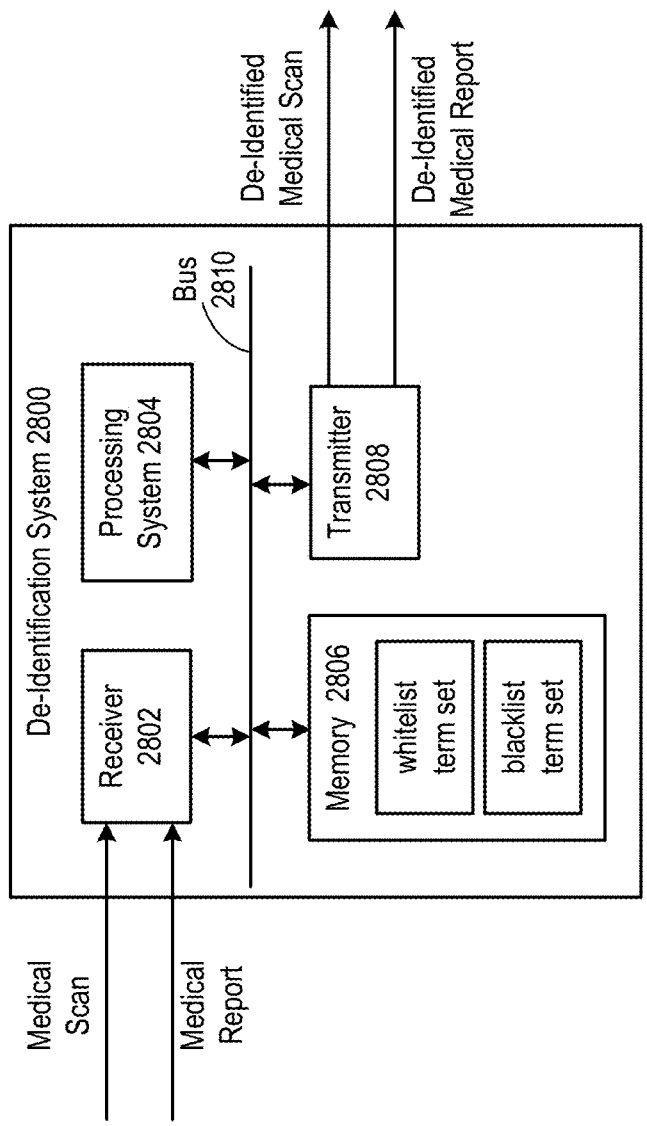
FIG. 10A is a schematic block diagram of a de-identification system in accordance with various embodiments.

FIG. 10A presents an embodiment of a de-identification system 2800. The de-identification system 2800 can be utilized to implement the de-identification system 2608 of FIGS. 8A-8F. In some embodiments, the de-identification system 2800 can be utilized by other subsystems to de-identify image data, medical report data, private fields of medical scan entries 352 such as patient identifier data 431, and/or other private fields stored in databases of the database memory device 340.

The de-identification system can be operable to receive, from at least one first entity, a medical scan and a medical report corresponding to the medical scan. A set of patient identifiers can be identified in a subset of fields of a header of the medical scan. A header anonymization function can be performed on each of the set of patient identifiers to generate a corresponding set of anonymized fields. A de-identified medical scan can be generated by replacing the subset of fields of the header of the medical scan with the corresponding set of anonymized fields.

A subset of patient identifiers of the set of patient identifiers can be identified in the medical report by searching text of the medical report for the set of patient identifiers. A text anonymization function can be performed on the subset of patient identifiers to generate corresponding anonymized placeholder text for each of the subset of patient identifiers. A de-identified medical report can be generated by replacing each of the subset of patient identifiers with the corresponding anonymized placeholder text. The de-identified medical scan and the de-identified medical report can be transmitted to a second entity via a network.

As shown in FIG. 10A, the de-identification system 2800 can include at least one receiver 2802 operable to receive medical scans, such as medical scans in a DICOM image format. The at least one receiver 2802 is further operable to receive medical reports, such as report data 449 or other reports containing natural language text diagnosing, describing, or otherwise associated the medical scans received by the de-identification system. The medical scans and report data can be received from the same or different entity, and can be received by the same or different receiver 2802 in accordance with the same or different communication protocol. For example, the medical scans can be received from the medical picture archive system 2620 of FIGS. 8A-8F and the report data can be received from the report database 2625 of FIGS. 8D-8F. In such embodiments, the receiver 2802 can be utilized to implement the receiver 2602 of FIG. 8B.

The de-identification system 2800 can further include a processing system 2804 that includes at least one processor, and a memory 2806. The memory 2806 can store operational instructions that, when executed by the processing system, cause the de-identification system to perform at least one patient identifier detection function on the received medical scan and/or the medical report to identify a set of patient identifiers in the medical scan and/or the medical report. The operational instructions, when executed by the processing system, can further cause the de-identification system to perform an anonymization function on the medical scan and/or the medical report to generate a de-identified medical scan and/or a de-identified medical report that do not include the set of patient identifiers found in performing the at least one patient identifier detection function. Generating the de-identified medical scan can include generating a de-identified header and generating de-identified image data, where the de-identified medical scan includes both the de-identified header and the de-identified image data. The memory 2806 can be isolated from Internet connectivity, and can be designated for PHI.

The de-identification system 2800 can further include at least one transmitter 2808, operable to transmit the de-identified medical scan and de-identified medical report. The de-identified medical scan and de-identified medical report can be transmitted back to the same entity from which they were received, respectively, and/or can be transmitted to a separate entity. For example, the at least one transmitter can transmit the de-identified medical scan to the de-identified image storage system 2610 of FIGS. 8A-8F and/or can transmit the de-identified medical scan to central server system 2640 via network 2630 of FIGS. 8A-8F. In such embodiments, the transmitter 2808 can be utilized to implement the interface 2655 of FIG. 8B. The receiver 2802, processing system 2804, memory 2806, and/or transmitter 2808 can be connected via bus 2810.

Some or all of the at least one patient identifier detection function and/or at least one anonymization function as discussed herein can be trained and/or implemented by one or subsystems 101 in the same fashion as other medical scan analysis functions discussed herein, can be stored in medical scan analysis function database 346 of FIG. 3, and/or can otherwise be characterized by some or all fields of a medical scan analysis function entry 356 of FIG. 5.

The de-identification system 2800 can perform separate patient identifier detection functions on the header of a medical report and/or medical scan, on the text data of the medical report, and/or on the image data of the medical scan, such as text extracted from the image data of the medical scan. Performance of each of these functions generates an output of its own set of identified patient identifiers. Combining these sets of patient identifiers yields a blacklist term set. A second pass of the header of a medical report and/or medical scan, on the text data of the medical report, and/or on the image data of the medical scan that utilizes this blacklist term set can catch any terms that were missed by the respective patient identifier detection function, and thus, the outputs of these multiple identification processes can support each other. For example, some of the data in the headers will be in a structured form and can thus be easier to reliably identify. This can be exploited and used to further anonymize these identifiers when they appear in free text header fields, report data, and/or in the image data of the medical scan. Meanwhile, unstructured text in free text header fields, report data, and/or image data of the medical scan likely includes pertinent clinical information to be preserved in the anonymization process, for example, so it can be leveraged by at least one subsystem 101 and/or so it can be leveraged in training at least one medical scan analysis function.

At least one first patient identifier detection function can include extracting the data in a subset of fields of a DICOM header, or another header or other metadata of the medical scan and/or medical report with a known type that corresponds to patient identifying data. For example, this patient identifying subset of fields can include a name field, a patient ID number field or other unique patient identifier field, a date field, a time field, an age field, an accession number field, SOP instance UID, and/or other fields that could be utilized to identify the patient and/or contain private information. A non-identifying subset of fields of the header can include hospital identifiers, machine model identifiers, and/or some or all fields of medical scan entry 352 that do not correspond to patient identifying data. The patient identifying subset of fields and the non-identifying subset of fields can be mutually exclusive and collectively exhaustive with respect to the header. The at least one patient identifier function can include generating a first set of patient identifiers by ignoring the non-identifying subset of fields and extracting the entries of the patient identifying subset of fields only. This first set of patient identifiers can be anonymized to generate a de-identified header as discussed herein.

In some embodiments, at least one second patient identifier detection function can be performed on the report data of the medical report. The at least one second patient identifier detection function can include identifying patient identifying text in the report data by performing a natural language analysis function, for example, trained by the medical scan natural language analysis system 114. For example, the at least one second patient identifier detection function can leverage the known structure of the medical report and/or context of the medical report. A second set of patient identifiers corresponding to the patient identifying text can be determined, and the second set of patient identifiers can be anonymized to generate a de-identified medical report. In some embodiments, a de-identified medical report includes clinical information, for example, because the portion of the original medical report that includes the clinical information was deemed to be free of patient identifying text and/or because the portion of the original medical report that includes the clinical information was determined to include pertinent information to be preserved.

In some embodiments, the medical report includes image data corresponding to freehand or typed text. For example the medical report can correspond to a digitized scan of original freehand text written by a radiologist or other medical professional. In such embodiments, the patient identifier detection function can first extract the text from the freehand text in the image data to generate text data before the at least one second patient identifier detection function is performed on the text of the medical report to generate the second set of patient identifiers.

In some embodiments, the at least one second patient identifier detection function can similarly be utilized to identify patient identifying text in free text fields and/or unstructured text fields of a DICOM header and/or other metadata of the medical scan and/or medical report data by performing a natural language analysis function, for example, trained by the medical scan natural language analysis system 114. A third set of patient identifiers corresponding to this patient identifying text of the free text and/or unstructured header fields can be determined, and the third set of patient identifiers can be anonymized to generate de-identified free text header field and/or unstructured header fields. In some embodiments, a de-identified free text header field and/or unstructured header field includes clinical information, for example, because the portion of the original corresponding header field that includes the clinical information was deemed to be free of patient identifying text and/or because the portion of the original corresponding header field that includes the clinical information was determined to include pertinent information to be preserved.

Patient identifiers can also be included in the image data of the medical scan itself. For example, freehand text corresponding to a patient name written on a hard copy of the medical scan before digitizing can be included in the image data, as discussed in conjunction with FIG. 10B. Other patient identifiers, such as information included on a patient wristband or other identifying information located on or within the vicinity of the patient may have been captured when the medical scan was taken, and can thus be included in the image. At least one third patient identifier detection function can include extracting text from the image data and/or detecting non-text identifiers in the image data by performing a medical scan image analysis function, for example, trained by the medical scan image analysis system 112. For example, detected text that corresponds to an image location known to include patient identifiers, detected text that corresponds to a format of a patient identifier, and/or or detected text or other image data determined to correspond to a patient identifier can be identified. The at least one third patient identifier detection function can further include identifying patient identifying text in the text extracted from the image data by performing the at least one second patient identifier detection function and/or by performing a natural language analysis function. A fourth set of patient identifiers corresponding to patient identifying text or other patient identifiers detected in the image data of the medical scan can be determined, and the fourth set of patient identifiers can be anonymized in the image data to generate de-identified image data of the medical scan as described herein. In particular, the fourth set of patient identifiers can be detected in a set of regions of image data of the medical scan, and the set of regions of the image data can be anonymized.

In some embodiments, only a subset of the patient identifier detection functions described herein are performed to generate respective sets of patient identifiers for anonymization. In some embodiments, additional patient identifier detection functions can be performed on the medical scan and/or medical report to determine additional respective sets of patient identifiers for anonymization. The sets of patient identifiers outputted by performing each patient identifier detection function can have a null or non-null intersection. The sets of patient identifiers outputted by performing each patient identifier function can have null or non-null set differences.

Cases where the sets of patient identifiers have non-null set differences can indicate that a patient identifier detected by one function may have been missed by another function. The combined set of patient identifiers, for example, generated as the union of the sets of sets of patient identifiers outputted by performing each patient identifier function, can be used to build a blacklist term set, for example, stored in memory 2806. The blacklist term set can designate the final set of terms to be anonymized. A second pass of header data, medical scans, medical reports, and/or any free text extracted from the header data, the medical scan, and/or the medical report can be performed by utilizing the blacklist term set to flag terms for anonymization that were not caught in performing the respective at least one patient identifier detection function. For example, performing the second pass can include identifying at least one patient identifier of the blacklist term set in the header, medical report, and/or image data of the medical scan. This can include by searching corresponding extracted text of the header, medical report, and/or image data for terms included in blacklist term set and/or by determining if each term in the extracted text is included in the blacklist term set.

In some embodiments, at least one patient identifier is not detected until the second pass is performed. Consider an example where a free text field of a DICOM header included a patient name that was not detected in performing a respective patient identifier detection function on the free text field of the DICOM header. However, the patient name was successfully identified in the text of the medical report in performing a patient identifier detection function on the medical report. This patient name is added to the blacklist term list, and is detected in a second pass of the free text field of the DICOM header. In response to detection in the second pass, the patient name of the free text field of the DICOM header can be anonymized accordingly to generate a de-identified free text field. Consider a further example where the patient name is included in the image data of the medical scan, but was not detected in performing a respective patient identifier detection function on the free text field of the DICOM header. In the second pass, this patient name can be detected in at least one region of image data of the medical scan by searching the image data for the blacklist term set.

In some embodiments, performing some or all of the patient identifier detection functions includes identifying a set of non-identifying terms, such as the non-identifying subset of fields of the header. In particular, the non-identifying terms can include terms identified as clinical information and/or other terms determined to be preserved. The combined set of non-identifying terms, for example, generated as the union of the sets of sets of non-identifying outputted by performing each patient identifier function, can be used to build a whitelist term set, for example, stored in memory 2806. Performing the second pass can further include identifying at least one non-identifying term of the whitelist term set in the header, medical report, and/or image data of the medical scan, and determining not to anonymize, or to otherwise ignore, the non-identifying term.

In various embodiments, some or all terms of the whitelist term set can be removed from the blacklist term set. In particular, at least one term previously identified as a patient identifier in performing one or more patient identifier detection functions is determined to be ignored and not anonymized in response to determining the term is included in the whitelist term set. This can help ensure that clinically important information is not anonymized, and is thus preserved in the de-identified medical scan and de-identified medical report.

In some embodiments, the second pass can be performed after each of the patient identifier detection functions are performed. For example, performing the anonymization function can include performing this second pass by utilizing the blacklist term set to determine the final set of terms to be anonymized. New portions of text in header fields, not previously detected in generating the first set of patient identifiers or the third set of patient identifiers, can be flagged for anonymization by determining these new portions of text correspond to terms of the blacklist term set. New portions of text the medical report, not previously detected in generating in the second set of patient identifiers, can be flagged for anonymization by determining these new portions of text correspond to terms of the blacklist term set. New regions of the image data of the medical scan, not previously detected in generating the fourth set of patient identifiers, can be flagged for anonymization by determining these new portions of text correspond to terms of the blacklist term set.

In some embodiments, the blacklist term set is built as each patient identifier detection function is performed, and performance of subsequent patient identifier detection functions includes utilizing the current blacklist term set. For example, performing the second patient identifier detection function can include identifying a first subset of the blacklist term set in the medical report by searching the text of the medical report for the blacklist term set and/or by determining if each term in the text of the medical report is included in the blacklist term set. Performing the second patient identifier detection function can further include identifying at least one term in the medical report that is included in the whitelist term set, and determining to ignore the term in response. The first subset can be anonymized to generate the de-identified medical report as discussed herein. New patient identifiers not already found can be appended to the blacklist term set, and the updated blacklist term set can be applied to perform a second search of the header and/or image data of the medical scan, and at least one of the new patient identifiers can be identified in the header in the second search of the header and/or in the image data in a second search of the image data. These newly identified patient identifiers in the header and/or image data are anonymized in generating the de-identified medical scan.

As another example, a second subset of the blacklist term set can be detected in a set of regions of image data of the medical scan by performing the medical scan image analysis function on image data of the medical scan, where the image analysis function includes searching the image data for the set of patient identifiers. For example, the medical scan image analysis function can include searching the image data for text, and the second subset can include detected text that matches one or more terms of the blacklist term set. In some embodiments, detected text that matches one or more terms of the whitelist term set can be ignored. The second subset can be anonymized to generate de-identified image data as discussed herein. New patient identifiers that are detected can be appended to the blacklist term set, and the updated blacklist term set can be applied to perform a second search of the header and/or metadata of the medical scan, and/or can be applied to perform a second search of the medical report. At least one of the new patient identifiers can be identified in the header as a result of performing the second search of the header and/or at least one of the new patient identifiers can be identified medical report as a result of performing the second search of the medical report. These newly identified patient identifiers can be anonymized in the header along with the originally identified blacklist term set in generating the de-identified header, and/or can be anonymized in the medical report along with the originally identified first subset in generating the de-identified medical report.

In some embodiments, the memory 2806 further stores a global blacklist, for example, that includes a vast set of known patient identifying terms. In some embodiments, the global blacklist is also utilized by at least one patient identifier detection function and/or in performing the second pass to determine patient identifying terms for anonymization. In some embodiments, the blacklist term set generated for a particular medical scan and corresponding medical report can be appended to the global blacklist for use in performing the second pass and/or in detecting patient identifiers in subsequently received medical scans and/or medical reports.

Alternatively or in addition, the memory 2806 can further store a global whitelist, for example, that includes a vast set of terms that can be ignored. In particular, the global whitelist can include clinical terms and/or other terms that are deemed beneficial to preserve that do not correspond to patient identifying information. In some embodiments, the global whitelist is utilized by at least one patient identifier detection function and/or in performing the second pass to determine terms to ignore in the header, image data, and/or medical report. In some embodiments, the whitelist term set generated for a particular medical scan and corresponding medical report can be appended to the global whitelist for use in performing the second pass and/or in ignoring terms in subsequently received medical scans and/or medical reports.

Alternatively or in addition, the memory 2806 can further store a global graylist, for example, that includes ambiguous terms that could be patient identifying terms in some contexts, but non-identifying terms in other contexts. For example, "Parkinson" could correspond to patient identifying data if part of a patient name such as "John Parkinson", but could correspond to non-patient identifying data meant to be ignored and preserved in the de-identified medical report and/or de-identified medical scan if part of a diagnosis term such as "Parkinson's disease." In some embodiments, the global graylist is also utilized in performing the second pass and/or in performing at least one patient identifier detection function to determine that a term is included in the graylist, and to further determine whether the term should be added to the blacklist term set for anonymization or whitelist term set to be ignored by leveraging context of accompanying text, by leveraging known data types of a header field from which the term was extracted, by leveraging known structure of the term, by leveraging known data types of a location of the image data from which the term was extracted, and/or by leveraging other contextual information. In some embodiments, the graylist term set can be updated based on blacklist and/or whitelist term sets for a particular medical scan and corresponding medical report.

In some embodiments, the at least one anonymization function includes a fiducial replacement function. For example, some or all of the blacklist term set can be replaced with a corresponding, global fiducial in the header, report data, and/or image data. In some embodiments, the global fiducial can be selected from a set of global fiducials based on a type of the corresponding patient identifier. Each patient identifier detected in the header and/or medical report can be replaced with a corresponding one of the set of global text fiducials. Each patient identifiers detected in the image data can be replaced with a corresponding one of the set of global image fiducials. For example, one or more global image fiducials can overlay pixels of regions of the image data that include the identifying patient data, to obfuscate the identifying patient data in the de-identified image data.

The global text fiducials and/or global image fiducials can be recognizable by inference functions and/or training functions, for example, where the global text fiducials and global image fiducials are ignored when processed in a training step to train an inference function and/or are ignored in an inference step when processed by an inference function. Furthermore, the global text fiducials and/or global image fiducials can be recognizable by a human viewing the header, medical report, and/or image data. For example, a radiologist or other medical professional, upon viewing a header, medical report, and/or image data, can clearly identify the location of a patient identifier that was replaced by the fiducial and/or can identify the type of patient identifier that was replaced by the fiducial.

As an example, the name "John Smith" can be replaced in a header and/or medical report with the text "% PATIENT NAME %", where the text "% PATIENT NAME %" is a global fiducial for name types of the header and/or the text of medical reports. The training step and/or inference step of medical scan natural language analysis functions can recognize and ignore text that matches "% PATIENT NAME %" automatically.

Figure 10B:
FIG. 10B is an illustration of an example of anonymizing patient identifiers in image data of a medical scan in accordance with various embodiments.

FIG. 10B illustrates an example of anonymizing patient identifiers in image data of a medical scan. In this example, the name "John Smith" and the date "May 4, 2010" is detected as freehand text in the original image data of a medical scan. The regions of the image data that include the patient identifiers can each be replaced by global fiducial in the shape of a rectangular bar, or any other shape. As shown in FIG. 10B, a first region corresponding to the location of "John Smith" in the original image data is replaced by fiducial 2820 in the de-identified image data, and a second region corresponding to the location of "May 4, 2010" in the original image data is replaced by fiducial 2822 in the de-identified image data. The size, shape, and/or location of each global visual fiducial can be automatically determined based on the size, shape, and/or location of the region that includes the patient identifier to minimize the amount of the image data that is obfuscated, while still ensuring the entirety of the text is covered. While not depicted in FIG. 10B, the fiducial can be of a particular color, for example, where pixels of the particular color are automatically recognized by the training step and/or inference step of medical scan image analysis functions to indicate that the corresponding region be ignored, and/or where the particular color is not included in the original medical scan and/or is known to not be included in any medical scans. The fiducial can include text recognizable to human inspection such as "% PATIENT NAME" and "% DATE" as depicted in FIG. 10B, and/or can include a QR code, logo, or other unique symbol recognizable to human inspection and/or automatically recognizable by the training step and/or inference step of medical scan image analysis functions to indicate that the corresponding region be ignored.

In some embodiments, other anonymization functions can be performed on different ones of the patient identifying subset of fields to generate the de-identified header, de-identified report data, and/or de-identified image data. For example, based on the type of identifying data of each field of the header, different types of header anonymization functions and/or text anonymization functions can be selected and utilized on the header fields, text of the report, and/or text extracted from the image data. A set of anonymization functions can include a shift function, for example, utilized to offset a date, time or other temporal data by a determined amount to preserve absolute time difference and/or to preserve relative order over multiple medical scans and/or medical reports of a single patient. FIG. 10B depicts an example where the shift function is performed on the date detected in the image data to generate fiducial 2822, where the determined amount is 10 years and 1 month. The determined amount can be determined by the de-identification system randomly and/or pseudo-randomly for each patient and/or for each medical scan and corresponding medical report, ensuring the original date cannot be recovered by utilizing a known offset. In various embodiments, other medical scans and/or medical reports are fetched for the same patient by utilizing a patient ID number or other unique patient identifier of the header. These medial scans and reports can be anonymized as well, where the dates and/or times detected in these medical scans and/or medical reports offset by the same determined amount, randomized or pseudo-randomized for particular patient ID number, for example, based on performing a hash function on the patient ID number.

The set of anonymization functions can include at least one hash function, for example utilized to hash a unique patient ID such as a patient ID number, accession number, and/or SOP instance UID of the header and/or text. In some embodiments, the hashed SOP instance UID, accession number, and/or patient ID number are prepended with a unique identifier, stored in a database of the memory 2806 and/or shared with the entities to which the de-identified medical scans and/or medical reports are transmitted, so that de-identified medical scans and their corresponding de-identified medical reports can be linked and retrieved retroactively. Similarly, longitudinal data can be preserved as multiple medical scans and/or medical reports of the same patient will be assigned the same hashed patient ID.

The set of anonymization functions can further include at least one manipulator function for some types of patient identifiers. Some values of header fields and/or report text that would normally not be considered private information can be considered identifying patient data if they correspond to an outlier value or other rare value that could then be utilized to identify the corresponding patient from a very small subset of possible options. For example, a patient age over 89 could be utilized to determine the identity of the patient, for example, if there are very few patients over the age of 89. To prevent such cases, in response to determining that a patient identifier corresponds to an outlier value and/or in response to determining that a patient identifier compares unfavorably to a normal-range threshold value, the patient identifier can be capped at the normal-range threshold value or can otherwise be manipulated. For example, a normal-range threshold value corresponding to age can be set at 89, and generating a de-identified patient age can include capping patient ages that are higher than 89 at 89 and/or can include keeping the same value for patient ages that are less than or equal to 89.

In some embodiments, the de-identified header data is utilized to replace the corresponding first subset of patient identifiers detected in the medical report with text of the de-identified header fields. In other embodiments, a set of text anonymization functions includes a global text fiducial replacement function, shift function, a hash function, and/or manipulator functions that anonymize the corresponding types of patient identifiers in the medical report separately.

In some embodiments where the image data of a medical scan includes an anatomical region corresponding to a patient's head, the image data may include an identifying facial structure and/or facial features that could be utilized to determine the patient's identity. For example, a database of facial images, mapped to a corresponding plurality of people including the patient, could be searched and a facial recognition function could be utilized to identify the patient in the database. Thus, facial structure included in the image data can be considered patient identifying data.

To prevent this problem and maintain patient privacy, the de-identification system can further be implemented to perform facial obfuscation for facial structure detected in medical scans. At least one region of the image data that includes identifying facial structure can be determined by utilizing a medical image analysis function. For example, the medical image analysis function can include a facial detection function that determines the regions of the image data that include identifying facial structure based on searching the image data for pixels with a density value that corresponds to facial skin, facial bone structure, or other density of an anatomical mass type that corresponds to identifying facial structure, and the facial obfuscation function can be performed on the identified pixels. Alternatively or in addition, the facial detection function can determine the region based on identifying at least one shape in the image data that corresponds to a facial structure.

The image obfuscation function can include a facial structure obfuscation function performed on the medical scan to generate de-identified image data that does not include identifying facial structure. For example, the facial structure obfuscation function can mask, scramble, replace with a fiducial, or otherwise obfuscate the pixels of the region identified by the facial detection function. In some embodiments, the facial structure obfuscation function can perform a one-way function on the region that preserves abnormalities of the corresponding portions of the image, such as nose fractures or facial skin legions, while still obfuscating the identifying facial structure such that the patient is not identifiable. For example, the pixels of the identifying facial structure can be altered such that they converge towards a fixed, generic facial structure. In some embodiments, a plurality of facial structure image data of a plurality of patients can be utilized to generate the generic facial structure, for example, corresponding to an average or other combination of the plurality of faces. For example, the pixels of the generic facial structure can be averaged with, superimposed upon, or otherwise combined with the pixels of the region of the image data identified by the facial detection function in generating the de-identified image data.

In some embodiments, a hash function can be performed on an average of the generic facial structure and the identified facial structure of the image data so that the generic facial structure cannot be utilized in conjunction with the resulting data of the de-identified image data to reproduce the original, identifying facial structure. In such embodiments, the hash function can alter the pixel values while still preserving abnormalities. In some embodiments, a plurality of random, generic facial structures can be generated by utilizing the plurality of facial structure image data, for example, where each if the plurality of facial structure image data are assigned a random or pseudo-random weight in an averaging function utilized to create the generic facial structure, where a new, random or pseudo-random set of weights are generated each time the facial structure obfuscation function is utilized to create a new, generic facial structure to be averaged with the identified facial structure in creating the de-identified image data to ensure the original identifying facial structure cannot be extracted from the resulting de-identified image data.

While facial obfuscation is described herein, similar techniques can be applied in a similar fashion to other anatomical regions that are determined to include patient identifiers and/or to other anatomical regions that can be utilized to extract patient identifying information if not anonymized.

In some embodiments, the at least one receiver 2802 is included in at least one transceiver, for example, enabling bidirectional communication between the medical picture archive system 2620 and/or the report database 2625. In such embodiments, the de-identification system 2800 can generate queries to the medical picture archive system 2620 and/or the report database 2625 for particular medical scans and/or medical reports, respectively. In particular, if the medical scan and medical report are stored and/or managed by separate memories and/or separate entities, they may not be received at the same time. However, a linking identifier, such as DICOM identifiers in headers or metadata of the medical scan and/or medical report, such accession number, patient ID number, SOP instance UID, or other linking identifier that maps the medical scan to the medical report can be utilized to fetch a medical report corresponding to a received medical scan and/or to fetch a medical scan corresponding to a received medical report via a query sent utilizing the at least one transceiver. For example, in response to receiving the medical scan from the medical picture archive system 2620, the de-identification system can extract a linking identifier from a DICOM header of the medical scan, and can query the report database 2625 for the corresponding medical report by indicating the linking identifier in the query. Conversely, in response to receiving the medical report from the report database 2625, the de-identification system can extract the linking identifier from a header, metadata, and/or text body of the medical report, and can query the medical picture archive system 2620 for the corresponding medical scan by indicating the linking identifier in the query. In some embodiments, a mapping of de-identified medical scans to original medical scans, and/or a mapping of de-identified medical reports to original medical reports can be stored in memory 2806. In some embodiments, linking identifiers such as patient ID numbers can be utilized to fetch additional medical scans, additional medical reports, or other longitudinal data corresponding to the same patient.

FIG. 11 presents a flowchart illustrating a method for execution by a de-identification system 2800 that stores executable instructions that, when executed by at least one processor, cause the de-identification to perform the steps below.

Step 2902 includes receiving from a first entity, via a receiver, a first medical scan and a medical report corresponding to the medical scan. Step 2904 includes identifying a set of patient identifiers in a subset of fields of a first header of the first medical scan. Step 2906 includes performing a header anonymization function on each of the set of patient identifiers to generate a corresponding set of anonymized fields. Step 2908 includes generating a first de-identified medical scan by replacing the subset of fields of the first header of the first medical scan with the corresponding set of anonymized fields. Step 2910 includes identifying a first subset of patient identifiers of the set of patient identifiers in the medical report by searching text of the medical report for the set of patient identifiers. Step 2912 includes performing a text anonymization function on the first subset of patient identifiers to generate corresponding anonymized placeholder text for each of the first subset of patient identifiers. Step 2914 includes generating a de-identified medical report by replacing each of the first subset of patient identifiers with the corresponding anonymized placeholder text. Step 2916 includes transmitting, via a transmitter, the de-identified first medical scan and the de-identified medical report to a second entity via a network.

In various embodiments, the medical scan is received from a Picture Archive and Communication System (PACS), where the medical report is received from a Radiology Information System (RIS), and where the first de-identified medical scan and the de-identified medical report are transmitted to a central server that is not affiliated with the PACS or the RIS. In various embodiments, first medical scan and the medical report are stored in a first memory for processing. The first memory is decoupled from the network to prevent the set of patient identifiers from being communicated via the network. The first de-identified medical scan and the de-identified medical report are stored in a second memory that is separate from the first memory. The first de-identified medical scan and the de-identified medical report are fetched from the second memory for transmission to the second entity.

In various embodiments, the header anonymization function performed on each of the set of patient identifiers is selected from a plurality of header anonymization functions based on one of a plurality of identifier types of the corresponding one of the subset of fields. In various embodiments, the plurality of identifier types includes a date type. A shift function corresponding to the date type is performed on a first date of the first header to generate the first de-identified medical scan, where the shift function includes offsetting the first date by a determined amount. A second medical scan is received, via the receiver, that includes a second header. A unique patient ID of the first header matches a unique patient ID of the second header. The shift function is performed on a second date of the second header by offsetting the second date by the determined amount to generate a second de-identified medical scan. The second de-identified medical scan is transmitted to the second entity via the network.

In various embodiments, the plurality of identifier types includes a unique patient ID type. A hash function corresponding the unique patient ID type is performed on the unique patient ID of the first header to generate the first de-identified medical scan. The hash function is performed on the unique patient ID of the second header to generate the second de-identified medical scan. An anonymized unique patient ID field of the first de-identified medical scan matches an anonymized unique patient ID field of the second de-identified medical scan as a result of the unique patient ID of the first header matching the unique patient ID of the second header.

In various embodiments, the plurality of identifier types includes a linking identifier type that maps the medical scan to the medical report. A hash function corresponding to the linking identifier type is performed on a linking identifier of the first header to generate a hashed linking identifier. A linking identifier field of the first de-identified medical scan includes the hashed linking identifier. Performing the text anonymization function on the first subset of patient identifiers includes determining one of the first subset of patient identifiers corresponds to linking identifier text and performing the hash function on the one of the first subset of patient identifiers to generate the hashed linking identifier, where the de-identified medical report includes the hashed linking identifier.

In various embodiments, a second subset of patient identifiers of the set of patient identifiers is identified in a set of regions of image data of the medical scan by performing an image analysis function on image data of the medical scan. The image analysis function includes searching the image data for the set of patient identifiers. An identifier type is determined for each of the second subset of patient identifiers. One of a plurality of image fiducials is selected for each of the second subset of patient identifiers based on the identifier type. De-identified image data is generated, where a set of regions of the de-identified image data, corresponding to the set of regions of the image data, includes the one of the plurality of image fiducials to obfuscate each of the second subset of patient identifiers. Generating the first de-identified medical scan further includes replacing the image data of the medical scan with the de-identified image data.

In various embodiments, a new patient identifier is identified in the medical report by performing a natural language analysis function on the medical report, where new patient identifier is not included in the set of patient identifiers. The set of patient identifiers is updated to include the new patient identifier prior to searching the image data of the medical scan for the set of patient identifiers, and the second subset of patient identifiers includes the new patient identifier.

In various embodiments, the memory further stores a global identifier blacklist. The natural language analysis function includes searching the medical report for a plurality of terms included in the global identifier blacklist to identify the new patient identifier. In various embodiments, the de-identification system determines that the global identifier blacklist does not include one of the set of patient identifiers, and the global identifier blacklist is updated to include the one of the set of patient identifiers.

In various embodiments, performing the image analysis function further includes identifying a new patient identifier in the image data, where new patient identifier is not included in the set of patient identifiers. Identifying text is extracted from a region of the image data corresponding to the new patient identifier. The new patient identifier is identified in the medical report by searching text of the medical report for the identifying text. The text anonymization function is performed on new patient identifier to generate anonymized placeholder text for the new patient identifier. Generating the de-identified medical report further includes replacing the identifying text with the anonymized placeholder text for the new patient identifier.

In various embodiments, generating the de-identified image data further includes detecting an identifying facial structure in the image data of the medical scan. Generating the de-identified image data includes performing a facial structure obfuscation function on the image data, and where the de-identified image data does not include the identifying facial structure.

FIGS. 12A-12G illustrate an embodiments of a medical scan hierarchical labeling system 3002. The medical scan hierarchical labeling system 3002 can be utilized to generate structured labeling data for medical scans via one or more client devices 120, based on user input to an interactive interface displayed on a display device corresponding to the one or more client devices.

As shown in FIGS. 12A-12G, the medical scan hierarchical labeling system 3002 can communicate bi-directionally, via network 150, with the medical scan database 342, medical scan analysis function database 346, and/or other databases of the database storage system 140, with one or more client devices 120, and/or, while not shown in FIG. 12A, one or more subsystems 101 of FIG. 1. In some embodiments, the medical scan hierarchical labeling system 3002 is an additional subsystem 101 of the medical scan processing system 100, implemented by utilizing the subsystem memory device 245, subsystem processing device 235, and/or subsystem network interface 265 of FIG. 2A. In some embodiments, the medical scan hierarchical labeling system 3002 is implemented by utilizing, or otherwise communicates with, the central server 2640. For example, some or all of the databases of the database storage system 140 are populated with de-identified data generated by the medical picture archive integration system 2600. In some embodiments, the medical scan hierarchical labeling system 3002 can receive de-identified medical scans, annotation data, and/or reports directly from the medical picture archive integration system 2600. For example, the medical scan hierarchical labeling system 3002 can request de-identified medical scans, annotation data, and/or reports that match requested criteria, for example, corresponding to training set criteria. In some embodiments, some or all of the medical scan hierarchical labeling system 3002 is implemented by utilizing other subsystems 101 and/or is operable to perform functions or other operations described in conjunction with one or more other subsystems 101. In some embodiments, the medical scan hierarchical labeling system 3002 is integrated within and/or utilizes the medical scan assisted review system 102 and/or the medical scan annotator system 106.

As shown in FIG. 12A, the medical scan hierarchical labeling system 3002 can store labeling application data 3020 of a labeling application associated with the medical scan hierarchical labeling system 3002. The labeling application data 3020 can include a plurality of prompt decision trees. The plurality of prompt decision trees can include a diagnosis prompt decision tree 3022, a characterization prompt decision tree 3024, and/or a localization prompt decision tree 3026. The labeling application data 3020 can be sent to the one or more client devices. The labeling application data can be stored as a client application as illustrated in FIG. 2A, stored in client memory device 240. The client processing device 230 can execute operational instructions of the labeling application data to enable the corresponding client device 120 to run the labeling application. The labeling application can include an interactive interface 3075 displayed on display device 270.

The client device can further receive a medical scan from the medical scan for labeling, for example, as a transmission from the medical scan hierarchical labeling system 3002, fetched directly from the medical scan database 342, and/or uploaded to the client device directly. As shown in FIG. 12B, the client device can utilize the labeling application to generate labeling data for the medical scan for transmission back to the medical scan hierarchical labeling system 3002. The labeling data can be mapped to the medical scan in the medical scan database, and can correspond to some or all fields of a medical scan entry 352, such as diagnosis data 440.

The medical scan database can correspond to a relational database and/or a database with a structured set of fields for the plurality of medical scan entries. The labeling data generated via the labeling application can correspond to the structured set of fields. In particular, each of the plurality of prompt decision trees can include leaf nodes that correspond to the structured set of fields, and the labeling application can display prompts to a user of the client device in accordance with the plurality of prompt decision trees. The labeling application can generate labeling data that corresponds to leaf nodes of the plurality of prompt decision tree, based on user input to the prompts indicating selections from sets of selection options that correspond to subsets of the structured set of fields. Requiring that all labeling data adheres to a uniform structure with a discrete set of possibilities in this fashion allows the labeling data to be consumable and easily utilized by other systems. For example, the labeling data can be utilized as training data for one or more other subsystems 101 train a medical scan analysis function.

The labeling application can be utilized by users such as radiologists and/or other labelers responsible for labeling and/or annotating medical scans of the medical scan database with diagnosis data. The interactive interface 3075 can display image data of the medical scan to such a user in conjunction with a plurality of prompts to provide diagnosis, characterization, and/or localization labeling of the medical scan for at least one abnormality identified by the user. The plurality of prompts can present a fixed set of differential diagnosis options allowing the user to select one or more of the differential diagnosis options corresponding to one or more abnormalities detected by the user in the medical scan. The plurality of prompts can present a fixed set of characterization options to classify, describe, or otherwise characterize the one or more differential diagnoses identified in the fixed set of diagnosis data options. The plurality of prompts can present a fixed set of localization options to indicate a region of interest and/or specific anatomical location associated with the one or more differential diagnoses identified in the fixed set of diagnosis data options.

The fixed sets of diagnosis options, characterization option, and/or localization options can correspond to a fixed set of hierarchical options, and can be characterized by a diagnosis prompt decision tree, a characterization prompt decision tree, and/or a localization prompt decision tree, respectively. FIGS. 12C, 12D, and 12E illustrate examples of a diagnosis prompt decision tree 3022, a characterization prompt decision tree 3024, and/or a localization prompt decision tree 3026, respectively. As illustrated, the diagnosis prompt decision tree 3022, the characterization prompt decision tree 3024, and/or the localization prompt decision tree 3026 can each include a root node, a plurality of internal nodes that each branch from the root node or another internal node, and a plurality of leaf nodes that each branch from the root node or an internal node. In particular, all of the fixed set of hierarchical diagnosis options, characterization options, and/or localization options can be represented by all of the leaf nodes of the diagnosis prompt decision tree, the characterization prompt decision tree, and/or the localization prompt decision tree, respectively. Each root node and internal node can include any number of branches corresponding to a plurality of options that can be selected in response to a prompt corresponding to the node. Each node can be located in one of a plurality of levels of the corresponding prompt decision tree, where each level is characterized by a number of branches from the root node.

The plurality of prompt decision trees can be stored in the application data as a data structures and/or abstract data type corresponding to trees in accordance with the structure of the corresponding decision trees. In some embodiments, other data structures and/or abstract data types are employed that indicate the plurality of decision trees and/or that cause the labeling application to select a set of prompts that are presented to the user as dictated by a corresponding prompt decision tree, to select a corresponding set of options for each prompt as dictated by a corresponding prompt decision tree, and/or to select an ordering of the set of prompts as dictated by a corresponding prompt decision tree, based on each user selection from the selected set of options. This can include filtering a total plurality of prompts and/or a total plurality of options based on user selections, in accordance with the corresponding decision tree. Thus, the labeling application can utilize a prompt selection algorithm that presents the prompts and options in accordance with at least one corresponding decision tree, even if the application data does not include any tree data structures. The examples presented in FIGS. 12C, 12D, and 12E present the behavior exhibited in execution of the labeling application by illustrating the prompt selection algorithm for selecting for the set of prompts that are presented to the user, the corresponding set of options for each prompt, and the ordering of the set of prompts. While the organization of data that includes these prompts and/or options can be stored in a corresponding tree structure in the application labeling data, any other data structure can be employed to organize storage of these prompts and/or options. Furthermore, any other data structure can be employed to organize storage of the instructions for such a prompt selection algorithm for selecting the prompts, the ordering of the prompts, and/or options associated with the prompts as discussed herein.

In presenting these prompt selection algorithms, FIGS. 12C-12E illustrate the distinction between different internal nodes and leaf nodes in accordance with the unique path from the root prompt. For example, diagnosis prompt 1.2 corresponds to the internal node reached after selecting selection option 1 from a set of selection options 1-N from the diagnosis root prompt to reach characterization prompt 1, and then selecting selection option 1.2 from a set of selection options 1.1-1.M. As presented in FIGS. 12C-12E, M, N, and R correspond to any integer number of branches from the corresponding node. The use of ellipses "[ . . . ]" as presented in FIGS. 12C-12E indicates that any number of additional selections were made to reach the corresponding node, and that the corresponding node can be at any level of the prompt decision tree. For example, leaf node 1.M. [ . . . ] indicates a leaf node that extends any number of branches from prompt 1.M. The prompt decision trees described herein can be of the same or different configurations presented in FIGS. 12C-12E.

The labeling application can require that a leaf node is reached in each prompt decision tree presented to the user, for example, where the interactive interface will not advance to a next prompt decision tree and/or will not exit until the user continues to make selections to ultimately advance to a leaf node. This ensures that the user's annotation of the medical fully characterizes at least one abnormality of the medical scan, while still producing structured, consumable labeling data.

Some or all of nodes of one or more prompt decision trees can correspond to a prompt presented to a user via the interactive interface, where a selected branch from the node to a next node away from the root node is determined based on user input corresponding to selection of an option corresponding to the branch. Furthermore, some or all nodes of one or more prompt decision trees can correspond to options presented to the labeling application internally, where selected branches from these nodes can be automatically determined for example, based on classifier data 420 of the scan itself such as the modality of the scan and/or anatomical region of the scan; based on leaf nodes reached in of other prompt decision trees; and/or based on another automatic determination that does not correspond to user input to the interactive interface. This can be utilized to advance from the root node to an internal node automatically, where a user is presented with the plurality of prompts of a prompt decision tree starting from this automatically selected internal node. This can also be utilized to automatically advance to an internal node or leaf node based on automatic determinations corresponding to selections of branches to advance down the decision tree, where the automatic determinations are made by the labeling application without user input.

The labeling application can include a plurality of diagnosis prompt decision trees, a plurality of characterization prompt decision trees, and a plurality of localization prompt decision trees for each modality, each anatomical regions, and/or for other scan classifier data 420. For example head CTs, chest x-rays, and chest CTs can each correspond to their own diagnosis prompt decision tree, a characterization prompt decision tree, and localization prompt decision tree. In such embodiments, the labeling application can automatically determine a modality, anatomical region, and/or other category of the medical scan, and can further automatically determine which of the plurality of trees will be used based on the determined category.

The interactive interface can display each of a plurality of prompts to a user of the client device, one at a time, in accordance with the diagnosis prompt decision tree, characterization prompt decision tree, and/or localization prompt decision tree of the labeling application data 3020. The user can select one of a fixed set of options indicated by each of the plurality of prompts of the diagnosis prompt decision tree as user input via interaction with the interactive interface 3075. The selected one of the plurality of options can dictate the next one of the plurality of prompts, in accordance with the corresponding prompt decision tree. These prompts can continue to be displayed in sequence to the user, progressing to the next prompt indicated by the prompt decision tree as the user selects one of the plurality of options presented in accordance with each prompt, until a leaf node of the prompt decision tree is reached. The leaf node can indicate some or all of the selections made by the user in previous nodes of the prompt decision tree from a root node to the leaf node.

Furthermore, each set of options presented for a prompt corresponding to an internal node can include only an appropriate set of options that are possible given the previous selections corresponding to branches from the root node to the diagnosis prompt node. This effectively filters the set of options presented to the user given the selections made so far, ensuring the set of presented options includes only valid options. These appropriate sets of options can be predetermined by an administrator or other user responsible for creating the prompt decision trees. In some embodiments, the medical scan hierarchical labeling system 3002 automatically determines the options presented for each prompt of a decision tree based on a known set of rules, for example, corresponding to possible options given modality, anatomical regions, and user selections that must be made to reach the corresponding node. In some embodiments, the medical scan hierarchical labeling system 3002 automatically optimizes an ordering of some or all of the prompts. In some embodiments, identical prompts are included in multiple paths of a prompt decision tree, but are presented in different orders. In some embodiments, an ordering of prompts to each leaf node is determined to optimize an expected number of branches necessary to reach a leaf node, optimize the average number of branches to reach a leaf node, to reduce or otherwise optimize the number of selection options presented in one or more prompts of one or more nodes, and/or to otherwise optimize the prompt decision tree. In some embodiments, the set of prompts to reach each leaf node is automatically determined to ensure the corresponding abnormality of each leaf node will be fully described in reaching the leaf node. In some embodiments, the number of this set of prompts is minimized, while still ensuring the corresponding abnormality of each leaf node will be described to a necessary extent in reaching the leaf node.

The interactive interface can first present the user with a prompt asking whether or not an abnormality is present, as shown in FIG. 12C. If the user selects "no", the diagnosis prompt decision tree can immediately branch to a leaf node indicating no abnormality is present, and the labeling data can correspond to a structured entry of the medical scan database indicating no abnormality is present. If the user selects the option indicating an abnormality is present, the interactive interface can display a diagnosis root prompt with a plurality of selection options 1-N. The user can select a single one of the N selection options to progress to the corresponding next diagnosis prompt 1-N. For example, the user can select option 1, and the interactive interface will display diagnosis prompt 1 in response, indicating a set of selection options 1.1-1.M. If the user selects option 1.1.1 in response to diagnosis prompt 1.1, leaf node 1.1.1 is reached. Labeling data corresponding to the diagnosis can indicate the diagnosis corresponding to leaf node 1.1.1. The leaf node can effectively indicate all of the selections made from the root node to reach the leaf node. Thus, the labeling data generated in response to selection of the leaf node can further indicate each of the individual selections made by the user to reach the leaf node, for example, where the labeling data indicates selection option 1, selection option 1.1, and selection option 1.1.1.

Each selection option 1, 1.1, and 1.1.1 can correspond to its own field of the relational database, and/or the relational database can include fields corresponding to only the set of leaf nodes, for example, with a binary indication of whether or not the diagnosis corresponding to each leaf node is present. In some embodiments, the database includes a single diagnosis field populated by one of the fixed set of options indicated by the one of the plurality of leaf nodes of the diagnosis prompt tree. The medical scan database can employ any structure with a discrete set of possible diagnosis entries corresponding to a corresponding discrete set of diagnosis options corresponding to the discrete set of leaf nodes of the diagnosis decision tree.

In some embodiments, the labeling application can automatically determine a starting node of the diagnosis decision tree, corresponding to one of the interior nodes rather than the root node. In particular, the labeling application can automatically determine the starting node of the diagnosis decision tree based a determined modality of the medical scan, based on a determined anatomical region of the medical scan, and/or other scan classifier data 420 of the medical scan. Leaf nodes branching from the selected starting node will only include diagnosis options corresponding to abnormalities that can be detected in the corresponding anatomical region of the medical scan and/or that can be detected in the corresponding modality of the medical scan.

For example, the labeling application automatically proceed to selection option 1 that indicates plurality of abnormalities associated with the head in response to determining that the medical scan is a head CT scan. In such embodiments, diagnosis prompt 1 will only present options corresponding to abnormalities that correspond to the head, and that can be detected in a head CT. Any leaf nodes 1.[ . . . ] that branch from diagnosis prompt 1 will only correspond to final diagnosis that correspond to the head, and that can be detected in a head CT. For example, the fixed set of options indicated by leaf nodes 1.[ . . . ] can include "brain tumor", and "brain bleed", but will not include "wrist fracture" or "pulmonary embolism."

As another example, the labeling application can proceed automatically to a selection option 2.1 in response to determining that the medical scan is a chest x-ray. For example, a selection option from the diagnosis root prompt can correspond to selecting the anatomical region of the medical scan from a set of anatomical regions, where selection option 2 corresponds to the chest. Diagnosis prompt 2 can correspond to selecting the modality from a plurality of modalities, where selection option 2.1 corresponds to an x-ray. In such embodiments, diagnosis prompt 2.1 will only present options corresponding to abnormalities that correspond to the chest, and that can be detected in an x-ray of the chest. Any leaf nodes 2.1.[ . . . ] that branch from diagnosis prompt 2.1 will only correspond to final diagnosis that correspond to the chest, and can be detected in a chest x-ray. For example, the fixed set of options indicated by leaf nodes 2.1.[ . . . ] can include "rib fracture" or "pneumonia" because they can be identified by a chest x-ray. However, "pulmonary embolism" is not included in the leaf nodes 2.1.[ . . . ], even though this condition is associated with the chest, because leaf nodes 2.1.[ . . . ] correspond to an x-ray modality, and because reviewing an x-ray alone is not sufficient to determine whether a pulmonary embolism is present or absent. However, if selection option 2.2 corresponds to a CT scan, any leaf nodes 2.2.[ . . . ] that branch from diagnosis prompt 2.2 will only correspond to a final diagnosis that corresponds to the chest and that can be detected in a chest CT. Thus, leaf nodes 2.2.[ . . . ] can include "pulmonary embolism" as a selection option because this condition can be determined to be present or absent in reviewing a chest CT.

In some embodiments, a medical scan entry can include any variable number of differential diagnosis, where each of the variable number of differential diagnosis are included in the same field or the variable number of different fields, and where each of the variable number of differential diagnosis corresponds to a different one of the discrete set of leaf nodes of the diagnosis decision tree. In such embodiments, after reaching a leaf node of the diagnosis decision tree, the user can be prompted with a question of whether or not there is another abnormality to characterize. In response to the user selecting "yes," the interactive interface can return to the root prompt, and/or the starting node determined based on the anatomical region and/or modality. Furthermore, a deeper starting node, branching from the initial starting node but further away from the root node, can be selected automatically as a result of selection of the first one or more leaf nodes that have already been selected, if these first one or more leaf nodes can narrow the set of options possible for additional differential diagnoses. In some embodiments, characterization and/or localization of the abnormality indicated in the first leaf node is completed in accordance with the characterization prompt decision tree and/or the localization prompt decision tree first, and once this characterization and/or localization is completed, the user is presented the option to identify, characterize, and/or localize additional abnormalities as differential diagnoses.

Once a leaf node is reached in the diagnosis decision tree and/or once it is indicated that no further abnormalities are present, the interactive interface can advance to prompts of the characterization prompt decision tree. FIG. 12D illustrates an example embodiment of a characterization prompt decision tree. The interactive interface can begin with the root node of the characterization prompt decision tree and/or the labeling application can automatically advance to an internal node based on the anatomical region and/or modality as discussed in conjunction with the diagnosis prompt decision tree Furthermore, as the set of options that can be used to characterize an abnormality depends on the type of abnormality itself, the labeling application can automatically advance to an even deeper internal node based on the leaf node of the diagnosis decision tree that was ultimately selected. For example, as shown in FIG. 12C, a characterization prompt X progressing from leaf node 1.1.1 can correspond to any characterization prompt node of the characterization prompt decision tree determined to be an automatic starting node given a diagnosis corresponding to leaf node 1.1.1. Other leaf nodes of the diagnosis prompt decision tree can also cause the interactive interface to automatically progress to their own pre-determined starting node of the characterization prompt decision tree.

From the selected starting node of the characterization prompt decision tree, the corresponding diagnosis can be characterized based on selections from the starting node, where the interactive interface presents successive prompts corresponding to the nodes branching based on selections to previous prompts, until a leaf node of the characterization prompt decision tree is reached. In embodiments where multiple leaf nodes for multiple abnormalities have already been selected from the diagnosis prompt decision tree, each of these abnormalities can be characterized separately, each with their own automatically determined starting node based on the corresponding leaf node, where a separate leaf node of the characterization decision tree is ultimately reached for each of these differential diagnoses.

The user can indicate if one or more differential diagnoses, identified via selection of multiple leaf nodes of the diagnosis prompt decision tree, correspond to side effects of a main one of the differential diagnoses. This can be performed in the plurality of characterization prompts, where one or more side effects are indicated and characterized as part of characterizing the main diagnosis. As one example, illustrated in FIG. 12D, once a diagnosis is characterized and a leaf node is reached, the user will be prompted with a question asking whether or not the diagnosis is further characterized by any side effects. If so, a selected starting diagnosis prompt Y of the diagnosis prompt decision tree will be presented, and the interactive interface will present prompts of the diagnosis prompt decision tree until a leaf node of the diagnosis prompt decision tree is ultimately selected for each side effect. Furthermore, each side effect can be further described via selection of leaf nodes in the characterization prompt decision tree and/or the localization prompt decision tree for the each side effect. As another example, after the user identifies a plurality of differential diagnoses, the interactive interface can present a prompt to select at least one main diagnosis from the plurality of differential diagnoses, and can further present a prompt to identify at least one of the remaining differential diagnoses as side effects of the main diagnosis.

For example, if a head CT includes a brain tumor, brain bleed, and fracture, the brain bleed and fracture can be indicated as side effects of the brain tumor. The user can reach leaf nodes of the diagnosis decision tree corresponding to each of "brain tumor", "brain bleed", and "fracture". In particular, after the "brain tumor" leaf node is reached in the diagnosis prompt decision tree, the user can be prompted to identify one or more side effects of the brain tumor as part of characterizing the brain tumor via the characterization prompt decision tree. In response to the user selecting to identify a side effect, prompts of the diagnosis prompt decision tree will be displayed until the leaf node corresponding to "brain bleed" is ultimately reached. In response to the user selecting to identify an additional side effect, prompts of the diagnosis prompt decision tree will be displayed until the leaf node corresponding to "fracture" is ultimately reached. In response to the user selecting that no more side effects are present, the user can continue characterizing and/or advance to localizing the brain tumor itself. The brain bleed and fracture can also each be characterized and localized by ultimately reaching leaf nodes of the characterization prompt decision tree and localization prompt decision tree for each of these side effects.

Once a leaf node is reached in the characterization decision tree and/or once the user indicates that no further side effects are present, the interactive interface can advance to prompts of the localization prompt decision tree 3026, presented in FIG. 12E. The interactive interface can begin with the root node of the localization prompt decision tree and/or the labeling application can automatically advance to an internal node based on the anatomical region and/or modality as discussed in conjunction with the diagnosis prompt decision tree and the characterization prompt decision tree. Furthermore, as the set of options that can be used to localize an abnormality can depend on the type of abnormality itself, the labeling application can automatically advance to an even deeper internal node based on the leaf node of the diagnosis prompt decision tree that was ultimately selected, and/or based on the leaf node of the characterization prompt decision tree that was ultimately selected. For example, as shown in FIG. 12D, a localization prompt Z progressing from leaf node 1.2.R can correspond to any localization prompt node of the localization prompt decision tree determined to be an automatic starting node given a diagnosis and/or characterization corresponding to leaf node 1.2.R. Other leaf nodes of the characterization prompt decision tree can also cause the interactive interface to automatically progress to their own pre-determined starting node of the localization prompt decision tree.

From the selected starting node of the localization prompt decision tree, the corresponding abnormality can be localized based on selections from the starting node, where the interactive interface presents successive prompts corresponding to the nodes branching based on selections to previous prompts, until a leaf node of the localization prompt decision tree is reached. In embodiments where multiple leaf nodes for multiple abnormalities have already been selected from the diagnosis prompt decision tree as differential diagnoses and/or side effects, each of these abnormalities can be localized separately, each with their own automatically determined starting node based on the corresponding leaf node, where a separate leaf node of the localization decision tree is ultimately reached for each of these abnormalities.

In some embodiments, as an abnormality might be located in multiple places, the user can select any number of leaf nodes to localize each abnormality. For example, as shown in FIG. 12E, after reaching a leaf node such as leaf node 1.1.1, the user can be presented with an option to identify other locations in which the abnormality is present. In response to the user selecting "yes," the interactive interface can return to the root prompt, and/or the starting node determined based on the anatomical region and/or modality. Furthermore, a deeper starting node, branching from the initial starting node but further away from the root node, can be selected automatically as a result of selection of the first one or more leaf nodes of the localization prompt decision tree that have already been selected, if these first one or more leaf nodes can narrow the set of options possible for additional locations diagnoses, such as narrowing to a set of adjacent locations or locations within proximity of locations selected thus far.

At least one internal node of the localization prompt decision tree can require that multiple leaf nodes are reached to characterize the abnormality. For example, as shown in FIG. 12G, localization prompt 1 indicates that a number Q leaf nodes are required. Once a leaf node, such as leaf node 1.2.1 is reached, if the required number Q leaf nodes have not yet been selected, localization prompt 1 will be presented and the user can progress to leaf nodes, returning to localization prompt 1 until the required number of leaf node selections Q have been made. While the diagnosis prompt decision tree of FIG. 12C nor the characterization prompt decision tree of FIG. 12D illustrate internal nodes or root nodes requiring multiple leaf nodes be reached, such nodes requiring multiple leaf node selections can similarly be included in the diagnosis prompt decision tree or the characterization prompt decision tree in other embodiments.

In some embodiments, this required number of leaf nodes can inherently be built into the localization prompt decision tree with single required selection from each node. For example, instead of returning to localization prompt 1 from leaf node 1.2.1, the leaf node 1.2.1 can instead be an internal node 1.2.1 presenting localization prompt 1, with the same set of M selection options this internal node, allowing the user to continue to eventually reach the Q leaf node selections as a result of progressing down deeper sets of branches and identifying each of the Q leaf nodes as selections to the final, Qth leaf node along the way.

As a particular example, if a leaf node corresponding to "brain tumor" is selected from the diagnosis prompt decision tree, at least one lobe and at least one compartment must be selected in the step of localizing the brain tumor. The localization prompt decision tree can present the user with a plurality of lobe selection options and a plurality of compartment selection options, and can require that at least one leaf node corresponding to a lobe is selected, and that at least one leaf node corresponding to a compartment is selected. For example, once a lobe is selected, the same prompt can be presented, excluding the lobe that has already been selected, until one of the plurality of compartment options is also selected. As another example, the localization prompt decision tree can present a first prompt with only a plurality of lobe options in an internal node, and once one of the plurality of lobe options is selected, can branch to the next node that presents a second prompt with only a plurality of compartment options, where the leaf node ultimately reached indicates the selected lobe and the selected compartment. In such embodiments, each of the plurality of lobe selection options can branch to the identical prompt nodes presenting the plurality of compartment options.

In some embodiments, based on the diagnosis leaf node, characterization leaf node, and/or localization leaf node, an additional set of questions may be necessary. For example, when leaf node N.[ . . . ] is reached, at least one additional prompt will be presented. This additional set of questions can correspond to prompts of at least one additional prompt decision tree, where the questions are hierarchical and dependent on previous questions, and/or where leaf nodes of each additional prompt decision tree must be reached. The additional prompt set can be the same or different for different leaf nodes. The additional prompt set can depend only on the diagnosis leaf node, characterization leaf node, localization leaf node, and/or on a combination of two or more nodes. The additional prompt set can be further based on differential diagnoses or side effects. The additional prompt set can be based on the modality of the medical scan and/or the anatomical region of the medical scan. For example, if the medical scan corresponds to a head CT, the additional question set includes ventricular system questions that will automatically be presented via the interactive interface in response to an automatic determination that the medical scan is a head CT. In some embodiments, the additional prompt set is inherently included as additional internal nodes of the diagnosis prompt decision tree, characterization prompt decision tree, and/or localization prompt decision tree, ultimately reaching a final leaf node that includes answers to the additional questions. The answers to the additional questions can be included in the fixed format of the labeling data, where each of the additional questions similarly presents a fixed set of options. Alternatively or in addition, at least one additional question can correspond to unstructured data, such as text or voice input by the user, drawings and/or or shapes outlining one or more abnormalities superimposed upon the medical scan as user input entered by the user, measurement data indicating size, shape, diameter, and/or volume of abnormalities as identified by the user, a report entered by the user, or other unstructured data. In some embodiments, this unstructured data can be mapped to the medical scan in the database, but can be separate from the rest structured labeling data.

In some embodiments, the medical scan includes a plurality of image slices. The user can be prompted to select a proper subset of slices and/or a single slice that includes an abnormality to be described in the labeling data. A user selection that indicates a selected subset of the plurality of images slices of the medical scan can be received via user input to the interactive interface. This prompt can be included in the localization prompt decision tree and can dictate further prompts of the localization prompt decision tree based on a narrowed anatomical location corresponding to the proper subset of slices and/or the single slice. Alternatively, this prompt can be presented separately from prompts of the localization prompt decision tree, and the starting localization prompt can be selected based on the selected subset of the plurality of image slices. For example, if a subset of slices selected by the user indicates the frontal lobe of a head CT, localization prompts presented by the user interface will include options corresponding to the selection of the frontal lobe.

The user can be prompted to provide an urgency ranking as part of a prompt decision tree, additional question set, and/or as a final prompt presented to the user. The urgency ranking prompt can similarly include a fixed set of urgency ranking options for selection by the user to indicate an urgency associated with the diagnosis, associated with further review of the medical scan, and/or associated with further scans, tests, or appointments with the patients that may be necessary. The urgency ranking can be included in the labeling data, and/or can be utilized in triaging of the medical scan by one or more subsystems.

In some embodiments, one or more of the nodes of one or more of the prompt decision trees can be optional, where a user selection is not required. Such nodes can include a "skip" branch, indicating that selection of one or more of the selection options is not necessary for this prompt. Selecting the skip option can correspond to a branch that advances to a next node in the prompt decision tree.

While the discussion thus far indicates that the user first selects a leaf node of the diagnosis prompt decision tree, then a leaf node of the characterization prompt decision tree, and finally a leaf node of the localization prompt decision tree, prompts of the diagnosis prompt decision tree, the characterization prompt decision tree, and the localization prompt decision tree can be presented in any order. For example, the user might first localize the abnormality, and then based on this localization, a starting node of the diagnosis prompt decision tree is determined based on types of abnormalities that can exist and/or be observed at the particular location indicated in the localization leaf node.

Furthermore, while FIGS. 12C-12E present the diagnosis prompt decision tree, characterization prompt decision tree, and localization prompt decision tree separately, prompts corresponding to diagnosis, characterization, and localization of one or more abnormalities can be included in a single prompt decision tree of the labeling application data, where reaching a leaf node of the single prompt decision tree includes selecting at least one diagnosis option from at least one internal node corresponding to a diagnosis prompt, selecting at least one characterization option from at least one internal node corresponding to a characterization prompt, and selecting at least one localization option from at least one internal node corresponding to a localization prompt. In some embodiments, the flow of prompts to at least one leaf node includes a plurality of diagnosis prompts, characterization prompts, and localization prompts in any order, for example, where first a localization prompt is presented, then a diagnosis prompt, then another localization prompt, and then a characterization prompt. In some embodiments, multiple prompt decision trees that includes this mix of diagnosis prompts, characterization prompts, and/or localization prompts are included in the labeling application data. Each of these multiple prompt decision trees can correspond to a different modality, a different anatomical region, a different modality/anatomical region pair, and/or other different scan classifier data 420.

The labeling application can be utilized by multiple client devices corresponding to multiple users, and each user can label multiple medical scans by utilizing the labeling application. Labeling data generated over time by one or more users for one or more medical scans can tracked in a user database 344, where the number of scans labeled by each user of each client device is tracked. The user database can further track how many scans have been labeled for each of a set of scan categories corresponding to different modalities, different anatomical regions, and/or other categories indicated by scan classifiers data 420. Users can be incentivized and/or rewarded for reaching a threshold number of labeled scans in one or more scan categories and/or reaching a total number of labeled scans. Similarly, users can be can be incentivized and/or rewarded for reaching and/or maintaining a threshold labeling rate in one or more scan categories and/or reaching and/or maintaining a threshold labeling rate overall. In some embodiments, users can be incentivized to label scans in categories with a count and/or labeling rate that is below a threshold for that user, encouraging the user to expand their skills and label scans of modalities and/or anatomical regions they do not typically label. In some embodiments, users can be incentivized to label scans in categories with a count and/or labeling rate that is below a global threshold across all users, for example, corresponding to scan types that are not addressed enough by users across the system, to encourage the user to meet this need. The incentives can include financial incentives, can include a favorable adjustment to performance score data and/or qualification data, and/or can include advancing a user to an expert status in one or more scan categories in which a number and/or labeling rate compares favorably.

In some embodiments, a medical scan can be automatically pre-processed to partition the medical scan in accordance with multiple anatomical regions included within the medical scan. For example, a full body scan can be partitioned into a set of medical scan portions, where each medical scan portion corresponds to each of a set of anatomical regions. For example, the full body scan can be partitioned into medical scan portions corresponding to the head, chest, arm, leg, etc. for individual labeling. These partitions can each be labeled by the same user or by different users. For example, the medical scan hierarchical labeling system 3002 can perform this pre-processing step prior to transmission of the medical scan to a client device. The different medical scan portions can be sent to different users for labeling based on determining each user has favorable qualification data and/or performance score data for the corresponding anatomical region. The labeling data can be retrieved from all of the users and can be compiled for the original medical scan to be mapped to the medical scan database. In some embodiments, the pre-processing step is performed after a medical scan is retrieved by a client device as part of execution of the labeling application. Each partition can be presented in conjunction with prompt decision trees corresponding to the anatomical region of each partition and/or in conjunction with starting nodes of the prompt decision trees determined based on the anatomical region of each partition.

As presented in FIGS. 12A and 12B, the labeling application is executed by the client device, allowing the client device to generate all of the labeling data locally, and this final labeling data is then transmitted back to the medical scan hierarchical labeling system 3002 via the network. In some embodiments, some or all of the steps performed by the client device in accordance with execution with the labeling application can be instead executed by the medical scan hierarchical labeling system 3002. This can be accomplished via additional transmissions between the medical scan hierarchical labeling system 3002 and the client device.

For example, some or all of the user input, such as user selection of a selection option of a prompt, can be transmitted via the network the medical scan hierarchical labeling system 3002. The medical scan hierarchical labeling system 3002 can utilize the corresponding prompt decision tree, stored in memory of the medical scan hierarchical labeling system 3002, to determine the next prompt that will be presented to the user and the corresponding set of options. This next prompt and corresponding set of options can be transmitted to the client device for display via the interactive interface, where one of this set of options is selected by the user via user input, and is transmitted back to the medical scan hierarchical labeling system 3002. Another next prompt and another next set of options is determined by medical scan hierarchical labeling system 3002 based on the prompt decision tree for transmission back to the client device. This process can continue until a leaf node is ultimately selected.

As another example, the medical scan hierarchical labeling system 3002 can automatically select the starting node for one or more of the prompt decision trees based on the anatomical region, modality, and/or other features of the medical scan, in conjunction with transmission of the medical scan. An indicator of the starting node can be transmitted to the client device, and the client device can present the plurality of prompts beginning with the starting node based on the indicator of the starting node received from the medical scan hierarchical labeling system 3002.

As another example, the medical scan hierarchical labeling system 3002 can automatically select the starting node for one or more of the prompt decision trees based on the anatomical region, modality, and/or other features of the medical scan that is transmitted to the client device. A subset of the corresponding one or more prompt decision trees is selected by the medical scan hierarchical labeling system 3002, where the root node of the subset is the selected starting node, and where the subset includes internal nodes and leaf nodes that extend from the starting node. This subset of the one or more prompt decision trees can transmitted to the client device for use, where the remainder of the one or more prompt decision trees is not transmitted to the client device and/or not stored by the client device. This subset of the one or more prompt decision trees can be utilized by the client device to present the plurality of prompts.

As shown in FIG. 12F, a medical scan training set can be retrieved from the medical scan database 342. The medical scan hierarchical labeling system 3002, or another subsystem 101, can perform a training step 3090, for example, by utilizing the medical scan image analysis system and performing training step 1352 of FIG. 7A. The medical scan training set can include medical scans that were labeled by one or more client devices by utilizing the medical scan hierarchical labeling system 3002 as discussed in conjunction with FIGS. 12A-12E. In particular, labeling data mapped to the medical scans of the medical scan training set was generated by client devices based leaf nodes reached in the diagnosis prompt decision tree, characterization prompt decision tree, and/or localization prompt decision tree. This labeling data is indicated for each medial scan in the medical scan training set, for example, as a structured entry in the medical scan database. The labeling data for each medical scan in the training set can be utilized as an output feature vector and/or output nodes of a neural network in the training step 3090, where the output feature vector and/or output nodes are structured in accordance with the fixed structure of the labeling data. The input feature vector and/or input nodes of the neural network can correspond to image data of each medical scan in the training set, patient history data of each medical scan in the training set, and/or other data of the corresponding medical scan entry of each medical scan in the training set. Once the model is trained, model data can be transmitted to the medical scan function analysis database 346 to be utilized by one or more other subsystems 101. Alternatively or in addition, the model data can be transmitted to the medical picture archive integration system 2600 to be utilized in performance of inference functions by the medical picture archive integration system 2600.

The model data can be utilized by the medical scan hierarchical labeling system 3002, or another subsystem 101, as shown in FIG. 12G to generate inference labeling data for one or more new medical scans to be labeled, for example, retrieved from the medical scan database 342, by performing an inference function 3095 that utilizes the trained model. For example, the medical scan image analysis system 112 and/or the inference step 1354, detection step 1372, and/or abnormality classification step 1374 of FIG. 7B can be utilized to generate inference labeling data for new medical scans. The inference labeling data can correspond to the same fixed structure of the labeling data generated by utilizing the labeling application, dictated by the fixed set of abnormality options, the fixed set of classification options, and the fixed set of localization options. The inference labeling data can indicate probability values for one or more of the fixed set of abnormality options, one or more of the fixed set of classification options, and/or one or more of the fixed set of localization options. These probability values can indicate probabilities that one or more of the fixed set of abnormality options is present in the scan and/or in a region of the scan corresponding to a probability matrix corresponding to the probability value, that one or more of the fixed set of classification options describes the one or more of the fixed set of abnormality options, and/or that the abnormality is located in the one or more of the fixed set of localization options. The inference labeling data can be mapped to the new medical scan in the medical scan database and/or can be transmitted to a client device for display to a user via a user interface.

In various embodiments, medical scan hierarchical labeling system includes a medical scan database that stores a plurality of medical scan entries, at least one processor, and a memory. The memory stores labeling application data that includes application operational instructions and a plurality of prompt decision trees. The plurality of prompt decision trees includes a diagnosis prompt decision tree, a characterization prompt decision tree, and a localization prompt decision tree. Each of the plurality of prompt decision trees includes a root node, a set of internal nodes, and a set of leaf nodes. Each root node and each of the set of internal nodes correspond to one of a plurality of prompts. Each root node and each of the set of internal nodes include a set of branches that each correspond to one of a discrete set of selection options for the one of the plurality of prompts. The memory further stores a medical scan relational database that stores a plurality of medical scan entries. The medical scan relational database includes a discrete set of fields corresponding to the leaf nodes of the plurality of prompt decision trees.

The executable instructions, when executed by the at least one processor, cause the medical scan hierarchical labeling system to transmit, via a network, labeling application data to a client device for storage. The application operational instructions of the labeling application data, when executed by at least one client device processor of the client device, cause the client device to execute a labeling application. The executable instructions further cause the medical scan hierarchical labeling system to transmit via the network, a medical scan to the client device.

Execution of the labeling application by the client device causes the client device to, in response to receiving the medical scan, display, via an interactive interface presented on a display device associated with the client device for display to a user associated with the client device, image data of the medical scan. The client device automatically determines a starting diagnosis prompt by selecting one of the set of internal nodes of the diagnosis prompt decision tree based on an anatomical region of the medical scan and further based on a modality of the medical scan. The client device displays, via the interactive interface, a plurality of diagnosis prompts of the diagnosis prompt decision tree, in succession, beginning with the starting diagnosis prompt, in accordance with corresponding nodes of the diagnosis prompt decision tree until a first one of the set of leaf nodes of the diagnosis prompt decision tree is ultimately selected. The interactive interface progresses to each next one of the plurality of diagnosis prompts by selecting one of the set of branches of each corresponding node in accordance with each of a plurality of corresponding user diagnosis selections, received via user input. Each of the plurality of corresponding user diagnosis selections corresponds to one of the discrete set of selection options for each one of the plurality of diagnosis prompts displayed via the interactive interface.

The client device automatically determines a starting characterization prompt by selecting one of the set of internal nodes of the characterization prompt decision tree based on the anatomical region of the medical scan, based on the modality of the medical scan, and further based on the first one of the set of leaf nodes of the diagnosis prompt decision tree. The client device displays, via the interactive interface, a plurality of characterization prompts, in succession, beginning with the starting characterization prompt, in accordance with corresponding nodes of the characterization prompt decision tree until a first one of the set of leaf nodes of the characterization prompt decision tree is ultimately selected. The interactive interface progresses to each next one of the plurality of characterization prompts by selecting one of the set of branches of each corresponding node in accordance with each of a plurality of corresponding user characterization selections, received via user input. Each of the plurality of corresponding user characterization selections corresponds to one of the discrete set of selection options for each one of the plurality of characterization prompts displayed via the interactive interface.

The client device automatically determines a starting localization prompt by selecting one of the set of internal nodes of the localization prompt decision tree based on the anatomical region of the medical scan, and further based on the modality of the medical scan. The client device displays via the interactive interface, a plurality of localization prompts, in succession, beginning with the starting localization prompt, in accordance with corresponding nodes of the localization prompt decision tree until a first one of the set of leaf nodes of the localization prompt decision tree is ultimately selected. The interactive interface progresses to each next one of the plurality of localization prompts by selecting one of the set of branches of each corresponding node in accordance with each of a plurality of corresponding user localization selections, received via user input. Each of the plurality of corresponding user localization selections corresponds to one of the discrete set of selection options for each one of the plurality of localization prompts displayed via the interactive interface.

The client device transmits, via the network, labeling data that includes a set of labels indicating the first one of the set of leaf nodes of the diagnosis prompt decision tree, the first one of the set of leaf nodes of the characterization prompt decision tree, and the first one of the set of leaf nodes of the localization prompt decision tree.

The executable instructions, when executed by the at least one processor of the medical scan hierarchical labeling system, further cause the medical scan hierarchical labeling system to receive, via the network, the set of labels from the client device, and to populate a medical scan entry of the medical scan in the medical scan relational database based on the set of labels.

FIGS. 13A-13B present embodiments of medical scan annotator system 106, for example, when utilized in conjunction with the medical scan hierarchical labeling system 3002. As illustrated in FIG. 13A, the medical scan annotator system 106 can select a medical scan from the medical scan database 342 for transmission via network 150 to one or more client devices 120 associated with a selected user set 4010 corresponding to one or more users in the user database 344. A medical scan can be selected for annotation based on an assigned priority and/or based on a turn-based queue, for example, based on the scan priority data 427 of the corresponding medical scan entry 352. The client device 120 of each user of the selected user set 4010 can display one or more received medical scans to the via the interactive interface 275 displayed by a display device corresponding to the client device 120, for example, by displaying medical scan image data 410 in conjunction with the medical scan assisted review sy stem 102.

The interactive interface 275 displayed by client devices 120 of each user in the selected user set 4010 can include a prompt to provide annotation data 4020 corresponding to the medical scan. This can include a prompt to provide a text and/or voice description via a keyboard and/or microphone associated with the client device. This can also include a prompt to indicate one or more abnormalities in the medical scan, for example, by clicking on or outlining a region corresponding to each abnormality via a mouse and/or touchscreen. For example, the interactive interface can prompt the user whether or not an abnormality is present. If the user indicates an abnormality is present, the interactive interface can prompt the user to identify the region that includes the abnormality. This can include allowing the user to scroll through one or more slices, to identify one or more slices that contain the abnormality, and to select a region of the one or more slices that contains the abnormality. Once the region is identified, the interactive interface can prompt the user to provide descriptive information classifying an abnormality based on its size, type, etc. To aid the user in providing this information, the user interface can automatically crop one or more slices based on the identified region and/or zoom in on the identified region. In various embodiments, the medical scan can be presented for annotation by utilizing the medical scan assisted review system 102, for example, presented in the new annotation mode. The interactive interface 275 can present the medical scan by utilizing interface features indicated in the display parameter data 470 and/or the interface preference data 560 of the user, and/or the user can indicate the annotation data via the interactive interface 275 by utilizing interface features indicated in the display parameter data 470 and/or the interface preference data 560 of the user. For example, some or all of the annotation data 4020 can correspond to, or be automatically generated based on, user input to the interactive interface.

Annotation data 4020 can be transmitted from each client device of users in the selected user set 4010 to the medical scan annotator system 106, for example, in response to receiving input data via the interactive interface indicating that the annotations are complete. The annotation data 4020 can be raw annotation data corresponding directly to the user input, or can be further processed by the client device before transmission. For example, a more precise region corresponding to each abnormality can be determined automatically based on the user input and by determining actual boundary points of the abnormality by utilizing image processing techniques and/or text and/or voice input can be processed and/or parsed, for example, by utilizing a medical scan natural language analysis function and/or medical report analysis function to generate medical codes 447 or other diagnosis data 440 corresponding to the medical scan. Such processing can also be performed by the medical scan annotation system 106 and/or another subsystem when the raw annotation data is received.

The medical scan annotator system 106 can evaluate the set annotation data 4020 received from the selected user set 4010 to determine if a consensus is reached, and/or generate a final consensus annotation 4030, for example, by performing an annotation consensus function 4040. For example, consider a selected user set 4010 that includes three users. If two users annotate a medical scan as "normal" and the third user annotates the medical scan as "contains abnormality", the annotation consensus function 4040 performed by medical scan annotator system 106 may determine that the final consensus annotation 4030 is "normal" by following a majority rules strategy. Alternatively, the medical scan annotator system 106 can determine that a consensus is not reached because one of the users indicated that an abnormality is present, and that the medical scan should not be passed off as normal because a level of confidence that the scan is normal, determined by a calculated consensus confidence score 4050, does not exceed a consensus confidence threshold. The confidence thresholds required for consensus can differ for different types of scans and/or severity of diagnosis.

If the medical scan annotator system 106 determines that a consensus is achieved, it can automatically generate the final consensus annotation 4030, and can map this final consensus annotation to the medical image in the medical scan database in diagnosis data 440, and/or transmit the consensus annotation to an originating entity of the medical scan. The medical scan annotator system 106 can also map the calculated consensus confidence score to the medical image in the confidence score data 460. In some embodiments, a truth flag 461 will automatically be assigned to all final consensus annotation 4030 in the confidence score data 460 and/or will automatically be assigned to final consensus annotation 4030 that exceeds a truth threshold. In some embodiments, annotation data 4020 received from each user and/or a corresponding annotation confidence score can also be stored in the medical database, mapped to the corresponding user and/or the corresponding performance score in the annotation author data 450.

In some embodiments, for example where annotation data 4020 includes several attributes, the annotation consensus function 4040 performed by the medical scan annotation system 106 can determine whether a consensus is reached by calculating a difference between two or more received annotation data 4020, for example, by generating a feature vector for annotation data 4020 received from each user. Each feature vector can be generated based on keywords, medical codes, abnormality location in the medical scan, abnormality size and/or shape in the medical scan, a classification of the abnormality, or other attributes listed in annotation data 4020 received from each user. Performing the annotation consensus function 4040 can further include calculating the Euclidian distance or other vector distance between the two or more feature vectors. Performing the annotation consensus function 4040 can further include determining if consensus is reached by determining if the average of these Euclidian distances is below a certain discrepancy threshold, for example, after determining and removing outlier annotations from the set. Similarly, the annotation consensus function 4040 can further include determining if consensus is reached by first generating the final consensus annotation 4030, and then calculating the Euclidian distance between each annotation feature vector and the final consensus annotation 4030, where consensus is determined to reached and the final consensus annotation is confirmed only if the average of these calculated Euclidian distances is below a certain discrepancy threshold. The annotation consensus function 4040 can calculate the final consensus annotation 4030 itself by creating a consensus feature vector, where each attribute of the consensus feature vector is determined by calculating a mean, median or mode of each corresponding annotation feature extracted from all of the received annotation data 4020. In this fashion, calculating the consensus confidence score 4050 can include calculating such an average Euclidian distance, where distances with larger magnitudes correspond to lower or otherwise less favorable consensus confidence scores 4050, and where distances with smaller magnitudes correspond to higher or otherwise more favorable consensus confidence scores 4050. Alternatively or in addition, the final consensus annotation 4030 can be generated based on the most closely matching annotations and/or based on another average, for example, calculating an average identified region that includes an abnormality.

The annotation consensus function 4040 further determine whether or not consensus is reached based on overall or categorized performance score data 530 and/or qualification data 540 of each user in the selected user set 4010. For example, each annotation data 4020 can be weighted based the performance scores and/or qualifications of the corresponding user. In the example where two users annotate a medical scan as "normal" and a third user annotates a medical scan as "contains abnormality", the medical scan annotator system 106 may determine that the consensus is "contains abnormality" based on the third user having a much higher performance score and/or being more highly qualified than the first two users. The final consensus annotation 4030 can be generated based on the annotation received from a user with the highest ranking in the category corresponding to the medical scan. The final consensus annotation 4030 can be generated based on calculating a weighted average annotation by computing a weighted consensus feature vector, where feature vectors of higher ranked users receive a higher weight. In some embodiments, each feature of the feature vector can be computed using a different set of user weights, for example, where the different feature weights for each user is determined based on corresponding category-based performance score data and/or qualification data.

Alternatively or in addition, the performance score data associated with the interface features of the interactive interface 275 used by each user to annotate the image can also be utilized to weight the different annotations in reaching consensus. Such weights can be applied when generating a consensus feature vector, where each annotation feature vector is weighted according to the performance score data of one or more corresponding interface features used by the corresponding user.

In some embodiments, confidence scores for each individual annotation can also be calculated for each user's annotation, and the consensus confidence score 4050 can be generated based on these confidence scores, for example, based on an average confidence score, based on confidence scores of annotation data that matches the final consensus annotation 4030, etc. In some embodiments, the final consensus annotation 4030 can be generated based on these confidence scores, for example, where annotation feature vectors are weighted based on a corresponding confidence score. The confidence scores for each annotation data 4020 can be generated automatically, for example, based on performance score data 530 as discussed herein. Individual confidence scores and/or a consensus confidence score 4050 can also be updated retroactively as new annotation data is received, for example, if new annotation data is received from another user, for example corresponding to an expert review when consensus is not reached, and/or if new annotation data is automatically generated by a subsystem after the consensus data is generated.

The medical scan annotator system 106 can also utilize auto-generated annotation data of the medical scan to determine if consensus is reached and/or to generate the final consensus annotation 4030. The auto-generated annotation data can be automatically generated by medical scan annotator system 106 by utilizing one or more medical scan analysis functions. The auto-generated annotation data can also be retrieved from the medical scan database 342 if it was generated by a subsystem 101 previously. One or more auto-generated annotations can be assigned their own weights and/or confidence scores, for example, based on the model accuracy data 631 and/or another determined performance of the function and/or subsystem responsible for creating each auto-generated annotation. Each auto-generated annotation data can be thus treated as an annotation from another user, and can be used to determine if consensus is reached and/or to generate the consensus annotation in the same fashion.

Alternatively, the auto-generated annotation can be merely verified based on the annotation data 4020 received from the selected user set 4010 by determining that the user annotations are close enough to the auto-generated annotation based on the discrepancy threshold. For example, this process may be utilized by the medical scan diagnosing system 108 to perform the output quality assurance step. The auto-generated annotation can be sent to the selected user set 4010 as part of this verification process, for example, displayed by each interactive interface 275 in conjunction with the medical scan assisted review system 102 as displayed annotation data, and the annotation data 4020 received from the selected user set 4010 can be include verification of and/or corrections of the auto-generated annotation. Alternatively, the medical scan can be sent without the auto-generated annotation and/or the auto-generated annotation can be hidden from view as part of a blind review, to ensure that the users are not biased in creating annotation data by the auto-generated annotation.

FIG. 13B illustrates an embodiment of the medical scan annotator system 106 upon determining that a consensus is not achieved, for example, because the calculated consensus confidence score 4050 does not exceed the consensus confidence threshold. The medical scan annotator system can select an expert user, for example, a user whose qualification data 540 indicates they are an expert in the category corresponding to the medical scan or who otherwise is identified as an expert based on their performance score data. The expert can receive the medical scan on a corresponding client device and annotate the image, for example, where the interactive interface 275 displays the medical scan image data 410 in conjunction with the medical scan assisted review system 102, and where the interactive interface utilizes interface features indicated in the display parameter data 470 of the medical scan and/or indicated in the interface preference data 560 of the user profile entry 354 of the expert user. The expert can view the annotation data 4020 generated by the selected user set 4010, for example, presented as the displayed annotation data of the medical scan assisted review system 102. Annotation data 4020 of each user can be displayed one at a time and the expert user can elect to advance to the next user's annotation data 4020. Alternatively, all of the annotation data 4020 can be displayed simultaneously for example, in different colors corresponding to each user's annotations and/or overlaid as translucent, highlighted regions, for example, where a portion of the highlighted region is more opaque when multiple users agree that the portion is included in the abnormality. In other embodiments, the annotation data 4020 can be hidden from the expert user, and the expert user can enter their own annotations in conjunction with a blind review to reduce bias.

Expert annotation data 4070 can be generated automatically, and can be transmitted automatically to the medical scan annotation system 106. The medical scan annotator system can automatically assign the received expert annotation data 4070 as the final consensus annotation 4030, and/or can assign a truth flag 461 to the expert annotation data 4070 in the confidence score data 460 of the medical scan. Alternatively, the expert annotation data 4070 can be compared to the previous annotation data 4020 and determine if consensus has been reached. For example, the expert annotation data 4070 and the annotation data 4020 can be collectively utilized by the annotation consensus function 4040, where the expert annotation data 4070 is assigned its own, higher weight than the other annotations. If consensus has still not been reached, the medical scan annotation system can continue to transmit the image other users and processing received annotations until consensus is reached, for example, selecting a new selected user set 4010 and/or selecting a new expert user.

The user profile entries 354 of each user in the selected user set 4010 and/or each expert user can be automatically updated by the medical scan annotator system 106 or another subsystem 101 by generating and/or updating performance score data 530 for each user based comparing their annotation to the final consensus annotation 4030. For example, the accuracy score data 531 of the performance score data 530 can be generated by calculating the Euclidian distance between a feature vector of a user's annotation and the feature vector of the consensus annotation as described previously, where a higher performance score is assigned to a user whose annotation is a smaller Euclidian distance from the consensus, and a lower performance score is assigned to a user whose annotation is a larger Euclidian distance from the consensus. The efficiency score data 532 of the performance score data can be automatically generated, for example, based on an annotation duration determined based on a difference between a first time that each user received the medical scan and a second time each user completed the annotation. The efficiency score data 532 can be further based on a difference between the annotation duration of each user and an average annotation duration computed for annotation durations of the selected user set. Aggregate performance data for each user can be generate and/or updated based on past accuracy and/or efficiency scores, based on how many scans have been annotated in total, based on measured improvement of the user over time, etc. Similarly, the performance score data 630 corresponding to medical scan analysis functions utilized to generate the auto-generated annotation data can be generated and/or updated by comparing the auto-generated annotation data to the final consensus annotation 4030 in a similar fashion and/or by comparing the computed annotation duration of a corresponding medical scan analysis functions to other computed annotation durations of other medical scan analysis functions that generated auto-generated annotation data for the medical scan.

The selected user set 4010 can be selected based on the performance score data 530 and/or qualification data 540 of each user corresponding to previous uses only the medical scan annotation system 106, or corresponding to usage of several subsystems 101. For example, a medical professional with a user profile indicating that he/she ranks above a certain threshold in annotating CT scans and/or indicating that he/she is highly qualified in the study of the lungs can be automatically selected by the medical scan annotator system to annotate a triaged medical scan identified as a lug CT scan. The size of the selected user set 4010 that receive a medical scan can be optimized based on the quality of the users selected, for example, based on calculating the probability of reaching consensus and/or calculating the probability that a consensus confidence score will be above a confidence threshold, and ensuring the probability falls above a probability threshold. For example, a first medical scan can be sent to a two medical professionals with high scores, qualifications, rankings, or correct annotation percentages. A second medical scan may be sent to ten medical professionals with lower scores or qualifications based on calculating that the probability of a correct consensus probability falls above a probability threshold.

In some embodiments, the medical scan annotator system 106 can first select a medical scan for annotation automatically, and in response, the selected user set 4010 can be determined automatically to annotate the selected medical scan based on determining users with highly ranked overall scores and/or based on categorized performance data 534 and/or qualification data 540 that corresponds to an identified scan classifier data 420 of the selected medical scan. Alternatively or in addition, the selected user set 4010 can be determined based on the size of a queue of medical scans already assigned to each user. For example, the selected user set 4010 can correspond to users with matching qualifications that correspond to the scan classifier data 420 and/or correspond to users with the lowest queues of other medical scans to annotate.

In other embodiments, the medical scan annotator system 106 can first determine one or more available users automatically, for example, based on medical scan queue lengths for each user in the system and/or in response to one or more users requesting to annotate a medical scan. In such cases, some or all of these identified users can be added to the selected user set 4010, and the medical scan can be selected based on corresponding categorized performance data 534, qualification data 540 or other relevant user profile data of users in the selected user set 4010.

Figure 13K:

FIGS. 13C-13V present example embodiments of a user interface of a medical scan annotator system 106, for example, presented in conjunction with the medical scan assisted review system 102. Some or all features presented in FIGS. 13C-13V can also be utilized in conjunction with other subsystems and can be included in the interface features. FIGS. 13C-13G present interface features for chest CT nodule characterization, and can be displayed in conjunction with a chest CT scan. Annotation data 4020 can be generated based on user selections in the user interface, and can be used to populate abnormality classification data 445 for abnormality classifier categories 444 such as "nodule spiculation", "nodule lobulation", "nodule texture", "nodule calcification", "nodule sphericity" and/or "nodule internal structure" for the associated medical scan. FIGS. 13H-13J present interface features for presentation to a user in conjunction with an identifying chest CT nodule, allowing a user to add new contours for one or more scans for a patient, for example, over multiple years, and indicate malignancy. As shown in FIG. 13K, the scan can be presented in conjunction with these interface features. FIGS. 13L-13O present interface features for presentation to a user in conjunction with identifying abnormalities in a chest x-ray. Users can classify each abnormality and draw a shape around each abnormality in the scan.

Figure 13P:
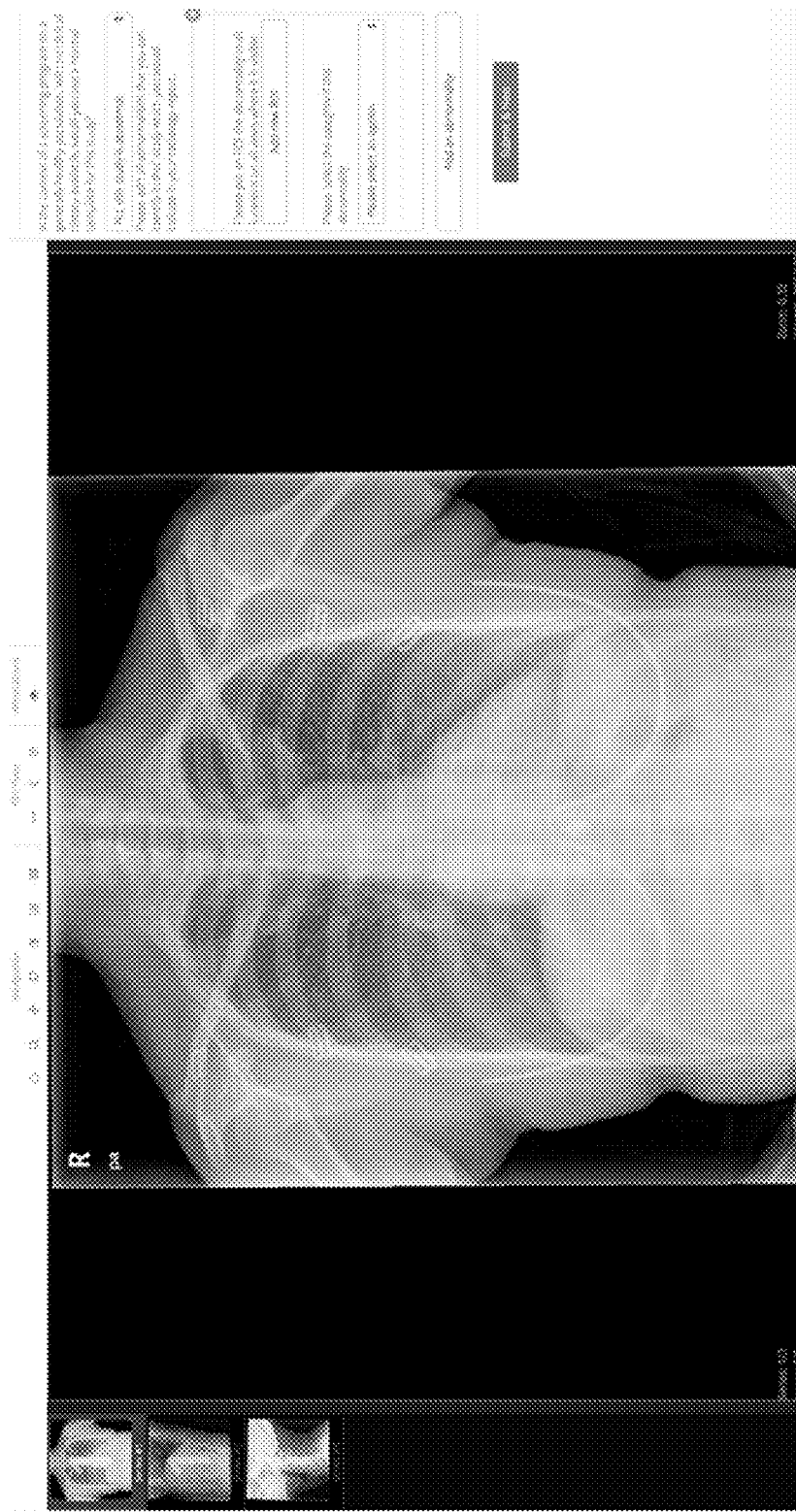
Figure 13Q:
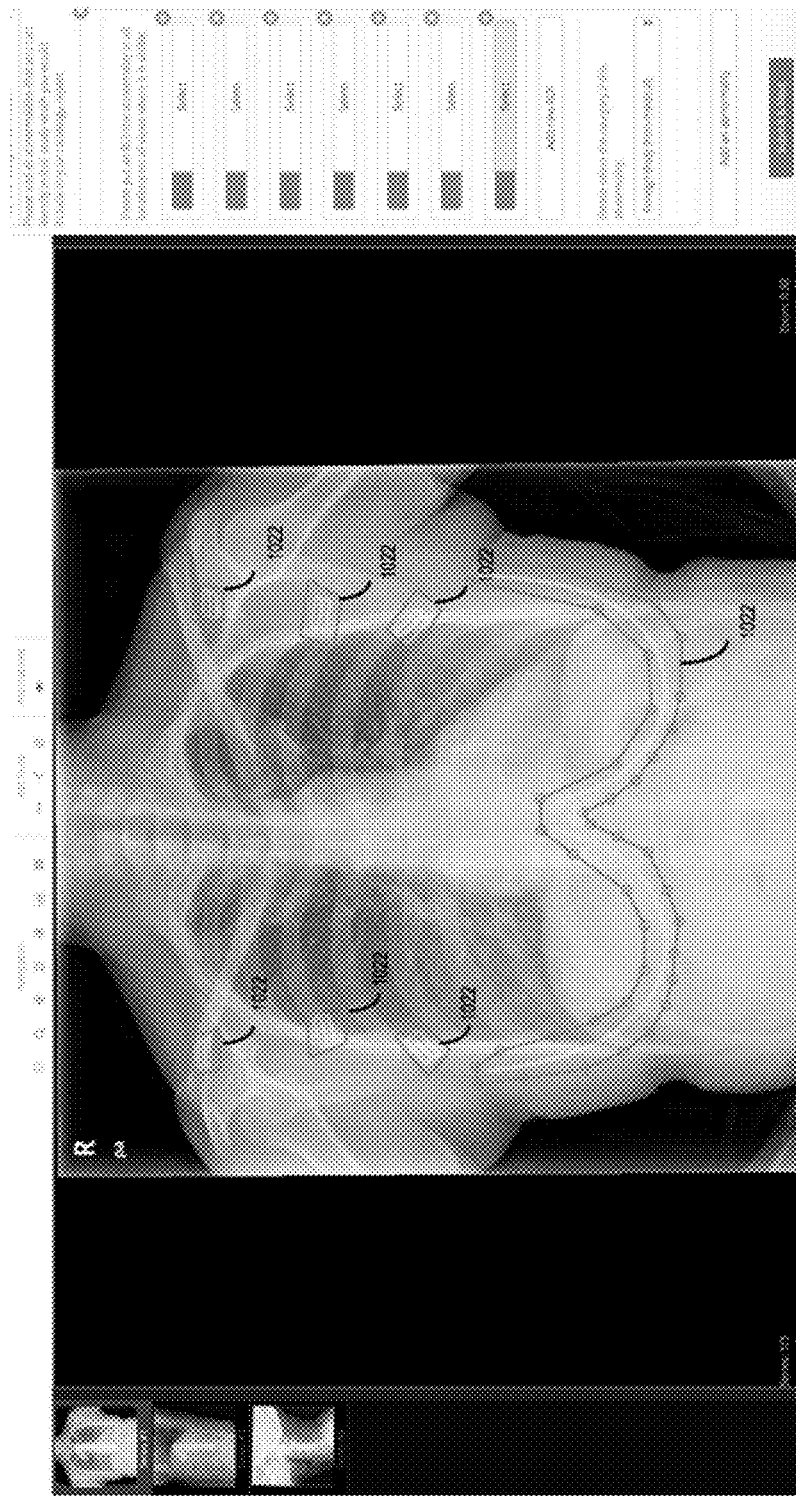
Figure 13R:
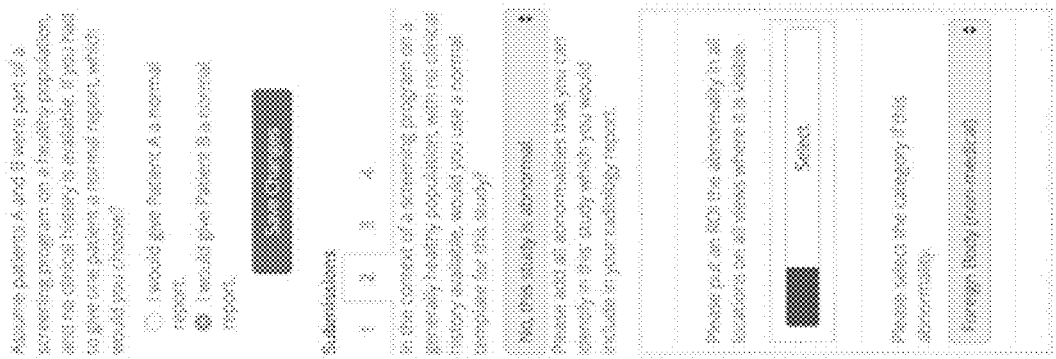

FIG. 13P presents a view of a chest x-ray presented via the interface before a user identifies regions of interest, and FIG. 13Q presents a view of the chest x-ray via the interface after the user identifies regions of interest of multiple abnormalities, indicated by seven polygons 1022. FIG. 13R presents interface features for comparing chest x-ray severity for multiple patients, displayed in conjunction with multiple x-rays that can be displayed in adjacent views or can be displayed one at a time where the user can toggle between them. A user can compare multiple scans corresponding to multiple patients, and provide feedback indicating differences between the patients, comparing if one patient's case is more severe than another, or determine which of two scans appears to be more normal.

FIGS. 13S-13V present interface features for chest x-ray triage classification, displayed in conjunction with a chest x-ray. A user can select abnormality classification data that can be used to generate annotation data 4020 and/or to populate abnormality classification data 445. As shown, some or all abnormality classification categories displayed, which can be determined based on abnormality classifier categories 444, can be presented, and hierarchal subcategories can be presented in response to a user selecting one of a plurality of abnormality classification categories that are present.

In some embodiments, the medical scan hierarchical labeling system 3002 is integrated within and/or utilizes features described in conjunction with the medical scan annotator system 106. In particular, the interfaces presented in some or all of FIGS. 13C-13V can be utilized by the medical scan hierarchical labeling system 3002, where options presented in in some or all of FIGS. 13C-13V can correspond to a set of selection options of a node in accordance with a prompt decision tree and/or where prompt decision trees of the medical scan hierarchical labeling system 3002 utilize at least one of the prompts and/or sets of options presented in in some or all of FIGS. 13C-13V as one or more prompts of one or more prompt decision trees, where the annotation data 4020 corresponding to the labeling data generated by the client device. The fixed set of diagnosis, characterization, and/or localization options can include some or all of the selections presented in in some or all of FIGS. 13C-13V, where fields of a medical scan entry correspond to some or all of the selections presented in in some or all of FIGS. 13C-13V and/or have valid entries corresponding to some or all of the selections presented in some or all of FIGS. 13C-13V.

The interactive interface can present hierarchical sets of options as a user advances through a prompt decision tree as presented in FIGS. 13S-13V, where each set of options is presented as an indented list in accordance with advancing to a deeper layer of the prompt decision tree, and where each set of options is not presented until the corresponding selection is made. For a hierarchical decision tree corresponding to the prompts presented in FIGS. 13S-13V, labeling data generated in response to a user selecting "submit and next" at FIG. 13V can indicate a leaf node of a first abnormality, with diagnosis, characterization, and localization data fully described as "pulmonary vasculature", "plethora", "diffuse", "left", and "lobe-left upper", and can further indicate a leaf node of a second abnormality with diagnosis, characterization, and localization data fully described as "mediastinum", "compression of structure", and "inferior-anterior".

FIGS. 14A-14C present an embodiment of a multi-label medical scan analysis system 5002. The multi-label medical scan analysis system can be operable to train a multi-label model, and/or can utilize the multi-label model to generate inference data for new medical scans, indicating probabilities that each of a set of abnormality classes are present in the medical scan. Heat maps for each of the set of abnormality can be generated based on probability matrices for display to via a display device.

As shown in FIGS. 14A-14C, the multi-label medical scan analysis system 5002 can communicate bi-directionally, via network 150, with the medical scan database 342 and/or with other databases of the database storage system 140, with one or more client devices 120, and/or, while not shown in FIG. 14A, with one or more subsystems 101 of FIG. 1.

In some embodiments, the multi-label medical scan analysis system 5002 is an additional subsystem 101 of the medical scan processing system 100, implemented by utilizing the subsystem memory device 245, subsystem processing device 235, and/or subsystem network interface 265 of FIG. 2A. For example, the multi-label medical scan analysis system 5002 can be implemented by utilizing the medical scan image analysis system 112 to train and/or utilize a computer vision model. In some embodiments, the multi-label medical scan analysis system 5002 utilizes, or otherwise communicates with, the central server system 2640. For example, the medical scan database 342 can be populated with de-identified data generated by the medical picture archive integration system 2600. The multi-label medical scan analysis system 5002 can receive de-identified medical scans of the training set with their corresponding annotation data, diagnosis data, and/or medical reports directly from the medical picture archive integration system 2600, for example, where the annotation data, diagnosis data, and/or medical reports are utilized to determine the medical labels for medical scans in the training set. As another example, the multi-label medical scan analysis system 5002 can perform an inference function on de-identified medical scans received from the medical picture archive integration system 2600, and probability matrix data and/or determined abnormality classes generated in the inference data can be assigned to the medical scan in the medical picture archive integration system 2600. As another example, the multi-label medical scan analysis system 5002 can request de-identified medical scans, annotation data, and/or reports that match requested criteria for the training set and/or for new medical scans to be labeled. In some embodiments, some or all of the multi-label medical scan analysis system 5002 is implemented by utilizing other subsystems 101 and/or is operable to perform functions or other operations described in conjunction with one or more other subsystems 101.

As shown in FIG. 14A, the multi-label medical scan analysis system can be operable to train a computer vision based model on a plurality of medical scans. A medical scan training set can be received from the medical scan database 342 and/or from another subsystem 101. The medical scan training set can include a plurality of medical scans of the same or different modality and/or anatomical region. For example, the medical scan training set can include exclusively chest x-rays. The medical scan training set can include a plurality of medical labels assigned to the plurality of medical scans. The medical labels assigned to a medical scan can correspond to at least one of a set of abnormality classes, and each medical scan in the training set can be labeled with zero, one, or a plurality of labels of the set of abnormality classes that are present in the medical scan. For example, when the training set includes chest x-rays, the set of abnormality classes can include atelectasis, effusion, mass, pneumonia, consolidation, emphysema, pleural thickening, cardiomegaly, infiltration, nodule, pneumothorax, edema, fibrosis, and/or hernia. The abnormality classes can correspond to some or all of the abnormality classifier categories 444, and/or can correspond to any set of abnormality types or categories, diagnosis types or categories, or medical conditions.

In some embodiments, the training set can further include region of interest data for some or all medical scans. The region of interest data can indicate a portion of the medical scan and/or an anatomical region where the medical label is present in the medical scan, and the model can be trained by utilizing this region of interest data. In other embodiments, no region of interest information is provided, and the at least one medical label assigned to a medical scan of the training data is considered a global label for the medical scan as a whole.

A training step 5010 can be applied to the medical scan training data to generate model parameters or other model data corresponding to a trained model. In some embodiments, multiple models are trained by utilizing multiple sets of training data, for example, where each set of training data corresponds to a different modality and/or anatomical region. Performing training step 5010 can include performing the training step 1352 of the medical scan image analysis system 112. In some embodiments, performing the training step 5010 includes training a neural network, for example where the image data of each the plurality of medical scans is the input data. A vector corresponding to the set of abnormality classes, populated by binary indicators corresponding to which medical labels correspond to each of the plurality of medical scans, can correspond the output data.

The output data of the training set can alternatively correspond to a N×N×K matrix, where the value of N corresponds to a highest-resolution level of a multi-resolution model, and where the value of K corresponds to number of abnormality classes in the set of abnormality classes. Each of the N×N values for each of the K classes can correspond to an image patch of two-dimensional image data, such as an x-ray or other two-dimensional medical image. When no region of interest data is available, each of the N×N values for each of the K classes can be populated with a binary indicator corresponding to whether the corresponding abnormality class is present in the image data as a whole, where each of the N×N values for the same K class are assigned to the same binary indicator. In the case where region of interest data is available in training, each of the N×N values for each of the K classes can be populated with a binary indicator corresponding to whether the corresponding abnormality class is present in the corresponding image patch of the image data.

In embodiments where the medical scans of the training set have a plurality of slices, an additional dimension M can correspond to the number of slices, where the output data of the training set corresponds to a N×N×M×K matrix, where each of the N×N×M values for each of the K classes corresponds to an image patch of the corresponding image slice. In some embodiments, other information of the medical scan accompanying the image data can be utilized as input data. For example, patient demographic and/or history data, and/or other fields of a corresponding medical scan entry 352 can be utilized to train the model along with the image data.

The model data generated by performing the training step 5010 can correspond to a multi-resolution model such as the model described in FIG. 15A. The model data can be transmitted to other subsystems 101 for use in implementing an inference function on new medical scans, can be transmitted to medical scan analysis function database 346 for access by one or more other subsystems 101, and/or can be stored locally by the multi-label medical scan analysis system 5002 for use in implementing an inference function on new medical scans.

As shown in FIG. 14B and FIG. 14C, the multi-label medical scan analysis system 5002 can receive new medical scans from the medical scan database 342 and/or from another subsystem 101. The multi-label medical scan analysis system 5002 can perform an inference function 5020 on the new medical scans by utilizing the model data generated as discussed in conjunction with FIG. 14A. The inference function can be performed on the image data alone, or can be performed on additional information along with the image data, such as metadata of the medical scan, patient demographic and/or history data, and/or other fields of a corresponding medical scan entry 352, for example, if the model was trained utilizing such information.

The output of the inference function 5020 can include a N×N×K matrix that indicates N×N probability values for each of the K classes. Each of the N×N values, for each of the K classes, can correspond to one of N×N image patches of the image data. Each of the N×N probability values for each of the K classes can correspond to a probability that the a corresponding one of the set of abnormality classes is present in the corresponding image patch. As discussed in conjunction with FIG. 14A, the value of N can correspond to a resolution of a plurality of resolution layers of the model. For example, if the size of the image data of the new medical scan is 1024×1024 pixels, the value of N can correspond to 64 for a total of $64^2$ image patches, each containing 16×16 pixels.

In some embodiments, the model data corresponds to a multi-resolution model consisting of multiple resolution layers, where low resolution layers capture context and/or semantic information, and high resolution layers capture finer details. In particular, the model can include a set of resolution layers, each with a different value n×n×K, where the value of n×n corresponds to the number of image patches the image is partitioned into at that resolution layer. Thus, higher values of n can correspond to higher-resolution of the layer. The set of resolution layers can include an 8×8 layer, a 16×16 layer, a 32×32 layer, and/or a 64×64 layer, and the 64×64 layer can correspond to the output layer.

In some embodiments, resolution of the input image data is reduced to lower and lower resolutions, for example, using ResNets. Resolution at each layer is preserved, for example, using DenseNets, to produce an initial feature map at each layer. Final feature maps can be generated at each layer, starting at the lowest resolution layer, and upsampling the results to generate the final feature maps at higher resolution layers. In particular, resolution preserving non-linear transformations can be incrementally applied be on a channel-wise concatenation of a previous feature map of the current layer and the upsampled feature map of the previous layer, for example, as discussed in conjunction with FIG. 15A. At the final, highest resolution layer, a probability matrix can be generated by applying a sigmoid function to the final feature map of the highest resolution layer, indicating probabilities for each instance (at 64×64 resolution), for each of the K classes. Spatial information is preserved by utilizing this coarse-to-fine approach, where at lower resolutions, weak localization cues can be further refined in subsequent higher resolutions. In particular, this preservation of spatial information allows abnormalities to be localized in inference function 5020 based on the output probability matrix, even in embodiments where no region of interest data was utilized in training step 5010.

In embodiments where the medical scans of the training set have a plurality of slices, an additional dimension M can correspond to the number of slices, where the output data of the training set corresponds to a N×N×M×K matrix, where each of the N×N×M values for each of the K classes corresponds to an image patch of the corresponding image slice. The value of M can be constant across each of the plurality of resolution layers of the model, where there is a plurality of n×n image patches for each of the M slices at each of the resolution layers. In other embodiments, the plurality of image patches are three-dimensional image subregions at some or all of the resolution layers, where the three-dimensional image subregions include pixels from multiple image slices. The slice-wise resolution can also improve with each resolution layer, for example, where the number of slices in each three-dimensional image subregion decreases at higher resolution layers. The number of slices in each three-dimensional image subregion at the highest resolution layer can be equal to one, or can be equal to a different lowest number.

In some embodiments, performing the inference function 5020 can include performing the inference step 1354 of FIG. 7B to generate one or more probability matrices 1371, with an added dimension K corresponding to each of the plurality of abnormality classes. Thus, the probability matrices 1371 can be generated for each of the K abnormality classes. The detection step 1372, abnormality classification step 1374, similar scan identification step 1376, and/or display parameter step 1378 can similarly be performed separately for each of the K abnormality classes.

The probability matrix data generated as output of the inference function 5020 can be transmitted to the client device 120 for display via a display device. Alternatively or in addition, the probability matrix data can be transmitted for use by another subsystem 101 and/or can be transmitted to the medical scan database to be mapped to the corresponding medical scan. Alternatively or in addition, the probability matrix data can be utilized by the multi-label medical scan analysis system 5002 to generate saliency maps, to generate region of interest data, to generate global probabilities for each class as illustrated in FIG. 14B, and/or to generate heat map visualization data as illustrated in FIG. 14C.

Generating the saliency maps can include assigning each value in the probability matrix to 1 or 0, and can be generated for each resolution level. Each value in the probability matrix can be assigned the value 1 or 0 by comparing the raw probability to a threshold. The threshold can be the same or different for each of the K abnormality classes, and/or can be the same or different for each of the N×N image patch locations. The saliency maps can be visually presented, for example, where image patches assigned a value of 1 are displayed in white or another first color, and where image patches assigned a value of 0 are displayed in black or another second color. The saliency maps can be transmitted to the client device 120 for display via a display device. Alternatively or in addition, the saliency maps can be transmitted for use by another subsystem 101 and/or can be transmitted to the medical scan database to be mapped to the corresponding medical scan.

Generating the region of interest data can include comparing values of each probability matrix to a probability threshold. The probability threshold can be the same or different for the plurality of abnormality classes. In some embodiments, the region of interest data indicates one or more image patches with a probability value that compared favorably to the probability threshold for at least one of the K abnormality classes. In some embodiments, the at least one of the K abnormality classes for which the probability value compared favorably to the probability threshold is further indicated in the region of interest data. The region of interest data can be transmitted for use by another subsystem 101 and/or can be transmitted to the medical scan database to be mapped to the corresponding medical scan. Alternatively or in addition, the region of interest data can be transmitted to the client device 120 for display via a display device. In particular, the region of interest data can be displayed in conjunction with the medical scan, for example, where the one or more image patches identified in the region of interest data are outlined, highlighted, or otherwise indicated visually. Furthermore, the at least one of the abnormality classes corresponding to the region of interest can be identified as text, and/or as a color or pattern used to identify the region interest. For example, for region of interest data of a medical scan with a first region of interest corresponding to a first abnormality class and a second region of interest corresponding to a second abnormality class, the first region of interest can be indicated via an interface displayed by the display device by overlaying the corresponding image patch of the image data of the medical scan with a first color and/or pattern, and the second region of interest can be indicated via the interface by overlaying the corresponding image patch of the image data of the medical scan with a second color and/or pattern. In some embodiments, the region of interest data is presented by utilizing the interface of the medical scan assisted review system 102. In some embodiments, the region of interest data is presented by the interface of a multi-label heat map display system.

FIG. 14B illustrates an embodiment of a multi-label medical scan analysis system 5002 that is implemented as a global multi-label generating system. The multi-label medical scan analysis system 5002 can generate global probabilities, for example, by performing a global labeling function 5030 on the probability matrix data. Generating the global probabilities can include evaluating the N×N probability matrix for each of the K classes and determining a global probability value for each of the K classes. In some embodiments, the global probability value for a given abnormality class is assigned a highest probability of the corresponding N×N probability matrix. In some embodiments, the global probability value for an abnormality class is based on an average of some or all of the probability values of the corresponding N×N probability matrix, and/or based on some other function of the values of the N×N probability matrix. In some embodiments, determining the global probability value includes applying a low-pass filter or other filter to the probability matrix.

In some embodiments, a final binary identifier is assigned for each of the K classes, indicating whether each of the K abnormality classes are determined to be present or absent in the medical scan, based on their global probabilities. For example, each of the K global probabilities can be compared to a probability threshold, which can be the same or different for each of the K abnormality classes. The abnormality can be determined to be present when the corresponding global probability value compares favorably to the probability threshold, and can be determined to be absent when the corresponding probability value compares unfavorably to the probability threshold.

The global probability data and/or final binary identifiers determined for some or all of the K classes can be transmitted to the client device 120 for display via a display device. Alternatively or in addition, the global probability data and/or final binary identifiers are transmitted for use by another subsystem 101 and/or are transmitted to the medical scan database to be mapped to the corresponding medical scan. In some embodiments a single, global binary identifier is generated, alternatively or in addition for the final binary identifiers for each of the K classes. The global binary identifier can be generated based on the probability matrix data, the global probability values, and/or final binary identifiers, and can indicate whether or not the medical scan is determined to include any abnormalities.

In some embodiments, the K abnormality classes are treated as independent variables. In such cases, the global probability for each abnormality class can be computed based only on corresponding the N×N matrix, independent of other N×N probability matrixes of the other K−1 abnormality classes. Similarly, the final binary identifier for each of the abnormality classes can be computed based only on the corresponding global probability, independent of the global probabilities of the other K−1 abnormality classes.

In other embodiments, dependency of some or all of the K abnormality classes is utilized in computing the global probabilities and/or the final binary identifiers. For example, correlation data that indicates correlations between pairs and/or subsets of the K abnormality classes can be determined and/or learned based on the training data, and the global probabilities and/or binary identifiers can be generated based on the correlation data. For example, the global probabilities can be computed as joint probabilities utilizing the correlation data. As another example, a global probability value for a first abnormality class can be set to a higher value in response to a high global probability value being computed for a second abnormality class that has a high correlation with the first abnormality class. In some embodiments, the correlations are learned and inherently integrated within the model and are reflected when the probability matrices are generated as output when the inference function is performed, and further consideration of abnormality class interdependencies is not necessary.

In various embodiments, a multi-label medical scan analysis system 5002 implemented as a global multi-label generating system is operable to receive, via a receiver, a plurality of medical scans and a plurality of global labels corresponding to the plurality of medical scans. Each of the plurality of global labels corresponds to one of a set of abnormality classes. A computer vision model is generated by training on the plurality of medical scans and the plurality of global labels. Probability matrix data is generated by performing an inference function that utilizes the computer vision model on a new medical scan. The probability matrix data includes, for each of a set of image patches of the new medical scan, a set of patch probability values corresponding to the set of abnormality classes. Each of the set of patch probability values indicates a probability that a corresponding one of the set of abnormality classes is present in the each of the set of image patches. Global probability data is generated based on the probability matrix data. The global probability data indicates a set of global probability values corresponding to the set of abnormality classes, and each of the set of global probability values indicates a probability that a corresponding one of the set of abnormality classes is present in the new medical scan. The global probability data is transmitted, via a transmitter, to a client device for display via a display device.

FIG. 14C illustrates an embodiment of the multi-label medical scan analysis system 5002 implemented as a multi-label heat map generating system. Heat map visualization data is generated, for example, by performing a heat map generator function 5040 on the probability matrix data. In particular, the heat map visualization data can indicate a heat map for each of the K abnormality classes, based on their corresponding N×N probability matrix. Each heat map can indicate pixel values or other color values, corresponding to grayscale and/or RGB color values, corresponding to each pixel of the input image data. In some embodiments, pixel values and/or other color values are only indicated for each image patch of the highest resolution, for example, where a single color value is computed for each of the values of the N×N probability matrix for each of the K classes. In some embodiments, heat maps are generated for each of the resolution layers, for example, where a single color value is computed for each image patch of the corresponding resolution layer.

The pixel values of each heat map can be proportional to the raw probability values of the N×N probability and/or can be computed as a deterministic function of the raw probability values. This results in a N×N resolution heat map, and if displayed by the same number of pixels as the input image, results in all pixels of the same image patch being assigned the same color. This can result in borders between image patches having a dramatic shift in color. For a more visually desirable heat map, a smoothing function can be utilized to smooth the color transitions between image patches and/or to otherwise soften the borders between image patches by changing color values gradually within each image patch in the direction towards each of up to four borders, based on the color of the neighboring image patch in each of the up to four directions. For example, when a 64×64 dimension probability matrix is outputted for a 1024× 1024 image for each abnormality class, smoothing techniques can be applied within each of the 16×16 dimension patches, for example, to smooth the borders between patches. In this case, the same image patch can include pixels of varying colors. Color value differentials between ones of a set of initial color values of neighboring pixels included in different ones of the set of image patches can be reduced as a result of applying the smoothing function. In some embodiments, the smoothing function is different for some or all of the K abnormality classes.

Alternatively or in addition, a segmentation masking function can be applied to some or all of the heat maps to mask one or more designated or determined regions, for example, based on borders of an anatomical region. For example, the segmentation masking function can mask everything outside of the heart. Masking can include not assigning pixel values for the masked region of the heat map and/or can include setting the pixel values for the masked region of the heat map to a mask color such as black, white, or other uniform, predetermined mask color. In some embodiments, the segmentation masking function is different for heat maps of each of the K different abnormality classes, for example, based on predetermined anatomical regions the different ones of the K abnormality classes pertain to. For example, for chest x-rays, heat maps for some of the K abnormality classes can mask regions outside the lungs, for example, when the corresponding abnormality class is prevalent in the lungs. As a further example, other ones of the K abnormality classes can mask regions outside the heart, for example, when the corresponding abnormality class is prevalent in the heart.

This heat map visualization data can be transmitted to a client device for display via a display device. In some embodiments, an interface displayed by the display device displays at least one of the heat maps for a corresponding one of the K abnormality classes. Each heat map can be displayed based on the corresponding color values for each pixel. In some embodiments, the raw pixel values of the heat map are displayed. In some embodiments, the heat map overlays the medical scan image data, where features of the original image data are still visible and the heat map highlights or shades the original image data in accordance with the color values of the heat map visualization data. The heat maps can be displayed in conjunction with text identifying the corresponding abnormality class, with the calculated global probability value for the corresponding abnormality class, and/or with the final binary identifier of the corresponding abnormality class. In some embodiments, the interface described in conjunction with the medical scan assisted review system 102 is utilized to display the heat maps and/or to allow a user to interact with the interface.

In various embodiments, a multi-label medical scan analysis system 5002 implemented as a multi-label heat map generating system is operable receiver, via a receiver, a plurality of medical scans and a plurality of global labels corresponding to the plurality of medical scans, where each of the plurality of global labels correspond to one of a set of abnormality classes. A computer vision model can be generated by training on the plurality of medical scans and the plurality of global labels. A new medical scan can be received, via the receiver. Probability matrix data can be generated by performing an inference function that utilizes the computer vision model on the new medical scan. The probability matrix data includes, for each of a set of image patches of the new medical scan, a set of patch probability values corresponding to the set of abnormality classes. Each of the set of patch probability values indicates a probability that a corresponding one of the set of abnormality classes is present in the each of the set of image patches. Heat map visualization data can be generated based on the probability matrix data. The heat map visualization data can indicate, for each of the set of abnormality classes, a color value for each pixel of the new medical scan. The heat map visualization data can be transmitted to a client device for display via a display device.

The discussion that follows in conjunction with FIGS. 15A-15D introduces an example embodiment of the model generated by multi-label medical scan analysis system 5002. Diagnostic imaging often requires the simultaneous identification of a multitude of findings of varied size and appearance. Beyond global indication of said findings, the prediction and display of localization information improves trust in and understanding of results when augmenting clinical workflow. Medical training data rarely includes more than global image-level labels as segmentations are time-consuming and expensive to collect. The example embodiment of the multi-label medical scan analysis system 5002 utilizes a novel architecture, which learns at multiple resolutions while generating saliency maps with weak supervision.

As used herein, $x \in \mathcal{R}^{w \times h \times c}$ denotes an input image with width w, height h, and channel c. In particular, x can correspond to the medical scan received by the multi-label medical scan analysis system 5002. As used herein, y is a binary vector of dimensionality K, where K is the total number of classes. In particular, K can correspond to the size of the set of abnormality classes discussed herein. For a specific class k, $y_k=0$ indicates its absence and $y_k=1$ its presence. The subscript indexes a particular example, for instance, $\{x_i; y_i\}$ is the i-th example. As used herein, $F \in \mathcal{R}^{w \times h \times c}$ denotes a feature map and $Q \in \mathcal{R}^{w \times h \times K}$ saliency map, with $Q \in [0,1]$. As used herein, two depth factors l and m accompany the feature and saliency maps. For instance, $F^l$ is the feature map as the result of a set of nonlinear transformation that changes the spatial resolution of $F^{l-1}$. On the other hand, $F_{m-1}$ and $F_m$ are consecutive feature maps that preserve the resolution during the nonlinear transformation.

FIG. 15A illustrates an example model that can be utilized by the of the multi-label medical scan analysis system 5002. In particular, FIG. 15A illustrates an example inference function 5020 that produces a saliency map with a resolution of 64×64, illustrating the process from input X-ray image to a predicted abnormality score. To reduce the resolution, a standard ResNet is firstly applied on the input image. To preserve the resolution, a standard DenseNet is applied per resolution. Upsampling and channel-wise concatenation fuse information from multiple resolutions. LSE-LBA pooling aggregates instance scores to the global probability Different numbers of resolution layers and/or different resolutions at each layer can be utilized in other embodiments. In some embodiments, the inference function 5020 and/or the global labeling function 5030 can be implemented by utilizing the model of FIG. 15A as discussed herein.

Each ResNet can contain several sub-modules, each of which is parameterized as $F^{l+1}=\sigma(g(F^l)+f(F^l))$. $F^{l+1}$ can be half the resolution of $F^l$, and/or can have twice the number of channels as $F^l$. σ can be is an element-wise nonlinearity. The functions g and $f$ can be composed of a series of 1×1 and 3×3 convolutions. The reduction in spatial resolution can be achieved by using convolutions with a stride size 2. A simple $f$ and complex g can be chosen such that $f$ is as close as possible to a simple identity transformation, leaving the heavy-lifting non-linear transformations to g to learn the residual. In some embodiments, spatial resolutions can be preserved with $F_{m+1}=\sigma(g(F_m)+F_m)$ in which case $f$ is chosen to be the identity function.

Because ResNets are susceptible to over-parameterization, which becomes critical when residual connections are used repeatedly on the horizontal data row in FIG. 15A without changing the spatial resolution. In the scenario where $F^{l+1}=\sigma(g(F^l)+f(F^l))$ is applied repeatedly, a model could simply learn to ignore the capacity in g, especially when σ is a rectified linear unit (relu). This would effectively defeat the purpose of inner-resolution propagation where a model is encouraged to specialize in making predictions under a selected resolution l. To solve this issue, the non-identity transformation on $F^l$ can be enforced explicitly, which can include removing the residual connections. Because the resulting model would lose the attraction of being easy to optimize, DenseNets can be utilized, where the resolution-preserving transformation is formulated as $F_m=\sigma(f(F_1 \oplus F_2 \oplus \ldots \oplus F_m))$, where ⊕ denotes the channel-wise concatenation of feature maps and $f$ denotes a series of resolution-preserving nonlinear transformations. This equation for $F_m$ enforces the nonlinear transformation $f$ on all previous feature maps without the possibility of skipping using identity mapping while still maintaining the desirable property of being easy to optimize due to the direct connections with all previous feature maps. Such a design effectively encourages the participation of all previous feature maps in propagation.

Fine-scale features, computed at high resolutions, capture detailed appearance information while coarse-scale features, computed from lower resolution representations of the data, capture semantic information and context. In deep neural networks utilized by the multi-label medical scan analysis system 5002, fine-scale features are learned in the earliest layers and coarse-scale features are learned in the subsequent layers, where the spatial resolution of the data has been reduced by repeated downsampling operations. Thus, the model learns to construct a feature hierarchy in a fine-to-coarse manner. While the coarse-scale features at the top of typical classification neural networks are suitable for image-level classification, spatial information required to precisely localize abnormalities is likely to be lost. If the model is expected to predict not only what abnormalities are present in the image but where they are, then the spatial information must be reintegrated.

The model illustrated in FIG. 15A performs this incrementally, in a coarse-to-fine manner, by repeatedly performing the operation $F_m^l=f(\mathcal{U}(F_n^{l+1}) \oplus (F_{m-1}^l))$, where $F_m^l$ denotes the m-th resolution-preserving feature map at resolution level l, where $F_n^{l+1}$ denotes the n-th feature map from the lower resolution level l+1, where denotes previous feature map at resolution level l, where $\mathcal{U}$ denotes the upsampling operation, and where ⊕ denotes the channel-wise concatenation. The upsampling operation $\mathcal{U}$, can be implemented in various ways including bilinear interpolation, nearest-neighbors interpolation, and/or learnable transposed convolutions. In the example embodiment discussed here, nearest-neighbors can be used to implement $\mathcal{U}$.

Log-Sum-Exp Pooling with Lower-bounded Adaptation can be utilized to take a saliency map S of a particular class k and produces a final score p, and can be defined as follows:

$$p = LSE\text{-}LBA(S) = \frac{1}{r_0 + \exp(\beta)} \log\left\{\frac{1}{wh}\sum_{i=1}^{w}\sum_{j=1}^{h} \exp((r_0 + \exp(\beta))S_{i,j})\right\}$$

As used herein, $S \in \mathbb{Z}^{w \times h \times 1}$ denotes a two-dimensional saliency map for a particular class k to be pooled. $S_{i,j}$ denotes the (i, j)-th element of S. In other embodiments, a Noisy-OR (NOR) function, generalized-mean (GM) function, and/or Log-Sum-Exponent (LSE) function can be utilized in performing the pooling function to generate the final score p. The final score p can correspond to the global probability determined for the corresponding abnormality class k as discussed in conjunction with FIG. 14B. For example, the global labeling function 5030 can be implemented by utilizing the LSE-LBA function, and/or another pooling function.

In addition to maintaining the benefits of using a pooling function which balances average and max pooling, the LBE-LSA pooling function is robust to the issue of numerical underflow when $S_{i,j}$ is very close to zero, compared with other pooling functions such as NOR and GM pooling, due to the removal of the exponential that directly acts on $S_{i,j}$. LSE-LBA also preserves probabilities. By bounding the values in S to be in the range [0; 1], the resulting score will also be in the same interval. Since the LSE-LBA function is monotonically increasing in $S_{i,j}$, it attains its maximum value when all $S_{i,j}=1$, and its minimum value when all $S_{i,j}=0$. When S is a map of all 0's, LSE-LBA(S)=0 and, and when S is a map of all 1's LSE-LBA(S)=1. A sigmoid activation function can be used on each $S_{i,j}$ to maintain this property. In addition to being numerically stable in computation, our the LSE-LBA function reparametrizes a hyperparameter r, used in LSE pooling, with $r=r_0+\exp(\beta)$ where $r_0$ is a positive constant and $\beta$ a learnable parameter. r can be lower bounded by $r_0$, expressing the sharpness prior of the pooling function. A large $r_0$ can encourage the learned saliency map to have less diffuse modes.

The model of FIG. 15A can be utilized in a weakly-supervised setting where pixel-wise labels are not available and only image-level annotations are utilized. Given the multi-resolution fused feature map at the highest level resolution $F^0 \in \mathcal{R}^{w \times h \times c}$, it is further divided into a grid of N×N, with N being the chosen resolution of the final saliency map. In some embodiments, N=w=h, resulting in $F^0 \in \mathcal{R}^{N \times N \times c}$. C Each of the $N^2$ c-dimensional vectors represents an instance $I_n(x)$ in the bag $F^0$, where n={1, ..., $N^2$}. The K-class instance probability is $P(I_n(x))=\text{sigmoid}(WI_n(x))$, where W is a K by c parameter matrix that is shared among all $N^2$ instances. This leads to the final probabilistic saliency map $S \in Q^{N \times N \times K}$. Following the LBE-LSA pooling function, $P(x)=LSE\text{-}LBA(S(x))$, where prediction P (x) is a K-dimensional vector and represents, according to the probability-preserving property of LSE-LBA pooling the probability of x belonging to K classes. Hence, a multi-class cross-entropy cost can be directly computed given y.

FIG. 15B illustrates example output saliency maps at various resolutions for an input chest x-ray. The model can produce all of the saliency maps, corresponding to each of the resolution levels, or can produce the highest level saliency map only. The model of FIG. 15A can also be utilized to generate probability matrix data and/or global probability data for any other types of medical scans described herein.

The model of FIG. 15A can be applied to datasets of medical scans, such as the NIH Chest X-ray dataset, which contains 112,120 frontal-view chest X-rays taken from 30,805 patients, where 51,708 images contain at least one of 14 labeled pathologies, in a PNG format with a standardized spatial resolution of 1024×1024. The 14 labeled pathologies can correspond to the set of abnormality classes, and can include, for example, atelectasis, effusion, mass, pneumonia, consolidation, emphysema, pleural thickening, cardiomegaly, infiltration, nodule, pneumothorax, edema, fibrosis, and/or hernia. Other clinical information including patients' age and gender are accessible in addition to the pathology labels, and while not used in this example embodiment, can be utilized in other example embodiments to train the model and/or implement the inference function.

For computational efficiency, the inputs of 1024×1024 can be downsampled to 512×512. Data augmentation can be applied during training, for example, where each image is zoomed by a factor uniformly sampled from [0.25; 0.75], translated in four directions by a factor uniformly sampled from [−50; 50] pixels, and/or rotated by a factor uniformly sampled from [−25; 25] degrees. After data augmentation, the inputs can be normalized to the interval [0; 1]. To further regularize the model, a weight decay can be applied, for example, with a coefficient of $10^{-5}$.

The model can be trained from scratch using only the NIH training set, for example, with an Adam optimizer and a learning rate of 0.001. Early stopping can be performed on the validation set based on the average AUC (Area Under the ROC curve) over all of the set of pathologies. For classification, the AUC per abnormality can be utilized.

In some embodiments, no bounding boxes are used at training time so that the model remains weakly supervised with respect to the task of localization. The best models on the classification task can then be evaluated on their localization performance. The quality of localization can be determined using the metric of intersection over detected bounding boxes (IoBB) with T(IoBB)=α, where α is set at a certain threshold. IoBB can be extremely sensitive to the choice of the discretization threshold by which the predicted probability score S is binarized before being compared with ground truth bounding boxes. IoBB can be very sensitive to the choice of a binarization threshold τ to discretize probabilistic saliency maps into binary foreground and background masks.

In some embodiments, the continuous version of DICE= $(2 \times S \times G)/(S^2+G^2)$ can be utilized as the cost function for training the model as a semantic segmentation model, where S is the probabilistic saliency map directly output by the model, and where G the ground truth binary bounding box downsampled to 512×512, the same resolution as the model input. The DICE cost function, or another cost function, can be selected to take into account the probability while avoiding the decision of having to select the discretization threshold T.

FIG. 15B presents a table illustrating an example of abnormality classification and weakly supervised localization performance on 14 abnormalities on the NIH Chest X-ray test set. Three models with different lower-bounded adaptation $r_0$ are included. In some embodiments, the impact of $r_0$ is much more pronounced in localization than in classification. In this example, the model is only trained on NIH data. In other embodiments, a pre-trained model, for example, trained on ImageNet without multi-resolution fusion. The bolded numbers of the table of FIG. 15B indicate the maxima other than statistical significance. Compared with classification, the choice of $r_0$ can have a more significant impact on abnormality localization due to their likely distinct visual appearance. For instance, when $r_0$ is small and the sharpness prior is weak, a model can tend to perform well on visually diffused abnormalities such as cardiomegaly, infiltration and pneumonia. As the sharpness prior is strengthened, localization of focalized and patchy abnormalities can be improved, as in the case of atelectasis and nodule. When choosing $r_0$ to be large, the performance of diffused abnormalities can degrade, such as atelectasis, cardiomegaly, effusion and pneumonia.

FIG. 15C includes an example of model-generated saliency maps. In particular, for each of the abnormality classes cardiomegaly, infiltration, nodule, effusion, mass, and pneumonia, FIG. 15C includes, from left to right, original images, ground truth bounding boxes, and model generated saliency maps for each of $r_0=0$, $r_0=5$, $r_0=10$, respectively. The corresponding DICE score for each model-generated saliency map, computed with respect to the ground truth, is also presented above the corresponding saliency map. FIG. 15C illustrates that increasing $r_0$ can result in overall sharper saliency maps. Using bounding boxes to delineate abnormalities can be limited by overestimating their true ROIs, which is illustrated in the cases of infiltration and pneumonia. As illustrated in FIG. 15C, some model findings can be incorrectly marked as false positives due to labeling noise where the ground-truth reader missed the finding.

FIG. 15D illustrates another example of saliency maps at multiple resolutions generated for a chest x-ray with mass by utilizing the four models, with an increasing target resolution, that were trained, for example, as discussed in conjunction with FIGS. 15A-15C, to produce the presented visualization. In particular, FIG. 15D illustrates how multi-resolution, lower-resolution maps can provide weak localization cues that are refined in higher-resolution layers. In some embodiments, only a highest resolution saliency map, such as a 64×64 resolution saliency map, is generated for an input medical scan.

FIGS. 16A-16E illustrate embodiments of a multi-model medical scan analysis system 6002. Multiple models can be trained to process medical scans of different views of a patient, medical scans of different modalities, and/or medical scans of different anatomical regions. Alternatively or in addition, some of the multiple models can be trained to detect/characterize different types of abnormality patterns and/or different characteristics of various types of abnormalities. When new medical scans are received for processing, one or more models can be selected based on the new medical scan, and inference data for the new medical scan can be generated by performing the one or more selected models. Inference data thus generated for new medical scans by selecting a proper subset of the set of models based on features of the new medical scans that correspond to criteria utilized to train the proper subset of models. This illustrates an improvement over existing systems, allowing more precise inference data to be generated by utilizing particular models trained to process the type of scan presented and/or trained to process a particular type of detected abnormality in the type of scan presented.

As shown in FIGS. 16A-16E, the multi-model medical scan analysis system 6002 can communicate bi-directionally, via network 150, with the medical scan database 342 and/or with other databases of the database storage system 140, with one or more client devices 120, and/or, while not shown in FIGS. 16A-16E, with one or more subsystems 101 of FIG. 1, with the central server system 2640, and/or with the medical picture archive system 2600.

In some embodiments, the multi-model medical scan analysis system 6002 is an additional subsystem 101 of the medical scan processing system 100, implemented by utilizing the subsystem memory device 245, subsystem processing device 235, and/or subsystem network interface 265 of FIG. 2A. For example, the multi-model medical scan analysis system 6002 can be implemented by utilizing the medical scan diagnosing system 108, the medical scan image analysis system 112, and/or the multi-label medical scan analysis system 5002 to train the plurality of computer vision models and/or to perform a plurality of inference functions by utilizing the plurality of computer vision models.

In some embodiments, the multi-model medical scan analysis system 6002 utilizes, or otherwise communicates with, the central server system 2640. For example, the medical scan database 342 can be populated with de-identified data generated by the medical picture archive integration system 2600. The multi-model medical scan analysis system 6002 can receive de-identified medical scans of the training set with their corresponding annotation data, diagnosis data, and/or medical reports directly from the medical picture archive integration system 2600, for example, where the annotation data, diagnosis data, and/or medical reports are utilized to determine the medical labels for medical scans in the training set. As another example, the multi-model medical scan analysis system 6002 can perform one or more inference functions on de-identified medical scans received from the medical picture archive integration system 2600, and abnormality data or other inference data generated as output of the plurality of the one or more inference functions can be assigned to the medical scan in the medical picture archive integration system 2600. As another example, the multi-model medical scan analysis system 6002 can request de-identified medical scans, annotation data, and/or reports that match requested criteria for the training set and/or for new medical scans to be labeled. As another example, one or more of the inference functions trained by the multi-model medical scan analysis system 6002 can be utilized by the annotating system 2612. In some embodiments, some or all of the multi-model medical scan analysis system 6002 is implemented by utilizing other subsystems 101 and/or is operable to perform functions or other operations described in conjunction with one or more other subsystems 101.

Figure 16A:
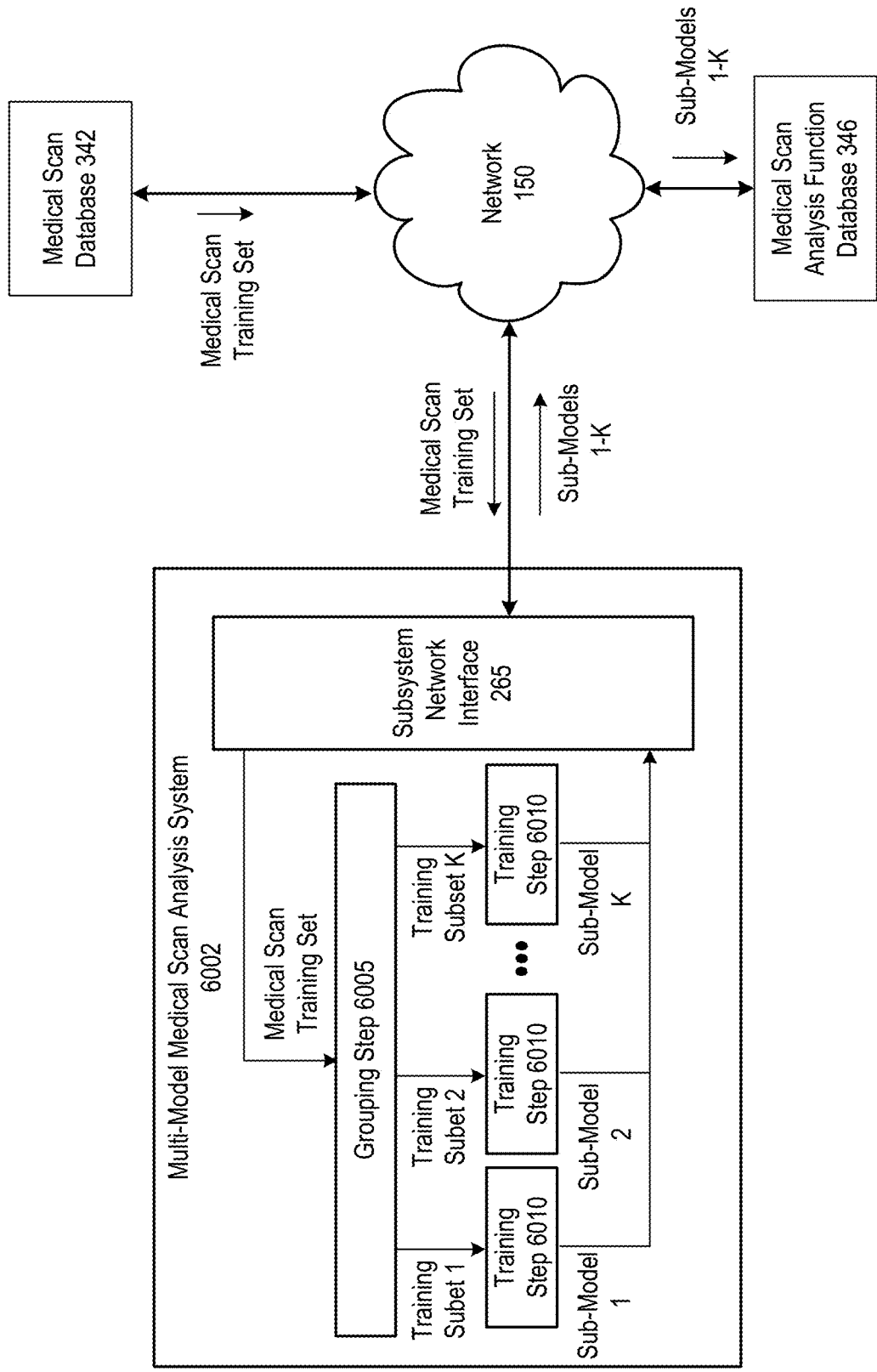

As shown in FIG. 16A, a training set of medical scans can be received, for example, from the medical scan database 342. Some or all medical scans in the training set of medical scans can include image data. Alternatively or in addition, some or all medical scans in the training set of medical scans can include raw sensor data captured by an modality machine, for example, prior to performing a Fourier transform to generate the image data of the medical scan. Alternatively or in addition, some or all medical scans in the training set of medical scans can include some or all of the fields of a corresponding medical scan entry 352. Alternatively or in addition, some or all medical scans in the training set of medical scans can correspond to DICOM images that includes a DICOM header. Alternatively or in addition, output labeling data that indicate and/or characterize at least one abnormality determined to be present in the medical scan can be received in conjunction with the corresponding medical scan for some or all medical scans in the medical scan training set.

A grouping step 6005 can be performed on the medical scan training set to form a plurality of training subsets 1-K. Some or all of the training subsets can have non-null intersections. Alternatively, training subsets 1-K can be mutually exclusive. Training subsets 1-K can be collectively exhaustive with respect to medical scans in the medical scan training set, or one or more medical scans of the medical scan training set can may be included in none of the training subsets 1-K. One or more of the training subsets 1-K can include all of the medical scans in the medical scan training set. One or more training subsets 1-K can include the same set of medical scans from the medical scan training set, but can be trained based on different criteria, for example, to detect different types of abnormalities.

The grouping step 6005 can include assigning the medical scans to the training subsets 1-K in accordance with grouping criteria, where medical scans that meet grouping criteria for one or more of the training subsets are included in the one or more training subsets. The grouping criteria can be based on characteristics of the scan itself, for example by utilizing some or all of scan classifier data 420, where medical scans are grouped by modality, anatomical region, view, sequence, originating entity, geographic region, date, and/or other data classifying the medical scan. Alternatively or in addition, the grouping criteria can be based on some or all of diagnosis data 440, for example, where medical scans are grouped by abnormality location data 443 and/or where medical scans are grouped by abnormality classifier category 444 and/or by abnormality pattern category 446. For example, grouping criteria for one of the training subsets can require medical scans that are Head CTs from a particular geographic region with abnormality data indicating a brain tumor. The corresponding sub-model can be trained to more accurately detect or to further characterize brain tumors for patients from the geographic region based on corresponding labeling data for the medical scans in this training subset.

Some or all of a medical scan's characteristics utilized to determine which group the medical scan is assigned to can be determined automatically by applying existing inference functions to generate the corresponding information for the medical scans. For example, modality, sequence, anatomical regions, and/or diagnosis data can be automatically determined by utilizing an existing computer vision model on the image data of the medical scan, such as the input quality assurance function 1106, and grouping medical scans in accordance with the determined scan category 1120.

Any fields, such as fields with discrete sets of options, of medical scan entries 352 can be utilized to group the medical scans, where only medical scans of the training set with one or more fields of a medical scan entry 352 that match and/or compare favorably to requirements for the one or more corresponding fields in the grouping criteria for one of the training subsets 1-K will be included in the one of the training subsets 1-K. In some embodiments, a discrete set of standardized fields in standardized DICOM headers or other metadata of the set of medical scans can be utilized to group the medical scans, where only medical scans of the training set with one or more DICOM fields of that match and/or compare favorably to requirements for the one or more corresponding fields in the grouping criteria for one of the training subsets 1-K are included in the one of the training subsets 1-K.

In some embodiments, a discrete set of standardized output labels are utilized to group the medical scans. This can include training on labeling data generated by user input to an interactive interface 3075 by utilizing the medical scan hierarchical labeling system 3002, and/or annotation data and/or additional annotation data generated by utilizing model-assisted annotating system of FIGS. 18A-18E, can be utilized to group the medical scans. For example, only medical scans of the training set with one or more output labels that match and/or compare favorably to requirements for the one or more corresponding output labels in the grouping criteria for one of the training subsets 1-K are included in the one of the training subsets 1-K. In some embodiments, the medical scans are grouped in accordance with internal nodes and/or leaf nodes of one or more prompt decision trees of the medical scan hierarchical labeling system. In some embodiments, medical scans with output labeling data that corresponds to a leaf node branching from a particular internal node of a prompt decision trees are grouped in the same training subset, where some or all training subsets correspond to different internal nodes of one or more prompt decision trees.

In some embodiments, performing the grouping step 6005 including partitioning data of at least one of the medical scans in the training set of medical scans. For example, in an embodiment where the grouping step groups different sequences, a medical scan can be partitioned into a plurality of different sequences, where each sequence is included a different one of the set of training subsets. As another example, in an embodiment where the grouping step groups different anatomical subregions, image data of a medical scan can be partitioned into a plurality of portions by different anatomical subregions, where each of the partitioned portions are included in a different one of the set of training subsets. In particular, different subsets of a set of image slices included in the medical scan can be included in different training subsets. As another example, one or more image slices can be partitioned into different cropped portions, where the different cropped portions are included in different training subsets.

As another example, in an embodiment where the grouping step groups by different types of input data, some or all fields of the medical scan entry can be partitioned and/or pre-processed. For example, image data of the medical scan can be included in at least one first training subset of the plurality of training subsets. Report data or unstructured text data of the medical scan can be included in at least one second training subset of the plurality of training subsets. Raw sensor data captured by the modality machine, prior to applying a Fourier to generate the image data, can be included in at least one third training subset of the plurality of training subsets. Patient history data of the medical scan can be included in at least one fourth training subset of the plurality of training subsets.

Performing the grouping step 6005 can include grouping the medical scans based on grouping criteria received from an administrator via user input to an interactive interface displayed by a display device of a client device 120. Alternatively or in addition, some or all of the grouping criteria can be determined automatically, for example, based on automatically determining features that best distinguish the training set of medical scans and grouping based on the set of automatically determined features. For example, statistically significant trends that differentiate medical scans corresponding to various criteria can be utilized to determine optimal groupings, where criteria that most differentiate generation of abnormality data for medical scans are grouped separately. Alternatively, in response to automatically determining that particular types of medical scans, when grouped together to train a single model, negatively impact the accuracy of the single model, and that training on the multiple types separately improves the accuracy abnormality data generated instead by separate models. As more training data is available overtime and/or as accuracy of different models are evaluated overtime, grouping criteria can be recalibrated to generate new grouping criteria. This can include reassigning groupings automatically to change grouping criteria of at least one of the groupings based on determining that one or more models is too overfit, based on determining new statistically significant trends that differentiate particular types of scans currently grouped together, and/or based on otherwise automatically determining accuracy would be improved by re-designating one or more particular types of scans into different groupings. Some or all of the trends utilized to determine groupings can be determined by utilizing the model-assisted annotating system of FIGS. 18A-18E.

Once the training subsets are formed, a training step 6010 can be performed separately on each of the training subsets 1-K to generate a plurality of sub-models 1-K. Each of the plurality of sub-models is thus trained to process types of medical scans that correspond to the grouping criteria utilized to determine the corresponding training subset. The training step 6010 can be the same or different for the each training subset. Performing the training step 6010 can include performing some or all of training step 5010 of FIG. 15A and/or some or all of training step 1352 of FIG. 7A. Performing the training step 6010 can include utilizing the training steps discussed in conjunction with the model-assisted annotating system of FIGS. 18A-18E. Some or all of the plurality of sub-models can correspond to same or different types of machine learning models. Some or all of the plurality of sub-models can correspond to neural networks with input nodes that correspond to image data of the medical scans and/or with output nodes that correspond abnormality data for the medical scans.

Some or all of the plurality of sub-models can be generated to process the same or different types of input and/or can include the and/or different number of input nodes. For example, the input to some or all of the plurality of sub-models can include pixels or subregions of one or more image slices of medical scans in the training subset, report data or other unstructured text data corresponding to medical scans in the training subset, raw sensor data captured by the modality machine prior to applying a Fourier to generate image data for medical scans in the training subset, and/or patient history data for medical scans in the training subset. One or more of the plurality of sub-models that utilizes report data and/or unstructured text data as input can utilize a natural language analysis function generated by the medical scan natural language analysis system 114 and/or can train the corresponding ones of the plurality of sub-models by training one or more natural language models.

Some or all of the plurality of sub-models can be configured generate the same or different types of output and/or can include the and/or different number of output nodes. For example, output to some or all inference functions that utilize of the plurality of sub-models can be configured to include probabilities indicating whether one or more types of abnormalities are present, can indicate region of interest data localizing one or more detected abnormalities, and/or can include characterization data describing size, volume, or other characterization data describing one or more detected abnormalities. Some or all of the output for some or all of the plurality of sub-models can correspond to some or all of the leaf nodes of one or more of the prompt decision trees of the medical scan hierarchical labeling system 3002 and/or can correspond to some or all of the annotation data and/or additional annotation data generated by utilizing the model-assisted annotating system of FIGS. 18A-18E. Some or all of the output for some or all of the plurality of sub-models can correspond to probability matrix data, global probability data, and/or heat map visualization data of the multi-label medical scan analysis system 5002.

In some embodiments, prior to performing the performing the training step 6010, the output labels of a training subset can be pre-processed. For example, in an embodiment where a sub-model is trained to detect a particular type of abnormality, the output labeling data of the corresponding training subset can be pre-processed to include a binary identifier indicating whether or not the corresponding abnormality type is present, based on the original output labeling data. Alternatively or in addition, some or all output labels for each medical scan in the training subset can be removed if they do not correspond to the intended output. For example, in the embodiment where a sub-model is trained to detect a particular type of abnormality, the output labeling data of the corresponding training subset can be pre-processed to remove output labels that do not correspond to the particular type of abnormality.

Figure 16B:
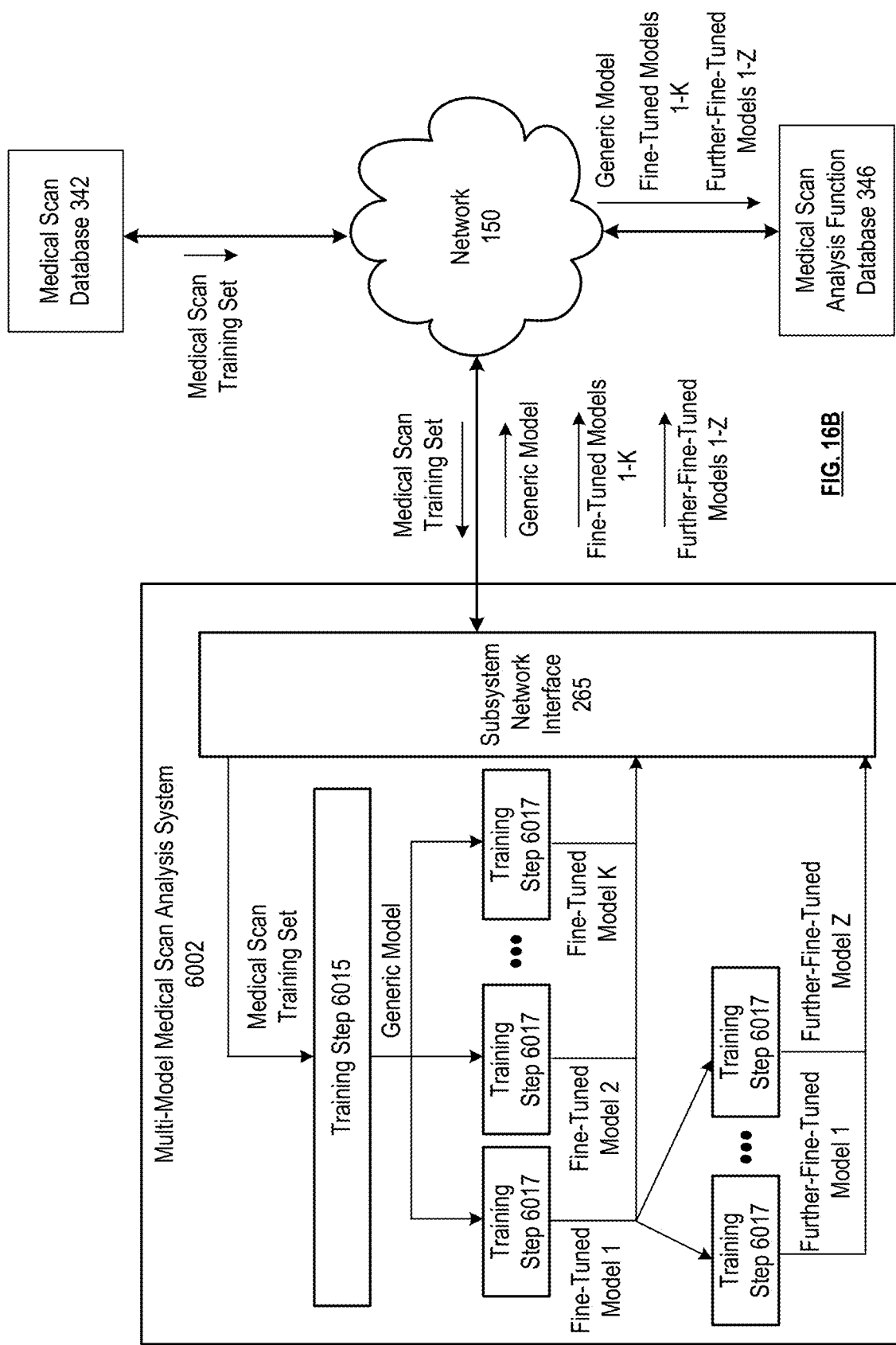
Figure 16C:
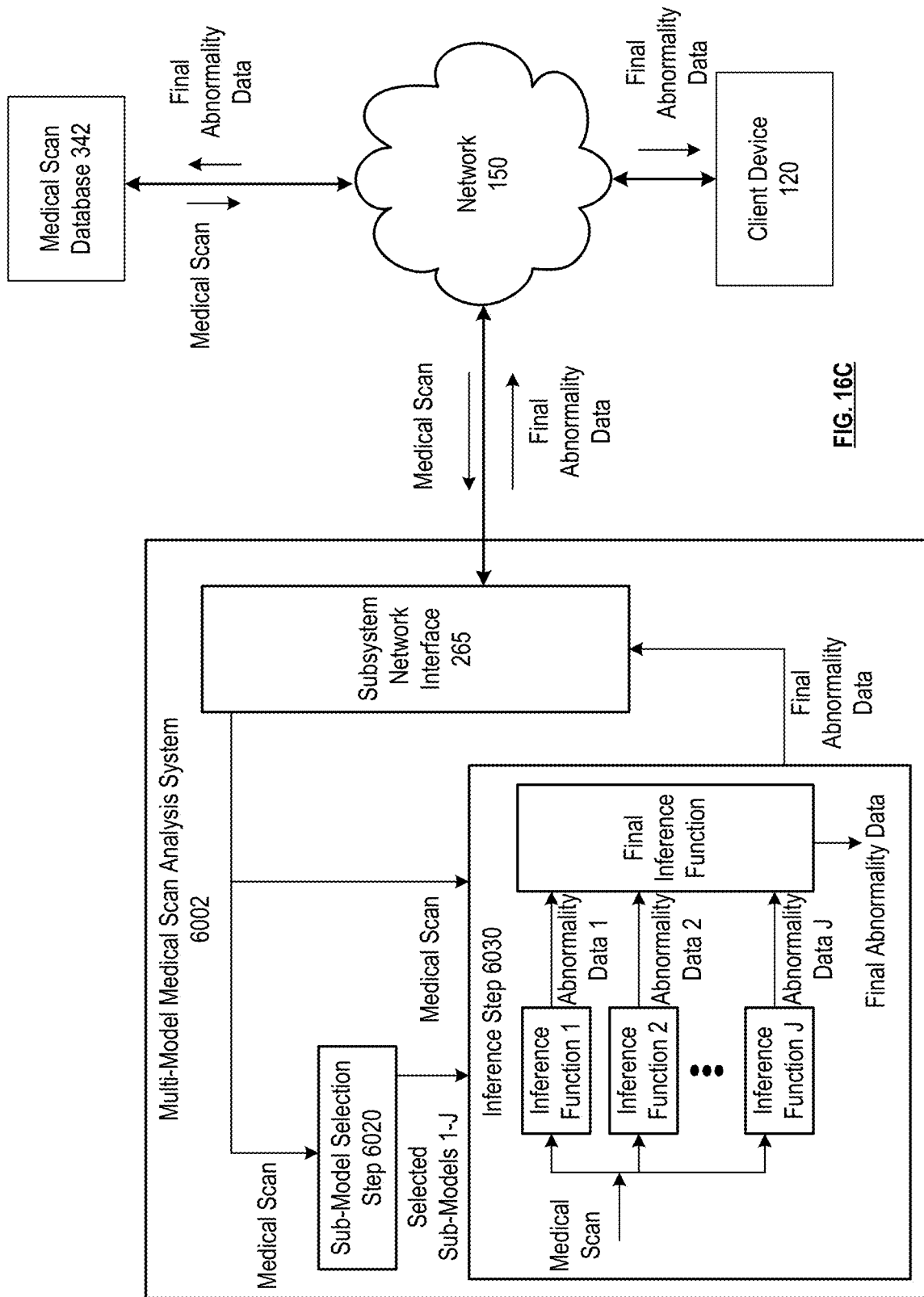
Figure 16D:
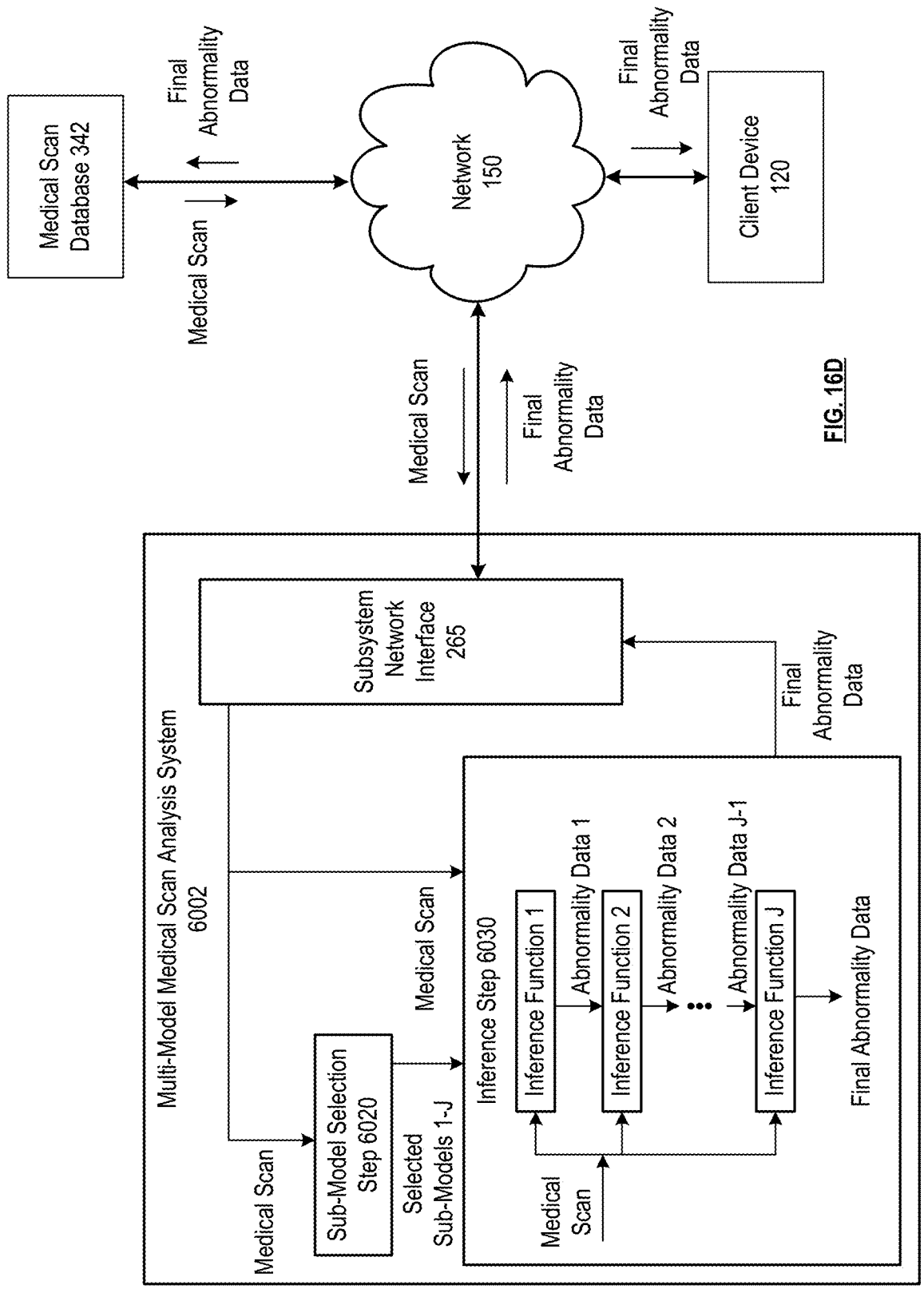
Figure 16E:
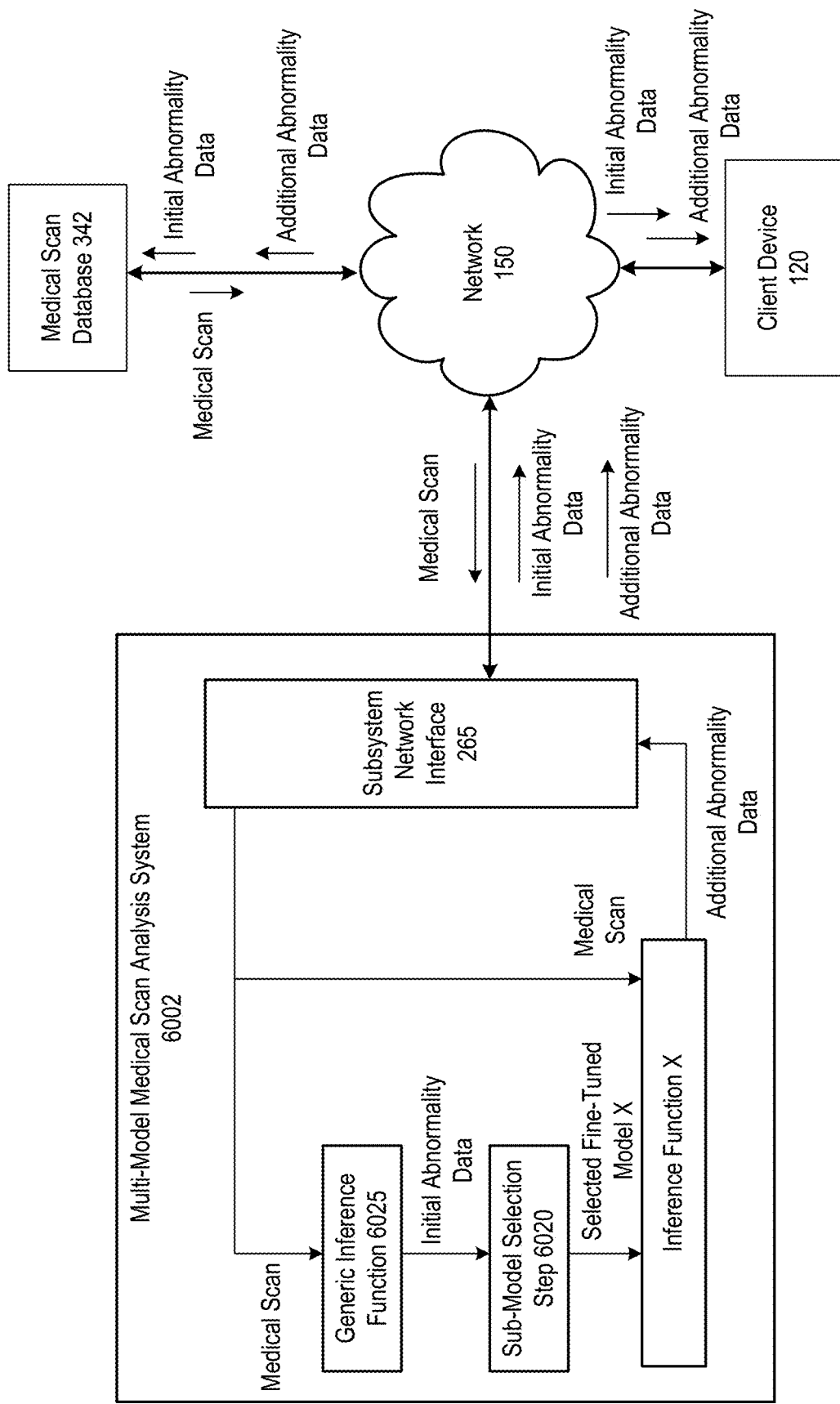

Weights, parameters, or other model data that characterize the sub-models 1-K can be stored locally for use by the multi-model medical scan analysis system 6002 to generate inference data for subsequently received medical scans, as illustrated in FIGS. 16C-16E. Alternatively or in addition, some or all of the model data for sub-models 1-K can be transmitted to the medical scan analysis function database 346.

In some embodiments, model parameters for the plurality of sub-models 1-K generated by the multi-model medical scan analysis system 6002 are sent to the medical picture archive integration system 2600 for use by the annotating system 2612. In such embodiments, the central server system 2640 can utilize and/or otherwise communicate with the multi-model medical scan analysis system 6002 to generate and/or receive the model parameters for transmission to the medical picture archive system 2600.

FIG. 16B illustrates an embodiment where the plurality of sub-models 1-K correspond to fine-tuned models of a generic model. In particular, the generic model can be generated by performing the training step 6015 on the entire medical scan training set, where the sub-models 1-K are generated by performing training steps 6017 on the generic model. Performing training steps 6015 and/or 6017 can include performing some or of training step 6010, and can be the same or different from training step 6010. In particular, performing training step 6017 can include modifying a plurality of weights of the generic model, for example, by starting from the generic model and by further training on a corresponding training subset to generate the corresponding fine-tuned model. Each fine-tuned model can include the same and/or different type of output as the generic model. Each fine-tuned model can correspond to an overfitted version of the generic model. Generating some or all of the fine-tuned models can include overfitting the generic model to better handle a more specific type of input data. Alternatively or in addition, generating some or all of the fine-tuned models can include overfitting the generic model to more accurately generate of output data and/or to provide output data that includes additional details.

In some embodiments, each fine-tuned model 1-K can correspond to a different one of a set of output labels of output labeling data for the medical scans in the training set.

In particular, if each output label in the output labeling data for the generic model corresponds to a probability that different one of a set of K abnormality types is present, each fine-tuned model can correspond to one of the set of K abnormality types. For example, each fine-tuned model can be configured to process medical scans to further characterize a type of abnormality, where the output corresponds to characterization labeling data for the type of abnormality. As another example, each fine-tuned model can be configured to process medical scans to more precisely detect a type of abnormality, where the output corresponds to a probability the type of abnormality is included in the medical scan. In such embodiments, the generic model can correspond to the multi-label model generated by the multi-label analysis system, where each fine-tuned model corresponds to a different one of the labels of the multi-label model.

In some embodiments, generating some or all of the fine-tuned models includes selecting a subset of the training set of medical scans and/or partitioning data of the training set medical scans. For example, the grouping step 6005 can be similarly performed as discussed in conjunction with FIG. 16A, and some or all of the fine-tuned models can be generated by retraining the generic model by utilizing only the corresponding training subset. Data for medical scans in the medical scan training set can similarly be partitioned into portions to generate training subsets, and the generic model can be retrained on different portions of data of the medical scans in the training set to generate the corresponding fine-tuned models.

In some embodiments, one or more of the fine-tuned models is further retrained or otherwise fine-tuned to generate a further-fine-tuned model. This can be accomplished by again applying the training step 6017 to the fine-tuned models, for example, where weights of the fine-tuned model are modified. For example, as illustrated in FIG. 16B, training step 6017 is applied to fine-tuned-model 1 to generate each further-fine-tuned model 1-Z. Generating a further-fine-tuned model can include by starting from the corresponding fine-tuned model and by further training on a smaller training subset and/or different output labels to generate the corresponding further-fine-tuned model. Determining the smaller training subset can include selecting only medical scans from the training subset that meet further refined criteria. Any number of further and further fine-tuned models can be generated from each fine-tuned model 1-K. For example, the grouping step 6005 can be applied to the training subset based on more refined criteria to generate a plurality of smaller subsets from the training subset, and each of the plurality of smaller subsets can be utilized to retrain the particular fine-tuned model to generate a plurality of further-fine-tuned models. In this fashion, a tree of fine-tuned models can effectively be generated, where each node in the tree corresponds to different training criteria, and where the criteria is more refined to create increasingly overfit models deeper and deeper down the tree.

Performing the fine-tuning step to generate one of the plurality of fine-tuned models corresponding to the first one of the plurality of abnormality types can include utilizing additional or otherwise different output labeling data of a subset of the plurality of medical scans. For example, each of the subset of the plurality of medical scans can have corresponding labeling data indicating the first one of the plurality of abnormality types is present in the each of the subset of the plurality of medical scans, as well as additional labeling data indicating characterization labels characterizing the first one of the plurality of abnormality types in the each of the subset of the plurality of medical scans. These characterization labels can be utilized as output data to generate the fine-tuned model. Each of the characterization labels can indicate whether or not a corresponding characterization category is present and/or can indicate a value or one of a discrete set of options for the corresponding characterization category. Some or all of the characterization labels can indicate abnormality classification data 445 of a corresponding abnormality classification category.

In some embodiments, each of a plurality of further-fine-tuned models correspond to internal nodes of one or more prompt decision trees. In particular, a subset of medical scans utilized to generate one of the fine-tuned models 1-K from the generic model can correspond to medical scans with output labeling data that compares favorably to a first internal node of a prompt decision tree. This fine-tuned model can be further refined to generate a further-fine-tuned model by retraining on a more refined subset, corresponding to medical scans with output labeling data that compares favorably to a second internal leaf node branching from the first internal node root node of a prompt decision tree. This further-fine-tuned model can be further and further fine-tuned by retraining on further refined models by further filtering the training set by only including medical scans that compare favorably to corresponding internal nodes deeper down the tree towards the leaf node. Some or all further-fine-tuned models can be generated by retraining subsequently generated further-fine-tuned models on further refined subsets corresponding to medical scans with output labeling data that compares favorably to a leaf node leaf node branching from a final internal node root node of a prompt decision tree.

In some embodiments, generating one or more of the fine-tuned models and/or further-fine-tuned models includes requesting additional training data. For example, additional training data can be requested in response to determining the subset of training data utilized to retrain the generic model or another previous model is too small, does not include a vast enough representation of medical scans, and/or when additional medical scans are otherwise determined to be necessary for training. The multi-label medical scan analysis system can generate a transmission to the medical scan database 342 for additional medical scans that meet criteria corresponding to a fine-tuned model and/or further-fine-tuned model identified to need more training data. Alternatively, the multi-label medical scan analysis system can forego generating the identified fine-tuned model and/or further-fine-tuned model until a time that the necessary additional training data is received via the network and/or is otherwise determined to be available. Alternatively, the multi-label medical scan analysis system can generate the identified fine-tuned model and/or further-fine-tuned model utilizing the corresponding training data that is available, and can generate an updated version of the identified fine-tuned model and/or further-fine-tuned model once a sufficient amount of additional training data is received.

FIGS. 16C-16E illustrate embodiments of utilizing the multi-model medical scan analysis system 6002 to generate inference data on new medical scans. As illustrated in FIG. 16C, a new medical scan can be received for processing, for example, from the medical scan database 342. A sub-model selection step 6020 can be performed to determine which sub-models 1-J will be applied to the medical scan, where J is less than or equal to K and where J is greater than or equal to one. For example, the header of the medical scan can be processed to determine a modality, anatomical region, or other scan classifier data 420 of the medical scan, and one or more sub-models correspond to the determined modality, anatomical region, or other scan classifier data 420 is selected. As another example, input quality assurance function 1106 can be utilized to determine a scan category 1120 for the new medical scan, and one or more sub-models can be selected based on the scan category 1120. A sub-model can be determined to correspond to a medical scan the determined modality, anatomical region, scan category 1120, or other scan classifier data 420 when medical scans from the training set were grouped into the training subset for the sub-model based on the same and/or substantially similar criteria. For example, one or more sub-models trained on a training subset corresponding to chest x-rays in a particular hospital setting can be selected in the sub-model selection step 6020 in response to determining the incoming medical scan is a chest x-ray captured in the same particular hospital setting. In some embodiments, all of the sub-models 1-K are applied to some or all incoming medical scans.

Once the sub-models 1-J are selected, a set of corresponding inference functions 1-J can be performed on the medical scan to generate corresponding abnormality data 1-J. Some or all of the inference functions 1-J can utilize medical scan analysis functions and/or other inference functions discussed herein. Some or all of the inference functions can utilize the inference function 5020 of the multi-label medical scan analysis system.

Each of the abnormality data 1-J can indicate at least one abnormality detected in the medical scan and/or can indicate the medical scan is normal. Some or all of the abnormality data 1-J can indicate its own probability matrix data, global probability data, and/or heat map visualization data discussed in conjunction with the multi-label medical scan analysis system 5002. Some or all of the abnormality data 1-J can indicate probabilities that one or more types of abnormalities are present and/or can further characterize and/or localize one or more particular types of abnormalities.

A final inference function can utilize the set of abnormality data 1-J to generate final abnormality data. The final abnormality data can include some or all of the abnormality data 1-J. For example, the final abnormality data can indicate a plurality of different abnormalities indicated in different ones of the abnormality data 1-J. Alternatively, the final abnormality data can include a final determination for at least one abnormality based on consolidating all of the abnormality data 1-J. This can include determining a medical scan is normal in response to a threshold number of the abnormality data 1-J indicating the medical scan is normal. This can include determining a medical scan includes an abnormality in response to a threshold number of the abnormality data 1-J indicates an abnormality is present. This can include determining a medical scan includes an abnormality in response to one of the abnormality data 1-J indicating an abnormality is present with a probability that exceeds a threshold. This can include determining that the medical scan includes an abnormality with a high probability value as a result of multiple ones of the abnormality data 1-J indicating an abnormality is present with lower probabilities than the high probability value. This can include computing a probability that an abnormality is present as a weighted average of probabilities that the abnormality is present in abnormality data 1-J. Ones of the abnormality data 1-J can be assigned higher weights in response to determining the corresponding sub-models are more accurate than other sub-models, where other ones of the abnormality data 1-J generated by utilizing the other, less accurate, sub-models are assigned lower weights. Weighted averages can be similarly applied to other features of the output labeling data, for example, to generate final probabilities that a detected abnormality corresponds to a particular type of abnormality, to generate final probability that one or more characterizing features of a detected abnormality are present, etc.

A first threshold required to determine that an abnormality is present in the final abnormality data can be equal to a first probability value when only one of the abnormality data 1-J indicates an abnormality is present. A second threshold probability required to determine whether an abnormality is present can be equal to a second probability value when more than one of the abnormality data 1-J compare favorably to the second threshold probability, where the second probability value is lower than the first probability value. Subsequent threshold probabilities required to determine whether an abnormality is present can be equal to subsequently lower values as more and more ones of the abnormality data 1-J indicate the abnormality is present. For example, if abnormality data generated by utilizing five inference functions indicates probabilities that an abnormality is present with probabilities 10%, 13%, 81%, 90%, and 2%, an abnormality can be determined to be present when a second threshold probability is equal to 80% because two of the five abnormality data indicate probabilities greater than 80%. As another example, if abnormality data generated by utilizing five inference functions indicates probabilities that an abnormality is present with probabilities 10%, 71%, 71%, 72%, and 2%, an abnormality can be determined to be present when a third threshold probability is equal to 70% because three of the five abnormality data indicate probabilities greater than 70%, even though the second probability threshold requiring two of the five abnormality data indicate probabilities greater than 80% is not met. This scheme can be similarly applied to other features of the output labeling data, for example, to determine whether detected abnormality corresponds to a particular type of abnormality, to determine whether one or more characterizing features of a detected abnormality are present, etc.

In some embodiments, each of the sub-models 1-K are trained to detect different types of abnormalities. For example, consider the embodiment where each sub-model 1-K is a fine-tuned model 1-K or a further-fine-tuned model generated as discussed in conjunction with FIG. 16B. Each inference function 1-J can be applied to the same input data, and each of the output labeling data 1-J can indicate a probability that one of the abnormalities types is present. The final abnormality data can indicate a global probability indicating a probability that any abnormality is present, and/or can indicate a global binary identifier indicating whether or not an abnormality is present. For example, the global binary identifier can indicate an abnormality is present in response to one of the 1-J output labeling data indicating a corresponding type of abnormality is present with a probability that exceeds a threshold, where the threshold is the same or different for each of the 1-J abnormality types. As another example, the global probability can be computed as a weighted average of the probabilities that each of the types of abnormalities is present. The global probability can utilize the global abnormality probability discussed in conjunction with the medical scan triaging system 8002.

In some embodiments, data for new medical scans can be partitioned into different portions, and the same or different set of sub-models 1-J can be selected for each of the different portions and can be applied to each different portion to generate the abnormality data. The different portions can correspond to different views of the same or different anatomical region. Alternatively or in addition, the different portions can correspond to different types of data corresponding to the medical scan. For example, each of the sub-models 1-J can process a different sequence of an incoming MRI scan and/or can process different views of a set of x-rays. As another example, one sub-model can process report data, and at least one other sub-model can process the corresponding image data, and/or at least one other sub-model can process raw sensor data. As another example, each of the sub-models 1-J can process different subsets of the image slices of the image data, and/or each of the sub-models 1-J can process different regions of image data for one or more the image slices. The final abnormality data can be generated by consolidating abnormality data generated for different types of input and/or for different portions of the image data to determine whether an abnormality is present, to determine one or more types of abnormality that are present, and/or to characterize one or more types of abnormalities determined to be present.

As another example, an entire study for a patient can be received that includes a plurality of different medical scans and/or reports for the patient. This can include longitudinal data collected for the patient over time and/or can include different modalities of medical scans and/or medical scans captured for different anatomical regions. The study can be partitioned into multiple medical scans and/or reports, and the same or different sub-models 1-J can be applied to each medical scan and/or report. All of the abnormality data generated by applying sub-models to all of the medical scans and/or reports in the study can be similarly consolidated in generating the final abnormality data.

The probability of one abnormality pattern identified by utilizing one model can influence probability of other abnormality patterns and/or can influence probability of characterization of other abnormalities in generating the final abnormality data. The probability of an abnormality based on one sequence and/or modality can influence probability of the same abnormality, or additional types of abnormalities corresponding to differing pathologies, detected based on additional sequences and/or modalities. This can be utilized to consolidate the set of abnormality data to generate the final abnormality data. Generating the final abnormality data can include utilizing a Bayesian model to generate a final probability that an abnormality is present, given the plurality of probabilities of the set of abnormality data for different types and/or portions of input such as different views, sequences, anatomical regions, report data, or other data for the medical scan. Alternatively or in addition, generating the final abnormality data can include utilizing a Bayesian model to generate a final probability that each of a plurality of abnormality types are present given a plurality of probabilities that each of a plurality of abnormality types are present.

Alternatively or in addition, generating the final abnormality data can include utilizing a plurality of known correlations between different types of abnormalities, where the final abnormality data is generated based on a known correlation value between the first type of abnormality and the second type of abnormality. For example, if the final inference function utilizes a model trained by the multi-model medical scan analysis system 6002, the plurality of known correlations can be automatically determined as a result of generating training model.

Consider an example where a first one of the subset of the set of sub-models is trained to detect a first type of abnormality and a second one of the subset of the set of sub-models is trained to detect a second type of abnormality. A first one of the set of abnormality data is generated as output of a first one of the subset of the set of inference functions that corresponds to the first one of the subset of the set of sub-models. A second one of the set of abnormality data is generated as output of a second one of the subset of the set of inference functions that corresponds to the first one of the subset of the set of sub-models. Suppose the first one of the set of abnormality data indicates a probability that the first type of abnormality is present, and the second one of the set of abnormality data indicates a second probability that second type of abnormality is present. The final inference function can utilize a Bayesian model and/or a known correlation between the first and second type of abnormality to determine final probabilities that the first and second types of abnormalities are present. For example, the final abnormality data can indicate an increase in the probability that the second type of abnormality is present in response to the set of abnormality data indicating the probability that the first type of abnormality is present compares favorably to a detection probability threshold and in response to the known correlation between the first type of abnormality and the second type of abnormality comparing favorably to a correlation threshold. As another example, the final abnormality data can indicate a decrease in the probability that the second type of abnormality is present in response to the set of abnormality data indicating the probability that the first type of abnormality is present compares unfavorably to a detection probability threshold and in response to the known correlation between the first type of abnormality and the second type of abnormality comparing favorably to a correlation threshold.

As illustrated in FIG. 16D, some or all of the sub-models can be applied in sequence, and can utilize abnormality data generated by previously applied sub-models. For example, a first one of the 1-J inference functions can be applied to the medical scan to generate abnormality data 1. A second one of the 1-J inference functions can be applied to the same or different portion of data the medical scan and/or to some or all of the abnormality data 1 to generate abnormality data 2. This process can continue until final abnormality data is generated, once inference function J is applied. The selection and/or ordering of the J inference function can be determined in the sub-model selection step 6020 and can be fixed until the final abnormality data is generated. Alternatively, the next inference function to be applied can be determined as output of applying a selection step after each abnormality data 1, 2, . . . , J−1 is generated, as a function of the abnormality data generated thus far.

In some embodiments, a different portion of the medical scans are applied to each inference function. In particular, smaller sub-regions can be selected from previous sub-regions of the image data for each subsequently applied inference function, based on localization data indicated in each subsequently generated abnormality data that further localizes a detected abnormality. For example, generating a sub-region from a previous sub-region can include selecting a proper subset of image slices and/or can include selecting a cropped portion of image data in one or more slices based on localization in the abnormality data of one or more previously applied sub-models. Some or all sub-regions can be successively smaller in size based on localization data in the abnormality data generated thus far, and/or can include different image data not included in a previous sub-region based on localization data in the abnormality data generated thus far.

FIG. 16E illustrates a particular example of sequentially applying inference functions. A first inference function, such as generic inference function 6025 corresponding to the generic model generated as discussed in conjunction with FIG. 16B, can be applied to the medical scan to generate initial abnormality data. Alternatively, the first inference function can be selected based on scan classier data of the medical scan by applying the sub-model selection step 6020. The initial abnormality data can indicate one of a plurality of types of abnormalities, and inference function X can be selected based on determining a corresponding one of the sub-models 1-K that is trained to detect, localize, and/or further characterize the detected type of abnormality in the initial abnormality data. For example, as illustrated in FIG. 16E, sub-model selection step 6020 can be applied to the initial abnormality data to select one of the fine-tuned models generated as discussed in conjunction with FIG. 16B, where the inference function X corresponds to the selected fine-tuned model. The additional abnormality output can indicate that the type of abnormality is detected with a higher confidence, or can alternatively indicate that the detected abnormality does not likely correspond to the type of abnormality initially detected, and perhaps corresponds to a different type. The additional abnormality output can localize and/or further localize the type of abnormality in the image data. The additional abnormality output can include characterization data for the type of abnormality. In particular, the characterization data can be specific to the type of abnormality, where different ones of the fine-tuned models generate different types of characterization data specific to their corresponding type of abnormality.

The additional abnormality data can indicate a plurality of probability values indicating whether each of a plurality of characterization types characterize one of the plurality of abnormality types indicated in the initial abnormality data, as a result of applying an inference function corresponding to the one of the plurality of abnormality types. The additional abnormality data can indicate a subset of the plurality of characterization types determined to characterize the first one of the plurality of abnormality types in response to corresponding ones of the plurality of probability values comparing favorably to a characterization threshold. The plurality of characterization types can correspond to a plurality of characterization labels included in output label data utilized to train the inference function.

While not illustrated in FIG. 16E, one or more further-fine-tuned models can be iteratively selected based the most recently generated additional abnormality data. The selection of further-fine-tuned models can correspond to models trained to further detect, characterize, and/or localize abnormalities. This can be determined based on a selecting an internal node and/or leaf node branching from a previous internal node, where the selected internal node and/or leaf node closely matches the additional abnormality data generated thus far, where the further-fine-tuned model was trained by a training subset that compares favorably to the labeling data that corresponds to findings in the additional abnormality data. Subsequently selected further-fine-tuned models can continue to be determined, based continuing to propagate down a prompt decision tree, where each next node is determined from the set of nodes branching from a current node based on determining which option most closely corresponds to the most recently generated additional abnormality data. This process can continue until a leaf node is reached, until no more models are available, and/or until probabilities of the additional abnormality data compare unfavorably to a threshold, indicating that further characterization is likely to be inconclusive and/or indicating that the abnormality cannot be further characterized.

If multiple abnormalities are detected in the one or more medical scans and/or reports, these multiple abnormalities can be processed separately. This can include consolidating the multiple abnormalities separately in the final abnormality data when applying the final inference function. Alternatively or in addition, this can include selecting separate fine-tuned functions for each abnormality detected by utilizing the generic algorithm, allowing each abnormality to be separately confirmed, characterized, and/or localized further.

In various embodiments, the multi-model medical scan analysis system 6002 includes at least one processor and a memory that stores operational instructions that, when executed by the at least one processor, cause the multi-model medical scan analysis system to perform the operations discussed herein. In particular, the multi-model medical scan analysis system can be operable to receive, via a receiver, a plurality of medical scans. A plurality of training sets can be generated from the plurality of medical scans. Each of a set of sub-models can be generated by performing a training step on a corresponding one of the plurality of training sets. A new medical scan can be received via the receiver, and subset of the set of sub-models can be selected based on the new medical scan. A set of abnormality data can be generated by applying a subset of a set of inference functions on the new medical scan, where the subset of the set of inference functions utilize the subset of the set of sub-models. Each of the set of abnormality data can be generated as output of performing one of the subset of the set of inference functions on the new medical scan. Final abnormality data can be generated by performing a final inference function on the set of abnormality data. The final abnormality data can be to a client device for display via a display device.

In various embodiments, the multi-model medical scan analysis system is operable to receive, via a receiver, a plurality of medical scans. Each of the plurality of medical scans can include corresponding labeling data indicating whether each of a plurality of abnormality types are present in the each of the plurality of medical scans. A generic model can be generated by performing a training step on image data of the plurality of medical scans and the corresponding labeling data. A plurality of fine-tuned models can be generated, where each of the plurality of fine-tuned models is generated by performing a fine-tuning step on the generic model, and where of the plurality of fine-tuned models corresponds to one of the plurality of abnormality types. A new medical scan can be received, via the receiver. Abnormality detection data can be generated for the new medical scan by performing a generic inference function on image data of the new medical scan. The generic inference function can utilize the generic model, and the abnormality detection data can indicate a plurality of probability values that each indicate a probability that a corresponding one of the plurality of abnormality types is present in the new medical scan. A first one of the plurality of abnormality types can be determined to be detected in the new medical scan by determining a corresponding one of the plurality of probability values compares favorably to a detection threshold. One of the plurality of fine-tuned models that corresponds to the first one of the plurality of abnormality types can be selected. Additional abnormality data can be generated for the new medical scan by performing a fine-tuned inference function on the image data of the new medical scan, where the fine-tuned inference function utilizes the one of the plurality of fine-tuned models. The additional abnormality data can be transmitted to a client device for display via a display device.

The multi-model medical scan analysis system 6002 can be implemented as a location-based medical scan analysis system 6004, as shown in FIG. 17. Factors such as patient population, imaging techniques/machinery, specialist training, definition of normal and abnormal, and/or other factors can vary across different geographic regions. These distinctions can be as small as between different hospitals, or as large as between different countries. Similarly, the type of hospital setting can affect trends of image data. In particular, whether the medical scan was taken in an inpatient setting, outpatient setting, emergency care setting, or other setting can further vary imaging data, for example, where test tubes are present in some settings and not others.

The location-based medical scan analysis system 6004 improves existing systems by presenting a solution to this problem. In particular, the location-based medical scan analysis system 6004 can be utilized to overfit one or more models based on specific trends of a particular location. The model can be overfit by hospital, by a larger geographic region, and/or by hospital setting to generate a plurality of models. Generating an overfit model for a particular location can be beneficial if the model is always run in the particular location and/or is always performed on medical scans generated in the particular location.

The multi-model medical scan analysis system 6002 can be utilized to generate such location-based models. In particular, some or all of the sub-models 1-K can correspond to different ones of a plurality of particular locations. As used herein, a particular location can correspond to any geographic region, any hospital-based location, and/or any hospital setting. The grouping step 6005 can be applied to training data to group medical scans based on their originating location to create training subsets grouped by geographic region, by hospital-based location, and/or by hospital setting. Some or all of the groupings can include one or more of the same medical scans. Alternatively, all of the groupings can be mutually exclusive. The grouping step 6005 can group medical scans only by particular location, and/or can also utilize other grouping criteria discussed in conjunction with FIG. 16A.

A training subset grouped by hospital setting can include medical scans from a plurality of different hospitals and/or geographic regions, so long as they were performed in the corresponding hospital setting. For example, an inpatient training subset can include medical scans taken in an inpatient setting across many different hospitals and/or different geographic regions. Alternatively, a training subset grouped by hospital setting can include medical scans from the same hospital and/or same geographic region. For example, multiple inpatient training subsets can be generated, each including medical scans taken in an inpatient setting in same hospital and/or in the same geographic region.

Determining which particular location each medical scan in the medical scan training set originated from can be accomplished by determining a location associated with an entity from which the medical scan was transmitted from. For example, if medical scans are transmitted to the location-based medical scan analysis system 6004 from different databases and/or different local systems 6050, a location associated with the database and/or local system from which each medical scan was transmitted can be utilized to determine the particular location associated with the medical scan. Alternatively or in addition, header data or other metadata associated with the medical scan, such as originating entity data 423 and/or geographic region data 424 can be utilized to determine the particular location. While not shown in FIG. 4A, medical scan entries can further indicate which of a plurality of hospital settings the medical scan was captured. Alternatively or in addition, patient data indicating a geographic region from which the patient is from can be utilized to determine the geographic region medical scan for the patient should be designated.

Training step 6010 can similarly be applied to all of the location-based training subsets to generate corresponding location-based sub-models 1-K. In some embodiments, a generic model is first created utilizing some or all of the medical scan training data, and each of the location-based sub-models correspond to fine-tuned models generated by retraining the generic model on the corresponding location-based training subset. In some embodiments, a location-based hierarchical tree is utilized to further refine one or more of the fine-tuned models. In particular, the generic model can utilize all of the training set of medical scans, a first sublayer of models can correspond to fine-tune models generated by retraining the generic model on training subsets corresponding to large geographic regions. A second sublayer of models can correspond to further-fine-tuned models corresponding to smaller geographic regions within the large geographic regions, where each of the second sublayer of models is generated by retraining one of the fine-tuned models on a training subset corresponding to a smaller geographic region within the large geographic region. For example, the first sublayer can correspond to models trained by country, and the second sublayer can correspond to models trained by hospitals within each country. Any number of sublayers of further-fine-tuned models by location can extend from the generic model.

The location-based medical scan analysis system 6004 can automatically determine grouping criteria for some or all of the location-based sub-models. In particular, the location-based medical scan analysis system 6004 can automatically determine to create distinct models across different geographic locations in response to determining statistically significant discrepancies between the locations. For example, the statistically significant discrepancies can be automatically determined in response to generating a generic model and by evaluating the performance across different particular locations. Any statistically significant discrepancies can be utilized to automatically group corresponding locations separately to create the corresponding location-based sub-models. In some embodiments, once a plurality of fine-tuned models are generated, some or all of the of fine-tuned models can be automatically evaluated for location-based discrepancies to automatically determine grouping criteria to generate one or more further-fine-tuned models. As more training data is available overtime and/or as accuracy of different models are evaluated overtime, sub-models can be retrained. This can include reassigning groupings automatically to change grouping criteria of at least one of the groupings based on determining that one or more models is too overfit, based on determining new statistically significant trends that differentiate particular locations currently grouped together, and/or based on otherwise automatically determining accuracy would be improved by re-designating one or more particular locations into different groupings.

Alternatively or in addition, some or all of the grouping criteria can be generated in response to receiving one or more requests for a location-based model from client devices associated with one or more particular locations. For example, a client device associated with a hospital or other medical entity, such as a client device associated with a local system 6050, can request its own location-based model for use on medical scans originating from that hospital or other medical entity. Alternatively or in addition, some or all of the grouping criteria can be generated based on administrator input to an interactive interface displayed via a display device of a client device 120 communicating with the location-based medical scan analysis system 6004.

In some embodiments, as illustrated in FIG. 17, a plurality of local systems 6050 communicate with the location-based medical scan analysis system 6004. The plurality of local systems can each be located in, or can otherwise be associated with, one of a plurality of particular locations. Each of the plurality of sub-models 1-K can be transmitted to a corresponding one of the local systems 6050, for example, as weight, parameters, inference function execution data, or other data characterizing the corresponding sub-models. The local system can receive its designated sub-model from the location-based medical scan analysis system 6004 via a network interface 6055. The local system can perform the corresponding inference function by its own processing system 6052, which can include one or more processors and memory that stores its own executable instructions that, when executed by the one or more processors, causes the processing system 6052 to utilize the sub-model to perform the corresponding inference function on new medical scans to generate corresponding abnormality data. For example, the processing system 6052 can be implemented by utilizing one or more subsystems 101. The processing system 6052 can communicate with one or more client devices 120, for example, via a wired and/or wireless network of the local system. For example, the abnormality data generated for new medical scans can be displayed to a user via an interactive interface displayed via a display device of the client device, for example, by utilizing the medical scan assisted review system 102.

At least one of the local processing systems can include its own medical scan database 342, for example, populated by medical scans generated in the particular location. For example, one or more modality machines located in the particular location can send imaging data to the medical scan database 342. The abnormality data generated for new medical scans by utilizing the sub-model received from the location-based medical scan analysis system 6004 can be sent to the medical scan database for storage in conjunction with the new medical scans. Alternatively, the abnormality data can be transmitted via the network interface 6055 to other databases and/or systems communicating via network 150. For example, the new medical scans and/or abnormality data can be transmitted back to the location-based medical scan analysis system 6004, and the location-based medical scan analysis system 6004 can utilize the new medical scans and/or abnormality data to retrain one or more sub-models and/or to retrain the generic model.

In some embodiments, each training subset 1-K utilized to train each sub-model is received separately from each of the of the local processing systems 6050 as its own medical scan training set 1-K. For example, each medical scan training set 1-K can be retrieved by a local system 6050 from the own medical scan database 342 for transmission to the location-based medical scan analysis system via the network interface 6055.

In some embodiments, multiple location-based sub-models can be trained by the location-based medical scan analysis system 6004 for each local processing system. For example, the location-based medical scan analysis system 6004 can receive medical scan training set 1 from a first one of the local systems, can perform grouping step 6005 as described in conjunction with FIG. 16A to generate a plurality of training subsets from the medical scan training set 1 to generate a plurality of sub-models particular to the first one of the local systems, where the plurality of sub-models are each configured to process different types of medical scans and/or generate different types of inference data as discussed herein. Alternatively, some or all of a plurality of location-independent sub-models generated to process different types of medical scans and/or generate different types of inference data can be further refined by location by utilizing medical scan training set 1 to generate the location-based sub-models. The set of sub-models overfitted for the particular location corresponding to the first local system 6050 by utilizing medical scan training set 1 can be sent back to the first local system 6050. The first local system 6050 can perform the sub-model selection step 6020 itself in response to determining to process a new medical scan to determine which of the set of its set of sub-models to utilize. The set of sub-models can be stored by the first local system 6050 in its own medical scan analysis function database 346. Each local system can receive the same or different set of sub-models overfitted for their own respective locations based on their respective training sets, and can similarly store their set of sub-models in their own medical scan analysis function database 346 or other memory.

Some or all of the plurality of local systems 6050 can be associated with particular hospitals or medical entities. Some or all of the plurality of local systems 6050 can be implemented by utilizing one or more subsystems 101 and/or by utilizing one or more client devices 120. Some or all of the of the plurality of local systems 6050 can be implemented by utilizing a medical picture archive integration system 2600, for example, where the central server system 2640 is implemented by utilizing the location-based medical scan analysis system 6004 and/or otherwise communicates with the location-based medical scan analysis system 6004. For example, the annotating system 2612 can receive, store, and utilize one or more sub-models overfitted for the location associated with the corresponding medical picture archive integration system 2600, received from the location-based medical scan analysis system 6004 and stored as the inference functions 1-K stored in memory 2684. The medical scan training set utilized for a local system can be anonymized by its de-identification system 2608 for transmission to the location-based medical scan analysis system 6004.

In various embodiments, a location-based medical scan analysis system 6004 includes at least one processor and a memory that stores operational instructions that, when executed by the at least one processor, cause the location-based medical scan analysis system to receive, via a receiver, a plurality of medical scans. A generic model is generated by performing a training step on image data of the plurality of medical scans. A plurality of location-based subsets of the plurality of medical scans is generated. Each of the plurality of location-based subsets is generated by including ones of the plurality of medical scans with originating locations that compare favorably to location grouping criteria for the each of the plurality of location-based subsets. A plurality of location-based models is generated. Each of the plurality of location-based models is generated by performing a fine-tuning step on the generic model, utilizing a corresponding one of the plurality of location-based subsets. Inference data is generated for a new medical scan by performing an inference function that utilizes one of the plurality of location-based models on the new medical scan.

An originating location associated with the new medical scan compares favorably to the location grouping criteria for one of the plurality of location-based subsets utilized to generate the one of the plurality of location-based models. The inference data is transmitted to a client device for display via a display device.

FIGS. 18A-18E illustrate an embodiment of a model-assisted annotating system 7002. One or more models can be continually updated over time as additional training data becomes available, by utilizing annotations generated via user input to a client device. Some or all of these human-generated annotations for subsequent sets of training data can be assisted via display of, and/or can be supplemented by, automatically-generated annotations generated by utilizing a current version of one or more models. The human-generated annotations can confirm accuracy of these automatically-generated annotations, can provide corrections and/or edits to the automatically-generated annotations, and/or utilize the automatically-generated annotations to provide additional, more detailed information. These human-generated annotations for subsequent sets of training data can then be utilized to update one or more models, and this process can be repeated over time to further improve models.

As shown in FIGS. 18A-18E, the model-assisted annotating system 7002 can communicate bi-directionally, via network 150, with the medical scan database 342, medical scan analysis function database 346, with other databases of the database storage system 140, with one or more client devices 120, and/or, while not shown in FIGS. 18A-18E, with one or more subsystems 101 of FIG. 1, with the central server system 2640, and/or with the medical picture archive system 2600.

In some embodiments, the model-assisted annotating system 7002 is an additional subsystem 101 of the medical scan processing system 100, implemented by utilizing the subsystem memory device 245, subsystem processing device 235, and/or subsystem network interface 265 of FIG. 2A. For example, the model-assisted annotating system 7002 can be implemented by utilizing the medical scan image analysis system 112, the multi-label medical scan analysis system 5002, and/or the multi-model medical scan analysis system 6002 to train one or more computer vision models and/or to perform one or more inference functions by utilizing the one or more computer vision models. Furthermore, the generation of human-generated annotation data via user input to interactive interfaces by utilizing client devices 120, as illustrated in FIGS. 18A and 18C, can be implemented by utilizing the medical scan assisted review system 102, the medical scan annotating system 106, and/or the medical scan hierarchical labeling system 3002.

In some embodiments, the model-assisted annotating system 7002 utilizes, or otherwise communicates with, the central server system 2640. For example, the medical scan database 342 can be populated with de-identified data generated by the medical picture archive integration system 2600. The model-assisted annotating system 7002 can receive de-identified medical scans of the training set with their corresponding annotation data, diagnosis data, and/or medical reports directly from the medical picture archive integration system 2600, for example, where the annotation data, diagnosis data, and/or medical reports are utilized to determine the medical labels for medical scans in the training set. As another example, the model-assisted annotating system 7002 can perform one or more inference functions on de-identified medical scans received from the medical picture archive integration system 2600, and abnormality data or other inference data generated as output of the plurality of the one or more inference functions can be assigned to the medical scan in the medical picture archive integration system 2600. As another example, the model-assisted annotating system 7002 can request de-identified medical scans, annotation data, and/or reports that match requested criteria for the training set and/or for new medical scans to be labeled. In some embodiments, some or all of the model-assisted annotating system 7002 is implemented by utilizing other subsystems 101 and/or is operable to perform functions or other operations described in conjunction with one or more other subsystems 101.

Figure 18A:
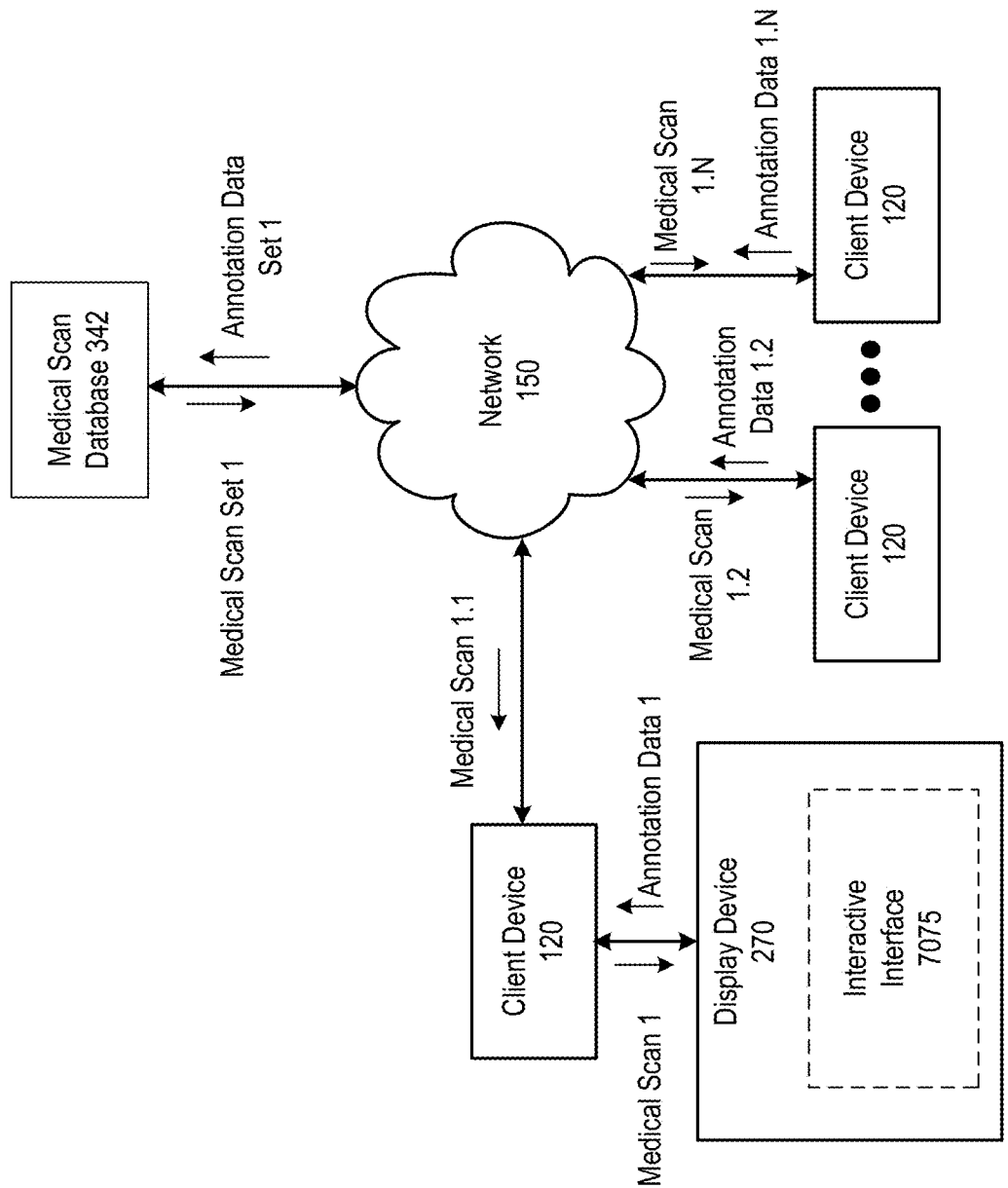

As illustrated in FIG. 18A, a first set of medical scans can be retrieved from a medical scan database for transmission to a plurality of client devices 120. The model-assisted annotating system 7002 can automatically determine which client devices the first set of medical scans are transmitted to and/or which medical scans in the first set of medical scans are sent to each client device, for example, based on performance data and/or qualification data of corresponding user and/or based on means utilized by the medical scan annotating system 106.

Each of the client devices can display one or more medical scans of the first set to a user via an interactive interface 7075, and can generate annotation data based on user input to the interactive interface in response to a prompt displayed by the interactive interface. The interactive interface 7075 can utilize features of the medical scan assisted review system 102 and/or the medical scan hierarchical labeling system 3002, for example where the interactive interface 7075 utilizes some or all features of interactive interface 3075 discussed in conjunction with the medical scan hierarchical labeling system 3002 and/or some or all features discussed in conjunction with FIGS. 13C-13V. For example, the medical scan 1.1 in the first medical scan set is displayed via a first client device, and corresponding annotation data 1.1 is generated by the first client device by utilizing user input to the interactive interface. Each annotation data 1.1-1.N can correspond to structured, standardized labeling data, such as the labeling discussed in conjunction with the medical scan hierarchical labeling system 3002. The annotation data 1.1-1.N can include any structured or unstructured data, and can indicate any of the diagnosis data 440 discussed herein. A first set of annotation data, which includes the annotation data 1.1-1.N corresponding to medical scans 1-N of the first set of medical scans, can be transmitted to the medical scan database for storage in conjunction with the first set of medical scans and can be transmitted to the model-assisted annotating system 7002.

Figure 18B:
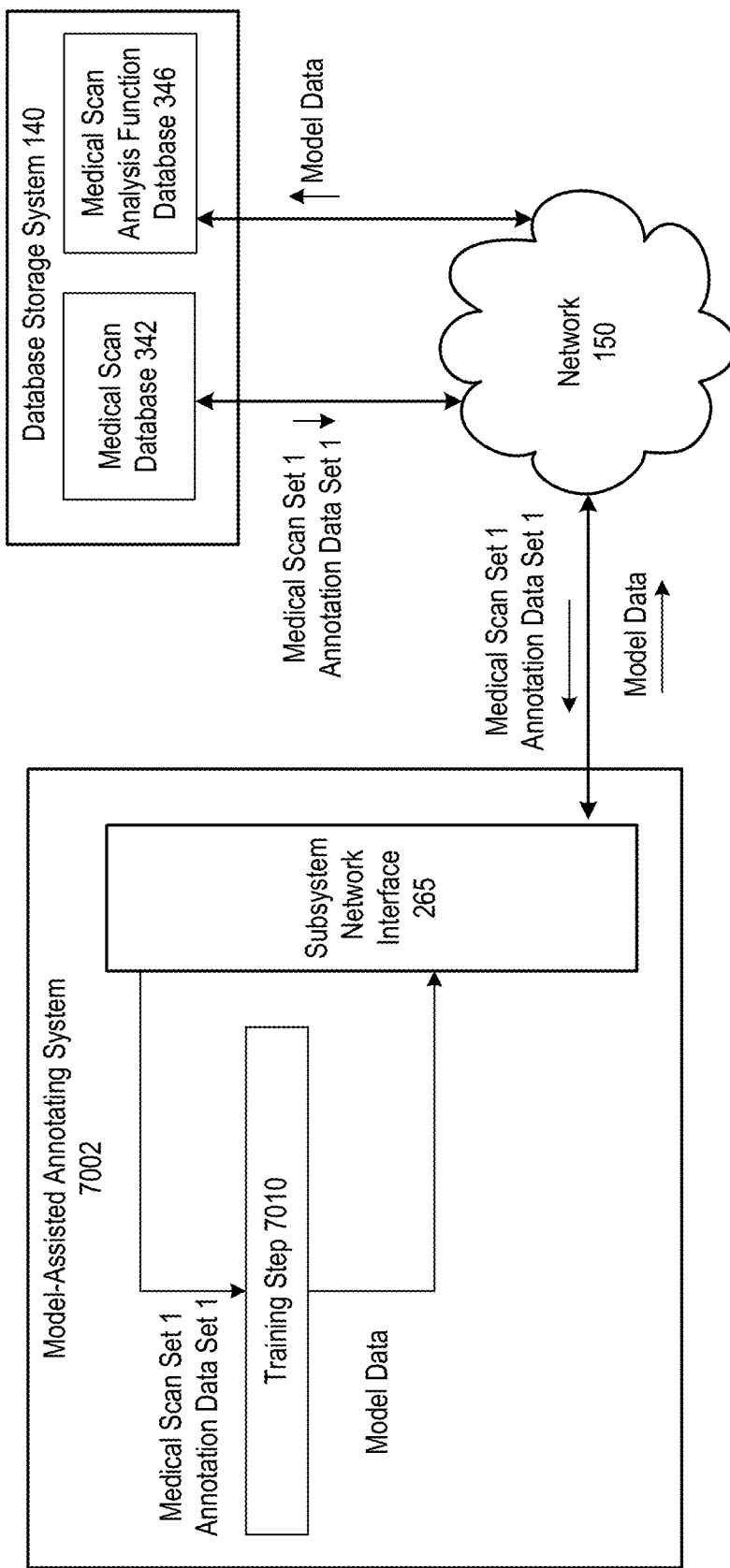
Figure 18C:
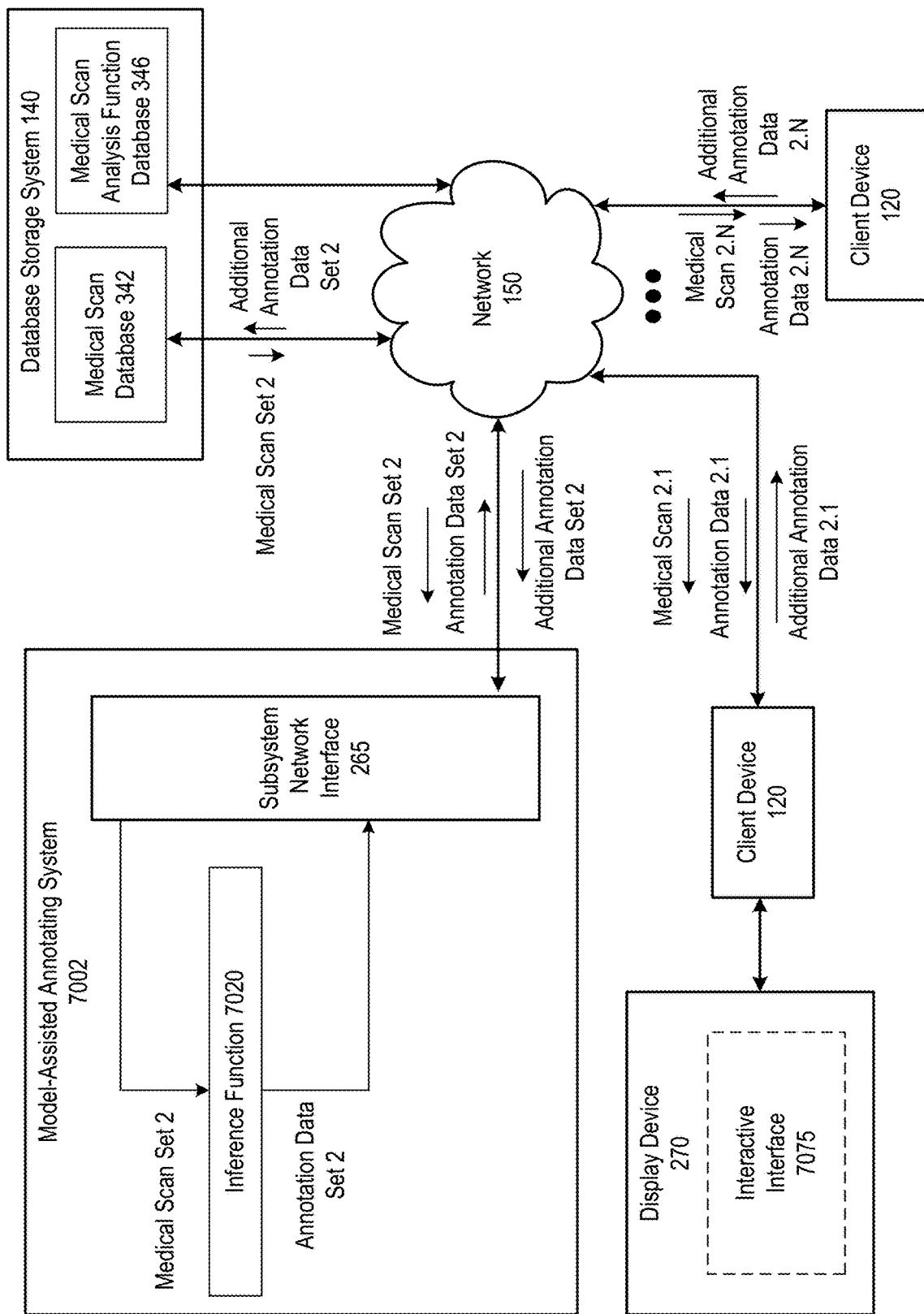

As illustrated in FIG. 18B, the model-assisted annotating system 7002 can utilize this first set of medical scans and corresponding annotation data to train a model, which can be utilized in performing any of the medical scan analysis functions or other inference functions discussed herein. For example, the model can correspond to a computer vision model that utilizes a neural network, where input labels correspond to image data of the medical scans and where output labels correspond to some or all of the annotation data. The training step 7010 utilized to train the model can be implemented by utilizing some or all of training step 5010 of the multi-label medical scan analysis system, for example, where the model corresponds to a multi-label model utilized to perform inference function 5020. Alternatively or in addition, the training step 7010 utilized to train the model can be implemented by utilizing some or all of training step 6010, for example, where a plurality of submodels 1-K are trained and are utilized to perform inference functions 1-K. Alternatively or in addition, the training step 7010 utilized to train the model can be implemented by utilizing some or all of training step 1352 of FIG. 7A. Model parameters for the trained model can be stored locally for further use by the model-assisted annotating system 7002 and/or can be transmitted to the medical scan function database for use by other subsystems 101 as any medical scan analysis function and/or inference function as discussed herein.

Over time, this model can be implemented by the model-assisted annotating system 7002 and/or other subsystems 101 to generate annotation data for new medical scans. As illustrated in FIG. 18C, a second set of medical scans can be received from the medical scan database, for example, where the second set of medical scans includes new medical scans not included in the first set of medical scans, such as more recent medical scans that were not previously available or otherwise were determined to not be included in the first set of medical scans. An inference function 7020 can be performed on each of the second set of medical scans to automatically generate annotation data for each of the second set of medical scans. Inference function 7020 can utilize the model generated by performing training step 7010 in FIG. 17D. Inference function 7020 can utilize inference step 6030 to perform one or more inference functions 1-J selected for the medical scan and/or a final inference function, where the annotation data corresponds to the final abnormality data. Inference function 7020 can utilize inference function 5020, global labeling function 5030, and/or heat map generator function 5040, where the annotation data includes the probability matrix data, global probability data, and/or heat map visualization data discussed in conjunction with FIGS. 14B and 14C. Inference function 7020 can utilize inference step 1354, detection step 1372, abnormality classification step 1374, similar scan identification step 1376, and/or display parameter step 1378 as discussed in conjunction with FIG. 7B. The annotation data generated as output to the inference function can include probabilities and/or can correspond to structured labeling data as discussed in conjunction with the medical scan hierarchical labeling system, for example, where the annotation data indicates probabilities for one or more internal nodes and/or leaf nodes of a prompt decision tree to characterize one or more abnormalities. Each of the second set of annotation data can indicate any of the diagnosis data 440 as discussed herein. While not shown in FIG. 18C, this second set of annotation data can be sent to the medical scan database for storage in conjunction with the second set of medical scans and/or can be transmitted to other subsystems 101 for use.

In particular, this annotation data can be utilized to aid users in generating additional annotation data via interaction with interactive interface 7075, as illustrated in FIG. 18C. The annotation data can be displayed in conjunction with a corresponding medical scan via interactive interface 7075. For example, a first client device can display a medical scan 2.1 of the second set of medical scans in conjunction with the corresponding annotation data 2.1 generated by the model-assisted annotating system 7002. The annotation data 2.1 can be displayed as text and/or can be utilized to visually indicate one or more abnormalities detected in the medical scan 2.1.

Some or all of the annotation data can be displayed visually, overlaying image data of the medical scan displayed by the interactive interface 7075. For example, the annotation data 2.1 can include localization data indicating a region of interest where an abnormality was detected, for example, based on probability matrix data. This localization data can include segmenting data automatically generated by the model-assisted annotating system 7002, and the segmenting data can be utilized to display a polygon shape outlining and/or surrounding a detected abnormality indicated in the annotation data, overlaying image data of the medical scan displayed by the interactive interface 7075. The annotation data can include the heat map visualization data of FIG. 14C, which can be displayed in conjunction with the medical scan via the interactive interface 7075. The annotation data can include measurement data indicating a diameter, area, and/or volume automatically calculated for an abnormality detected in the medical scan, and the measurement data can be displayed upon an abnormality detected in the image data. For example, a diameter measurement can be displayed upon an abnormality detected in the image data.

Alternatively or in addition, some or all of the annotation data 2.1 can be displayed by automatically making one or more prompt selections as discussed in conjunction with the medical scan hierarchical labeling system. In particular, one or more of the hierarchical interface features, such as those illustrated in FIGS. 13S-13V, can be automatically selected, where checked boxes or other visual indications of selection automatically appear based on corresponding labels being indicated in the annotation data 2.1. Furthermore, the prompt decision tree can automatically progress to an internal node prompt based on one or more decisions already made as indicated in the annotation data. For example, a user can be automatically presented with an interface as displayed in FIG. 13T in response to the automatically generated annotation data 2.1 indicating that the medical scan includes an abnormality characterized as pulmonary vasculature, plethora, and diffuse, where these selections are already visually indicated, and where the user is automatically prompted to select from "left", or "right."

Client devices can generate additional annotation data based on user input to the interactive interface 7075. The generation of the additional annotation data can be assisted based on the already-generated annotation data presented to the user via the interactive interface 7075. The additional annotation data can include correction and/or edits to the annotation data, indicating that some of the annotation data is incorrect. Alternatively, the additional annotation data can indicate all of the annotation data is correct, and can include further detail, for example, to further characterize and/or localize an abnormality indicated in the annotation data. The additional annotation data can indicate both the originally generated annotation data as well as new data inputted by the user, and/or can include only additional information and/or corrections made by the user.

For example, the interactive interface 7075 can automatically outline, highlight, zoom-in on, or otherwise visually indicate at least one automatically detected abnormality indicated in the annotation data. The interactive interface 7075 can prompt the user to confirm whether or not each detected abnormality is indeed an abnormality and/or to confirm and/or edit a type of abnormality determined for the detected abnormality. The interactive interface 7075 can prompt the user to edit any automatically generated characterization data of each abnormality, for example, via interaction with a text box and/or by allowing the user to de-select any automatically made selections, such as automatically determined selections of a hierarchical labeling display such as that of FIGS. 13S-13V.

The interactive interface 7075 can prompt the user to provide additional characterization data for an abnormality indicated in the image data. For example, the user can be automatically presented with an interface as displayed in FIG. 13T in response to the automatically generated annotation data 2.1 indicating that the medical scan includes an abnormality characterized as pulmonary vasculature, plethora, and diffuse, as discussed. The user can then be prompted to make final selections until a leaf node of the prompt decision tree is reached, for example, where the final selections of "left" and "lobe—left upper" are selected via user input as illustrated in FIG. 13U. These selections can be included in the additional annotation data.

The user can be prompted to provide and/or edit measurement data for a detected abnormality, where a user is prompted to draw a diameter for a lesion presented to the user, indicate endpoints of a diameter of a lesion presented to the user, and/or otherwise provide measurement data for a lesion presented to the user. The user can be prompted to provide and/or edit segmentation data for the detected abnormality, where the user is prompted to draw and/or indicate vertices for a polygon surrounding the detected abnormality. These selections can be included in the additional annotation data.

The user can be further prompted to identify, characterize, and/or localize any additional abnormalities that were not indicated in the annotation data. These selections can be included in the additional annotation data.

Figure 18D:
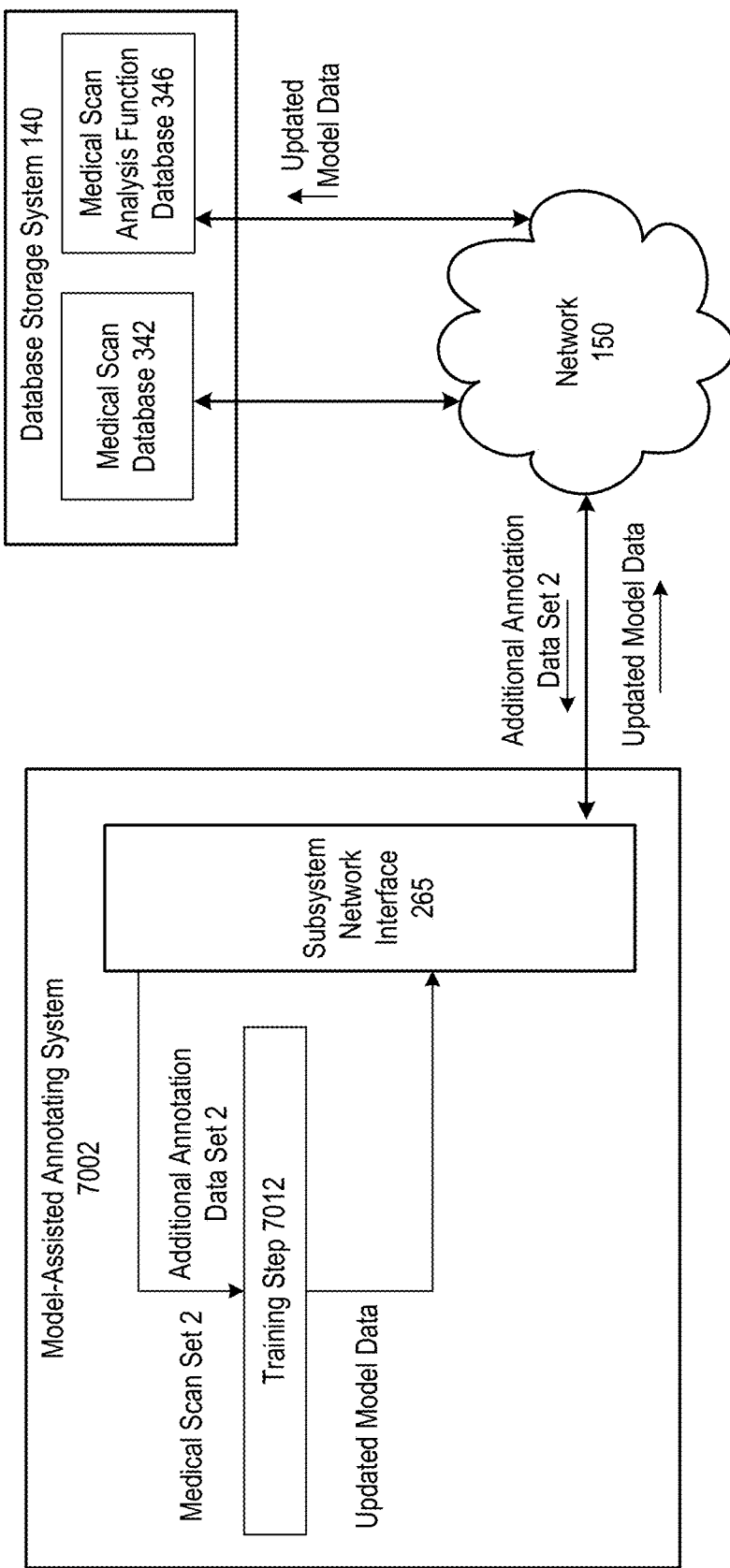

The additional annotation data 2.1-2.N generated for each of the medical scans in the second set of medical scans can be transmitted to the medical scan database for storage in conjunction with the corresponding medical scans. Furthermore, as illustrated in FIG. 18D, this second set of additional annotation data can be utilized to update the current model and/or to update a plurality of sub-models. Training step 7012 can be performed and can include retraining the current model based on corrected annotation data of the additional annotation data, for example, by utilizing the weights and/or other parameters of the current model and by retraining and/or overfitting the current model to modify the current set of weights to generate an updated model and/or an updated plurality of sub-models. Image data of the second set of medical scans can be utilized as input data and the additional annotation data can be utilized as output labels to retrain and/or fine-tune the current model. Some or all of the automatically generated annotation data can also be included in the output labels, for example, for medical scans of the second set with automatically generated annotation data determined to be correct and/or complete. The updated model can correspond to one or more new, fine-tuned models generated by fine-tuning an existing model as discussed in conjunction with FIG. 16B.

Parameters, weights and/or other data for the updated model and/or updated plurality of sub-models can be transmitted to the medical scan analysis function database 346 for use by other subsystems 101. The updated model can also be stored locally by the model-assisted annotating system for further use, as illustrated in FIG. 18E.

The updated model can correspond to a more accurate version and/or more comprehensive of the current model, trained on additional training data that can include more types of medical scans and/or types of abnormalities not sufficiently included in the original training data of the first set of medical scans and the first set of annotation data. Furthermore, the automatic assistance provided via interactive interface 7075 to generate the additional annotation data can increase accurate detection of abnormalities, leading to more accurate annotation data provided by users to generate a more accurate model. The assistance provided via interactive interface 7075 to generate the additional annotation data can increase efficiency, allowing users to more quickly annotate medical scans and leading to a greater volume of annotation data provided by users, allowing for larger training sets to generate a more comprehensive model.

In some embodiments, the current model generates a first type of output, such as abnormality detection data with no characterization data. The updated model can utilize additional information provided in the set of additional annotation data to improve the functionality of the current model, for example, where a second type of output is utilized to train the updated model, where the second type of output includes characterization data and/or other new output labels that were not included in the current model. Thus, the updated model can provide additional functionality, where output of the corresponding inference function included additional probabilities for additional labels not included in the current model, and/or otherwise generates additional information not generated by the current model. This can include generating one or more new types of models, such as one or more of the sub-models 1-K that were not previously available, based additional types of medical scans and/or abnormality data included in the second set of medical scans and/or second set of additional abnormality data. This can also include generating one or more further-fine-tuned models, for example, increasing functionality of an existing fine-tuned-model by training on more detailed characterization and/or localization labels indicated in the additional annotation data to generate a model that can process medical scans and can similarly generate more detailed characterization and/or localization labels.

Figure 18E:
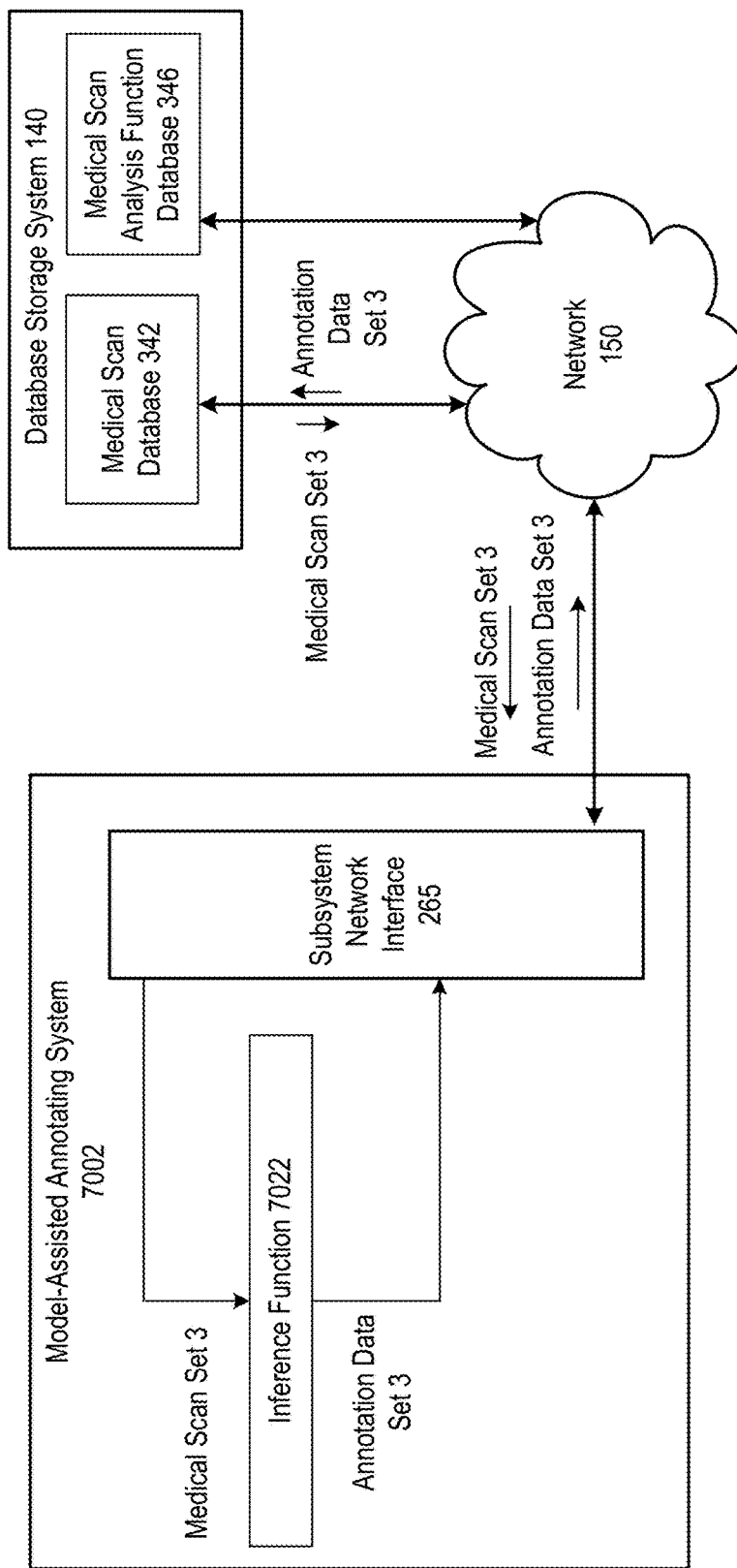

As illustrated in FIG. 18E, a third set of medical scans can be received via the network, and a corresponding third set of annotation data can be generated by utilizing an inference function 7022. The inference function 7022 can utilize the updated model generated by performing training step 7012 in FIG. 17D. Inference function 7022 can utilize inference step 6030 to perform one or more inference functions 1-J selected for the medical scan and/or a final inference function, where the annotation data corresponds to the final abnormality data. Inference function 7022 can utilize inference function 5020, global labeling function 5030, and/or heat map generator function 5040, where the annotation data includes the probability matrix data, global probability data, and/or heat map visualization data discussed in conjunction with FIGS. 14B and 14C. Inference function 7022 can utilize inference step 1354, detection step 1372, abnormality classification step 1374, similar scan identification step 1376, and/or display parameter step 1378 as discussed in conjunction with FIG. 7B.

The third set of annotation data can be transmitted to the medical scan database 342 as illustrated in FIG. 18E, for example, in response to the updated model being determined to be complete and/or sufficiently accurate. Alternatively, the process illustrated in FIGS. 18C and 18D can repeat for this third set of medical scans, where the third set of medical scans and corresponding set of annotation data are sent to the same or different set of client devices, and where additional annotation data is generated by the client devices based on user input the interactive interface 3075 in response to a prompt displayed via the interactive interface 3075 in conjunction with display of one or more of the third set of medical scans and corresponding set of automatically generated annotation data. This third set of additional annotation data can be utilized to further update the current model and/or one or more of a plurality of sub-models.

This process can continue to repeat for subsequent sets of medical scans, where the model and/or a plurality of submodels are further updated over time to improve accuracy and/or increase functionality. The model-assisted annotating system 7002 can automatically determine when this process should be repeated, for example, in response to determining a generic model and/or one or more sub-models are not sufficiently accurate, do not generate enough information to fully characterize one or more types of abnormalities, and/or were not trained on a sufficient amount of training data corresponding to one or more specific types of medical scans and/or corresponding to one or more specific types of abnormalities, resulting in the generic model and/or one or more sub-models not sufficiently handling the one or more specific types of medical scans and/or not sufficiently detecting and/or characterizing the one or more specific types of abnormalities. Retraining one or more models as discussed in conjunction with FIGS. 18C and 18D can be included in a remediation step 1140, in response to determining to temporarily decommission one or of the models and/or in response to determining the one or more models needs to be retrained by utilizing new training data.

In some embodiments, subsequent rounds of training include increasing characterization functionality, for example, based on more and more detailed characterization indicated by the characterization prompt decision tree and/or another prompt decision tree. In particular, early rounds of training can automatically generate detection data and/or less detailed characterization data corresponding to internal nodes of the characterization prompt decision tree that are close to the root node. The additional annotation data can include standardized labeling data corresponding to one or more deeper layers of the prompt decision tree and/or leaf nodes. The training step 7012 can include fine-tuning an existing model trained to characterize a particular type by introducing additional output labels corresponding to selections made in a deeper layer of the prompt decision tree. This process can repeat as additional training data is available to enable automatic characterization corresponding to deeper and deeper layers of the prompt decision tree, for example, where corresponding further-fine-tuned models are trained by overfitting a model trained in a previous iteration, based on the additional annotation data, for enable even more characterization functionality. This process can similarly be implemented for localization by utilizing the localization prompt decision tree.

The model-assisted annotating system 7002 can further determine what type of training data is necessary for subsequent rounds of updated training, and can request specific types of medical scans from the medical scan database by automatically generating medical scan criteria indicating particular scan classifier data 420 such as one or more particular modalities, anatomical regions, sequences, geographic regions, hospital settings, and/or originating entities. Furthermore, for medical scans that may already have diagnosis data 440 in the medical scan database generated by a client device based on user input and/or automatically generated by another subsystem 101, the medical scan criteria can further indicate particular diagnosis data 440, indicating particular types of abnormalities and/or particular abnormality classification data 445 for one or more abnormality classifier categories 444 and/or abnormality pattern categories 446. A set of medical scans corresponding to this automatically generated medical scan criteria can be automatically retrieved from the medical scan database 342. A set of annotation data can be automatically generated utilizing one or more existing models, and this annotation data can be sent to the same or different set of client devices with the corresponding set of medical scans. The additional annotation data can be generated as discussed in conjunction with FIG. 18C. A generic model and/or one or more sub-models can be automatically updated by performing the same or different training step 7012 to increase accuracy of one or more existing models, to improve functionality of one or more existing models, and/or to create one or more new models, for example, configured to handle medical scans and/or abnormalities identified in the automatically generated medical scan criteria.

Generating the medical scan criteria can include identifying weak categories based on evaluating the annotation data generated across a set of medical scans. These identified weak categories can be utilized to automatically dictate types of training data that should be prioritized to improve the model, and can be used to identify additional scans to include in the training data to train an improved model.

For example, the automatically generating medical scan criteria can be generated for subsequent rounds of updated training based on automatically detecting weak categories of medical scans. This can include evaluating a set of annotation data generated for a set of medical scans on a most current model and/or a most current one or more sub-models. Confidence levels and/or a confusion matrix of the annotation data for the set of scans can be compared to thresholds across multiple scan classifier categories to identify weak categories. This can include utilizing the probabilities indicated in probability matrix data generated by performing an inference step 1354 and/or inference function 5020.

A weak scan classifier categories can include medical scans of with scan classifier data 420 or one or more particular categories where a threshold number the medical scans in the identified scan classifier category have corresponding annotation data that has confidence levels confusion matrices that compare unfavorably to the threshold, for example, indicating abnormalities are identified with weak levels of confidence. Similarly, additional annotation data received from client devices indicating a threshold number of medical scans of a particular scan classifier category with incorrect annotation data can be utilized to identify the particular scan classifier category as a weak scan classifier category. This weak scan classifier category can be indicated in the medical scan criteria, and a set of medical scans corresponding to the weak scan classifier category can be received in response for transmission to client devices with or without corresponding automatically generated annotation data. This set of medical scans and the additional annotation data received from the set of client devices can be utilized to perform training step 7012 to generate updated and/or new sub-models and/or to generate an updated generic model.

As another example, the automatically generating medical scan criteria can be generated for subsequent rounds of updated training based on automatically detecting weak categories of output labels. This can include evaluating a set of annotation data generated for a set of medical scans on a most current model and/or a most current one or more sub-models. Confidence levels and/or a confusion matrix of the annotation data for the set of scans can be compared to thresholds across multiple output label categories to identify weak categories. A weak output label category can correspond to an output label with corresponding confidence levels and/or corresponding probability values in a probability matrix that compare unfavorably to the threshold, indicating these output labels are identified with weak levels of confidence. For example, one or more types of abnormalities of a multi-label model generated as discussed in conjunction with the multi-label medical scan analysis system can be identified as weak when a threshold number of abnormality data indicates the corresponding output labels have corresponding probabilities that compare unfavorably to the threshold.

Similarly, additional annotation data received from client devices indicating a threshold number of automatically generated annotation data indicating the type of abnormality was incorrect can be utilized to identify the type of abnormality as a weak type of abnormality. The weak output label can be indicated in the medical scan criteria, and a set of medical scans corresponding to the weak output label can be received in response. For example, medical scans with already-generated diagnosis data 440 matching the weak output label can be retrieved. This set of medical scans can be sent to client devices to allow the already-generated diagnosis data 440 to be confirmed and/or edited in the additional annotation data, and this additional annotation data can be received from the set of client devices can be utilized to perform training step 7012 to generate updated and/or new sub-models and/or to generate an updated generic model. Alternatively, the set of medical scans and the already-generated diagnosis data 440 corresponding to the weak label can be utilized perform training step 7012 without the need for additional annotation data.

Other problematic trends across the automatically generated annotation data can be identified based on a set of rules. For example, detecting an instance or trend that the global abnormal score is high where no individual abnormality pattern is high can be used to flag a problem with the model. Similarly, detecting an instance or trend where the global abnormality score is low and one or more individual scores is high can also be used to flag a problem with the model. As another example, the set of rules can include sets of findings with required dependencies, indicating sets of findings that should or shouldn't occur in tandem. Detecting an instance or trend that one of these sets of findings occurs in tandem can be used to flag a problem with the model. These identified problematic trends can also be used to automatically dictate types of training data that should be prioritized to improve the model.

When one of the set of rules is broken by a threshold number of the set of annotation data, retraining can be determined to be necessary. If one of more of the set of rules is broken by a threshold number of the set of annotation data for scans of a particular type, medical scans with the corresponding scan classifier data for these scans can be requested as additional training data. one or more particular output labels are determined to be included in a set of required dependencies that is broken by a threshold number of the set of annotation data, additional medical scans with these output labels can be requested as additional training data.

A set of required dependencies in the set of rules can indicate output labels for findings that should occur in tandem, and this rule can be determined to be broken for annotation data with one of the output labels of the required dependency having a corresponding probability of being present in the medical scan that compares favorably to a detection probability threshold, and with a second one of the output labels of the required dependency having a corresponding probability of being present in the medical scan that compares unfavorably to the same or different detection probability threshold. The set of required dependencies can indicate output labels for findings that should not occur in tandem, and this rule can be determined to be broken for annotation data with two or more of the output labels of the required dependency having corresponding probabilities of being present in the medical scan that compare favorably to the same or different detection probability thresholds. Alternatively or in addition, determining whether or not findings have occurred in tandem in the annotation data can include calculating a difference between detection probabilities of the corresponding findings, where the findings are determined not to occur in tandem if the difference between the detection probabilities exceeds a difference threshold.

The annotation data can indicate a global abnormality probability, indicating a probability that any abnormality is present. The annotation data can further include a plurality of abnormality type probabilities, each indicating a probability that one of a set of corresponding abnormality types is present. The set of rules can dictate that when the global probability compares favorably to a detection probability threshold, then at least one of the abnormality type probabilities must compare favorably to the same or different detection probability threshold. The set of rules can dictate that when at least one of the abnormality type probabilities compares favorably to a detection probability threshold, then the global probability must compare favorably to the same or different detection probability threshold. The set of rules can dictate that when the global probability compares unfavorably to a detection probability threshold, then all of the abnormality type probabilities must compare unfavorably to the same or different detection probability threshold. The set of rules can dictate that when all of the abnormality type probabilities compare unfavorably to a detection probability threshold, then the global probability must compare unfavorably to the same or different detection probability threshold.

The set of rules can be generated based on user input to an interactive interface displayed via a display device in response to a prompt to indicate the set of rules. Alternatively or in addition, the set of rules can be generated based on automatically determining trends in training data, such as automatically identifying findings that always or often occur in tandem and/or automatically identifying findings that rarely or never occur in tandem, and/or otherwise automatically determining pair or other sets of findings that have a high correlation that is determined to be statistically significant.

In various embodiments, a model-assisted annotating system 7002 includes at least one processor and a memory that stores operational instructions that, when executed by the at least one processor, cause the model-assisted annotating system to receive, via a receiver, a first set of medical scans for review. The first set of medical scans can be transmitted, via a transmitter, to a set of client devices associated with a set of users. Each of the first set of medical scans can be displayed to one of the set of users via an interactive interface displayed by a display device associated with a corresponding one of the set of client devices. A first set of annotation data can be received from the set of client devices. Each of the first set of annotation data can be generated by one of the set of client devices in response to a prompt via the interactive interface displayed by the display device to provide annotation data for one of the first set of medical scans displayed by the one of the set of client devices.

A first training step can be performed to train a computer vision model by utilizing image data of the first set of medical scans as input labels and by utilizing the first set of annotation data as output labels. A second set of medical scans can be received, via the receiver, for review. A second set of annotation data can be generated by performing an inference function on image data of the second set of medical scans. The inference function can utilize the computer vision model. Each of the second set of annotation data can be generated as output of performing the inference function on a corresponding one of the second set of medical scans.

The second set of medical scans and the second set of annotation data can be transmitted, via the transmitter, the to the set of client devices, wherein each of the second set of medical scans is displayed to one of the set of users in conjunction with a corresponding one of the second set of annotation data via the interactive interface. A set of additional annotation data can be received from the set of client devices. Each of the set of additional annotation data can be generated by one of the set of client devices in response to a prompt via the interactive interface displayed by the display device to provide additional annotations to the corresponding one of the second set of annotation data displayed in conjunction with one of the second set of medical scans by the one of the set of client devices. A second training step can be performed to generate an updated computer vision model by utilizing the set of additional annotation data to update the computer vision model.

A third set of medical scans can be received, via the receiver, for review. A third set of annotation data can be generated by performing an updated inference function on image data of the third set of medical scans. The updated inference function can utilize the updated computer vision model, and each of the third set of annotation data can be generated as output of performing the updated inference function on a corresponding one of the third set of medical scans. The third set of medical scans and the third set of annotation data can be transmitted, via the transmitter, to the set of client devices. Each of the third set of medical scans can be displayed to one of the set of users in conjunction with a corresponding one of the third set of annotation data via the interactive interface.

FIG. 19 presents a medical scan triaging system 8002. The medical scan triaging system 8002 can be utilized to automatically forego human-review of medical scans that are determined to be normal with a high enough probability. In particular, human-review of these medical scans can be waived based on determining global abnormality thresholds generated by performing an inference function on these medical scans compares unfavorably to a triage probability threshold, where the triage probability threshold is generated automatically or generated via administrator input. The remaining medical scans with a high enough probability that some abnormality exists can be triaged for review by a plurality of users via interaction with an interactive interface displayed via display devices of a plurality of client devices. In particular, the remaining medical scans are designated for human review based on determining global abnormality thresholds generated by performing an inference function on these medical scans compares favorably to a triage probability threshold. These triaged scans can be queued in a designated order and/or can be designated for particular users based on the type of scan, based on types of abnormalities detected, and/or based on a determined severity, rarity, and/or time-sensitivity of detected abnormalities.

As shown in FIG. 19, the medical scan triaging system 8002 can communicate bi-directionally, via network 150, with the medical scan database 342 and/or with other databases of the database storage system 140, with one or more client devices 120, and/or, while not shown in FIG. 19, with one or more subsystems 101 of FIG. 1, with the central server system 2640, and/or with the medical picture archive system 2600.

In some embodiments, the medical scan triaging system 8002 is an additional subsystem 101 of the medical scan processing system 100, implemented by utilizing the subsystem memory device 245, subsystem processing device 235, and/or subsystem network interface 265 of FIG. 2A. For example, the medical scan triaging system 8002 can be implemented by utilizing the medical scan image analysis system 112, the multi-label medical scan analysis system 5002, the multi-model medical scan analysis system 6002, and/or the model-assisted annotating system 7002 to train one or more computer vision models and/or to perform one or more inference functions by utilizing the one or more computer vision models. Furthermore, the generation of human-generated annotation data via user input to interactive interfaces by utilizing client devices 120, as illustrated in FIG. 19, can be implemented by utilizing the medical scan assisted review system 102, the medical scan annotating system 106, the medical scan hierarchical labeling system 3002, and/or the model-assisted annotating system 7002.

In some embodiments, the medical scan triaging system 8002 utilizes, or otherwise communicates with, the central server system 2640. For example, the medical scan database 342 can be populated with de-identified data generated by the medical picture archive integration system 2600. The medical scan triaging system 8002 can receive de-identified medical scans of with their corresponding annotation data, diagnosis data, and/or medical reports directly from the medical picture archive integration system 2600, for example, where the annotation data, diagnosis data, and/or medical reports are utilized to determine the medical labels for medical scans in a training set utilized to train one or more inference functions utilized by the medical scan triaging system 8002. As another example, the medical scan triaging system 8002 can perform one or more inference functions on de-identified medical scans received from the medical picture archive integration system 2600, and abnormality data or other inference data generated as output of the plurality of the one or more inference functions can be assigned to the medical scan in the medical picture archive integration system 2600. As another example, the medical scan triaging system 8002 can request de-identified medical scans, annotation data, and/or reports that match requested criteria medical scans to be triaged. In some embodiments, some or all of the medical scan triaging system 8002 is implemented by utilizing other subsystems 101 and/or is operable to perform functions or other operations described in conjunction with one or more other subsystems 101.

As illustrated in FIG. 19, a set of medical scans 1-N can be received by the medical scan triaging system 8002. For example, these medical scans can correspond to new medical scans to be reviewed, and can be transmitted to the medical scan triaging system 8002 as they are captured by imaging machines and/or can be requested by the medical scan triaging system 8002. The medical scan triaging system 8002 can perform an inference function 8010 to generate inference data for the plurality of medical scans 1-N. The inference function utilize a computer vision model trained on training set of medical scans and corresponding labeling data. For example, the corresponding labeling data utilized to train the inference function 8010 can include a global abnormality label indicating whether each scan in the training set is normal or includes at least one abnormality. As another example, the inference function 8010 can utilize inference function 7020, inference function 7022, inference step 6030, inference function 5020, inference step 1354, and/or detection step 1372 to generate inference data.

The inference data generated by the inference function 8010 can include a global abnormality probability indicating whether any abnormality is present. This global abnormality probability can be determined by performing the final inference function of FIG. 16C based on abnormality data of a plurality of sub-models performed on each medical scan. The global abnormality probability can be generated based on evaluating whether any of a plurality of output labels generated as output to the inference function 8010 indicate that a corresponding one of a plurality of abnormalities is present, for example, by utilizing one or more probability matrices 1371 and/or probability matrix data generated by utilizing inference function 5020. For example, the global abnormality probability can be generated by utilizing the global probability data generated by performing the global labeling function 5030 on the probability matrix data generated by performing inference function 5020.

In some embodiments, the inference data for a medical scan includes only one output label, indicating a single probability that any abnormality is present. In other embodiments, the inference data for a medical scan includes a plurality of probabilities that a plurality of abnormality types are present, and the global abnormality probability is generated as a function the plurality of probabilities of the plurality of abnormality types. In some embodiments, the inference data for a medical scan includes a plurality of probabilities corresponding to a plurality of regions of the image data of the medical scan, where the global abnormality probability is generated as a function the plurality of probabilities of the plurality of regions.

The global abnormality probability can indicate a highest probability across a plurality of probabilities that each of a plurality of abnormality types are present. The global abnormality probability can indicate a higher probability than any of the plurality of probabilities that each of the plurality of abnormality types are present in response to determining that multiple ones of the plurality of abnormality types have a probability of being present in the medical scan that are higher than a detection probability threshold. The global abnormality probability can indicate a higher probability than any of a plurality of probabilities that each of a plurality of abnormalities are present in response to determining that multiple abnormalities are detected in different regions of the image data, each with a probability of being present in the medical scan that is higher than a detection probability threshold.

In some embodiments, when probability matrix data indicates a plurality of probabilities that each of a plurality of regions of image data of a medical scan include a probability, the global abnormality probability can be higher in response to a higher number of adjacent regions indicating a probability that an abnormality exists that is higher than a detection probability threshold. For example, the global abnormality probability can be higher than any of the probabilities of the plurality of adjacent regions, and the increase in value of the global abnormality probability from an average or highest probability of the adjacent regions can be an increasing function of the number of adjacent regions.

In some embodiments, when a single region indicates a probability that an abnormality exists that is higher than a detection probability threshold, surrounded by adjacent regions that are substantially lower than the detection probability threshold, the global abnormality probability is generated to be lower than the probability in the single region. In some embodiments, a filtering and/or smoothing step can be applied to probability matrix data generated as output to the inference function 8010, where the probabilities of these single regions are considered extraneous probabilities that are removed and/or lowered, and where the global abnormality probability is generated to indicate a probability that an abnormality is present that is lower than the detection probability threshold despite these extraneous probabilities of the probability matrix data.

While the global abnormality probability discussed herein indicates a value that increases with probability that an abnormality is present, the global abnormality probability can instead be represented as a global normal probability. The value of the a global normal probability can be equal to one minus the global abnormality probability, and can indicate a value that increases with probability that no abnormality is present. The inference data generated as output to the inference function 8010 can indicate either the global abnormality probability or the global abnormality probability.

A triage assignment function 8020 can be performed once the global abnormalities are generated for the set of medical scans 1-N. The triage assignment function 8020 can group the medical scans into two groups: a normal group of medical scans determined to be normal, where review by a human is determined not to be necessary, and a triaged group of medical scans, where review by a human review is determined to be necessary. Dividing the medical scans into the two groups can be performed by comparing the global abnormality probability to a triage probability threshold. Medical scans with global abnormality probabilities that compare favorably to the triage probability threshold can be included in the triaged group, and medical scans that compare unfavorably to the triage probability threshold can be included in the normal group. The triage probability threshold can be determined automatically by the medical scan triaging system 8002 and/or can be determined based on receiving a triage probability threshold from a client device 120 based on user input to an interactive interface 8075 displayed on a display device, in response to a prompt to select a triage probability threshold displayed on the interactive interface 7075. For example, an administrator can set the triage probability threshold, and can change the triage probability threshold to a higher or lower value at a later time.

The triage probability threshold can correspond to a very strict standard, for example, where medical scans must have a global normal probability of at least 99% or other substantially high probability that no abnormalities exist to be placed in the normal group. The triage probability threshold can be the same or different from any of the detection probability thresholds discussed herein. The triage probability threshold can be the same or different for different types of medical scans and/or for different types of abnormalities, and a plurality of triage probability thresholds for these different groups can be individually set via user input to interactive interface 8075.

Medical scans assigned to the triage group can be automatically assigned to one or more particular users for review, for example based on performance data and/or qualification data for these users in the user database. In particular, users can be selected as discussed in conjunction with the medical scan annotation system 106, for example, based on the type of medical scan, based on one or more types of detected abnormalities in the inference data, and/or based on an urgency value in the inference data indicating a time-sensitivity of the one of more detected abnormalities. Alternatively or in addition, the users be selected based on availability of the users, based on a queue size of other scans triaged to the users, and/or based on a random or pseudo-random selection.

The corresponding client devices 120 can be determined based on the selected users, and the medical scan triaging system 8002 can facilitate transmission of each medical scans in the triage group to one or more corresponding client devices 120 based on determined assignments. Alternatively, the medical scan triaging system 8002 can transmit triage data to the medical scan database 342 and/or another entity indicating identifiers of the medical scans in the triage group, and the medical scans in the triage group can be retrieved from or automatically transmitted to the client devices 120 accordingly. For example, as illustrated in FIG. 19, medical scans 1-R assigned to the triage group correspond to a proper subset of the set of medical scans 1-N. Identifiers indicating the medical scans medical scans 1-R in the triage group can be transmitted via the network, for example, the medical scan database. Each of the medical scans 1-R can be sent to one or more corresponding client devices 120 for review from the medical scan database 342 and/or from the medical scan triaging system 8002. Alternatively, the identifiers indicating the medical scans 1-R and/or a subset of the identifiers indicating a subset of the triaged scans assigned to each user can be sent to each corresponding client device, and the client devices can retrieve triaged medical scans accordingly by utilizing the corresponding identifiers.

The medical scans in the normal group can identified as not needing additional review, and identifiers indicating the medical scans in the normal group can similarly be sent to the medical scan database 342 and/or another entity. For example, these medical scans can be flagged as normal, can be flagged as review already having been completed, and/or can be flagged as not needing review in a corresponding entry of the medical scan database. For example, as illustrated in FIG. 19, medical scans 1-Q assigned to the normal group correspond to a proper subset of the set of medical scans 1-N. The set of scans 1-R and the set of scans 1-Q can be mutually exclusive and collectively exhaustive with regards to the set of scans 1-N. Identifiers indicating the medical scans medical scans 1-Q in the normal group can be transmitted via the network, for example, the medical scan database. Alternatively or in addition, these medical scans can be removed from a set of scans previously designated for triage. Alternatively or in addition, the identifiers indicating the medical scans in the normal group can be sent to one or more client devices, where users are alerted that these scans do not need review via a display on interactive interface 8077.

In some embodiments where only the global abnormality probability is indicated in the output of inference function 8010, additional inference functions can be applied to medical scans in the triage group. For example, once a medical scan is determined to be designated as needing further review, the sub-model selection step 6020 can be applied to the medical scan, and one or more selected sub-models 1-J can be applied to generate additional inference data by applying inference step 6030. In some embodiments, the additional inference data can be utilized for determining which user will be selected for triage, for example, by utilizing additional details such as a type of abnormality and/or localization data for an abnormality to select a user with corresponding qualifications. The additional inference data can indicate time-sensitivity data, which can be utilized to determine to select a user that will be available to review the scan or see the patient in person more quickly. The additional inference data can indicate corresponding probabilities for some or all of this information, and more qualified users can be selected in response to determining an abnormality's presence in the image data is more uncertain, and that more scrutiny will be necessary to review the scan. Similarly, less qualified users can be selected to review a medical scan in response to determining an abnormality's presence in the image data is more certain and/or is characterized with more detail and/or with higher confidence, where less scrutiny may be required to review the scan. Some or all of this additional information provided by performing subsequent inference functions can instead be indicated in the original inference data generated as output of inference function 8010.

Interactive interface 8077 can display medical scans triaged to the corresponding client device via a corresponding display device to the user. Interactive interface 8077 can allow the user to enter annotation data, report data, diagnosis data, or other data describing any abnormalities determined to be included in the medical scans, for example by utilizing interface features of the medical scan assisted review system 102 and/or the medical scan hierarchical labeling system 3002. Some or all of the additional information generated by the inference function 8010 and/or any additional inference functions performed can be transmitted in conjunction with medical scans to client devices 120 for display to assist users in reviewing the medical scans, for example, as discussed in conjunction with the medical scan assisted review system 102 and/or as discussed in conjunction with the model-assisted annotation system 7002. Alternatively, the medical scans can be reviewed in their original form. The annotation data generated for medical scans reviewed by a user of a client device 120 can be transmitted to the medical scan database for storage, for example, as some or all of diagnosis data 440. As shown in FIG. 19, each annotation data 1-R, corresponding to the triaged medical scans 1-R, can be transmitted from the client devices 120 to the medical scan database 342 for storage, for example, as some or all of diagnosis data 440. Each annotation data 1-R can include structured labeling data, region of interest data, unstructured text, and/or any other diagnosis data 440 as discussed herein.

When the triage probability threshold is changed automatically or based on user input to interactive interface 8075, subsequently received medical scans can be assigned to the triage group or the normal group in accordance with the new triage probability threshold. Furthermore, some of the already-sorted medical scans 1-N can be switched to a different group accordingly. For example, when the triage probability threshold becomes stricter, requiring a higher global normal probability for scans to be placed in the normal category, one or more medical scans included in the normal category because they compared unfavorably to a prior triage probability threshold can be assigned for triage in response to comparing favorably to the new, stricter triage probability threshold. These medical scans can be similarly designated for review by one or more particular users and/or can be queued for review. The medical scan database can be updated to change the designation of these scans from normal to needing review, until review is complete.

When the triage probability threshold becomes looser, requiring a lower global normal probability for scans to be placed in the normal category, one or more medical scans included in the triage category because they compared favorably to a prior triage probability threshold can be assigned as normal in response to comparing unfavorably to the new, looser triage probability threshold. If these medical scans were already transmitted for review to one or more client devices 120, they can be removed from a queue of scans to review and/or a notification can be transmitted to the client device 120 to indicate these medical scans no longer require review. Identifiers for these medical scans can be transmitted to the medical scan database, and these medical scans can be flagged as normal and/or as not requiring review in the medical scan database.

The triage probability threshold can automatically be adjusted by the medical scan triaging system 8002 at any time. For example, the medical scan triaging system 8002 can determine to change the triage probability threshold to a stricter triage probability threshold in response to determining that the accuracy of the inference function 8010 has worsened and/or compares unfavorably to a threshold. The medical scan triaging system 8002 can determine to change the triage probability threshold to a stricter triage probability threshold in response to determining an expected average review time compares favorably to a low review time threshold, and thus more medical scans can be designated for review without overloading users in the system and/or without delaying the expected average review time to compare unfavorably to the low review time threshold.

The medical scan triaging system 8002 can determine to change the triage probability threshold to a looser triage probability threshold in response to determining the accuracy of the inference function 8010 has improved and/or compares favorably to a threshold. The medical scan triaging system 8002 can determine to change the triage probability threshold to a looser triage probability threshold in response to determining the expected average review time to compares unfavorably to the low review time threshold to ensure that medical scans are being reviewed more quickly.

Performing the triage assignment function 8020 can include generating priority data for the medical scans in the triage group, for example where medical scans are designated for a review in an order designated by a plurality of priority values generated for the plurality of medical scans. The priority values be a function of global abnormality probability, and can be assigned a higher values for higher probabilities that an abnormality exists, as dictated by the global abnormality probability. The priority values can be function of a severity level and/or rarity level corresponding to one or more types of abnormalities detected in the medical scan, where medical scans with detected types of abnormalities determined to be more rare or more severe are assigned higher probability values. The priority values can be function of a global time-sensitivity value indicated in the inference data generated by performing inference function 8010, for example, where the time-sensitivity value is based on one or more output labels in the inference data, and where the inference function 8010 was trained by utilizing output labels for the training set of medical scans that indicated one or more time-sensitivity values based on an determined time-sensitivity for the training set of medical scans. The priority value can be assigned a higher value for higher time-sensitivity values. The priority value can be determined as a weighted sum, weighted average, or other function of multiple criteria including one or more of the global abnormality probability, severity value, rarity value, time-sensitivity value, and/or other output labels indicated in the inference data.

The medical scans can be queued for review in an order dictated by the corresponding priority values, where medical scans with the highest priority values are queued for review first. Selecting which users will review each medical scan can further be based on the ordering of priority values, where users determined to be available to review medical scans more quickly and/or more accurately are selected to review medical scans with higher priority values, and/or where a plurality of medical scans with highest priority values are divided amongst multiple users, ensuring each of these users can review these highest priority medical scans first and ensuring that all of the highest priority scans are reviewed in a timely fashion. A subset of medical scans designated for a particular user can be queued for that user in accordance with the priority values, where the interactive interface 8077 presents the medical scans to the user one at a time for review in accordance with the ordering dictated by the priority values.

In some embodiments, some medical scans with global abnormality probabilities that compare unfavorably to the triage probability threshold can still be designated for triage. For example, if a severity, rarity, and/or time-sensitivity value determined in the inference data for a medical scan exceeds a corresponding severity, rarity, and/or time-sensitivity threshold, these medical scans can similarly be designated for review. For example, consider a medical scan with inference data indicating a particular type of abnormality may possibly being present with a low probability, where global abnormality probabilities is not high enough for the medical scan to be designated for triage. If this particular type of abnormality is not particularly severe, rare, and/or time-sensitive, accidently placing this medical scan in the normal group may not be particularly detrimental. However, if this particular type of abnormality is particularly severe, rare, and/or time-sensitive, accidently placing this medical scan in the normal group could be very detrimental. The severity, rarity, and/or time-sensitivity threshold for triage can be determined based on user input to interactive interface 8075 and/or can be determined automatically by the medical scan triaging system 8002. Additional triaging probability thresholds for one or more corresponding probabilities for one or more particular types of abnormalities can also be utilized to dictate whether a severe, rare, and/or time-sensitive type of finding has a high enough probability of warranting review. Thus, determining whether a medical scan is grouped in the triage group can be a function of its severity, rarity, and/or time-sensitivity value in addition to its global abnormality probability.

In various embodiments, a medical scan triaging system 8002 includes at least one processor and a memory that stores operational instructions that, when executed by the at least one processor, cause the medical scan triaging system to receive, via a receiver, a plurality of medical scans for review. Abnormality data can be generated for each of the plurality of medical scans by performing an inference function on image data of each of the plurality of medical scans. The inference function can utilize a computer vision model trained on a training set of medical scans, and the abnormality data for the each of the plurality of medical scans can indicate a global abnormality probability indicating a probability that an abnormality is present in the each of the plurality of medical scans. A triage probability threshold can be determined based on user input to a first client device in response to a prompt presented via an interactive interface. The interactive interface can be displayed on a first display device associated with the first client device.

A first subset of the plurality of medical scans can be determined by identifying ones of the plurality of medical scans with a corresponding global abnormality probability that compares favorably to the triage probability threshold. A second subset of the plurality of medical scans can be determined by identifying ones of the plurality of medical scans with a corresponding global abnormality probability that compares unfavorably to the triage probability threshold. The first subset of the plurality of medical scans can be designated for human review, and the second subset of the plurality of medical scans can be designated as normal, where human review of the second subset of the plurality of medical scans is automatically waived. Transmission of the first subset of the plurality of medical scans to a plurality of client devices associated with a plurality of users can be facilitated. The first subset of the plurality of medical scans can be displayed to the plurality of users via a plurality of display devices associated with the plurality of users.

FIG. 20 presents a flowchart illustrating a method for execution by a multi-model medical scan analysis system 6002 that stores executable instructions that, when executed by at least one processor, cause the multi-model medical scan analysis system 6002 to perform the steps below.

Step 9002 includes receiving, via a receiver, a plurality of medical scans. Step 9004 includes generating a plurality of training sets from the plurality of medical scans. Step 9006 includes generating each of a set of sub-models by performing a training step on a corresponding one of the plurality of training sets of the plurality of medical scans. Step 9008 includes receiving, via the receiver, a new medical scan. Step 9010 includes selecting a subset of the set of sub-models based on the new medical scan. Step 9012 includes generating a set of abnormality data by applying a subset of a set of inference functions on the new medical scan. The subset of the set of inference functions utilize the subset of the set of sub-models, and each of the set of abnormality data is generated as output of performing one of the subset of the set of inference functions on the new medical scan. Step 9014 includes generating final abnormality data by performing a final inference function on the set of abnormality data. Step 9016 includes transmitting the final abnormality data to a client device for display via a display device.

In various embodiments, each of the set of sub-models corresponds to one of a set of medical scan classification categories. Each of the plurality of training sets are generated to include ones of the plurality of medical scans of a corresponding one of the set of medical scan classification categories. The subset of the set of sub-models are selected by determining a corresponding subset of the set of medical scan classification categories that compare favorably to the new medical scan. In various embodiments, the set of medical scan classification categories correspond to a plurality of medical scan modalities, a plurality of medical scan views, and/or a plurality of anatomical regions.

In various embodiments, the new medical scan is received in a study for a patient that includes a plurality of medical scans. The subset of the set of sub-models is selected based on the plurality of medical scans in the study, and at least two of the subset of the set of inference functions are performed on different ones of the plurality of medical scans to generate the set of abnormality data. In various embodiments, the set of abnormality data indicates a plurality of probabilities that indicate whether an abnormality is present in the different ones of the plurality of medical scans. The final inference function utilizes a Bayesian model to generate a final probability that the abnormality is present in the patient given the plurality of probabilities of the set of abnormality data.

In various embodiments, a first one of the subset of the set of sub-models is trained to detect a first type of abnormality, and a second one of the subset of the set of sub-models is trained to detect a second type of abnormality. A first one of the set of abnormality data is generated as output of a first one of the subset of the set of inference functions that corresponds to the first one of the subset of the set of sub-models. A second one of the set of abnormality data is generated as output of a second one of the subset of the set of inference functions that corresponds to the first one of the subset of the set of sub-models. The first one of the set of abnormality data indicates a probability that the first type of abnormality is present, and the second one of the set of abnormality data indicates a second probability that second type of abnormality is present.

In various embodiments, the set of abnormality data indicates a plurality of probabilities that indicate whether a plurality of abnormality types are present. The final inference function utilizes a Bayesian model to generate final probabilities that each of the plurality of abnormality types are present given the plurality of probabilities of the set of abnormality data. In various embodiments, the final inference function utilizes a plurality of known correlations between different types of abnormalities, and the final abnormality data is generated based on a known correlation between the first type of abnormality and the second type of abnormality.

In various embodiments, a training step is performed on a plurality of sets of abnormality data to generate a hyper-model. Each of the plurality of sets of abnormality data indicate whether each of the plurality of types of abnormalities are present in a corresponding study in a training set of studies, where the final inference function utilizes the hyper-model, and where the plurality of known correlations are determined as a result of generating the hyper-model.

In various embodiments, the final abnormality data indicates an increase in the probability that the second type of abnormality is present in response to the set of abnormality data indicating the probability that the first type of abnormality is present compares favorably to a detection threshold and in response to the known correlation between the first type of abnormality and the second type of abnormality comparing favorably to a correlation threshold. In various embodiments, the final abnormality data indicates a decrease in the probability that the second type of abnormality is present in response to the set of abnormality data indicating the probability that the first type of abnormality is present compares unfavorably to a detection threshold and in response to the known correlation between the first type of abnormality and the second type of abnormality comparing favorably to a correlation threshold.

In various embodiments, the method further includes partitioning data of the plurality of medical scans into at least two partitioned data portions in accordance with a plurality of partitioning categories. At least two of the plurality of training sets are generated to include partitioned data portions of a corresponding one plurality of partitioning categories. The set of sub-models includes at least two sub-models that are each generated by performing the training step on the partitioned data portions of a corresponding one of the at least two of the plurality of training sets. Data of the new medical scan is partitioned into at least two new partitioned data portions. Each of at least two inference functions corresponding to the at least two sub-models are applied to a corresponding one of the at least two new partitioned data portions to generate the set of abnormality data.

In various embodiments, the set of abnormality data indicates a plurality of probabilities that indicate whether an abnormality is present in different partitioned data portions of the new medical scan. The final inference function utilizes a Bayesian model to generate a final probability that the abnormality is present in the new medical scan given the plurality of probabilities of the set of abnormality data.

In various embodiments, image data of the medical scans is partitioned by a plurality of anatomical subregion types. The plurality of training sets includes a set of anatomical subregion type subsets that each include image data of the plurality of medical scans of a corresponding one of the plurality of anatomical subregion types. The image data of the new medical scan is partitioned into a plurality of sub-regions in accordance with the plurality of anatomical sub-region types. At least two of the subset of the set of inference functions are performed on of different ones of the plurality of sub-regions of the image data of the new medical scan.

In various embodiments, the plurality of medical scans include image data and text data. Generating the plurality of training sets includes generating at least one image data training set that includes image data of the plurality of medical scans. Generating the plurality of training sets further includes generating at least one text data training set that includes text data of the plurality of medical scans. A first one of the set of abnormality data is generated by applying a first one of the set of inference functions on image data of the new medical scan, where the first one of the set of inference functions utilizes a computer vision model generated by performing the training step on the image data training set. A second one of the set of abnormality data is generated by applying a second one of the set of inference functions on text data of the new medical scan, where the second one of the set of inference functions utilizes a natural language model generated by performing the training step on the text data training set.

In various embodiments, the medical scans are partitioned by sequence. The plurality of training sets includes a set of sequence type subsets that each include sequences of the plurality medical scans of a corresponding one of a plurality of sequence types. The new medical scan includes a plurality of sequences, and at least two of the subset of the set of inference functions are performed on different ones of the plurality of sequences.

In various embodiments, a first one of the set of abnormality data is generated as output of performing a first one of the subset of the set of inference functions on a first one of the plurality of sequences of the new medical scan that corresponds to a first type of sequence. The first one of the subset of the set of inference functions utilizes a first one of the subset of the set of sub-models that was trained on the first type of sequence. A second one of the set of abnormality data is generated as output of performing a second one of the subset of the set of inference functions on a second one of the plurality of sequences of the new medical scan that corresponds to a second type of sequence. The second one of the subset of the set of inference functions utilizes a second one of the subset of the set of sub-models that was trained on the second type of sequence. The first one of the set of abnormality data indicates a first probability that an abnormality is present in the first one of the plurality of sequences. The second one of the set of abnormality data indicates a second probability that the abnormality is present in the second one of the plurality of sequences. The final abnormality data indicates a final probability that the abnormality is present in the new medical scan, where the final probability is generated based on the first probability and the second probability.

In various embodiments, a first one of the set of sub-model is selected for performance on the new medical scan, based on the new medical scan. First abnormality data is generated by applying a first one of the set of inference functions on the new medical scan, where the first one of the set of inference functions utilizes the first one of the set of sub-models. A second one of the set of sub-models is selected for performance on the new medical scan based on the first abnormality data. Second abnormality data is generated by applying a second one of the set of inference functions on the new medical scan. The second one of the set of inference functions utilizes the second one of the set of sub-models. The final abnormality data is generated based on the second abnormality data.

In various embodiments, a sub-region of image data of the new medical scan is selected based on the first abnormality data. One of the set of sub-models that is trained on one of a plurality of anatomical sub-region types that corresponds to the sub-region is selected as the second one of the set of sub-models, where the second one of the set of inference functions is performed only on the sub-region of the image data of the new medical scan.

FIG. 21 presents a flowchart illustrating a method for execution by a multi-model medical scan analysis system 6002 that stores executable instructions that, when executed by at least one processor, cause the multi-model medical scan analysis system 6002 to perform the steps below. Some or all of the steps of FIG. 21 can be performed by the multi-model medical scan analysis system 6002 instead of or in addition to some or all of the steps of FIG. 20.

Step 9102 includes receiving, via a receiver, a plurality of medical scans. Each of the plurality of medical scans includes corresponding labeling data indicating whether each of a plurality of abnormality types are present in the each of the plurality of medical scans. In various embodiments, the plurality of medical scans correspond to chest x-rays. Step 9104 includes generating a generic model by performing a training step on image data of the plurality of medical scans and the corresponding labeling data. Step 9106 includes generating a plurality of fine-tuned models, where each of the plurality of fine-tuned models is generated by performing a fine-tuning step on the generic model, and where each of the plurality of fine-tuned models corresponds to one of the plurality of abnormality types. Step 9108 includes receiving, via a receiver, a new medical scan. Step 9110 includes generating abnormality detection data for the new medical scan by performing a generic inference function on image data of the new medical scan. The generic inference function utilizes the generic model, and the abnormality detection data indicates a plurality of probability values that each indicate a probability that a corresponding one of the plurality of abnormality types is present in the new medical scan. Step 9112 includes determining a first one of the plurality of abnormality types that is detected in the new medical scan by determining a corresponding one of the plurality of probability values compares favorably to a detection threshold. Step 9114 includes selecting one of the plurality of fine-tuned models that corresponds to the first one of the plurality of abnormality types. Step 9116 includes generating additional abnormality data for the new medical scan by performing a fine-tuned inference function on the image data of the new medical scan, where the fine-tuned inference function utilizes the one of the plurality of fine-tuned models. Step 9118 includes transmitting the additional abnormality data to a client device for display via a display device. The abnormality can also be transmitted to the client device for display via the display device.

In various embodiments, the additional abnormality data includes a new probability value indicating whether the first one of the plurality of abnormality types is present. In various embodiments, the additional abnormality data indicates an increased confidence that first one of the plurality of abnormality types is present in the new medical scan in response to the new probability value indicating a higher probability value than the corresponding one of the plurality of probability values of the abnormality detection data. In various embodiments, the additional abnormality data indicates that the first one of the plurality of abnormality types is not present in the new medical scan in response to the new probability value comparing unfavorably to the detection threshold.

In various embodiments, performing the fine-tuning step includes modifying a plurality of pre-tuned weights of the generic model. In various embodiments, performing the fine-tuning step includes performing a training step on a subset of the plurality of medical scans that have corresponding labeling data indicating the first one of the plurality of abnormality types is present in the each of the subset of the plurality of medical scans. Performing the training step includes utilizing a set of initial weights corresponding to the plurality of pre-tuned weights of the generic model.

In various embodiments, performing the fine-tuning step to generate one of the plurality of fine-tuned models corresponding to the first one of the plurality of abnormality types includes utilizing additional labeling data of a subset of the plurality of medical scans. Each of the subset of the plurality of medical scans have corresponding labeling data indicating the first one of the plurality of abnormality types is present in the each of the subset of the plurality of medical scans. The additional labeling data indicates characterization labels characterizing the first one of the plurality of abnormality types in the each of the subset of the plurality of medical scans. The additional abnormality data indicates output data for the characterization labels.

In various embodiments, the output data indicates a plurality of probability values indicating whether each of a plurality of characterization types characterize the first one of the plurality of abnormality types. In various embodiments, the output data indicates a subset of the plurality of characterization types determined to characterize the first one of the plurality of abnormality types in response to corresponding ones of the plurality of probability values comparing favorably to a characterization threshold.

In various embodiments, a second one of the plurality of abnormality types is determined by determining a second corresponding one of the plurality of probability values compares favorably to the detection threshold. A second one of the plurality of fine-tuned models that corresponds to the second one of the plurality of abnormality types is selected. Second additional abnormality data is generated for the new medical scan by performing a second fine-tuned inference function on the image data of the new medical scan. The second fine-tuned inference function utilizes the second one of the plurality of fine-tuned models. The second additional abnormality data is transmitted to a client device for display via a display device in conjunction with the additional abnormality data. In various embodiments, the abnormality detection data indicates region of interest data indicating a location of the first one of the plurality of abnormality types in the image data of the new medical scan. A sub-region of the image data of the new medical scan is selected based on the region of interest data, and the fine-tuned inference function is performed only on the sub-region of the image data of the new medical scan.

In various embodiments, the method includes determining a subset of the plurality of medical scans that have corresponding labeling data indicating the first one of the plurality of abnormality types is present in the each of the subset of the plurality of medical scans. A plurality of sub-regions are selected by selecting a sub-region of the image data of each of the subset of the plurality of medical scans based on region interest data of the corresponding labeling data indicating a location of the first one of the plurality of abnormality types in the image data of the each of the subset of the plurality of medical scans. A training step is performed on the plurality of sub-regions to generate the one of the plurality of fine-tuned models.

FIG. 22A presents a flowchart illustrating methods for execution by a multi-model medical scan analysis system 6002 implemented as a location-based medical scan analysis system 6004 that stores executable instructions that, when executed by at least one processor, cause the location-based medical scan analysis system 6004 to perform the steps below.

Step 9202 includes receiving, via a receiver, a plurality of medical scans. Step 9204 includes generating a generic model by performing a training step on image data of the plurality of medical scans. Step 9206 includes generating a plurality of location-based subsets of the plurality of medical scans. Each of the plurality of location-based subsets is generated by including ones of the plurality of medical scans with originating locations that compare favorably to location grouping criteria for the each of the plurality of location-based subsets. Step 9208 includes generating a plurality of location-based models, where each of the plurality of location-based models is generated by performing a fine-tuning step on the generic model, utilizing a corresponding one of the plurality of location-based subsets.

Inference data is generated for a new medical scan by performing an inference function that utilizes one of the plurality of location-based models on the new medical scan. An originating location associated with the new medical scan compares favorably to the location grouping criteria for one of the plurality of location-based subsets utilized to generate the one of the plurality of location-based models. The inference data is transmitted to a client device for display via a display device.

As illustrated in FIG. 22A, the method can further include step 9210, which includes receiving, via the receiver, the new medical scan. The method can further include step 9212, which includes selecting the one of the plurality of location-based models based on determining the location grouping criteria for the one of the plurality of location-based subsets utilized to generate the one of the plurality of location-based models compares favorably to the originating location of the new medical scan. The method can further include step 9214, which includes performing the inference function that utilizes the one of the plurality of location-based models on the new medical scan to generate the inference data is generated for a new medical scan. The method can further include step 9216, which includes transmitting the inference data to the client device for display via the display device. In various embodiments, the method can further include determining the originating location of the new medical scan based on determining a location of a transmitting entity, where the new medical scan was transmitted to the location-based medical scan analysis system by the transmitting entity.

Alternatively or in addition, the method can further include transmitting the model data for each of the plurality of location-based models to at least one of a plurality of local systems, where each of the plurality of local systems is associated with a location that compares favorably to the location grouping criteria for one of the plurality of location-based subsets utilized to generate the one of the plurality of location-based models associated with the model data. In various embodiments, at least one of the plurality of local systems utilizes a medical picture archive integration system. In various embodiments, some or all of the plurality of local systems includes at least one second processor and a second memory that stores second executable instructions that, when executed by the at least one second processor, causes a corresponding one of the plurality of local systems to perform the steps illustrated in FIG. 22B.

Step 9218 includes receiving model data for one of the plurality of location-based models from the location-based medical scan analysis system. Step 9220 includes receiving the new medical scan via a receiver of the one of the plurality of local systems. Step 9222 includes performing the inference function that utilizes the one of the plurality of location-based models on the new medical scan to generate the inference data. Step 9224 includes transmitting the inference data to the client device for display via the display device.

In various embodiments, the location grouping criteria for the plurality of location-based subsets indicates geographic region criteria. Some or all of the plurality of location-based subsets include medical scans originating from each of a plurality of different geographic regions. In various embodiments, the location grouping criteria for the plurality of location-based subsets indicates hospital criteria. Some or all of the plurality of location-based subsets include medical scans originating from each of a plurality of different hospitals. In various embodiments, the location grouping criteria for the plurality of location-based subsets indicates hospital setting criteria. Some or all of the plurality of location-based subsets include medical scans originating from each of a plurality of different hospital settings. The plurality of different hospital settings include an in-patient setting, an out-patient setting, an emergency care setting, and/or any other types of hospital settings.

In various embodiments, a plurality of location groupings that optimize accuracy of the plurality of location-based models are automatically determined, where the plurality of location-based subsets are determined in accordance with the plurality of location groupings. In various embodiments, at least one location-based trend in the image data of the plurality of medical scans is automatically determined. At least one of the plurality of location groupings is determined based on a trend location associated with the location-based trend.

In various embodiments, an updated generic model is generated by performing a retraining step on the generic model. The retraining step utilizes the new medical scan and the inference data. A plurality of updated location-based models are generated, where each of the plurality of updated location-based models is generated by performing a fine-tuning step on the updated generic model. Second inference data is generated for a second new medical scan by performing an inference function that utilizes one of the plurality of updated location-based models on the second new medical scan. A second originating location associated with the second new medical scan compares favorably to the location grouping criteria for one of the plurality of location-based subsets utilized to generate the one of the plurality of location-based models. The second inference data is transmitted to the client device for display via the display device. In various embodiments, the retraining step further utilizes model parameters of at least one of the plurality of location-based models. In various embodiments, generating the plurality of updated location-based models includes changing the location grouping criteria for at least one of the plurality of location-based subsets.

FIG. 23 presents a flowchart illustrating a method for execution by a model-assisted annotating system 7002 that stores executable instructions that, when executed by at least one processor, cause the model-assisted annotating system 7002 to perform the steps below.

Step 9302 includes receiving, via a receiver, a first set of medical scans for review. Step 9304 includes transmitting, via a transmitter, the first set of medical scans to a set of client devices associated with a set of users. Each of the first set of medical scans is displayed to one of the set of users via an interactive interface displayed by a display device associated with a corresponding one of the set of client devices. Step 9306 includes receiving a first set of annotation data from the set of client devices. Each of the first set of annotation data is generated by one of the set of client devices in response to a prompt via the interactive interface displayed by the display device to provide annotation data for one of the first set of medical scans displayed by the one of the set of client devices. Step 9308 includes performing a first training step to train a computer vision model by utilizing image data of the first set of medical scans as input labels and by utilizing the first set of annotation data as output labels. Step 9310 includes receiving, via the receiver, a second set of medical scans for review. Step 9312 includes generating a second set of annotation data by performing an inference function on image data of the second set of medical scans. The inference function utilizes the computer vision model, and each of the second set of annotation data is generated as output of performing the inference function on a corresponding one of the second set of medical scans. Step 9314 includes transmitting, via the transmitter, the second set of medical scans and the second set of annotation data to the set of client devices. Each of the second set of medical scans is displayed to one of the set of users in conjunction with a corresponding one of the second set of annotation data via the interactive interface. Step 9316 includes receiving a set of additional annotation data from the set of client devices. Each of the set of additional annotation data is generated by one of the set of client devices in response to a prompt via the interactive interface displayed by the display device to provide additional annotations to the corresponding one of the second set of annotation data displayed in conjunction with one of the second set of medical scans by the one of the set of client devices. Step 9318 includes performing a second training step to generate an updated computer vision model by utilizing the set of additional annotation data to update the computer vision model. Step 9320 includes receiving, via the receiver, a third set of medical scans for review. Step 9322 includes generating a third set of annotation data by performing an updated inference function on image data of the third set of medical scans. The updated inference function utilizes the updated computer vision model, and each of the third set of annotation data is generated as output of performing the updated inference function on a corresponding one of the third set of medical scans. Step 9324 includes transmitting, via the transmitter, the third set of medical scans and the third set of annotation data to the set of client devices. Each of the third set of medical scans is displayed to one of the set of users in conjunction with a corresponding one of the third set of annotation data via the interactive interface.

In various embodiments, the set of additional annotation data includes a set of corrected annotation data. Each of the set of corrected annotation data is generated by one of the set of client devices in response to a prompt via the interactive interface displayed by the display device to provide corrections to the corresponding one of the second set of annotation data displayed in conjunction with one of the second set of medical scans. The second training step utilizes image data of the second set of medical scans as input labels and utilizes the set of corrected annotation data as output labels.

In various embodiments, performing the first training step includes utilizing image data as input labels and further includes utilizing a global binary abnormality label for each of the first set of annotation data as output labels. The second set of annotation data includes a global binary abnormality label for each of the second set of medical scans. The set of additional annotation data includes a set of abnormality characterization data, where each of the set of abnormality characterization data is generated by one of the set of client devices in response to a prompt via the interactive interface displayed by the display device to characterize an abnormality indicated in the corresponding one of the second set of annotation data displayed in conjunction with one of the second set of medical scans. The second training step utilizes image data of the second set of medical scans as input labels and utilizes the set of abnormality characterization data as output labels.

In various embodiments, the third set of annotation data includes abnormality characterization data generated as output of the updated inference function. The abnormality characterization data of each of the third set of annotation data is displayed to one of the set of users in conjunction with a corresponding one of the third set of annotation data via the interactive interface.

In various embodiments, the second set of annotation data includes region of interest data generated as output of the inference function, where the region of interest data of one of the second set of annotation data is utilized to indicate a location of an abnormality indicated in the one of the second set of annotation data in the display of a corresponding one of the second set of medical scans via the interactive interface. In various embodiments, the interactive interface displays segmentation data outlining the abnormality overlaying the image data of the corresponding one of the second set of medical scans.

In various embodiments, inference trend data is generated by automatically evaluating the third set of annotation data to identify at least one trend. A third training step is performed to generate a second updated computer vision model based on the inference trend data. In various embodiments, each of the third set of annotation data includes a confusion matrix indicating a plurality of probability values for a plurality of labels. Generating the inference trend data includes identifying at least one weak label of the plurality of labels based on determining corresponding probability values in confusion matrices of the third set of annotation data compare unfavorably to a confidence threshold.

In various embodiments, additional training data criteria corresponding to the at least one weak label is determined. A request for additional training data that indicates the additional training data criteria is transmitted, via the transmitter. A fourth set of medical scans is received, via the receiver, in response to the request for additional training data. Performing the third training step includes utilizing the fourth set of medical scans as input labels and further includes utilizing a fourth set of annotation data for the fourth set of medical scans as output labels.

In various embodiments, the additional training data criteria indicates at least one type of abnormality. In various embodiments, the third set of medical scans correspond to a plurality of scan types. Generating the inference trend data further includes grouping the third set of medical scans by the plurality of scan types into a plurality of groupings and separately evaluating the third set of annotation data for each of the plurality of groupings. The at least one weak label is identified for one of the plurality of groupings, and the additional training data criteria indicates one of the plurality of scan types corresponding to the one of the plurality of groupings.

In various embodiments, the fourth set of medical scans is transmitted, via the transmitter, to the set of client devices. Each of the fourth set of medical scans is displayed to one of the set of users via the interactive interface displayed by a display device associated with a corresponding one of the set of client devices. The fourth set of annotation data is received from the set of client devices. Each of the fourth set of annotation data is generated by one of the set of client devices in response to a prompt via the interactive interface displayed by the display device to provide annotation data for one of the fourth set of medical scans displayed by the one of the set of client devices.

In various embodiments, each of the third set of annotation data includes a confusion matrix indicating a plurality of probability values for a plurality of labels. A plurality of desired label dependency rules are determined. Each of the plurality of desired label dependency rules indicates at least two of the plurality of labels and each of the plurality of desired label dependency rules further indicates a desired relationship between a corresponding at least two of the plurality of probability values for the at least two of the plurality of labels. Generating the inference trend data includes determining probability values in confusion matrices of the third set of annotation data compare unfavorably to at least one of the plurality of desired label dependency rules. In various embodiments, the plurality of labels includes a global abnormality label. One of the plurality of probability values for the global abnormality label indicates a probability that any abnormality is present. The plurality of labels further includes a set of abnormality classification labels. Each one of a set of the plurality of probability values for the set of abnormality classification labels indicates a probability that an abnormality of a classification indicated by a corresponding one of the set of abnormality classification labels is present.

A first one of the set of the plurality of desired label dependency rules indicates that if at least one of the set of the plurality of probability values for the set of abnormality classification labels exceeds a detection probability threshold, then the one of the plurality of probability values for the global abnormality label should also exceed the detection probability threshold. A second one of set of the plurality of desired label dependency rules indicates that if the one of the plurality of probability values for the global abnormality label exceeds the detection probability threshold, then at least one of the set of the plurality of probability values for the set of abnormality classification labels should also exceed the detection probability threshold. A third one of the set of the plurality of desired label dependency rules indicates that if none of the set of the plurality of probability values for the set of abnormality classification labels exceed the detection probability threshold, then the one of the plurality of probability values for the global abnormality label should not exceed the detection probability threshold. A fourth one of the set of the plurality of desired label dependency rules indicates that if the one of the plurality of probability values for the global abnormality label does not exceed the detection probability threshold, then none of the set of the plurality of probability values for the set of abnormality classification labels should exceed the detection probability threshold.

FIG. 24 presents a flowchart illustrating a method for execution by a medical scan triaging system 8002 that stores executable instructions that, when executed by at least one processor, cause the medical scan triaging system 8002 to perform the steps below.

Step 9402 includes receiving, via a receiver, a plurality of medical scans for review. Step 9404 includes generating abnormality data for each of the plurality of medical scans by performing an inference function on image data of each of the plurality of medical scans. The inference function utilizes a computer vision model trained on a training set of medical scans, and the abnormality data for the each of the plurality of medical scans indicates a global abnormality probability indicating a probability that an abnormality is present in the each of the plurality of medical scans. Step 9406 includes determining a triage probability threshold based on user input to a first client device in response to a prompt presented via an interactive interface. The interactive interface is displayed on a first display device associated with the first client device. Step 9408 includes determining a first subset of the plurality of medical scans by identifying ones of the plurality of medical scans with a corresponding global abnormality probability that compares favorably to the triage probability threshold. Step 9410 includes determining a second subset of the plurality of medical scans by identifying ones of the plurality of medical scans with a corresponding global abnormality probability that compares unfavorably to the triage probability threshold. Step 9412 includes designating the first subset of the plurality of medical scans for human review. Step 9414 includes designating the second subset of the plurality of medical scans as normal, where human review of the second subset of the plurality of medical scans is automatically waived. Step 9416 includes facilitating transmission of the first subset of the plurality of medical scans to a plurality of client devices associated with a plurality of users. The first subset of the plurality of medical scans are displayed to the plurality of users via a plurality of display devices associated with the plurality of users.

In various embodiments, an updated triage probability threshold is determined based on user input to the first client device in response to a second prompt presented via an interactive interface. An updated first subset of the plurality of medical scans is determined by identifying ones of the plurality of medical scans with a corresponding global probability that compares favorably to the updated triage probability threshold. An updated second subset of the plurality of medical scans is determined by identifying ones of the plurality of medical scans with a corresponding global probability that compares unfavorably to the updated triage probability threshold. The updated first subset of the plurality of medical scans is designated for human review. The updated second subset of the plurality of medical scans is designated as normal, where human review of the updated second subset of the plurality of medical scans is automatically waived.

In various embodiments, the updated triage probability threshold is determined based on second user input to the first client device in response to a second prompt presented via the interactive interface. In various embodiments, at least one of the plurality of medical scans has a global abnormality probability that greater than a first probability value indicated by the triage probability threshold and is less than a second probability value indicated by the updated triage probability threshold. The at least one of the plurality of medical scans in the first subset is removed to generate the updated first subset and is added to the second subset to generate the updated second subset, and where a notification is transmitted to at least one of the plurality of client devices indicating that the at least one of the plurality of medical scans no longer needs review.

In various embodiments, at least one of the plurality of medical scans has a global abnormality probability that less than a first probability value indicated by the triage probability threshold and is greater than a second probability value indicated by the updated triage probability threshold, where at least one of the plurality of medical scans in the second subset is removed to generate the updated second subset and is added to the first subset to generate the updated first subset, and where transmission of the at least one of the plurality of medical scans is transmitted to at least one of the plurality of client devices for display to at least one of the plurality of users.

In various embodiments, an expected average review time is determined based on a number of medical scans in the first subset of the plurality of medical scans. The method further includes automatically determining to update the triage probability threshold in response to determining the expected average review time compares favorably to a low review time threshold.

In various embodiments, the abnormality data for at least one of the plurality of medical scans further includes a time-sensitivity value indicating a time-sensitivity of a detected abnormality in the abnormality data. A triage time-sensitivity threshold is determined based on user input to the first client device in response to a second prompt presented via the interactive interface. A third subset of the plurality of medical scans is determined by identifying ones of the second subset of the plurality of medical scans with a corresponding time-sensitivity value that compares favorably to the triage time-sensitivity threshold. The third subset of the plurality of medical scans is designated for human review. Transmission of the third subset of the plurality of medical scans to the plurality of client devices associated with the plurality of users is facilitated. The third subset of the plurality of medical scans are displayed to the plurality of users via a plurality of display devices associated with the plurality of users.

In various embodiments, review assignment data is generated by assigning each of the first subset of the plurality of medical scans to one of the plurality of users for review. Transmission of the first subset of the plurality of medical scans to the plurality of client devices is facilitated in accordance with the review assignment data. In various embodiments, the abnormality data for each of the plurality of medical scans further includes a time-sensitivity value indicating a time-sensitivity of a detected abnormality in the abnormality data. Priority data is generated by determining a priority value for each the first subset of the plurality of medical scans in as a function of the global abnormality probability and the time-sensitivity value. The review assignment data is generated based on the priority data.

In various embodiments, one of the plurality of users is assigned at least two of the first subset of the plurality of medical scans in the review assignment data. Review ordering data is generated for the at least two of the first subset of the plurality of medical scans based on the priority data. The at least two of the first subset of the plurality of medical scans are displayed to the one of the plurality of users in an ordering dictated by the review ordering data.

In various embodiments, the review assignment data is generated by assigning each of the first subset of the plurality of medical scans to one of the plurality of users with qualification data that corresponds to an anatomical region of the each of the first subset of the plurality of medical scans. In various embodiments, the abnormality data for each of the plurality of medical scans further includes abnormality classification data characterizing the abnormality. The review assignment data is generated by assigning each of the first subset of the plurality of medical scans to one of the plurality of users with qualification data that corresponds to the abnormality classification data of the each of the first subset of the plurality of medical scans.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "configured to", "operably coupled to", "coupled to", and/or "coupling" includes direct coupling between items and/or indirect coupling between items via an intervening item (e.g., an item includes, but is not limited to, a component, an element, a circuit, and/or a module) where, for an example of indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "configured to", "operable to", "coupled to", or "operably coupled to" indicates that an item includes one or more of power connections, input(s), output(s), etc., to perform, when activated, one or more its corresponding functions and may further include inferred coupling to one or more other items. As may further be used herein, the term "associated with", includes direct and/or indirect coupling of separate items and/or one item being embedded within another item. As may still further be used herein, the term "automatically" refers to an action caused directly by a processor of a computer network in response to a triggering event and particularly without human interaction.

As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1. As may be used herein, the term "compares unfavorably", indicates that a comparison between two or more items, signals, etc., fails to provide the desired relationship.

As may also be used herein, the terms "processing module", "processing circuit", "processor", "processing device" and/or "processing unit" may be a single processing device or a plurality of processing devices. Such a processing device may be a microprocessor, micro-controller, digital signal processor, graphics processing unit, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module, module, processing circuit, and/or processing unit may be, or further include, memory and/or an integrated memory element, which may be a single memory device, a plurality of memory devices, and/or embedded circuitry of another processing module, module, processing circuit, and/or processing unit. Such a memory device may be a read-only memory, random access memory, volatile memory, non-volatile memory, static memory, dynamic memory, flash memory, cache memory, and/or any device that stores digital information. Note that if the processing module, module, processing circuit, and/or processing unit includes more than one processing device, the processing devices may be centrally located (e.g., directly coupled together via a wired and/or wireless bus structure) or may be distributedly located (e.g., cloud computing via indirect coupling via a local area network and/or a wide area network). Further note that if the processing module, module, processing circuit, and/or processing unit implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element may store, and the processing module, module, processing circuit, and/or processing unit executes, hard coded and/or operational instructions corresponding to at least some of the steps and/or functions illustrated in one or more of the Figures and/or described herein. Such a memory device or memory element can be included in an article of manufacture. While the processing module, module, processing circuit, and/or processing unit device may be a general purpose computing device, the execution of the hard coded and/or operational instructions by the processing module, module, processing circuit, and/or processing unit configures such a general purpose computing device as a special purpose computing device to implement the corresponding steps and/or functions illustrated in one or more of the Figures and/or described herein. In particular, the hard coded and/or operational instructions by the processing module, module, processing circuit, and/or processing unit implement acts and algorithms performed by the processing module, module, processing circuit, and/or processing unit. Such acts and algorithms can be identified by name, can be illustrated via flowchart and/or described in words.

One or more embodiments have been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claims. Further, the boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality.

To the extent used, the flow diagram block boundaries and sequence could have been defined otherwise and still perform the certain significant functionality. Such alternate definitions of both functional building blocks and flow diagram blocks and sequences are thus within the scope and spirit of the claims. One of average skill in the art will also recognize that the functional building blocks, and other illustrative blocks, modules and components herein, can be implemented as illustrated or by discrete components, application specific integrated circuits, processors executing appropriate software and the like or any combination thereof.

In addition, a flow diagram may include a "start" and/or "continue" indication. The "start" and "continue" indications reflect that the steps presented can optionally be incorporated in or otherwise used in conjunction with other routines. In this context, "start" indicates the beginning of the first step presented and may be preceded by other activities not specifically shown. Further, the "continue" indication reflects that the steps presented may be performed multiple times and/or may be succeeded by other activities not specifically shown. Further, while a flow diagram indicates a particular ordering of steps, other orderings are likewise possible provided that the principles of causality are maintained.

The one or more embodiments are used herein to illustrate one or more aspects, one or more features, one or more concepts, and/or one or more examples. A physical embodiment of an apparatus, an article of manufacture, a machine, and/or of a process may include one or more of the aspects, features, concepts, examples, etc. described with reference to one or more of the embodiments discussed herein. Further, from figure to figure, the embodiments may incorporate the same or similarly named functions, steps, modules, etc. that may use the same or different reference numbers and, as such, the functions, steps, modules, etc. may be the same or similar functions, steps, modules, etc. or different ones.

The term "system" is used in the description of one or more of the embodiments. A system implements one or more functions via a device such as a processor or other processing device or other hardware that may include or operate in association with a memory that stores operational instructions. A system may operate independently and/or in conjunction with software and/or firmware. As also used herein, a system may contain one or more sub-system, each of which may be one or more systems.

As may further be used herein, a computer readable memory includes one or more memory elements. A memory element may be a separate memory device, multiple memory devices, or a set of memory locations within a memory device. Such a memory device may be a read-only memory, random access memory, volatile memory, non-volatile memory, static memory, dynamic memory, flash memory, cache memory, and/or any device that stores digital information. The memory device may be in a form a solid state memory, a hard drive memory, cloud memory, thumb drive, server memory, computing device memory, and/or other physical medium for storing digital information.

While particular combinations of various functions and features of the one or more embodiments have been expressly described herein, other combinations of these features and functions are likewise possible. The present disclosure is not limited by the particular examples disclosed herein and expressly incorporates these other combinations.

What is claimed is:

1. A multi-model medical scan analysis system, comprising:
   at least one processor; and
   a memory that stores operational instructions that, when executed by the at least one processor, cause the multi-model medical scan analysis system to:
   receive, via a receiver, a plurality of medical scans;
   generate a plurality of training sets from the plurality of medical scans;
   generate each of a set of sub-models by performing a training step on a corresponding one of the plurality of training sets of the plurality of medical scans, wherein a first one of the set of sub-models is trained to detect a first type of abnormality, and wherein a second one of the set of sub-models is trained to detect a second type of abnormality;
   receive, via the receiver, a new medical scan;
   select a subset of the set of sub-models based on the new medical scan that includes the first one of the set of sub-models and the second one of the set of sub-models;
   generate a set of abnormality data indicating a plurality of probabilities of abnormality detection by applying a subset of a set of inference functions on the new medical scan, wherein the subset of the set of inference functions utilize the subset of the set of sub-models, wherein each of the set of abnormality data is generated as output of performing one of the subset of the set of inference functions, wherein a first one of the set of abnormality data is generated as output of a first one of the subset of the set of inference functions that corresponds to the first one of the set of sub-models, wherein a second one of the set of abnormality data is generated as output of a second one of the subset of the set of inference functions that corresponds to the second one of the set of sub-models, wherein the first one of the set of abnormality data indicates a first probability that the first type of abnormality is present, wherein the second one of the set of abnormality data indicates a second probability that second type of abnormality is present, and wherein the plurality of probabilities includes the first probability and the second probability;
   generate final abnormality data by performing a final inference function on the set of abnormality data, wherein the final abnormality data indicates at least one final probability of abnormality detection based on the plurality of probabilities of abnormality detection; and wherein the at least one final probability includes a global probability indicating a probability that any abnormality is present based on the plurality of probabilities; and
   transmit the final abnormality data to a client device for display via a display device.

2. The multi-model medical scan analysis system of claim 1, wherein at least two of the set of sub-models each correspond to different ones of a set of medical scan classification categories, wherein at least two of the plurality of training sets are generated to include ones of the plurality of medical scans of a corresponding one of the set of medical scan classification categories, and wherein the subset of the set of sub-models are selected by determining a corresponding subset of the set of medical scan classification categories that compare favorably to the new medical scan.

3. The multi-model medical scan analysis system of claim 2, wherein the set of medical scan classification categories correspond to at least one of: a plurality of medical scan modalities, a plurality of medical scan views, or a plurality of anatomical regions.

4. The multi-model medical scan analysis system of claim 2, wherein the new medical scan is received in a study for a patient that includes a plurality of medical scans that each include a plurality of image slices, wherein the subset of the set of sub-models is selected based on the plurality of medical scans in the study, and wherein at least two of the subset of the set of inference functions are performed on different ones of the plurality of medical scans to generate the set of abnormality data.

5. The multi-model medical scan analysis system of claim 4, wherein the plurality of probabilities indicate whether an abnormality is present in the different ones of the plurality of medical scans, and wherein the final inference function utilizes a Bayesian model to generate the at least one final probability to further include a probability that the abnormality is present in the patient given the plurality of probabilities of the set of abnormality data.

6. The multi-model medical scan analysis system of claim 1, wherein the plurality of probabilities that indicate whether a plurality of abnormality types are present, and wherein the final inference function utilizes a Bayesian model to generate the at least one final probability to further include a plurality of final probabilities indicating whether each of the plurality of abnormality types are present given the plurality of probabilities of the set of abnormality data.

7. The multi-model medical scan analysis system of claim 1, wherein the final inference function utilizes a plurality of known correlations between different types of abnormalities, and wherein the final abnormality data is generated based on a known correlation between the first type of abnormality and the second type of abnormality.

8. The multi-model medical scan analysis system of claim 7, wherein the operational instructions, when executed by the at least one processor, further cause the multi-model medical scan analysis system to perform a training step on a plurality of sets of abnormality data to generate a hyper-model, wherein each of the plurality of sets of abnormality data indicate whether each of the plurality of types of abnormalities are present in a corresponding study in a training set of studies, wherein the final inference function utilizes the hyper-model, and wherein the plurality of known correlations are determined as a result of generating the hyper-model.

9. The multi-model medical scan analysis system of claim 7, wherein one of: the final abnormality data indicates an increase in the second probability that the second type of abnormality is present in response to the set of abnormality data indicating the first probability that the first type of abnormality is present comparing favorably to a detection threshold and in response to the known correlation between the first type of abnormality and the second type of abnormality comparing favorably to a correlation threshold; or the final abnormality data indicates a decrease in the second probability that the second type of abnormality is present in response to the set of abnormality data indicating the first probability that the first type of abnormality is present comparing unfavorably to a detection threshold and in response to the known correlation between the first type of abnormality and the second type of abnormality comparing favorably to a correlation threshold.

10. The multi-model medical scan analysis system of claim 1, wherein the operational instructions, when executed by the at least one processor, further cause the multi-model medical scan analysis system to:
partition image data of one of the plurality of medical scans into at least two partitioned image data portions in accordance with a plurality of partitioning categories, wherein a first one of the plurality of training sets includes a first partitioned image data portion of the least two partitioned image data portions, and wherein a second one of the plurality of training sets includes a second partitioned image data portion of the least two partitioned image data portions; and
partition image data of the new medical scan into at least two new partitioned image data portions, wherein the first one of the subset of the set of inference functions is performed upon a first new partitioned image data portion of the at least two new partitioned image data portions, and wherein the second one of the subset of the set of inference functions is performed upon a second new partitioned image data portion of the at least two new partitioned image data portions.

11. The multi-model medical scan analysis system of claim 10, wherein partitioning the image data of the one of the plurality of medical scans into at least two partitioned image data portions includes one of: partitioning a set of images slices included in the one of the plurality of medical scans into different subsets of the set of image slices for inclusion in different ones of the plurality of training sets; or cropping at least one image slice included in the one of the plurality of medical scans into different cropped portions for inclusion in different ones of the plurality of training sets.

12. The multi-model medical scan analysis system of claim 10, wherein the plurality of probabilities indicate whether an abnormality is present in different ones of the at least two new partitioned image data portions of the new medical scan, and wherein the final inference function utilizes a Bayesian model to generate a final probability that the abnormality is present in the new medical scan given the plurality of probabilities of the set of abnormality data.

13. The multi-model medical scan analysis system of claim 10, wherein image data of each of the plurality of medical scans is partitioned by a plurality of anatomical subregion types, wherein the plurality of training sets includes a set of anatomical subregion type subsets that each include image data of the plurality of medical scans of a corresponding one of the plurality of anatomical subregion types, wherein the image data of the new medical scan is partitioned into a plurality of sub-regions in accordance with the plurality of anatomical subregion types, and wherein at least two of the subset of the set of inference functions are performed on of different ones of the plurality of sub-regions of the image data of the new medical scan.

14. The multi-model medical scan analysis system of claim 1, wherein the plurality of medical scans include image data and text data, wherein generating the plurality of training sets includes generating at least one image data training set that includes image data of the plurality of medical scans, wherein generating the plurality of training sets includes generating at least one text data training set that includes text data of the plurality of medical scans, wherein the first one of the set of abnormality data is generated by applying the first one of the subset of the set of inference functions on image data of the new medical scan, wherein the first one of the subset of the set of inference functions utilizes a computer vision model generated by performing the training step on the at least one image data training set, wherein a third one of the set of abnormality data is generated by applying a third one of the set of inference functions on text data of the new medical scan, and wherein the third one of the set of inference functions utilizes a natural language model generated by performing the training step on the text data training set.

15. The multi-model medical scan analysis system of claim 1, wherein the medical scans are partitioned by sequence, wherein the plurality of training sets includes a set of sequence type subsets that each include sequences of the plurality of medical scans of a corresponding one of a plurality of sequence types, wherein the new medical scan includes a plurality of sequences, and wherein at least two of the subset of the set of inference functions are performed on different ones of the plurality of sequences.

16. The multi-model medical scan analysis system of claim 15, wherein a third one of the set of abnormality data is generated as output of performing a third one of the subset of the set of inference functions on a third one of the plurality of sequences of the new medical scan that corresponds to a third type of sequence, wherein the third one of the subset of the set of inference functions utilizes a third one of the set of sub-models that was trained on the third type of sequence, wherein a fourth one of the set of abnormality data is generated as output of performing a fourth one of the subset of the set of inference functions on a fourth one of the plurality of sequences of the new medical scan that corresponds to a fourth type of sequence, wherein the fourth one of the subset of the set of inference functions utilizes a fourth one of the set of sub-models that was trained on the fourth type of sequence, wherein the third one of the set of abnormality data indicates a third probability that an abnormality is present in the third one of the plurality of sequences, wherein the fourth one of the set of abnormality data indicates a fourth probability that the abnormality is present in the fourth one of the plurality of sequences, wherein the final abnormality data indicates a final probability that the abnormality is present in the new medical scan, and wherein the at least one final probability is generated based on the third probability and the fourth probability.

17. The multi-model medical scan analysis system of claim 1, wherein the operational instructions, when executed by the at least one processor, further cause the multi-model medical scan analysis system to:
   select the first one of the set of sub-models to perform on the new medical scan, based on the new medical scan;
   generate first abnormality data by applying a first one of the subset of the set of inference functions on the new medical scan, wherein the first one of the subset of the set of inference functions utilizes the first one of the set of sub-models;
   select the second one of the set of sub-models to perform on the new medical scan based on the first abnormality data; and
   generate second abnormality data by applying the second one of the subset of the set of inference functions on the new medical scan, wherein the second one of the subset of the set of inference functions utilizes the second one of the set of sub-models, wherein the final abnormality data is generated based on the second abnormality data.

18. The multi-model medical scan analysis system of claim 17, wherein the operational instructions, when executed by the at least one processor, further cause the multi-model medical scan analysis system to:
   select a sub-region of image data of the new medical scan based on the first abnormality data; and
   select one of the set of sub-models that is trained on one of a plurality of anatomical sub-region types that corresponds to the sub-region as the second one of the set of sub-models, wherein the second one of the subset of the set of inference functions is performed only on the sub-region of the image data of the new medical scan.

19. A method for execution by a multi-model medical scan analysis system, the method comprising:
   receiving, via a receiver, a plurality of medical scans;
   generating a plurality of training sets from the plurality of medical scans;
   generating each of a set of sub-models by performing a training step on a corresponding one of the plurality of training sets of the plurality of medical scans, wherein a first one of the set of sub-models is trained to detect a first type of abnormality, and wherein a second one of the set of sub-models is trained to detect a second type of abnormality;
   receiving, via the receiver, a new medical scan;
   selecting a subset of the set of sub-models based on the new medical scan that includes the first one of the set of sub-models and the second one of the set of sub-models;
   generating a set of abnormality data indicating a plurality of probabilities of abnormality detection by applying a subset of a set of inference functions on the new medical scan, wherein the subset of the set of inference functions utilize the subset of the set of sub-models, wherein each of the set of abnormality data is generated as output of performing one of the subset of the set of inference functions, wherein a first one of the set of abnormality data is generated as output of a first one of the set of inference functions that corresponds to the first one of the set of sub-models, wherein a second one of the set of abnormality data is generated as output of a second one of the subset of the set of inference functions that corresponds to the second one of the set of sub-models, wherein the first one of the set of abnormality data indicates a first probability that the first type of abnormality is present, wherein the second one of the set of abnormality data indicates a second probability that second type of abnormality is present, and wherein the plurality of probabilities includes the first probability and the second probability;
   generating final abnormality data by performing a final inference function on the set of abnormality data, wherein the final abnormality data indicates at least one final probability of abnormality detection based on the plurality of probabilities of abnormality detection; and wherein the at least one final probability includes a global probability indicating a probability that any abnormality is present based on the plurality of probabilities; and
   transmitting the final abnormality data to a client device for display via a display device.

* * * * *